United States Patent
Bennett et al.

(10) Patent No.: US 8,268,990 B2
(45) Date of Patent: Sep. 18, 2012

(54) COMPOUNDS

(75) Inventors: Nicholas J. Bennett, Loughborough (GB); Thomas McInally, Loughborough (GB); Stephen Thom, Loughborough (GB)

(73) Assignees: AstraZeneca AB, Sodertalje (SE); Dainippon Sumitomo Pharma Co., Ltd., Osaka (JP)

( * ) Notice: Subject to any disclaimer, the term of this patent is extended or adjusted under 35 U.S.C. 154(b) by 367 days.

(21) Appl. No.: 12/274,915

(22) Filed: Nov. 20, 2008

(65) Prior Publication Data

US 2009/0209524 A1    Aug. 20, 2009

Related U.S. Application Data

(60) Provisional application No. 61/013,699, filed on Dec. 14, 2007.

(30) Foreign Application Priority Data

Nov. 22, 2007   (SE) .................................... 0702577

(51) Int. Cl.
   *C07D 201/16* (2006.01)
(52) U.S. Cl. ............... 540/1; 514/235.8; 514/252.11; 514/255.05; 540/575; 544/122; 544/295; 544/297
(58) Field of Classification Search ............. 514/235.8, 514/252.11, 255.05; 540/575; 544/122, 544/295, 297
See application file for complete search history.

(56) References Cited

U.S. PATENT DOCUMENTS

| | | | |
|---|---|---|---|
| 4,179,562 A | 12/1979 | Ponsford | |
| 4,689,338 A | 8/1987 | Gerster | |
| 4,698,348 A | 10/1987 | Gerster | |
| 4,714,701 A | 12/1987 | Beauchamp | |
| 4,912,112 A | 3/1990 | Seydel et al. | |
| 5,736,549 A | 4/1998 | Beasley et al. | |
| 5,994,361 A | 11/1999 | Penney et al. | |
| 6,028,076 A | 2/2000 | Hirota et al. | |
| 6,110,923 A | 8/2000 | Ely | |
| 6,329,381 B1 | 12/2001 | Kurimoto et al. | |
| 6,376,501 B1 | 4/2002 | Isobe et al. | |
| 6,458,798 B1 | 10/2002 | Fujita et al. | |
| 6,951,866 B2 * | 10/2005 | Fujita et al. | 514/275 |

(Continued)

FOREIGN PATENT DOCUMENTS

EP    1550662    7/2005

(Continued)

OTHER PUBLICATIONS

Hirota et al. "Discovery of 8-hydroxydenines as a novel type of interferon inducer" J. Med. Chem. 45(25):5419-5422 (2002).

(Continued)

*Primary Examiner* — Brandon Fetterolf
*Assistant Examiner* — Jean Cornet
(74) *Attorney, Agent, or Firm* — Morgan, Lewis & Bockius LLP

(57) ABSTRACT

The present invention provides compounds of formula (I)

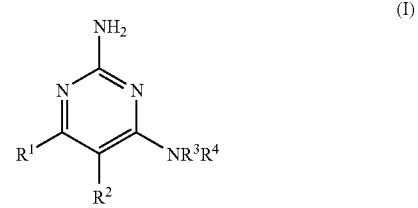

wherein $R^1$, $R^2$, $R^3$ and $R^4$ are as defined in the specification, and pharmaceutically acceptable salts thereof, as well as processes for their preparation, pharmaceutical compositions containing them and their use in therapy.

4 Claims, 2 Drawing Sheets

| XRPD of Monosaccharin salt of Example 57 | | XRPD of Monosaccharin salt of Example 57 | |
|---|---|---|---|
| 2Ø (°) | d space (Å) | 2Ø (°) | d space (Å) |
| 6.3591 | 13.89953 | 19.7576 | 4.49356 |
| 6.9124 | 12.78817 | 20.0967 | 4.41851 |
| 7.3269 | 12.06562 | 20.4436 | 4.34431 |
| 8.3939 | 10.53409 | 20.6797 | 4.29524 |
| 9.8676 | 8.96393 | 20.9564 | 4.23914 |
| 10.8454 | 8.15784 | 21.3643 | 4.15912 |
| 11.7549 | 7.52861 | 22.0341 | 4.03418 |
| 12.4448 | 7.11275 | 22.8587 | 3.89049 |
| 12.7113 | 6.96421 | 23.0919 | 3.85172 |
| 12.9682 | 6.82685 | 23.2947 | 3.81865 |
| 13.6976 | 6.46492 | 23.6138 | 3.76776 |
| 14.4166 | 6.14407 | 24.1901 | 3.6793 |
| 14.6521 | 6.04582 | 24.7329 | 3.59976 |
| 16.2142 | 5.4667 | 25.5475 | 3.4868 |
| 16.4918 | 5.37531 | 26.0651 | 3.41873 |
| 16.7975 | 5.27818 | 27.0187 | 3.30019 |
| 17.224 | 5.14843 | 28.7768 | 3.10244 |
| 17.6001 | 5.03925 | 29.788 | 2.99938 |
| 17.7692 | 4.99165 | 31.0299 | 2.88212 |
| 18.1766 | 4.88069 | 31.2805 | 2.8596 |
| 18.6503 | 4.75779 | 37.1333 | 2.42123 |
| 19.1041 | 4.64577 | | |

Accuracy - +/- 0.1° 2Ø

U.S. PATENT DOCUMENTS

| | | | |
|---|---|---|---|
| 7,157,465 | B2 | 1/2007 | Isobe et al. |
| 8,012,964 | B2 | 9/2011 | Kurimoto et al. |
| 2002/0128264 | A1 | 9/2002 | Taylor |
| 2003/0191086 | A1 | 10/2003 | Hanus |
| 2004/0214192 | A1 | 10/2004 | Hashida et al. |
| 2005/0054590 | A1 | 3/2005 | Averett |
| 2005/0119273 | A1 | 6/2005 | Lipford et al. |
| 2006/0052403 | A1 | 3/2006 | Isobe et al. |
| 2007/0190071 | A1 | 8/2007 | Kurimoto et al. |
| 2007/0225303 | A1* | 9/2007 | Ogita et al. ............ 514/263.22 |
| 2008/0269240 | A1 | 10/2008 | Hashimoto et al. |
| 2008/0300244 | A1 | 12/2008 | Bonnert et al. |
| 2009/0082332 | A1 | 3/2009 | Abbot et al. |
| 2009/0099216 | A1 | 4/2009 | Millichip et al. |
| 2009/0105212 | A1 | 4/2009 | Isobe et al. |
| 2009/0118263 | A1 | 5/2009 | Hashimoto et al. |
| 2009/0143400 | A1 | 6/2009 | McInally et al. |
| 2009/0192153 | A1 | 7/2009 | Hashimoto et al. |
| 2009/0264447 | A1 | 10/2009 | Dietz et al. |
| 2010/0087443 | A1 | 4/2010 | Bonnert et al. |
| 2010/0093998 | A1 | 4/2010 | Isobe et al. |
| 2010/0099870 | A1 | 4/2010 | Isobe et al. |
| 2010/0130491 | A1 | 5/2010 | Bonnert et al. |
| 2010/0240623 | A1 | 9/2010 | Cook et al. |
| 2010/0280001 | A1 | 11/2010 | Bonnert et al. |
| 2010/0298364 | A1 | 11/2010 | Bennett et al. |
| 2011/0028715 | A1 | 2/2011 | Isobe et al. |
| 2011/0046369 | A1 | 2/2011 | Hashimoto et al. |
| 2011/0054168 | A1 | 3/2011 | Kurimoto et al. |
| 2011/0136801 | A1 | 6/2011 | Isobe et al. |

FOREIGN PATENT DOCUMENTS

| | | |
|---|---|---|
| EP | 1728793 | 12/2006 |
| EP | 2246353 | 11/2010 |
| GB | 1375162 | 11/1974 |
| JP | 08-165292 | 6/1996 |
| JP | 347422/1997 | 11/1997 |
| JP | 367449/1997 | 12/1997 |
| JP | 367451/1997 | 12/1997 |
| JP | 11-193282 | 7/1999 |
| WO | WO 99/50249 | 10/1999 |
| WO | WO 01/07027 | 2/2001 |
| WO | WO 2005/009978 | 2/2005 |
| WO | WO 2005/092892 | 10/2005 |
| WO | WO 2005/092893 | 10/2005 |
| WO | WO 2006/137706 | 12/2006 |
| WO | WO 2007/031726 | 3/2007 |
| WO | WO 2007/031829 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2008/001070 | 1/2008 |
| WO | WO 2008/004948 | 1/2008 |
| WO | WO 2008/015250 | 2/2008 |
| WO | WO 2008/083465 | 7/2008 |
| WO | WO 2008/114006 | 9/2008 |
| WO | WO 2008/114008 | 9/2008 |
| WO | WO 2008/114817 | 9/2008 |
| WO | WO 2008/114819 | 9/2008 |
| WO | WO 2008/135791 | 11/2008 |
| WO | WO 2009/078798 | 6/2009 |
| WO | WO 2009/091031 | 7/2009 |
| WO | WO 2009/091032 | 7/2009 |
| WO | WO 2010/033074 | 3/2010 |

OTHER PUBLICATIONS

Isobe et al. "Synthesis and biological evaluation of novel 9-substituted-8-hydroxyadenine derivatives as potent interferon inducers" J. Med. Chem. 49(6):2088-2095 (2006).

Isobe et al. "Synthesis and structure-activity relationships of 2-substituted-8-hydroxyadenine derivatives as orally available interferon inducers without emetic side effects" Bioorganic & Medicinal Chemistry 11:3641-3647 (2003).

Krueger et al. "Tilorone hyrdrochloride: an orally active antiviral agent" Science 169(3951):1213-1214 (1970).

Kurimoto et al. "Prodrugs of 9-benzyl-8-hydroxy-2-(2-hydroxyethylthio)adenine: Potent interferon inducing agents in monkeys" Chemical and Pharmaceutical Bulletin 52(4):466-469 (2004).

Kurimoto et al. "Synthesis and evaluation of 2-substituted 8-hydroxyadenines as potent interferon inducers with improved oral bioavailabilities" Bioorganic & Medicinal Chemistry 12:1091-1099 (2004).

Kurimoto et al. "Synthesis and structure-activity relationships of 2-amino-8-hydroxyadenines as orally active interferon inducing agents" Bioorganic & Medicinal Chemistry 11:5501-5508 (2003).

Lee et al. "Molecular basis for the immunostimulatory activity of guanine nucleoside analogs: Activation of Toll-like receptor 7" Proc. Natl. Acad. Sci. USA 100(11):6646-6651 (2003).

Nichol et al. "Stimulation of murine interferon by a substituted pyrimidine" Antimicrobial Agents and Chemotherapy 9(3):433-439 (1976).

Reiter et al. "Cytokine induction in mice by the immunomodulator imiquimod" Journal of Leukocyte Biology 55(2):234-240 (1994).

Stringfellow et al. "Antiviral and interferon-inducing properties of 1,5-diamino anthraquinones" Antimicrobial Agents and Chemotherapy 15(1); 111-118 (1979).

Falco et al., "2,4-Diaminopyrimidines as Antimalarials. I.1 5-Aryloxyl and 5-Alkoxyl Derivatives," J. Am. Chem. Soc., 73 (8): 3753-3758 (1951).

Yoshimoto et al., "ation analysis of Baker's studies on enzyme inhibition. 2. Chymotrypsin, trypsin, thymidine phosphorylase, uridine phosphorylase, thymidylate synthetase, cytosine nucleoside deaminase, dihydrofolate reductase, malate dehydrogenase, glutamate dehydrogenase, lactate dehydrogenase, and glyceraldehyde-phosphate dehydrogenase," J. Med. Chem., 19(1): 71-98 (1976).

Aoki et al., "Weekly dosing of AZD8848/DSP-3025, a novel TLR7 agonist antedrug, demonstrates a prolonged period of control against markers of pulmonary inflammation in an alergen challenge model in the mouse," ATS, New Orleans, May 2010.

Bell et al., "AZD8848/DSP-3025, a novel potent TLR7 agonist antedrug, demonstrates negligible systemic activity and a prolonged period of control after cessation of weekly dosing in a brown Norway rat ovalbumin challenge model," ATS, New Orleans, May 2010.

Biffen et al., "Biological activity of a novel TLR7 agaonist antedrug for the treatment of allergic diseases," ATS, New Orleans, May 2010.

Ikeda et al., "AZD8848/DSP-3025, a novel potent TLR7 agonist antedrug, demonstrates efficacy against airway obstruction and other inflammatory endpoint in Guinea pig models of Rhinitis and asthma with acute and weekly dosing," ATS, New Orleans, May 2010.

Kurimoto et al. "Synthesis and biological evaluation of novel 9-substituted-8-hydroxyadenine derivatives as potent interferon inducers" Journal of Medicinal Chemistry 49(6): 2088-2095 (2006).

Kurimoto et al., "Synthesis and biological evaluation of 8-oxoadenine derivatives as Toll-like Receptor 7 agonists introducing the antedrug concept," J. Med. Chem., 2010, 53, pp. 2964-2972.

Lee et al. "Activation of anti-hepatitis C virus responses via Toll-like receptor 7" Proc. Natl. Acad. Sci. USA 103(6): 1828-1833 (2006).

Matsui et al., "Mechanisms of inhibition of type-2 Cytokines by novel TLR7 agonist antedrugs," ATS New Orleans, May 2010.

McInally et al, "Identification of a novel TLR7 agonist antedrug," EFMC-ISMC 201, Brussels, Belgium, Sep. 5-9, 2010.

McInally, "Identification and pharmacology of novel TLR7 agonist antedrugs," RSC BMSC Inflammation meeting Nov. 18, 2010.

Tojo et al., "Synthesis and biological evaluation of a novel TLR7 agonist with an antedrug strategy," EFMC-ISMC 201, Brussels, Belgium, Sep. 5-9, 2010.

English translation of Opposition against Costa Rican Patent Application No. 11451.

Eiho et al. "Mechanism of long-lasting suppression against Th2 immune response in the lung by a novel antedrug TLR7 agonist," European Respiratory Society Annual Congress, Amsterdam, Sep. 24-28, 2011, Abstract and Poster.

Greiff et al. "Repeated intranasal TLR7 stimulation reduces allergen responsiveness in allergic rhinitis," European Respiratory Society Annual Congress, Amsterdam, Sep. 24-28, 2011, Abstract and Poster.

Biffen et al. "Novel TLR7 agonists for the treatment of allergic diseases," Toll 2011 Meeting, Riva del Garda, Italy, May 4-7, 2011, Abstract.

* cited by examiner

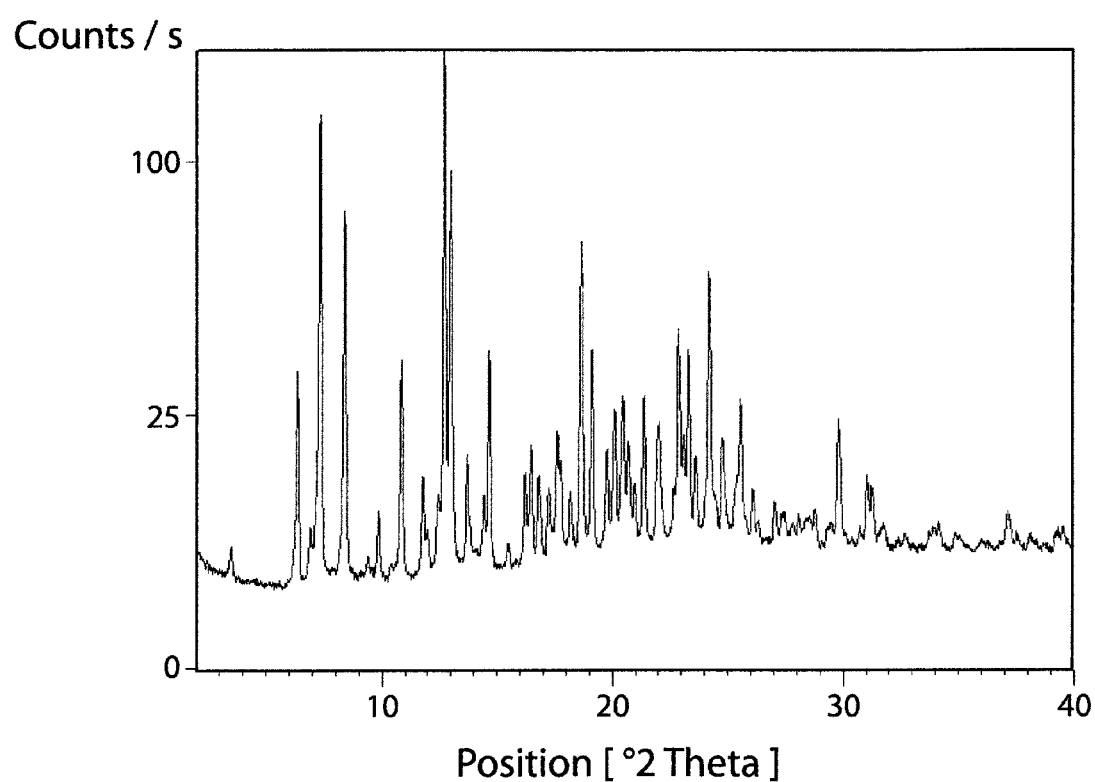
Fig. 1A (MONOSACCHARIN SALT)

Fig. 1B

| XRPD of Monosaccharin salt of Example 57 | | XRPD of Monosaccharin salt of Example 57 | |
|---|---|---|---|
| 2Ø (°) | d space (Å) | 2Ø (°) | d space (Å) |
| 6.3591 | 13.89953 | 19.7576 | 4.49356 |
| 6.9124 | 12.78817 | 20.0967 | 4.41851 |
| 7.3269 | 12.06562 | 20.4436 | 4.34431 |
| 8.3939 | 10.53409 | 20.6797 | 4.29524 |
| 9.8676 | 8.96393 | 20.9564 | 4.23914 |
| 10.8454 | 8.15784 | 21.3643 | 4.15912 |
| 11.7549 | 7.52861 | 22.0341 | 4.03418 |
| 12.4448 | 7.11275 | 22.8587 | 3.89049 |
| 12.7113 | 6.96421 | 23.0919 | 3.85172 |
| 12.9682 | 6.82685 | 23.2947 | 3.81865 |
| 13.6976 | 6.46492 | 23.6138 | 3.76776 |
| 14.4166 | 6.14407 | 24.1901 | 3.6793 |
| 14.6521 | 6.04582 | 24.7329 | 3.59976 |
| 16.2142 | 5.4667 | 25.5475 | 3.4868 |
| 16.4918 | 5.37531 | 26.0651 | 3.41873 |
| 16.7975 | 5.27818 | 27.0187 | 3.30019 |
| 17.224 | 5.14843 | 28.7768 | 3.10244 |
| 17.6001 | 5.03925 | 29.788 | 2.99938 |
| 17.7692 | 4.99165 | 31.0299 | 2.88212 |
| 18.1766 | 4.88069 | 31.2805 | 2.8596 |
| 18.6503 | 4.75779 | 37.1333 | 2.42123 |
| 19.1041 | 4.64577 | | |

Accuracy - +/- 0.1° 2Ø

COMPOUNDS

CROSS-REFERENCE TO RELATED APPLICATIONS

This application claims the benefit of Sweden Patent Application No. 0702577-8, filed Nov. 22, 2007 and U.S. Provisional Application No. 61/013,699, filed Dec. 14, 2007, both of which are herein incorporated by reference in their entirety.

NAMES OF PARTIES TO A JOINT RESEARCH AGREEMENT

The subject matter claimed in this application was made as a result of activities undertaken within the scope of a joint research agreement dated Dec. 19, 2003, between AstraZeneca AB and Sumitomo Pharmaceuticals Co., Ltd. All of the rights and obligations of Sumitomo Pharmaceuticals Co., Ltd. as defined in the joint research agreement between AstraZeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct. 3, 2005.

BACKGROUND OF THE INVENTION

The present invention relates to pyrimidine derivatives, processes for their preparation, pharmaceutical compositions containing them and their use in therapy.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha (IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

This patent application describes a class of pyrimidine derivatives having immunomodulating properties that act via TLR7 which are useful in the treatment of viral or allergic diseases and cancers.

In accordance with the present invention, there is therefore provided a compound of formula (I)

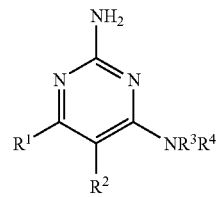

(I)

wherein
$R^1$ represents $C_1$-$C_6$ alkyl, $C_1$-$C_6$ alkoxy or $C_1$-$C_6$ alkylthio;
$R^2$ represents either

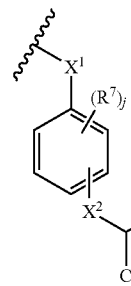

(Ia)

or

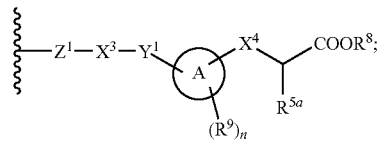

(Ib)

$R^3$ represents a hydrogen atom or a $C_1$-$C_3$ alkyl group;
$R^4$ represents,
(i) $C_3$-$C_8$ cycloalkyl, $C_1$-$C_8$ alkyl, $C_2$-$C_8$ alkenyl or $C_2$-$C_8$ alkynyl, each of which may be optionally substituted by one or more substituents independently selected from halogen, hydroxyl, $C_1$-$C_6$ alkoxy, $C_1$-$C_6$ alkylthio and $C_3$-$C_6$ cycloalkyl, or
(ii) a group

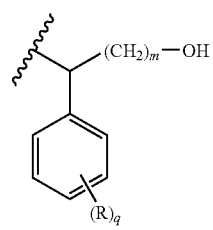

(Ic)

in which m is 1 or 2, q is 0, 1 or 2 and each $R^3$ independently represents a halogen atom or a hydroxyl, methyl, cyano, trifluoromethyl, $S(O)_n$-methyl or methoxy group;
$X^1$ represents an oxygen or sulphur atom or a group NH or $CH_2$;
$X^2$ and $X^4$ each independently represent a bond or an oxygen or sulphur atom;
$R^5$ and $R^{5a}$ each independently represent a hydrogen atom or a $C_1$-$C_3$ alkyl group;

$R^6$ represents a $C_1$-$C_6$ alkyl group optionally substituted by one or more substituents independently selected from halogen, cyano, hydroxyl, $C_1$-$C_3$ alkoxy, methylsulphonyl, methylthiazolyl and $NR^{10}R^{11}$, or $R^6$ represents a saturated heterocyclic ring optionally substituted by $C_1$-$C_6$ alkyl;

j is 1 or 2;

each $R^7$ independently represents a hydrogen or halogen atom or a hydroxyl, methyl, cyano, halomethoxy or methoxy group;

$Z^1$ represents a $C_2$-$C_6$ alkylene or $C_3$-$C_8$ cycloalkylene group;

$X^3$ represents $NR^{12}$, >N—$COR^{12}$, $CONR^{12}$, $NR^{12}CO$, $SO_2NR^{12}$, >N—$SO_2R^{12}$, $NR^{12}SO_2$, $NR^{12}CONR^{13}$ or $NR^{13}CONR^{12}$, $S(O)_p$ or O;

p is 0, 1 or 2;

$Y^1$ represents a single bond or $C_1$-$C_6$ alkylene;

A represents a monocyclic or bicyclic $C_6$-$C_{10}$ aryl or a monocyclic or bicyclic $C_5$-$C_{12}$ heteroaryl group containing 1 to 3 ring heteroatoms;

$R^8$ represents a $C_1$-$C_6$ alkyl group optionally substituted by one or more substituents independently selected from halogen, cyano, hydroxyl, $NR^{10}R^{11}$ and $C_1$-$C_3$ alkoxy;

n is 0, 1 or 2;

each $R^9$ independently represents halogen, cyano, hydroxy, thiol, $C_1$-$C_3$ alkyl, $C_1$-$C_3$ hydroxyalkyl, $C_1$-$C_3$ haloalkyl, $C_1$-$C_3$ alkoxy, $C_1$-$C_3$ haloalkoxy, $C_1$-$C_3$ alkylthio, $C_1$-$C_3$ alkylsulfonyl or $C_1$-$C_3$ alkylsulfinyl;

$R^{10}$ and $R^{11}$ each independently represent hydrogen, $C_1$-$C_6$ alkyl or $C_3$-$C_6$ cycloalkyl, or $R^{10}$ and $R^{11}$ together with the nitrogen atom to which they are attached form a 4- to 7-membered saturated heterocyclic ring which may optionally contain a further ring heteroatom selected from oxygen, $S(O)_v$ or $NR^{36}$, the heterocyclic ring being optionally substituted by $C_1$-$C_6$ alkyl (which is itself optionally substituted by $C_1$-$C_6$ alkoxy) or di-$C_1$-$C_6$ alkylamino;

$R^{12}$ represents a hydrogen atom, a 3- to 8-membered saturated or unsaturated heterocyclic ring comprising at least one ring group O, $S(O)_t$, N or $NR^{14}$, a $C_1$-$C_6$ alkyl group or $C_3$-$C_6$ cycloalkyl group, the latter two groups being optionally substituted by one or more substituents independently selected from $NR^{15}R^{16}$ and $R^{17}$, or $R^{12}$ is a $C_1$-$C_6$ alkylene which may be linked to a carbon atom within a $C_2$-$C_6$ alkylene group $Z^1$ so as to form a saturated 4- to 7-membered nitrogen-containing ring;

$R^{14}$, $R^{22}$ and $R^{35}$ each independently represent a hydrogen atom, $CO_2R^{18}$, $S(O)_wR^{18}$, $COR^{19}$, or a $C_1$-$C_6$ alkyl, $C_2$-$C_6$ alkenyl, $C_2$-$C_6$ alkynyl or $C_3$-$C_8$ cycloalkyl group, each of which may be optionally substituted by one or more substituents independently selected from halogen, cyano, $OR^{20}$ and $NR^{20}R^{21}$;

$R^{15}$ and $R^{16}$ each independently represent a hydrogen atom, a 3- to 8-membered saturated heterocyclic ring comprising at least one ring group O, $S(O)_z$ or $NR^{22}$, $C_1$-$C_6$ alkyl or $C_3$-$C_6$ cycloalkyl, the latter two groups being optionally substituted by one or more substituents independently selected from halogen, cyano, $S(O)_dR^{23}$, $OR^{24}$, $CO_2R^{24}$, $OC(O)R^{24}$, $SO_2NR^{24}R^{25}$, $CONR^{24}R^{25}NR^{24}R^{25}$, $NR^{24}SO_2R^{26}$, $NR^{24}COR^{25}$, or a 3- to 8-membered saturated heterocyclic ring comprising at least one ring group O, $S(O)_b$ or $NR^{25}$, or $R^{15}$ and $R^{16}$ together with the nitrogen atom to which they are attached form a 3- to 8-membered saturated heterocyclic ring comprising a ring nitrogen atom and optionally one or more further ring heteroatoms independently selected from nitrogen, oxygen, sulphur and sulphonyl, the heterocyclic ring being optionally substituted by one or more substituents independently selected from halogen, cyano, $S(O)_fR^{27}$, $OR^{27}$, $CO_2R^{27}$, $COR^{27}$, $OC(O)R^{27}$, $SO_2NR^{27}R^{28}$, $CONR^{27}R^{28}$, $NR^{27}R^{28}$, $NR^{27}SO_2R^{29}$, $NR^{27}COR^{28}$, $C_1$-$C_6$ haloalkyl, $C_3$-$C_8$ cycloalkyl, $C_1$-$C_6$ alkyl, aryl and heteroaryl, the latter four groups being optionally substituted by one or more substituents independently selected from halogen, cyano, $S(O)_gR^{30}$, $OR^{30}$, $CO_2R^{30}$, $SO_2NR^{30}R^{31}$, $CONR^{30}R^{31}$ and $NR^{30}R^{31}$;

$R^{17}$ represents halogen, cyano, $C_1$-$C_3$ haloalkoxy, $CO_2R^{32}$, $S(O)_gR^{32}$, $OR^{32}SO_2NR^{32}R^{34}$, $CONR^{32}R^{34}$, $NR^{32}SO_2R^{33}$, $NR^{32}CO_2R^{33}$, $NR^{32}COR^{34}$ or a 3- to 8-membered saturated heterocyclic ring comprising a ring group $NR^{35}$;

a, b, d, f, g, h, t, v, w and z each independently represent 0, 1 or 2;

$R^{18}$, $R^{26}$, $R^{29}$ and $R^{33}$ each independently represent a $C_1$-$C_6$ alkyl or $C_3$-$C_6$ cycloalkyl group;

$R^{13}$, $R^{19}$, $R^{20}$, $R^{21}$, $R^{23}$, $R^{24}$, $R^{25}$, $R^{27}$, $R^{28}$, $R^{30}$, $R^{31}$, $R^{32}$ and $R^{34}$ each independently represent a hydrogen atom or a $C_1$-$C_6$ alkyl or $C_3$-$C_6$ cycloalkyl group; and $R^{36}$ represents a hydrogen atom or a $C_1$-$C_3$ alkyl group;

or a pharmaceutically acceptable salt thereof.

In the context of the present specification, unless otherwise stated, an alkyl, alkenyl or alkynyl substituent group or an alkyl, alkenyl or alkenyl moiety in a substituent group may be linear or branched. Examples of $C_1$-$C_8$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl, n-hexyl, n-heptyl and n-octyl. Examples of $C_2$-$C_8$ alkenyl groups/moieties include ethenyl, propenyl, 1-butenyl, 2-butenyl, 1-pentenyl, 1-hexenyl, 1-heptenyl, 1-octenyl, 1,3-butadienyl, 1,3-pentadienyl, 1,4-pentadienyl and 1,4-hexadienyl. Examples of $C_2$-$C_8$ alkynyl groups/moieties include ethynyl, 1-propynyl, 2-propynyl (propargyl) or 2-butynyl.

Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene. A $C_3$-$C_8$ cycloalkyl(ene) group is a cyclopropyl(ene), cyclobutyl(ene), cyclopentyl(ene), cyclohexyl(ene), cycloheptyl(ene) or cyclooctyl(ene) group. A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl. A $C_1$-$C_6$ hydroxyalkyl substituent group/moiety will comprise at least one hydroxyl group, e.g. one, two, three or four hydroxyl groups, examples of which include —$CH_2OH$, —$CH_2CH_2OH$, —$CH_2CH_2CH_2OH$ and —$CH(CH_2OH)_2$. An unsaturated (heterocyclic) ring will be partially or fully unsaturated. The alkyl groups in a di-$C_1$-$C_6$ alkylamino group may be the same or different. When $R^6$ represents a $C_1$-$C_6$ alkyl group optionally substituted by $NR^{10}R^{11}$ where $R^{10}$ and $R^{11}$ together with the nitrogen atom to which they are attached form an optionally substituted 4- to 7-membered saturated heterocyclic ring which may optionally contain a further ring heteroatom selected from oxygen, $S(O)_v$ or $NR^{36}$, it will be appreciated that the ring may be attached to the alkyl chain via any suitable ring atom, whether a carbon atom or a heteroatom. The same comment applies to the 3- to 8-membered saturated or unsaturated heterocyclic ring defined in $R^{12}$, and the heterocyclic rings defined in $R^{15}$, $R^{16}$ and $R^{17}$.

An aryl group/moiety may contain from 6 to 10 carbon atoms and may be monocyclic or polycyclic (e.g. bicyclic or tricyclic) in which the two or more rings are fused.

Heterocyclic groups are rings which may be saturated, partially unsaturated or unsaturated, and contain from 3 to 20 atoms, at least one and suitably from 1 to 4 atoms are heteroatoms selected from oxygen, sulphur and nitrogen. Rings may be monocyclic, fused, bridged, or spiro bicyclic heterocyclic ring system(s). Monocyclic heterocyclic rings contain from about 3 to 12 ring atoms, with from 1 to 5 heteroatoms selected from N, O, and S, and suitably from 3 to 7 member atoms, in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems.

Examples of heterocyclic groups which are saturated or partially saturated include cyclic ethers (oxiranes) such as ethyleneoxide, tetrahydrofuran, dioxane, and substituted cyclic ethers. Heterocycles containing nitrogen include, for example, azetidine, pyrrolidine, piperidine, piperazine, tetrahydrotriazine, tetrahydropyrazole, and the like. Typical sulfur containing heterocycles include tetrahydrothiophene, dihydro-1,3-dithiol-2-yl, and hexahydrothiepin-4-yl. Other heterocycles include dihydro-oxathiol-4-yl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene. A suitable value for a heterocyclyl group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

Heterocyclic groups which are aromatic in nature are referred to as "heteroaryl" groups. These groups are aromatic mono-, bi-, or polycyclic heterocyclic ring incorporating one or more (for example 1-4) heteroatoms selected from N, O, and S. The term heteroaryl includes both monovalent species and divalent species. Examples of heteroaryl groups include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers ring systems wherein at least one ring is an aromatic ring containing 1 or more heteroatoms selected from O, S and N and one or more of the other rings is a non-aromatic, saturated or partially unsaturated ring optionally containing one or more heteroatoms selected from O, S and N, for example 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

For the avoidance of doubt, it should be understood that the definitions of the heterocyclic rings in formula (I) are not intended to include unstable structures or any O—O, O—S or S—S bonds and that a substituent, if present, may be attached to any suitable ring atom.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

FIG. 1A is an X-ray powder diffraction pattern of 4-(Dimethylamino)butyl 2-(4-((2-amino-4-methyl-6-(pentylamino)pyrimidin-5-yl)methyl)phenyl)acetate, monosaccharin salt.

FIG. 1B is a table listing the 2θ (2 theta) values and d-spacings corresponding to the peaks shown in the X-ray diffraction pattern of FIG. 1A.

$R^1$ represents $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy, isopropoxy, n-butoxy, isobutoxy, tert-butoxy, n-pentoxy or n-hexoxy), or $C_1$-$C_6$, preferably $C_1$-$C_4$, alkylthio (e.g. methylthio, ethylthio, n-propylthio, isopropylthio, n-butylthio, isobutylthio, tert-butylthio, n-pentylthio or n-hexylthio).

In an embodiment of the invention, $R^1$ represents a $C_1$-$C_6$ alkyl group, particularly methyl group.

In an embodiment of the invention, $R^3$ represents a hydrogen atom.

In an embodiment of the invention, $R^4$ represents a $C_3$-$C_8$, preferably $C_3$-$C_6$, cycloalkyl, $C_1$-$C_8$, preferably $C_4$-$C_8$ or $C_5$-$C_7$, alkyl, $C_2$-$C_8$, preferably $C_4$-$C_7$, alkenyl or $C_2$-$C_8$, preferably $C_4$-$C_7$, alkynyl group, each of which may be optionally substituted by one or more substituents (e.g. one, two, three or four substituents) independently selected from halogen (e.g. fluorine, chlorine, bromine or iodine), hydroxyl, $C_1$-$C_6$, preferably $C_1$-$C_4$, alkoxy, $C_1$-$C_6$, preferably $C_1$-$C_4$, alkylthio and $C_3$-$C_6$, preferably $C_5$-$C_6$, cycloalkyl.

In another embodiment, $R^4$ represents $C_1$-$C_8$ alkyl group, in particular a $C_4$-$C_7$ alkyl group which is optionally substituted by a hydroxyl group.

In one embodiment of the invention, $R^2$ represents a group (Ia).

In an embodiment of the invention, $X^1$ represents a sulphur atom or, in particular, $CH_2$.

$X^2$ preferably represents a bond or an oxygen atom.

In one embodiment, $X^2$ represents a bond.

$R^5$ preferably represents a hydrogen atom.

$R^6$ represents a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group optionally substituted by one or more substituents (e.g. one, two, three or four substituents) independently selected from halogen, cyano, hydroxyl, $C_1$-$C_3$ alkoxy, methylsulphonyl, methylthiazolyl and $NR^{10}R^{11}$, or $R^6$ represents a saturated heterocyclic ring, e.g. a 5- to 6-membered saturated heterocyclic ring such as piperidine, optionally substituted by $C_1$-$C_6$, preferably $C_1$-$C_4$, alkyl, in particular methyl.

In one aspect $R^6$ represents a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group optionally substituted by one or more substituents (e.g. one, two, three or four substituents) independently selected from halogen (e.g. fluorine, chlorine, bromine or iodine), cyano, hydroxyl, $C_1$-$C_3$ alkoxy and $NR^{10}R^{11}$. In another aspect, $R^6$ represents a $C_1$-$C_6$ alkyl group, particularly methyl group. In still another aspect, $R^6$ represents a $C_1$-$C_6$ alkyl group substituted by $NR^{10}R^{11}$.

Each $R^7$ independently represents a hydrogen or halogen (e.g. fluorine, chlorine, bromine or iodine) atom or a hydroxyl, methyl, cyano, halomethoxy or methoxy group. In one aspect, j is 1 and $R^7$ represents hydrogen, hydroxyl, fluorine or methoxy.

$R^{10}$ and $R^{11}$ each independently represent hydrogen, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) or $C_3$-$C_6$, preferably $C_5$-$C_6$, cycloalkyl, or $R^{10}$ and $R^{11}$ together with the nitrogen atom to which they are attached form a 4- to 7-membered, preferably 5- to 6-membered, saturated heterocyclic ring which may optionally contain a further ring heteroatom selected from oxygen, $S(O)_v$ or $NR^{36}$, the heterocyclic ring being optionally substituted by $C_1$-$C_6$ preferably $C_1$-$C_4$, alkyl (which is itself optionally substituted by $C_1$-$C_6$, preferably $C_1$-$C_4$, alkoxy, e.g. methoxy or ethoxy) or di-$C_1$-$C_6$ alkylamino (e.g. dimethylamino).

In one aspect $R^{10}$ and $R^{11}$ each independently represent hydrogen, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) or $C_3$-$C_6$, preferably $C_5$-$C_6$, cycloalkyl, or $R^{10}$ and $R^{11}$ together with the nitrogen atom to which they are attached form a 4- to 7-membered, preferably 5- to 6-membered, saturated heterocyclic ring which may optionally contain a further ring heteroatom selected from oxygen, $S(O)_v$ or $NR^{36}$.

In another aspect, $R^{10}$ and $R^{11}$ each represent a methyl group, or $R^{10}$ and $R^{11}$ together with the nitrogen atom to which they are attached form a 5- to 6-membered, saturated heterocyclic ring which may optionally contain a further ring heteroatom selected from oxygen, $S(O)_v$ or $NR^{36}$, the heterocyclic ring being optionally substituted by $C_1$-$C_2$ alkyl (which is itself optionally substituted by methoxy) or dimethylamino.

In a further aspect, $R^{10}$ and $R^{11}$ each represent a methyl group, or $R^{10}$ and $R^{11}$ together with the nitrogen atom to which they are attached form a 6-membered saturated heterocyclic ring containing a further ring heteroatom selected from oxygen or $NR^{36}$.

In an alternative embodiment, $R^2$ represents a group (Ib).

$Z^1$ represents a $C_2$-$C_6$, preferably $C_2$-$C_4$, alkylene or $C_3$-$C_8$, preferably $C_5$-$C_6$, cycloalkylene group. In one aspect, $Z^1$ represents a linear $C_2$-$C_6$ alkylene, in particular a linear $C_3$-$C_4$ alkylene, group.

In one aspect, $X^3$ represents $NR^{12}$, $>$N—$COR^{12}$, $NR^{12}CO$ or $>$N—$SO_2R^{12}$.

$Y^1$ represents a single bond or a $C_1$-$C_6$, preferably $C_1$-$C_4$, alkylene group. In one aspect, $Y^1$ represents a $C_1$-$C_6$ alkylene, particularly methylene, group.

$X^4$ preferably represents a bond or an oxygen atom.

In one embodiment, $X^4$ represents a bond.

$R^{5a}$ preferably represents a hydrogen atom.

A represents a monocyclic or bicyclic $C_6$-$C_{10}$ aryl or a monocyclic or bicyclic $C_5$-$C_{12}$ heteroaryl group containing 1 to 3 ring heteroatoms independently selected from nitrogen, oxygen and sulphur. In one aspect, A represents a phenyl ring.

$R^8$ represents a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group optionally substituted by one or more substituents (e.g. one, two, three or four substituents) independently selected from halogen (e.g. fluorine, chlorine, bromine or iodine), cyano, hydroxyl, $NR^{10}R^{11}$ and $C_1$-$C_3$ alkoxy.

In one aspect, $R^8$ represents a $C_1$-$C_6$ alkyl group, particularly methyl group.

When n is 1 or 2, each $R^9$ independently represents halogen (e.g. fluorine, chlorine, bromine or iodine), cyano, hydroxy, thiol, $C_1$-$C_3$ alkyl (e.g. methyl or ethyl), $C_1$-$C_3$ hydroxyalkyl (e.g. hydroxymethyl), $C_1$-$C_3$ haloalkyl (e.g. trifluoromethyl), $C_1$-$C_3$ alkoxy (e.g. methoxy or ethoxy), $C_1$-$C_3$ haloalkoxy (e.g. trifluoromethoxy), $C_1$-$C_3$ alkylthio (e.g. methylthio or ethylthio), $C_1$-$C_3$ alkylsulfonyl (e.g. methylsulfonyl) or $C_1$-$C_3$ alkylsulfinyl (e.g. methylsulfinyl).

In one aspect, n is 0.

$R^{12}$ represents a hydrogen atom, a 3- to 8-, particularly 5- to 8-membered saturated or unsaturated heterocyclic ring comprising at least one ring group (e.g. one, two, three or four ring groups independently selected from) O, $S(O)_t$, N or $NR^{14}$, a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group or $C_3$-$C_6$, preferably $C_5$-$C_6$, cycloalkyl group, the latter two groups being optionally substituted by one or more substituents (e.g. one, two or three substituents) independently selected from $NR^{15}R^{16}$ and $R^{17}$, or $R^{12}$ is a $C_1$-$C_6$ alkylene which may be linked to a carbon atom within a $C_2$-$C_6$ alkylene group $Z^1$ so as to form a saturated 4- to 7-membered nitrogen-containing ring.

In one embodiment of the invention, $R^{12}$ represents a hydrogen atom, a 5- or 6-membered saturated or unsaturated heterocyclic ring comprising one or two ring groups independently selected from N and $NR^{14}$, or a $C_1$-$C_6$, preferably $C_1$-$C_4$, alkyl group optionally substituted by one or more substituents (e.g. one, two or three substituents) independently selected from $NR^{15}R^{16}$ and $R^{17}$.

In a further embodiment, $R^{12}$ represents a hydrogen atom, a 5-membered unsaturated heterocyclic ring comprising two ring groups independently selected from N and $NR^{14}$, or a $C_1$-$C_3$ alkyl group optionally substituted by $NR^{15}R^{16}$ or $R^{17}$.

In an embodiment of the invention, $R^{14}$ represents a $C_1$-$C_6$ alkyl group, particularly methyl group.

$R^{15}$ and $R^{16}$ each independently represent a hydrogen atom, a 3- to 8-membered saturated heterocyclic ring comprising at least one ring group O, $S(O)_z$ or $NR^{22}$, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group or $C_3$-$C_6$, preferably $C_5$-$C_6$, cycloalkyl group, the latter two groups being optionally substituted by one or more substituents (e.g. one, two, three or four substituents) independently selected from halogen (e.g. fluorine, chlorine, bromine or iodine), cyano, $S(O)_aR^{23}$, $OR^{24}$, $CO_2R^{24}$, $OC(O)R^{24}$, $SO_2NR^{24}R^{25}$, $CONR^{24}R^{25}$, $NR^{24}R^{25}$, $NR^{24}SO_2R^{26}$, $NR^{24}COR^{25}$, or a 3- to 8-membered saturated heterocyclic ring comprising at least one ring group O, $S(O)_b$ or $NR^{25}$, or $R^{15}$ and $R^{16}$ together with the nitrogen atom to which they are attached form a 3- to 8-membered saturated heterocyclic ring comprising a ring nitrogen atom and optionally one or more (e.g. one, two or three) further ring heteroatoms independently selected from nitrogen, oxygen, sulphur and sulphonyl, the heterocyclic ring being optionally substituted by one or more substituents (e.g. one, two, three or four substituents) independently selected from halogen (e.g. fluorine, chlorine, bromine or iodine), cyano, $S(O)_dR^{27}$, $OR^{27}$, $CO_2R^{27}$, $COR^{27}$, $OC(O)R^{27}$, $SO_2NR^{27}R^{28}$, $CONR^{27}R^{28}$, $NR^{27}R^{28}$, $NR^{27}SO_2R^{29}$, $NR^{27}COR^{28}$, $C_1$-$C_6$, preferably $C_1$-$C_4$, haloalkyl, $C_3$-$C_8$, preferably $C_3$-$C_6$, cycloalkyl, $C_1$-$C_6$, preferably $C_1$-$C_4$, alkyl, aryl and heteroaryl, the latter four groups being optionally substituted by one or more substituents (e.g. one, two, three or four substituents) independently selected from halogen, cyano, $S(O)_fR^{30}$, $OR^{30}$, $CO_2R^{30}$, $SO_2NR^{30}R^{31}$, $CONR^{30}R^{31}$ and $NR^{30}R^{31}$.

In an embodiment of the invention, $R^{15}$ and $R^{16}$ each independently represent a hydrogen atom or a $C_1$-$C_6$, preferably $C_1$-$C_4$, alkyl group optionally substituted by one or more substituents (e.g. one, two, three or four substituents) independently selected from halogen, cyano, $S(O)_aR^{23}$, $OR^{24}$, $CO_2R^{24}$, $OC(O)R^{24}$, $SO_2NR^{24}R^{25}$, $CONR^{24}R^{25}$, $NR^{24}R^{25}$, $NR^{24}SO_2R^{26}$, $NR^{24}COR^{25}$, or a 3- to 8-membered saturated heterocyclic ring comprising at least one ring group O, $S(O)_b$ or $NR^{25}$.

In another embodiment, $R^{15}$ and $R^{16}$ each independently represent a $C_1$-$C_6$, preferably $C_1$-$C_4$, more preferably $C_1$-$C_2$, alkyl group optionally substituted by $OR^{24}$.

In an alternative embodiment, $R^{15}$ and $R^{16}$ together with the nitrogen atom to which they are attached form a 3- to 8-, particularly 5- to 7-membered saturated heterocyclic ring comprising a ring nitrogen atom and optionally one or more (e.g. one, two or three) further ring heteroatoms independently selected from nitrogen, oxygen, sulphur and sulphonyl, the heterocyclic ring being optionally substituted by one or more substituents (e.g. one, two, three or four substituents) independently selected from halogen (e.g. fluorine, chlorine, bromine or iodine), cyano, $OR^{27}$, $CO_2R^{27}$, $COR^{27}$, $C_1$-$C_6$, preferably $C_1$-$C_4$, alkyl and aryl, the latter two groups being optionally substituted by one or more substituents (e.g. one, two, three or four substituents) independently selected from halogen, cyano, $S(O)_fR^{30}$, $OR^{30}$, $CO_2R^{30}$, $SO_2NR^{30}R^{31}$, $CONR^{30}R^{31}$ and $NR^{30}R^{31}$.

In a further embodiment, $R^{15}$ and $R^{16}$ together with the nitrogen atom to which they are attached form a 5- to 7-membered saturated heterocyclic ring comprising a ring nitrogen atom and optionally a second ring nitrogen or oxygen atom, the heterocyclic ring being optionally substituted by $OR^{27}$, $CO_2R^{27}$, $COR^{27}$, $C_1$-$C_3$ alkyl or phenyl, the latter two groups being optionally substituted by $S(O)_fR^{30}$ or $NR^{30}R^{31}$.

In an embodiment of the invention, $R^{17}$ represents $CO_2R^{32}$.

$R^{18}$, $R^{26}$, $R^{29}$ and $R^{33}$ each independently represent a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group or $C_3$-$C_6$, preferably $C_5$-$C_6$, cycloalkyl group.

$R^{13}$, $R^{19}$, $R^{20}$, $R^{21}$, $R^{23}$, $R^{24}$, $R^{25}$, $R^{27}$, $R^{28}$, $R^{30}$, $R^{31}$, $R^{32}$ and $R^{34}$ each independently represent a hydrogen atom or a $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) group or $C_3$-$C_6$, preferably $C_5$-$C_6$, cycloalkyl group.

In an embodiment of the invention,
$R^1$ represents methyl;
$R^2$ represents either $R^5$ represents a hydrogen atom;
$R^6$ represents a $C_1$-$C_6$ alkyl group optionally substituted by $NR^{10}R^{11}$;
j is 1;
$R^7$ represents a hydrogen or halogen (particularly fluorine) atom or a methoxy group;
$Z^1$ represents a $C_3$-$C_4$ alkylene;
$X^3$ represents $NR^{12}$, $>N-COR^{12}$, $NR^{12}CO$ or $>N-SO_2R^{12}$;
$Y^1$ represents methylene;
$X^4$ represents a bond or an oxygen atom;
$R^{5a}$ represents a hydrogen atom;
A represents a monocyclic or bicyclic $C_6$-$C_{10}$ aryl (particularly phenyl) group;
$R^8$ represents methyl;
n is 0;
$R^{10}$ and $R^{11}$ each represent a methyl group, or $R^{10}$ and $R^{11}$ together with the nitrogen atom to which they are attached form a 6-membered saturated heterocyclic ring containing a further ring heteroatom selected from oxygen or $NR^{36}$;
$R^{12}$ represents a hydrogen atom, a 5-membered unsaturated heterocyclic ring comprising two ring groups independently selected from N and $NR^{14}$, or a $C_1$-$C_3$ alkyl group optionally substituted by $NR^{15}R^{16}$ or $R^{17}$;
$R^{14}$ represents methyl;
$R^{15}$ and $R^{16}$ each independently represent a $C_1$-$C_2$ alkyl group optionally substituted by $OR^{24}$, or
$R^{15}$ and $R^{16}$ together with the nitrogen atom to which they are attached form a 5- to 7-membered saturated heterocyclic ring comprising a ring nitrogen atom and optionally a second ring nitrogen or oxygen atom, the heterocyclic ring being optionally substituted by $OR^{27}$, $CO_2R^{27}$, $COR^{27}$, $C_1$-$C_3$ alkyl or phenyl, the latter two groups being optionally substituted by $S(O)_fR^{30}$ or $NR^{30}R^{31}$;
f is 2;
$R^{17}$ represents $CO_2R^{32}$; and
$R^{24}$, $R^{27}$, $R^{30}$, $R^{31}$ and $R^{32}$ each independently represent a hydrogen atom or a methyl group.

In another embodiment of the invention,
$R^1$ represents methyl;
$R^2$ represents either

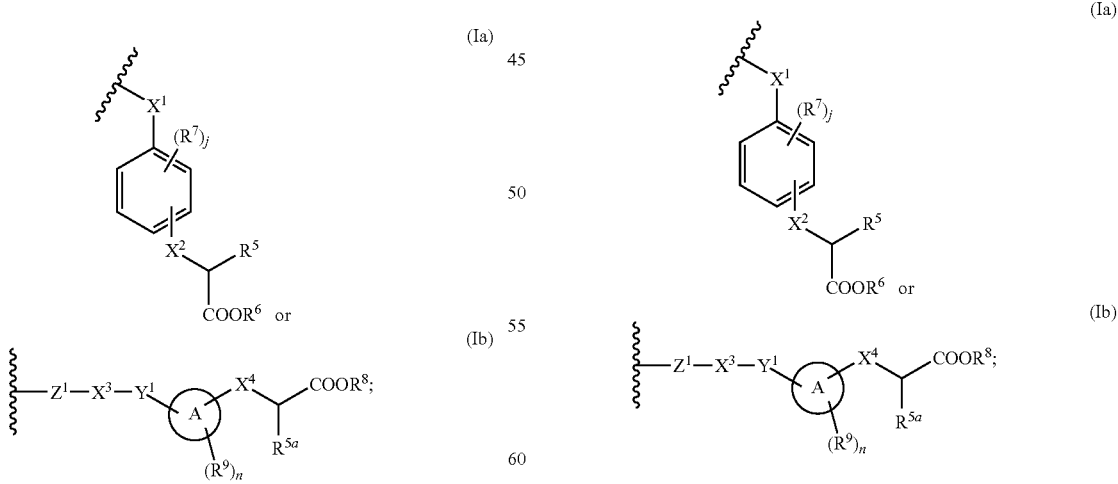

$R^3$ represents a hydrogen atom;
$R^4$ represents a $C_4$-$C_7$ alkyl group optionally substituted by a hydroxyl group;
$X^1$ represents $CH_2$;
$X^2$ represents a bond or an oxygen atom;

$R^3$ represents a hydrogen atom;
$R^4$ represents a $C_4$-$C_7$ alkyl group optionally substituted by a hydroxyl group;
$X^1$ represents a sulphur atom or $CH_2$;
$X^2$ represents a bond or an oxygen atom;
$R^5$ represents a hydrogen atom;

$R^6$ represents a $C_1$-$C_6$ alkyl group optionally substituted by hydroxyl, methylsulphonyl, methylthiazolyl or $NR^{10}R^{11}$, or $R^6$ represents a 5- to 6-membered saturated heterocyclic ring optionally substituted by $C_1$-$C_6$ alkyl;

j is 1;

$R^7$ represents a hydrogen or halogen (particularly fluorine) atom or a hydroxyl or methoxy group;

$Z^1$ represents a $C_3$ alkylene;

$X^3$ represents $NR^{12}$, >N—$COR^{12}$, $NR^{12}CO$ or >N—$SO_2R^{12}$;

$Y^1$ represents methylene;

$X^4$ represents a bond or an oxygen atom;

$R^{5a}$ represents a hydrogen atom;

A represents a monocyclic or bicyclic $C_6$-$C_{10}$ aryl (particularly phenyl) group;

$R^8$ represents methyl;

n is 0;

$R^{10}$ and $R^{11}$ each represent a methyl group, or $R^{10}$ and $R^{11}$ together with the nitrogen atom to which they are attached form a 5- or 6-membered saturated heterocyclic ring optionally containing a further ring heteroatom selected from oxygen, $S(O)_v$ or $NR^{36}$, the heterocyclic ring being optionally substituted by $C_1$-$C_6$ alkyl (which is itself optionally substituted by $C_1$-$C_6$ alkoxy) or di-$C_1$-$C_6$ alkylamino;

v is 2;

$R^{12}$ represents a hydrogen atom, a 5- or 6-membered saturated or unsaturated heterocyclic ring comprising one or two ring groups independently selected from N and $NR^{14}$, or a $C_1$-$C_3$ alkyl group optionally substituted by $NR^{15}R^{16}$ or $R^{17}$;

$R^{14}$ represents methyl;

$R^{15}$ and $R^{16}$ each independently represent a $C_1$-$C_2$ alkyl group optionally substituted by $OR^{24}$, or $R^{15}$ and $R^{16}$ together with the nitrogen atom to which they are attached form a 5- to 7-membered saturated heterocyclic ring comprising a ring nitrogen atom and optionally a second ring nitrogen or oxygen atom, the heterocyclic ring being optionally substituted by $OR^{27}$, $CO_2R^{27}$, $COR^{27}$, $C_1$-$C_3$ alkyl or phenyl, the latter two groups being optionally substituted by $S(O)_fR^{30}$ or $NR^{30}R^{31}$;

f is 2;

$R^{17}$ represents $CO_2R^{32}$ or $S(O)_gR^{32}$;

g is 0; and $R^{24}$, $R^{27}$, $R^{30}$, $R^{31}$ and $R^{32}$ each independently represent a hydrogen atom or a methyl group.

Examples of compounds of the invention include

Methyl 2-(3-((3-(2-Amino-4-methyl-6-(pentylamino)pyrimidin-5-yl)propylamino)methyl)phenyl)acetate, Methyl 2-(4-((3-(2-amino-4-methyl-6-(pentylamino)pyrimidin-5-yl)propylamino)methyl)phenyl)acetate, Methyl 2-(3-((N-(3-(2-amino-4-methyl-6-(pentylamino)pyrimidin-5-yl)propyl)-2-(dimethylamino)acetamido)methyl)phenyl)acetate, Methyl 2-(4-((N-(3-(2-amino-4-methyl-6-(pentylamino)pyrimidin-5-yl)propyl)-2-(dimethylamino)acetamido)methyl)phenyl)acetate, (S)-Methyl 1-(2-((3-(2-amino-4-methyl-6-(pentylamino)pyrimidin-5-yl)propyl)(3-(2-methoxy-2-oxoethyl)benzyl)amino)-2-oxoethyl)pyrrolidine-2-carboxylate, Methyl 2-(3-((N-(3-(2-amino-4-methyl-6-(pentylamino)pyrimidin-5-yl)propyl)-2-(4-methylpiperazin-1-yl)acetamido)methyl)phenyl)acetate, Methyl 2-(3-((N-(3-(2-amino-4-methyl-6-(pentylamino)pyrimidin-5-yl)propyl)-2-(4-hydroxypiperidin-1-yl)acetamido)methyl)phenyl)acetate, Methyl 2-(3-((2-(4-acetyl-1,4-diazepan-1-yl)-N-(3-(2-amino-4-methyl-6-(pentylamino)pyrimidin-5-yl)propyl)acetamido)methyl)phenyl)acetate, Methyl 2-(3-((N-(3-(2-amino-4-methyl-6-(pentylamino)pyrimidin-5-yl)propyl)-2-(4-(3-(dimethylamino)propyl)piperazin-1-yl)acetamido)methyl)phenyl)acetate, Methyl 2-(3-((N-(3-(2-amino-4-methyl-6-(pentylamino)pyrimidin-5-yl)propyl)-2-((2-hydroxyethyl)(methyl)amino)acetamido)methyl)phenyl)acetate, Methyl 4-((3-(2-amino-4-methyl-6-(pentylamino)pyrimidin-5-yl)propyl)(3-(2-methoxy-2-oxoethyl)benzyl)amino)-4-oxobutanoate, Methyl 2-(3-((N-(3-(2-amino-4-methyl-6-(pentylamino)pyrimidin-5-yl)propyl)-4-(dimethylamino)butanamido)methyl)phenyl)acetate, Methyl 2-(3-((N-(3-(2-amino-4-methyl-6-(pentylamino)pyrimidin-5-yl)propyl)methylsulfonamido)methyl)phenyl)acetate, Methyl 2-(3-((N-(3-(2-amino-4-methyl-6-(pentylamino)pyrimidin-5-yl)propyl)-1-methyl-1H-imidazole-4-sulfonamido)methyl)phenyl)acetate, Methyl 2-(4-((N-(3-(2-amino-4-methyl-6-(pentylamino)pyrimidin-5-yl)propyl)-2-((2-methoxyethyl)(methyl)amino)acetamido)methyl)phenyl)acetate, Methyl 2-(3-((N-(3-(2-amino-4-methyl-6-(pentylamino)pyrimidin-5-yl)propyl)-3-(dimethylamino)propanamido)methyl)phenyl)acetate, Methyl 2-(3-((4-(2-amino-4-methyl-6-(pentylamino)pyrimidin-5-yl)butylamino)methyl)phenyl)acetate, (S)-Methyl 2-(4-((3-(2-amino-4-(1-hydroxyheptan-3-ylamino)-6-methylpyrimidin-5-yl)propylamino)methyl)phenyl)acetate, (S)-Methyl 2-(4-((N-(3-(2-amino-4-(1-hydroxyheptan-3-ylamino)-6-methylpyrimidin-5-yl)propyl)-2-(dimethylamino)acetamido)methyl)phenyl)acetate, Methyl 2-(3-((2-amino-4-methyl-6-(pentylamino)pyrimidin-5-yl)methyl)phenyl)acetate, Methyl 2-(4-((2-amino-4-methyl-6-(pentylamino)pyrimidin-5-yl)methyl)-3-methoxyphenyl)acetate, Methyl 2-(4-((2-amino-4-methyl-6-(pentylamino)pyrimidin-5-yl)methyl)-3-fluorophenyl)acetate, Methyl 2-(4-(2-(3-(2-amino-4-methyl-6-(pentylamino)pyrimidin-5-yl)propylamino)-2-oxoethyl)phenyl)acetate, Methyl 2-(3-(2-(3-(2-amino-4-methyl-6-(pentylamino)pyrimidin-5-yl)propylamino)-2-oxoethyl)phenyl)acetate, Methyl 2-(3-((3-(2-amino-4-methyl-6-(pentylamino)pyrimidin-5-yl)propylamino)methyl)phenoxy)acetate, Methyl 2-(4-((N-(3-(2-amino-4-methyl-6-(pentylamino)pyrimidin-5-yl)propyl)-2-(3-(4-(methylsulfonyl)phenyl)piperidin-1-yl)acetamido)methyl)phenyl)acetate, Methyl 2-(4-((1N-(3-(2-amino-4-methyl-6-(pentylamino)pyrimidin-5-yl)propyl)-2-morpholinoacetamido)methyl)phenyl)acetate, Methyl 2-(4-((N-(3-(2-amino-4-methyl-6-(pentylamino)pyrimidin-5-yl)propyl)-2-(4-phenylpiperidin-1-yl)acetamido)methyl)phenyl)acetate, Methyl 2-(4-((N-(3-(2-amino-4-methyl-6-(pentylamino)pyrimidin-5-yl)propyl)-2-(piperidin-1-yl)acetamido)methyl)phenyl)acetate, (S)-Methyl 2-(4-((2-amino-4-(1-hydroxypentan-2-ylamino)-6-methylpyrimidin-5-yl)methyl)-3-methoxyphenyl)acetate, (S)-Methyl 2-(4-((2-amino-4-(1-hydroxyheptan-3-ylamino)-6-methylpyrimidin-5-yl)methyl)-3-methoxyphenyl)acetate, (S)-Methyl 2-(4-((2-amino-4-(1-hydroxyhexan-2-ylamino)-6-methylpyrimidin-5-yl)methyl)-3-methoxyphenyl)acetate, (S)-Methyl 2-(4-((2-amino-4-(1-hydroxyheptan-3-ylamino)-6-methylpyrimidin-5-yl)methyl)-3-fluorophenyl)acetate,
Methyl 2-(4-((2-amino-4-methyl-6-(pentylamino)pyrimidin-5-yl)methyl)phenyl)acetate,
2-Morpholinoethyl 2-(4-((2-amino-4-methyl-6-(pentylamino)pyrimidin-5-yl)methyl)phenyl)acetate,
2-(Dimethylamino)ethyl 2-(4-((2-amino-4-methyl-6-(pentylamino)pyrimidin-5-yl)methyl)phenyl)acetate,
3-(Dimethylamino)propyl 2-(4-((2-amino-4-methyl-6-(pentylamino)pyrimidin-5-yl)methyl)phenyl)acetate,
2-(4-Methylpiperazin-1-yl)ethyl 2-(4-((2-amino-4-methyl-6-(pentylamino)pyrimidin-5-yl)methyl)phenyl)acetate,
Methyl 2-(3-((2-amino-4-methyl-6-(pentylamino)pyrimidin-5-yl)methyl)-4-hydroxyphenyl)acetate,
Methyl 2-(4-((2-amino-4-methyl-6-(pentylamino)pyrimidin-5-yl)methyl)-3-methoxyphenoxy)acetate,
Methyl 2-(4-((2-amino-4-(butylamino)-6-methylpyrimidin-5-yl)methyl)phenyl)acetate,
(S)-Methyl 2-(3-((2-amino-4-(1-hydroxyhexan-3-ylamino)-6-methylpyrimidin-5-yl)methyl)-4-fluorophenyl)acetate,
5 (S)-Methyl 2-(4-((2-amino-4-(1-hydroxypentan-2-ylamino)-6-methylpyrimidin-5-yl)methyl)phenyl)acetate,
(S)-Methyl 2-(4-((2-amino-4-(1-hydroxyhexan-2-ylamino)-6-methylpyrimidin-5-yl)methyl)phenyl)acetate,
(S)-Methyl 2-(4-((2-amino-4-(1-hydroxyhexan-3-ylamino)-6-methylpyrimidin-5-yl)methyl)-3-fluorophenyl)acetate,
Methyl 2-(4-((2-amino-4-(butylamino)-6-methylpyrimidin-5-yl)methyl)-3-methoxyphenyl)acetate,
(S)-Methyl 2-(4-((2-amino-4-(1-hydroxypentan-2-ylamino)-6-methylpyrimidin-5-yl)methyl)-3-fluorophenyl)acetate,
(S)-Methyl 2-(4-((2-amino-4-(1-hydroxyhexan-3-ylamino)-6-methylpyrimidin-5-yl)methyl)-3-methoxyphenyl)acetate,
(S)-Methyl 2-(4-((2-amino-4-(1-hydroxyhexan-3-ylamino)-6-methylpyrimidin-5-yl)methyl)phenyl)acetate,
(S)-Methyl 2-(4-((2-amino-4-(1-hydroxyheptan-3-ylamino)-6-methylpyrimidin-5-yl)methyl)phenyl)acetate,
Methyl 2-(4-((N-(3-(2-amino-4-methyl-6-(pentylamino)pyrimidin-5-yl)propyl)-1-methylpiperidine-4-carboxamido)methyl)phenyl)acetate,
Methyl 2-(4-((N-(3-(2-amino-4-methyl-6-(pentylamino)pyrimidin-5-yl)propyl)-2-(methylthio)acetamido)methyl)phenyl)acetate,
(S)-Methyl 2-(4-((2-amino-4-(2-hydroxybutylamino)-6-methylpyrimidin-5-yl)methyl)-3-methoxyphenyl)acetate,
Methyl 2-(3-((2-amino-4-methyl-6-(pentylamino)pyrimidin-5-yl)methyl)-4-methoxyphenyl)acetate,
3-(Dimethylamino)-2,2-dimethylpropyl 2-(4-((2-amino-4-methyl-6-(pentylamino)pyrimidin-5-yl)methyl)phenyl)acetate,
3-(4-Methylpiperazin-1-yl)propyl 2-(4-((2-amino-4-methyl-6-(pentylamino)pyrimidin-5-yl)methyl)phenyl)acetate,
4-(Dimethylamino)butyl 2-(4-((2-amino-4-methyl-6-(pentylamino)pyrimidin-5-yl)methyl)phenyl)acetate.
3-Morpholinopropyl 2-(4-((2-amino-4-methyl-6-(penylamino)pyrimidin-5-yl)methyl)phenyl)acetate,
1-Methylpiperidin-4-yl 2-(4-((2-amino-4-methyl-6-(pentylamino)pyrimidin-5-yl)methyl)phenyl)acetate,
(1-Methylpiperidin-4-yl)methyl 2-(4-((2-amino-4-methyl-6-(pentylamino)pyrimidin-5-yl)methyl)phenyl)acetate,
4-(Pyrrolidin-1-yl)butyl 2-(4-((2-amino-4-methyl-6-(pentylamino)pyrimidin-5-yl)methyl)phenyl)acetate,
(1-(2-Methoxyethyl)piperidin-4-yl)methyl 2-(4-((2-amino-4-methyl-6-(pentylamino)pyrimidin-5-yl)methyl)phenyl)acetate,
4-(4-Methylpiperazin-1-yl)butyl 2-(4-((2-amino-4-methyl-6-(pentylamino)pyrimidin-5-yl)methyl)phenyl)acetate,
4-(1,1-Dioxidothiomorpholin-4-yl)butyl(4-{[2-amino-4-methyl-6-(pentylamino)pyrimidin-5-yl]methyl}phenyl)acetate,
4-Morpholinobutyl 2-(4-((2-amino-4-methyl-6-(pentylamino)pyrimidin-5-yl)methyl)phenyl)acetate,
2-(1-Methylpiperidin-4-yl)ethyl 2-(4-((2-amino-4-methyl-6-(pentylamino)pyrimidin-5-yl)methyl)phenyl)acetate,
Piperidin-4-ylmethyl 2-(4-((2-amino-4-methyl-6-(pentylamino)pyrimidin-5-yl)methyl)phenyl)acetate,
4-(4-(Dimethylamino)piperidin-1-yl)butyl 2-(4-((2-amino-4-methyl-6-(pentylamino)pyrimidin-5-yl)methyl)phenyl)acetate,
(1-Methylpiperidin-4-yl)methyl 2-(4-((2-amino-4-(butylamino)-6-methylpyrimidin-5-yl)methyl)phenyl)acetate,
(S)-4-(Dimethylamino)butyl 2-(4-((2-amino-4-(1-hydroxypentan-2-ylamino)-6-methylpyrimidin-5-yl)methyl)phenyl)acetate,
(S)-(1-Methylpiperidin-4-yl)methyl 2-(4-((2-amino-4-(1-hydroxypentan-2-ylamino)-6-methylpyrimidin-5-yl)methyl)-3-methoxyphenyl)acetate,
(1-Methylpiperidin-4-yl)methyl 2-(4-((2-amino-4-(butylamino)-6-methylpyrimidin-5-yl)methyl)-3-methoxyphenyl)acetate,
4-(Pyrrolidin-1-yl)butyl 2-(4-((2-amino-4-(butylamino)-6-methylpyrimidin-5-yl)methyl)-3-methoxyphenyl)acetate,
(S)-(1-Methylpiperidin-4-yl)methyl 2-(4-((2-amino-4-(1-hydroxyhexan-3-ylamino)-6-methylpyrimidin-5-yl)methyl)-3-fluorophenyl)acetate,
(S)-Methyl 2-(4-((2-amino-4-(1-hydroxyhexan-3-ylamino)-6-methylpyrimidin-5-yl)methyl)-3-hydroxyphenyl)acetate,
(S)-(1-Methylpiperidin-4-yl)methyl 2-(4-((2-amino-4-(1-hydroxypentan-2-ylamino)-6-methylpyrimidin-5-yl)methyl)-3-hydroxyphenyl)acetate,
Methyl 2-(4-((2-amino-4-(butylamino)-6-methylpyrimidin-5-yl)methyl)-3-hydroxyphenyl)acetate,
(S)-4-(Pyrrolidin-1-yl)butyl 2-(4-((2-amino-4-(1-hydroxyhexan-3-ylamino)-6-methylpyrimidin-5-yl)methyl)-3-hydroxyphenyl)acetate,
4-(Pyrrolidin-1-yl)butyl 2-(4-((2-amino-4-(butylamino)-6-methylpyrimidin-5-yl)methyl)-3-hydroxyphenyl)acetate,
(S)-Methyl 2-(3-((2-amino-4-(1-hydroxypentan-2-ylamino)-6-methylpyrimidin-5-yl)methyl)-4-methoxyphenyl)acetate,
(S)-(1-Methylpiperidin-4-yl)methyl 2-(4-((2-amino-4-(2-hydroxybutylamino)-6-methylpyrimidin-5-yl)methyl)phenyl)acetate,
4-(Pyrrolidin-1-yl)butyl 2-(4-((2-amino-4-(butylamino)-6-methylpyrimidin-5-yl)methyl)phenyl)acetate,
(1-Methylpiperidin-4-yl)methyl 2-(3-((2-amino-4-(butylamino)-6-methylpyrimidin-5-yl)methyl)-4-methoxyphenyl)acetate,
4-(Pyrrolidin-1-yl)butyl 2-(3-((2-amino-4-methyl-6-(pentylamino)pyrimidin-5-yl)methyl)phenyl)acetate,
(1-Methylpiperidin-4-yl)methyl 2-(3-((2-amino-4-methyl-6-(pentylamino)pyrimidin-5-yl)methyl)phenyl)acetate,
(S)-4-(Dimethylamino)butyl 2-(4-((2-amino-4-(1-hydroxyhexan-3-ylamino)-6-methylpyrimidin-5-yl)methyl)-3-fluorophenyl)acetate,
(S)-4-(4-Methylpiperazin-1-yl)butyl 2-(4-((2-amino-4-(1-hydroxyhexan-3-ylamino)-6-methylpyrimidin-5-yl)methyl)-3-fluorophenyl)acetate,
(S)-Methyl 2-(4-((2-amino-4-(1-hydroxypentan-2-ylamino)-6-methylpyrimidin-5-yl)methyl)-3-hydroxyphenyl)acetate, 2-Hydroxyethyl 2-(4-((2-amino-4-(butylamino)-6-methylpyrimidin-5-yl)methyl)-3-methoxyphenyl)acetate,
4-(4-(Dimethylamino)piperidin-1-yl)butyl 2-(4-((2-amino-4-(butylamino)-6-methylpyrimidin-5-yl)methyl)-3-methoxyphenyl)acetate,
4-Hydroxybutyl 2-(4-((2-amino-4-(butylamino)-6-methylpyrimidin-5-yl)methyl)-3-methoxyphenyl)acetate,
3-(Methylsulfonyl)propyl 2-(4-((2-amino-4-(butylamino)-6-methylpyrimidin-5-yl)methyl)-3-methoxyphenyl)acetate,
3-Hydroxypropyl 2-(4-((2-amino-4-(butylamino)-6-methylpyrimidin-5-yl)methyl)-3-methoxyphenyl)acetate,
(S)-4-(Dimethylamino)butyl 2-(4-((2-amino-4-(1-hydroxyhexan-3-ylamino)-6-methylpyrimidin-5-yl)methyl)phenyl)acetate,
(1-Methylpiperidin-4-yl)methyl 2-(4-(2-amino-4-(butylamino)-6-methylpyrimidin-5-ylthio)phenyl)acetate,
4-(Pyrrolidin-1-yl)butyl 2-(4-(2-amino-4-(butylamino)-6-methylpyrimidin-5-ylthio)phenyl)acetate,
4-(Dimethylamino)butyl 2-(3-((2-amino-4-(butylamino)-6-methylpyrimidin-5-yl)methyl)-4-methoxyphenyl)acetate,
Methyl 2-(3-((2-amino-4-(butylamino)-6-methylpyrimidin-5-yl)methyl)-4-methoxyphenyl)acetate,
Methyl 2-(3-((2-amino-4-(butylamino)-6-methylpyrimidin-5-yl)methyl)-4-hydroxyphenyl)acetate,
(S)-2-(1-Methylpiperidin-4-yl)ethyl 2-(4-((2-amino-4-(1-hydroxyhexan-3-ylamino)-6-methylpyrimidin-5-yl)methyl)-3-fluorophenyl)acetate,
2-(4-Methylthiazol-5-yl)ethyl 2-(4-((2-amino-4-(butylamino)-6-methylpyrimidin-5-yl)methyl)-3-methoxyphenyl)acetate,
(1-Methylpiperidin-4-yl)methyl 2-(4-((2-amino-4-(butylamino)-6-methylpyrimidin-5-yl)methyl)-3-hydroxyphenyl)acetate,
4-(Dimethylamino)butyl 2-(4-((2-amino-4-(butylamino)-6-methylpyrimidin-5-yl)methyl)-3-hydroxyphenyl)acetate,
or pharmaceutically acceptable salts thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises (a) when $R^2$ represents a group of formula (Ia), reacting a compound of formula (II)

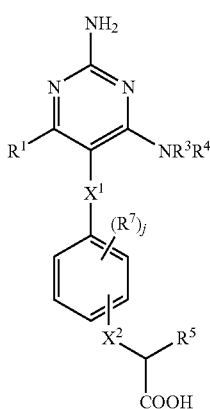
(II)

wherein j, $X^1$, $X^2$, $R^1$, $R^3$, $R^4$, $R^5$ and $R^7$ are as defined in formula (I), with a compound of formula (III), $R^6$—OH, where $R^6$ is as defined in formula (I); or (b) when $R^2$ represents a group of formula (Ib), reacting a compound of formula (IV)

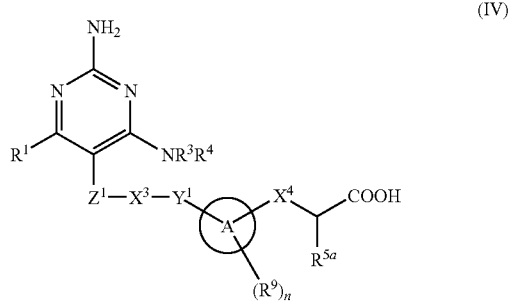
(IV)

wherein n, A, $X^3$, $X^4$, $Y^1$, $Z^1$, $R^1$, $R^3$, $R^4$, $R^{5a}$ and $R^9$ are as defined in formula (I), with a compound of formula (V), $R^8$—OH, where $R^8$ is as defined in formula (I); or (c) when $R^2$ represents a group of formula (Ib) in which $X^3$ represents NH and $Y^1$ represents $C_1$-$C_6$ alkylene, reacting a compound of formula (VI)

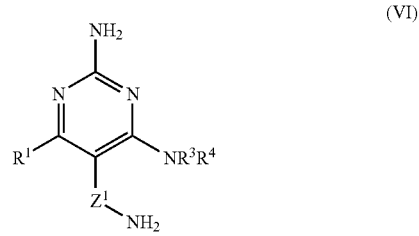
(VI)

wherein $R^1$, $R^3$, $R^4$ and $Z^1$ are as defined in formula (I), with a compound of formula (VII)

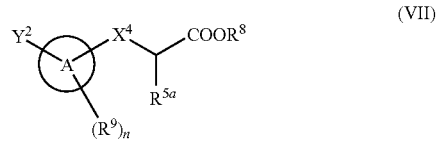
(VII)

wherein $Y^2$ represents —$(C_1$-$C_5$alkyl$)_j$-CHO, j is 0 or 1, and A, n, $X^4$, $R^{5a}$, $R^8$ and $R^9$ are as defined in formula (I);

and optionally after (a), (b) or (c) carrying out one or more of the following procedures:
  converting a compound of formula (I) into another compound of formula (I)
  removing any protecting groups
  forming a pharmaceutically acceptable salt.

Process (a) may be carried out under acidic conditions in the presence of, for example, hydrochloric or sulphuric acid and the appropriate alcohol of formula (III) as solvent. Alternatively, the reaction may be carried out by activation of the formula (II) acid with a coupling agent such as PyBop (benzotriazol-1-yloxytripyrrolidinophosphonium hexafluorophosphate) or HATU (O-(7-azabezotriazol-1-yl)-N,N,N',N'-tetramethyluronium hexafluorophosphate) in an organic solvent such as N-methylpyrrolidinone, N,N-dimethylformamide, acetonitrile or tetrahydrofuran, usually in the presence of a suitable base (e.g. triethylamine, Hunigs base) at a temperature, for example, in the range from 0 to 50° C.

Process (b) may be carried out in an analogous manner to process (a).

Process (c) may conveniently be carried out in the presence of a suitable reducing agent (e.g. sodium triacetoxyborohydride) in an organic solvent such as 1-methyl-2-pyrrolidinone, 1,2-dichloroethane or tetrahydrofuran at a temperature, for example, in the range from 0 to 150° C. Alternatively, an imine intermediate can be preformed by stirring the compounds of formulae (VI) and (VII) in a suitable solvent such as tetrahydrofuran, optionally in the presence of an acid, such as acetic acid, at a temperature, for example, in the range from room temperature to 150° C. A reducing agent, such as sodium borohydride, can then be added to give a compound of formula (I) when $R^2$ represents a group of formula (Ib).

A compound of formula (IV) may be prepared by reacting a compound of formula (VI) with a compound of formula (VIIa) in which the substituents have the meanings defined in formula (VII), using process (c) above

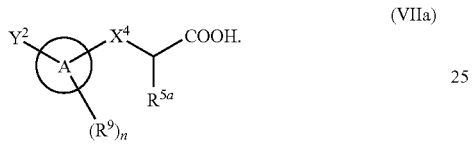

(VIIa)

Alternatively, compounds of formula (IV) may be prepared by dealkylating a corresponding compound of formula (I) according to techniques known in the art.

Compounds of formula (II) in which $X^1$ represents $CH_2$, $X^2$ represents a bond and $R^5$ represents a hydrogen atom may be prepared as described in the following reaction scheme 1 in which j, $R^1$, $R^3$, $R^4$ and $R^7$ are as defined in formula (II), Et represents an ethyl group LG represents a leaving group and $R^{40}$ represents a $C_1$-$C_6$ alkyl group.

Scheme 1

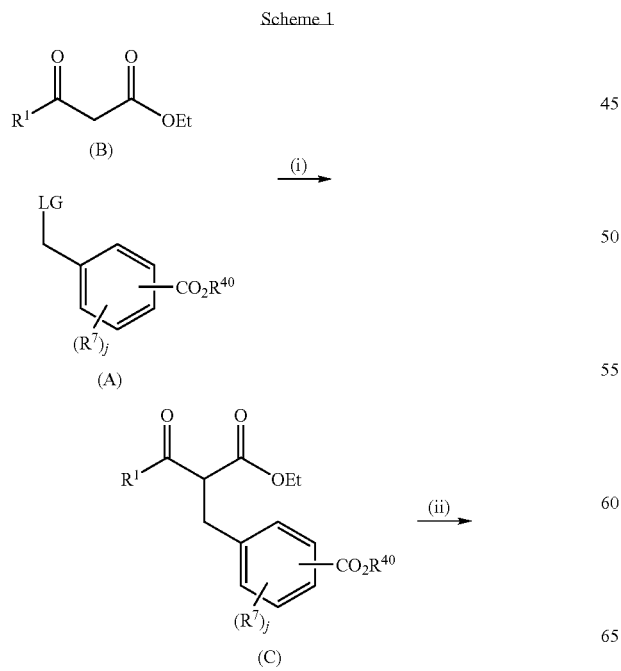

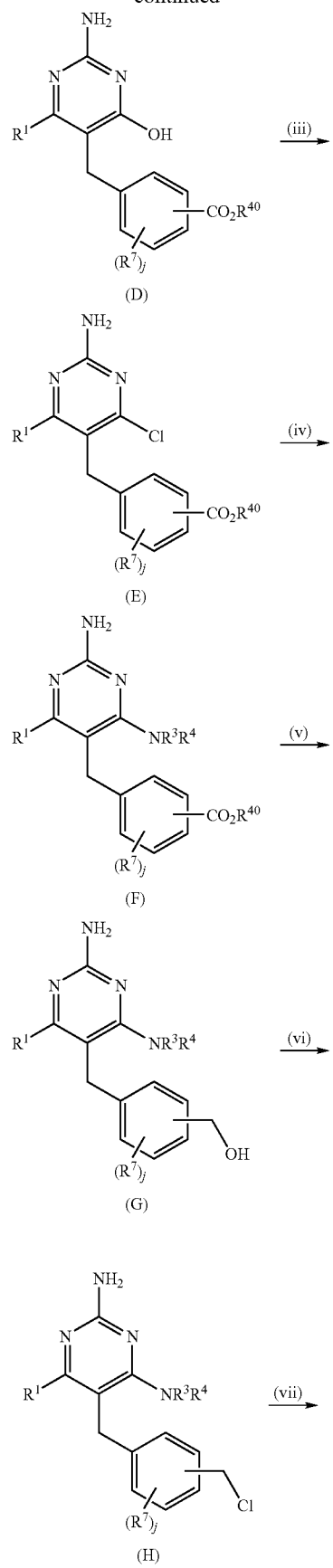

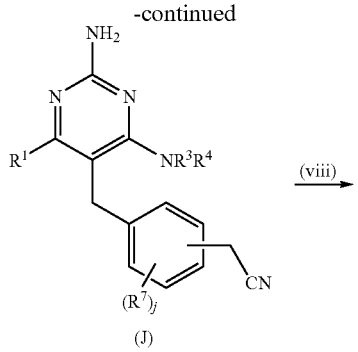

Compounds of formula (C) may be prepared by reacting a compound of formula (B) with a base, such as sodium hydride, in a suitable solvent such as tetrahydrofuran or N,N-dimethylformamide at a temperature, for example, from 0° C. to room temperature (20° C.), followed by addition of a compound of formula (A). The reaction is then preferably heated at a temperature, for example, from 50° C. to 100° C., optionally in the presence of an additive such as potassium iodide.

Compounds of formula (D) may be prepared by reacting a compound of formula (C) with guanidine or guanidine carbonate in a suitable solvent such as methanol or ethanol at a temperature, for example, in the range from 50° C. to 150° C.

Compounds of formula (E) may be prepared by reacting a compound of formula (D) with phosphorous oxychloride, at a temperature, for example, from 50° C. to 110° C.

Compounds of formula (F) may be prepared by reacting a compound of formula (E) with excess of an amine of formula $R_3R_4NH$, in a suitable solvent such as butanol or 1,2-dioxane at a temperature, for example, from 50° C. to 150° C. Alternatively, the reaction can be performed in a microwave at a temperature, for example, from 50° C. to 200° C.

Compounds of formula (G) may be prepared by reacting a compound of formula (F) with a reducing agent, such as lithium aluminium hydride, in a suitable solvent such as tetrahydrofuran at a temperature, for example, from 0° C. to 60° C.

Compounds of formula (H) may be prepared by reacting a compound of formula (G) with a chlorinating agent, such as thionyl chloride, in a suitable solvent such as dichloromethane at a temperature, for example, from 0° C. to 50° C.

Compounds of formula (J) may be prepared by reacting a compound of formula (H) with a cyanide salt, such as potassium cyanide, in a suitable solvent such as dimethylsulfoxide or N,N-dimethylformamide (or a mixture of both solvents) at a temperature, for example, from room temperature to 50° C.

Compounds of formula (II) may be prepared by reacting a compound of formula (J) with an alkali base, such as potassium hydroxide, in a suitable solvent such as methanol or ethanol and water at a temperature, for example, from 50° C. to 100° C.

Alternatively the order of the steps in reaction scheme 1 may be changed, for example, a compound of formula (E) can be subjected to steps (v) to (vi) then displaced by an amine $R_3R_4NH$ as in step (iv).

In reaction scheme 1, compounds of formula (A) may be prepared easily using known techniques. For example, a compound of formula (A), designated (Av) in which LG represents a leaving group, $R^{40}$ represents a $C_1$-$C_6$ alkyl group, j is 1 and $R^7$ is hydroxyl protected by a protecting group $P^1$.

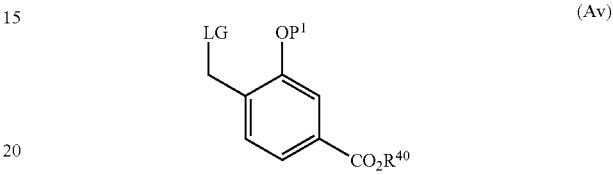

may be prepared by the following route:

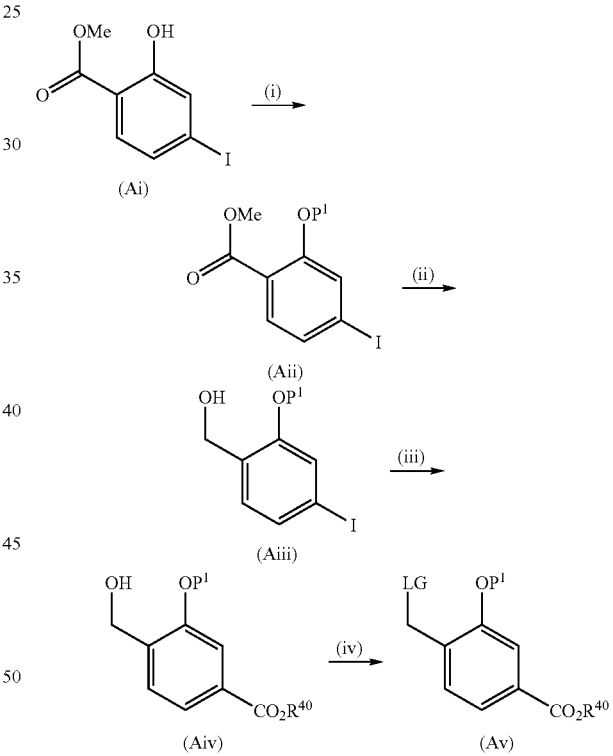

Compounds of formula (Aii) may be prepared by reacting a compound of formula (Ai) with an alkylating agent of formula, $P^1LG$, where LG is a leaving group and $P^1$ represents a suitable hydroxyl-protecting group such as methyl or benzyl, in the presence of a base such as potassium carbonate, in a suitable solvent such as tetrahydrofuran or N,N-dimethylformamide at a temperature, for example, from room temperature to 100° C.

Compounds of formula (Aiii) may be prepared by reacting a compound of formula (Aii) with a reducing agent, for example, diisobutylaluminium hydride (DIBAL-H) in a suitable solvent such as tetrahydrofuran at a temperature, for example, from −60° C. to room temperature.

Compounds of formula (Aiv) may be prepared by carbonylating a compound of formula (Aiii) in the presence of an alcohol, $R^{40}OH$. The reaction may be performed in a carbonylator under a pressure of carbon monoxide (1-5 bar) with a palladium catalyst, such as dichloro[1,1'-bis(diphenylphosphino)ferrocene]Pd (II) dichloromethane adduct, at a temperature from 30° C. to 150° C.

Compounds of formula (Av), where LG is a chloride leaving group, may be prepared by reacting a compound of formula (Aiv), with a chlorinating agent, such as thionyl chloride, in a suitable solvent such as dichloromethane at a temperature, for example, from 0° C. to 50° C.

Compounds of formula (F) can also be prepared by reaction of a compound of formula (VIII) with excess of an amine of formula $R_3R_4NH$, where j, $R^1$, $R^3$, $R^4$, $R^7$ and $R^{40}$ are as defined above and $R^{41}$ is defined as a $C_1$-$C_6$ alkyl or a phenyl ring substituted by one or more $C_1$-$C_6$ alkyl groups.

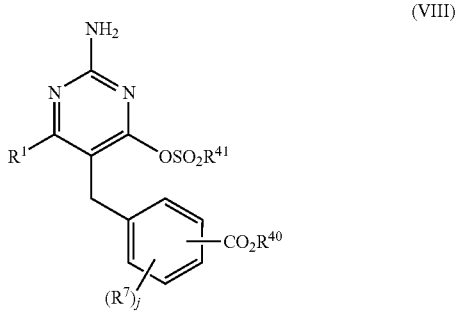

(VIII)

The reaction may be carried out in a suitable solvent such as butanol or 1,2-dioxane at a temperature, for example, from 50° C. to 150° C. Alternatively, the reaction can be performed in a microwave at a temperature, for example, from 50° C. to 200° C.

A compound of formula (VIII) may be prepared by reacting a compound of formula (D) with a compound of formula (IX), $^{41}RSO_2Cl$. The reaction may be carried out in a suitable solvent, such as DCM, and a base such as triethylamine or Hunigs base at a temperature, for example, from 0° C. to 50° C.

A compound of formula (J) may also be prepared by reaction of a compound of formula (VIIIa) with an amine of formula $R_3R_4NH$

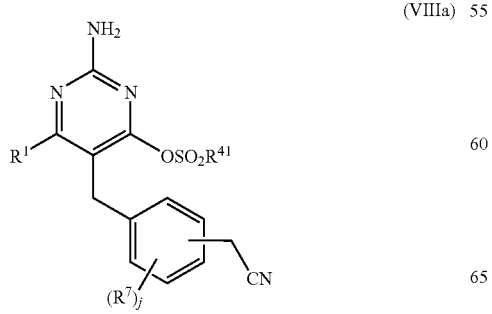

(VIIIa)

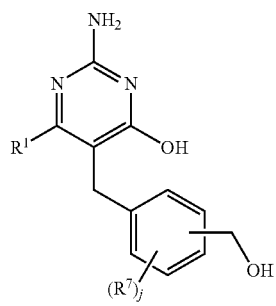

(VIIIb)

in which the substituents have the meanings defined above. A compound of formula (VIIIa) may be prepared from a compound of formula (VIIIb) using the schemes and reaction conditions above.

A compound of formula (VIIIb) may prepared according to reaction scheme 1 steps (i) and (ii) by substituting the compound of formula (A) with a compound of formula (VIIIc) in which LG represents a leaving group, P represents a hydroxyl-protecting group and j and $R^7$ are as defined in formula (VIIIb), followed by removal of the hydroxyl-protecting group P,

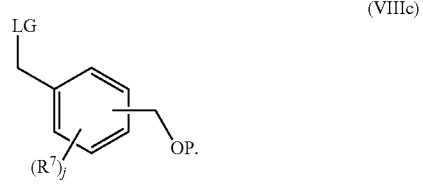

(VIIIc)

Compounds of formula (C) can also be prepared by reduction of a compound of formula (X)

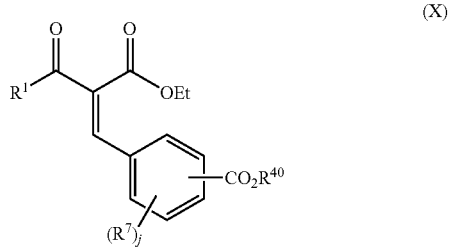

(X)

wherein j, $R^1$, $R^7$ and $R^{40}$ are as defined above. The reaction may be carried out with a catalyst such as palladium on carbon under a hydrogen atmosphere (1-20 bar) in a suitable solvent such as ethanol at a temperature, for example, from 20° C. to 100° C.

A compound of formula (X) can be prepared by reaction of a compound of formula (B) with a compound of formula (XI)

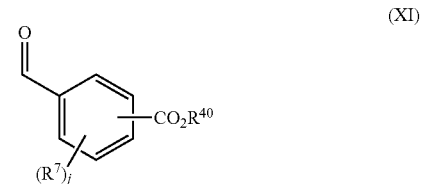

(XI)

wherein j, $R^7$ and $R^{40}$ are as defined above. The reaction may be carried out in the presence of acetic acid and piperidine in a suitable solvent such as toluene at a temperature, for example, from 50° C. to 150° C.

Compounds of formula (J) may also be prepared as described in the following reaction scheme Ia:

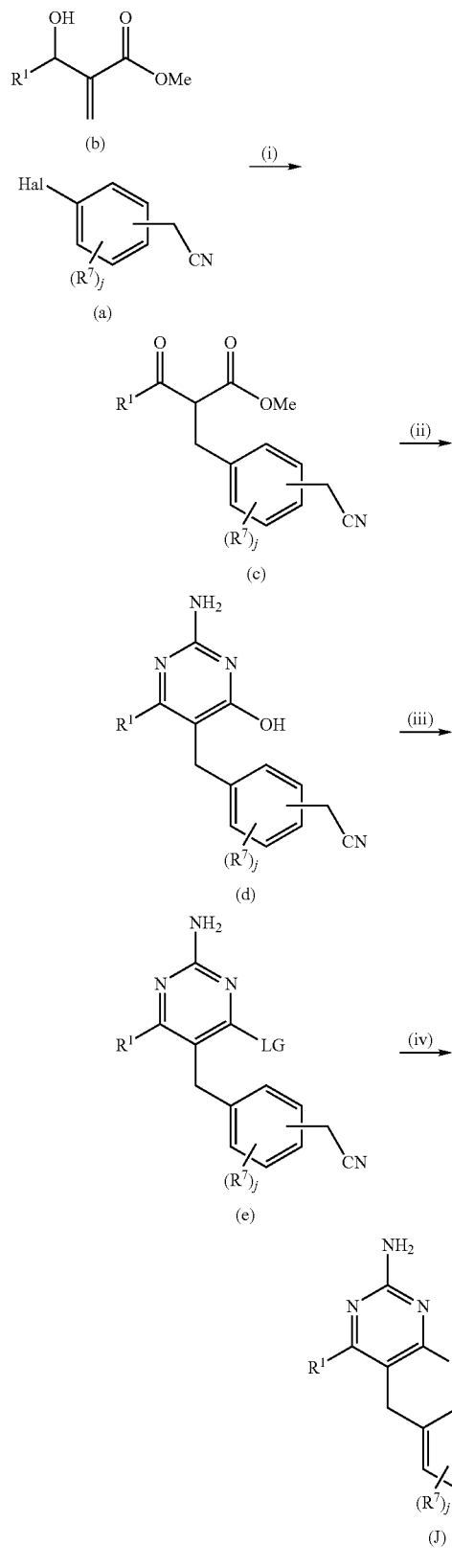

Compounds of formula (c) may be prepared by a Heck reaction between a compound of formula (b) and a compound of formula (a) where Hal=bromine or iodine and j, $R^1$ and $R^7$ are as defined in reaction scheme 1. The reaction may be carried out using a palladium catalyst, such as $Pd(OAc)_2$ or Pd-118, a base such as sodium hydrogencarbonate or dicyclohexylmethylamine, and tetrabutylammonium chloride or bromide. The reaction is performed in a suitable solvent such as tetrahydrofuran or dimethylacetamide at a temperature, for example, from 50° C. to 150° C.

Compounds of formula (d) may be prepared by reacting a compound of formula (c) with guanidine or guanidine carbonate in a suitable solvent such as methanol or ethanol at a temperature, for example, in the range from 50° C. to 150° C.

Compounds of formula (e), where LG is a leaving group such as halogen or an alkylsulphonyl or benzylsulphonyl group, may be prepared by reacting a compound of formula (d) with phosphorous oxychloride, at a temperature, for example, from 50° C. to 110° C. Alternatively a compound of formula (e) may be prepared by reacting a compound of formula (d) with, for example, an alkylsulphonyl chloride. The reaction is conveniently carried out in a solvent, such as dichloromethane, in the presence of a base such as triethylamine or Hunigs base at a temperature, for example, from 0° C. to 50° C.

Compounds of formula (J) may be prepared by reacting a compound of formula (e) with excess of an amine of formula $R_3R_4NH$, in a suitable solvent such as butanol or 1,4-dioxane at a temperature, for example, from 50° C. to 150° C. Alternatively, the reaction can be performed in a microwave at a temperature, for example, from 50° C. to 200° C.

Compounds of formula (a) are commercially available or may be prepared easily using known techniques. For example, a compound of formula (a), designated (av), in which Hal is iodine, j is 1 and $R^7$ is hydroxyl protected by a protecting group $P^1$ (e.g. methyl, ethyl or benzyl)

may be prepared using the route below.

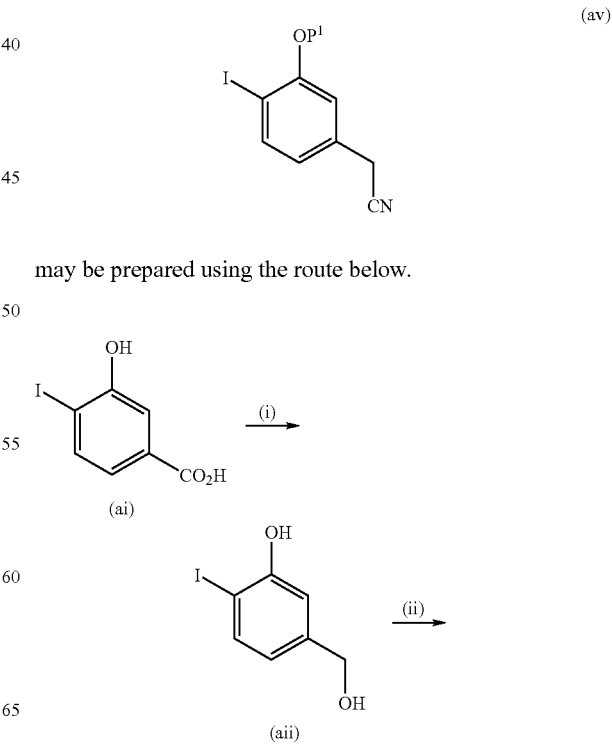

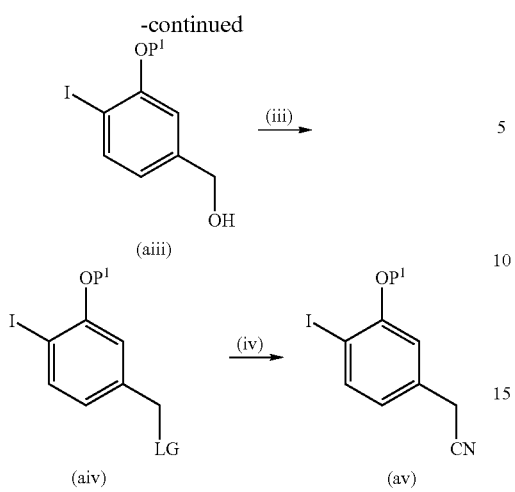

Compounds of formula (aii) may be prepared by reacting a compound of formula (ai) with a reducing agent, for example, borane-tetrahydrofuran complex, in a suitable solvent such as tetrahydrofuran at a temperature, for example, from room temperature to 80° C.

Compounds of formula (aiii) may be prepared by reacting a compound of formula (aii) with an alkylating agent of formula, P¹LG, where LG is a leaving group and P¹ is a hydroxyl-protecting group, in the presence of a base such as potassium carbonate, in a suitable solvent such as tetrahydrofuran or N,N-dimethylformamide, at a temperature, for example, from room temperature to 100° C.

Compounds of formula (aiv), where LG is a chloride leaving group, may be prepared by reacting a compound of formula (aiii), with a chlorinating agent, such as thionyl chloride, in a suitable solvent such as dichloromethane at a temperature, for example, from 0° C. to 50° C.

Compounds of formula (av) may be prepared by reacting a compound of formula (aiv) with a cyanide salt, such as potassium cyanide, in a suitable solvent such as dimethylsulfoxide or N,N-dimethylformamide (or a mixture of both solvents) at a temperature, for example, from room temperature to 50° C.

A compound of formula (I), where $R^2$ represents a group of formula (Ia) in which $X^1$ represents $CH_2$, $X^2$ represents a bond and $R^5$ represents a hydrogen atom, may be prepared by reacting a compound of formula (f)

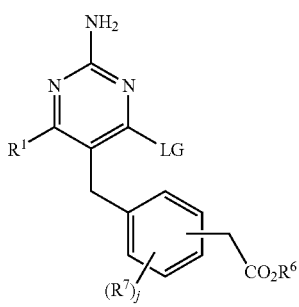

in which LG represents a leaving group and j, $R^1$, $R^6$ and $R^7$ are as defined in formula (I), with an amine of formula $R_3R_4NH$ in which $R^3$ and $R^4$ are as defined in formula (I), in a suitable solvent such as 1,4-dioxane at a temperature, for example, from 50° C. to 150° C. Alternatively, the reaction can be performed in a microwave at a temperature, for example, from 50° C. to 200° C.

A compound of formula (f) may be prepared according to reaction scheme 1a above, starting with a compound of formula (c1).

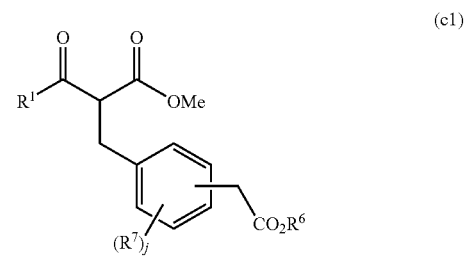

A compound of formula (c1) may be prepared according to reaction scheme 1a step (i) using an appropriate aromatic bromide or iodide (g), or from a compound (h) or (j) using the methods hereinbefore described:

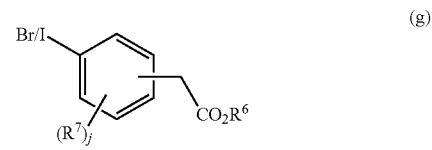

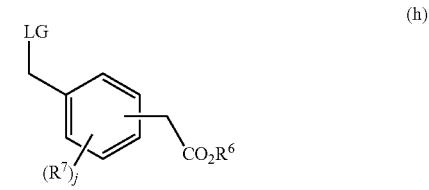

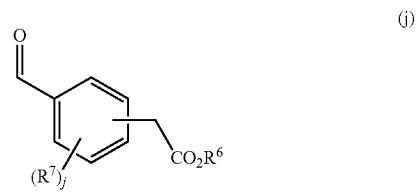

A compound of formula (C) in reaction scheme 1 may also be prepared using Heck chemistry as above with a compound of formula (k):

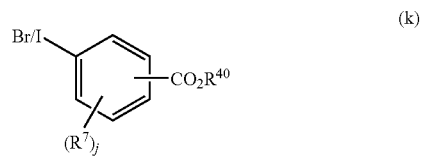

Compounds of formula (J) in reaction scheme 1a may also be prepared from a compound of formula (e) where LG is chloro, by a palladium catalysed coupling reaction with a protected amino-alcohol of formula (P^a), (P<sup>a</sup>)

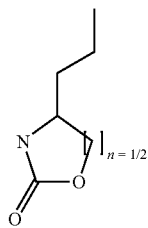

The reaction may be performed in a suitable solvent such as 1,4-dioxane with a palladium catalyst formed from palladium acetate and 9,9-dimethyl-4,5-bis(diphenylphosphino) xanthene and a base such as potassium carbonate. The reaction may be performed at a temperature, for example, from 50° C. to 150° C.

A compound of formula (II) in which $X^1$ represents a sulphur atom may be prepared by reacting a compound of formula (XII) with a compound of formula (XIII) or (XIIIa) in which j, $R^1$, $R^7$ and $R^{40}$ are as defined above, and then by following the steps in reaction scheme 1 from formula (D), or the compound of formula (II) may be prepared from the compound of formula (XIIIb) in which j, $R^1$ and $R^7$ are as defined above, following reaction scheme 1 steps (vi)-(vii), (iii)-(iv) and then (viii).

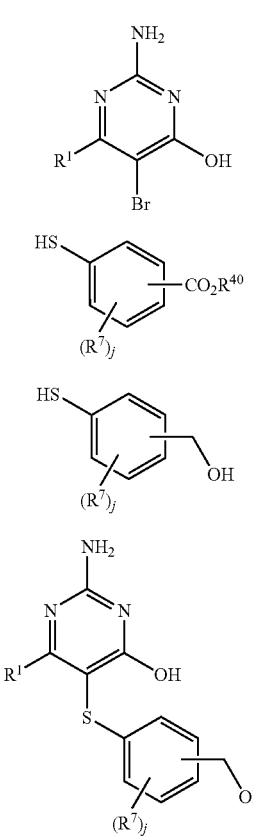

The reaction may be carried out in a suitable solvent, such as ethylene glycol, and a base such as potassium carbonate at a temperature, for example, from 80° C. to 200° C.

A compound of formula (II) in which $X^1$ represents an oxygen atom may be prepared by reacting a compound of formula (XIV) with a compound of formula (XV), where $R^{42}$ represents a suitable leaving group and j, $R^1$, $R^7$ and $R^{40}$ are as defined above, and then by following the steps in reaction scheme 1 from formula (C)

(XIV)

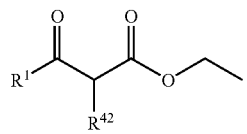

(XV)

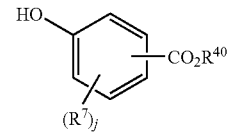

The reaction may be carried out in a suitable solvent, such as tetrahydrofuran, and a base such as potassium carbonate at a temperature, for example, from 20° C. to 100° C.

A compound of formula (II) in which $X^1$ represents a group NH may be prepared by reacting a compound of formula (XVI) with a compound of formula (XVII) where and j, $R^1$, $R^7$ and $R^{40}$ are as defined above, then by following the steps in reaction scheme 1 from formula (C). The benzyl protecting group may be removed by hydrogenation at a convenient step in the route.

(XVI)

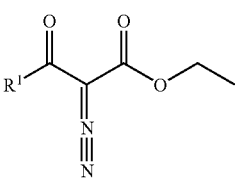

(XVII)

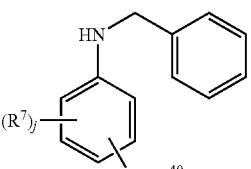

The reaction may be carried out in a suitable solvent, such as toluene, and a catalyst such as rhodium acetate at a temperature, for example, from 50° C. to 150° C.

Compounds of formula (VI) in which $Z^1$ represents a linear $C_3$-$C_6$ alkylene group may be prepared according to the following reaction scheme 2 in which PG represents a nitrogen-protecting group and $R^1$, $R^3$ and $R^4$ are as defined in formula (I).

Scheme 2

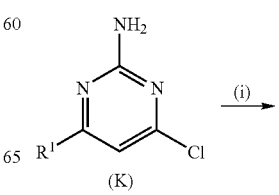

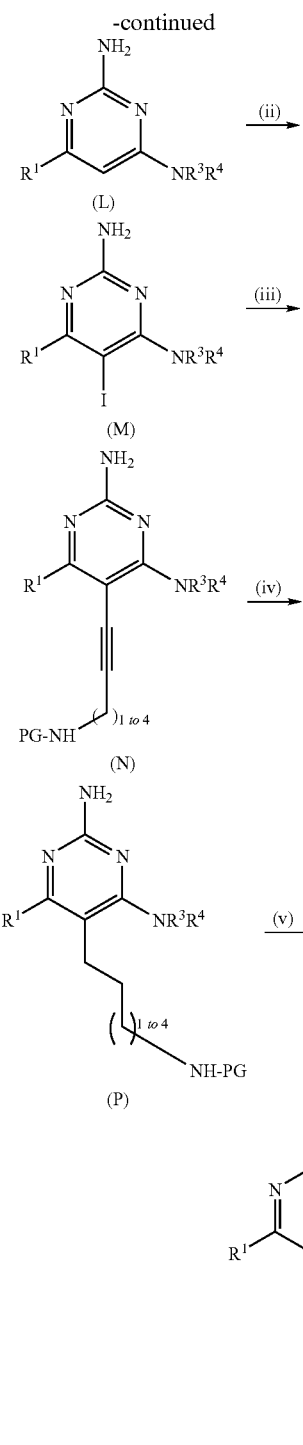

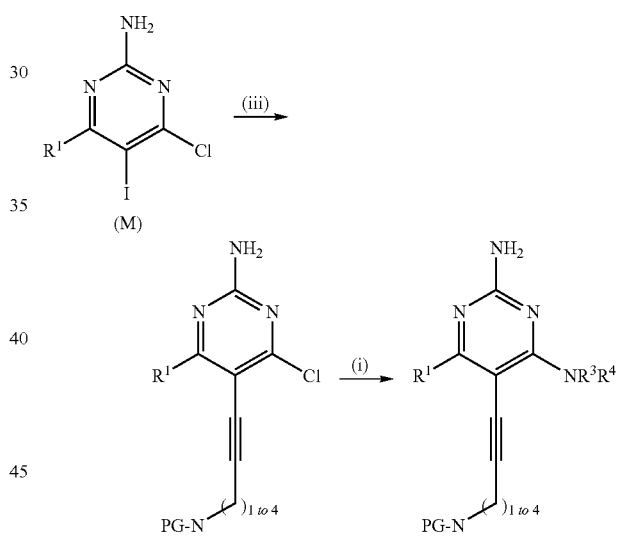

as dichloromethane and with water. The reaction is preferably performed at a temperature, for example, from 50° C. to 150° C.

Compounds of formula (N) may be prepared by reacting a compound of formula (M) with a compound of formula (XVIII), HC≡C(CH$_2$)$_{1-4}$N-PG, where PG is a nitrogen-protecting group. The reaction may be carried out in the presence of a palladium catalyst such as tetrakis(triphenylphosphine)palladium (0), copper(I) iodide and a base such as triethylamine. The reaction may be carried out in a suitable solvent, such as tetrahydrofuran, at a temperature, for example, from 50° C. to 150° C.

Compounds of formula (P) may be prepared by the reduction of a compound of formula (N) under hydrogenation conditions. The reaction may be carried out with a catalyst such as palladium on carbon under a hydrogen atmosphere (1-20 bar) in a suitable solvent such as ethanol at a temperature, for example, from 20° C. to 100° C.

Compounds of formula (VI) may be prepared by removing the nitrogen-protecting group from a compound of formula (P) according to techniques known in the art.

Alternatively the order of the steps in scheme 2 may be changed as follows:

Scheme 3

Compounds of formula (P) may also be prepared according to reaction scheme 4, where LG$^1$ is a leaving group and R$^1$ and PG are as defined above.

Scheme 4

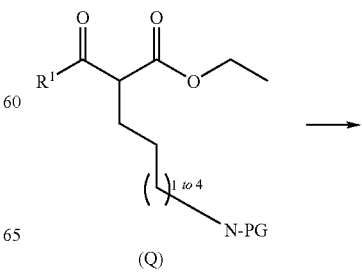

Compounds of formula (L) may be prepared by reacting a compound of formula (K) with excess of an amine of formula R$_3$R$_4$NH where R$^3$ and R$^4$ are as defined above, in a suitable solvent such as butanol or 1,2-dioxane at a temperature, for example, from 50° C. to 150° C. Alternatively the reaction can be performed in a microwave at a temperature, for example, from 50° C. to 200° C.

Compounds of formula (M) may be prepared by reacting a compound of formula (L) with iodine in the presence of a base such as sodium hydroxide, in a suitable organic solvent such

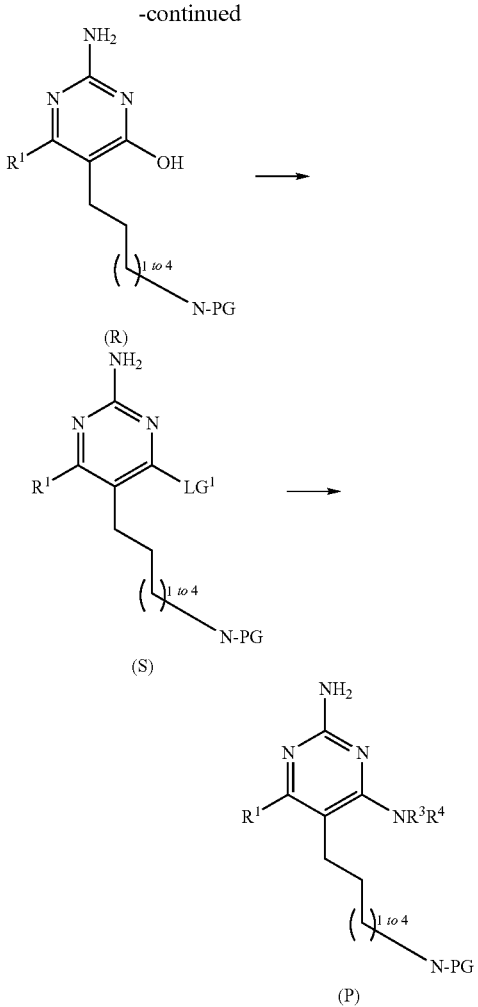

Compounds of formula (Q) and (R) can be prepared in a similar method as shown above.

A compound of formula (S) can be prepared from a compound of formula (R) by activation of the hydroxyl group. When $LG^1$ represents chlorine the reaction may be performed by reacting a compound of formula (R) with phosphorous oxychloride, at a temperature, for example, from 50° C. to 110° C. Alternatively when $LG^1$ represents $OSO_2R^{41}$ as defined in formula (VIII), a compound of formula (R) may be reacted with a compound of formula $^{41}RSO_2Cl$. The reaction may be carried out in a suitable solvent, such as dichloromethane, and a base such as triethylamine or Hunigs base at a temperature, for example, from 0° C. to 50° C.

Compounds of formula (P) may be prepared by reacting a compound of formula (S) with excess of an amine of formula $R_3R^4NH$ where $R^3$ and $R^4$ are as defined above, in a suitable solvent such as butanol or 1,2-dioxane at a temperature, for example, from 50° C. to 150° C. Alternatively the reaction can be performed in a microwave at a temperature, for example, from 50° C. to 200° C.

Compounds of formulae (III), (V), (VI), (VII), (VIIa), (VIII), (VIIIa), (VIIIb), (VIIIc), (IX), (X), (XI), (XII), (XIII), (XIIIa), (XIIIb), (XIV), (XV), (XVI), (XVII), (XVIII) and further compounds of formula (II) are either commercially available, are well known in the literature or may be prepared easily using known techniques.

Compounds of formula (I) may be converted to other compounds of formula (I) using conventional methods. For example, a compound of formula (I) in which $R^2$ represents a group of formula (Ib) and $X^3$ is NH can be converted to a corresponding compound of formula (I) in which $X^3$ is $>NSO_2R^{12}$ by reaction with a compound of formula $R^{12}SO_2Cl$. The reaction is suitably carried out in an organic solvent such as dichloromethane or acetonitrile, in the presence of a base such as pyridine or triethylamine. Temperatures in the range from 0° C. to 80° C. are suitably employed.

Further, a compound of formula (I) in which $R^2$ represents a group of formula (Ib) and $X^3$ is NH can be converted to a corresponding compound of formula (I) in which $X^3$ is $>NCOR^{12}$ by reaction with a compound of formula $R^{12}COCl$. The reaction is suitably carried out in an organic solvent such as dichloromethane or acetonitrile, in the presence of a base such as pyridine or triethylamine. Temperatures in the range from 0° C. to 80° C. are suitably employed. Alternatively the reaction may be carried out by activation of an acid of formula $R^{12}CO_2H$ with a coupling agent such as HATU or PyBOP in an organic solvent such as N-methylpyrrolidinone, N,N-dimethylformamide, acetonitrile or tetrahydrofuran usually in the presence of a suitable base (e.g. triethylamine, Hunigs base) at a temperature, for example, in the range from 0° C. to 50° C.

Still further, a compound of formula (I) in which $R^2$ represents a group of formula (Ib) and $X^3$ is NH can be converted to a corresponding compound of formula (I) in which $X^3$ is $>NCOCH_2NR^{15}R^{16}$ by reaction with chloroacetyl chloride followed by an amine of formula $R^{15}R^{16}NH$. The first stage is suitably carried out in an organic solvent such as dichloromethane or acetonitrile, with one equivalent of chloroacetyl chloride. Temperatures in the range from 0° C. to 30° C. are suitably employed. In the second stage the reaction is suitably carried out in an organic solvent such as dichloromethane or acetonitrile, with excess of an amine $R^{15}R^{16}NH$. Temperatures in the range from 0° C. to 100° C. are suitably employed.

A compound of formula (I), where $R^2$ represents a group of formula (Ib) and $X^3$ represents $NR^{12}CO$ or $NR^{12}SO_2$ may be prepared by reacting a compound of formula (XIX) with a compound of formula (XX)

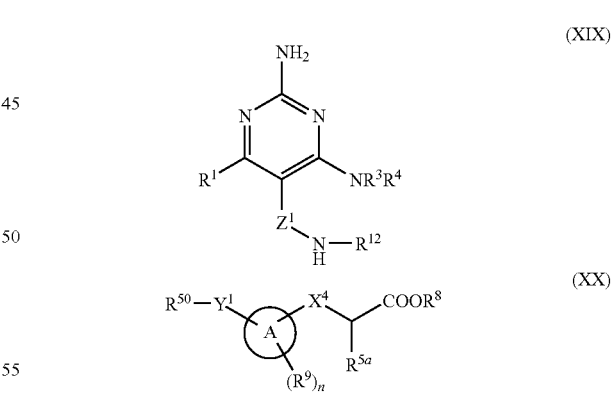

where $R^{50}$ represents $SO_2\text{-}LG^2$ or $CO\text{-}LG^2$, $LG^2$ is a suitable leaving group such as chlorine and the remaining substituents are as defined in formula (I). The reaction is suitably carried out in an organic solvent such as dichloromethane or acetonitrile, in the presence of a base such as pyridine or triethylamine. Temperatures in the range from 0° C. to 80° C. are suitably employed. Alternatively when $R^{50}=CO_2H$, the reaction may be carried out by activation with a coupling agent such as HATU, $T_3P$ (1-propanephosphonic acid cyclic anhydride) or PyBOP in an organic solvent such as N-methylpyrrolidinone, N,N-dimethylformamide, acetonitrile or tetrahydrofuran usually in the presence of a suitable base (e.g. triethylamine, Hunigs base) at a temperature, for example, in the range from 0° C. to 50° C.

A compound of formula (IV) where $R^2$ represents a group of formula (Ib) and $X^3$ represents $NR^{12}CO$ or $NR^{12}SO_2$, may be prepared by reaction of a compound of formula (XIX) with a compound of formula (XXI) using similar conditions to those above.

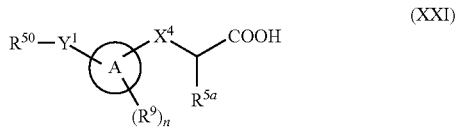

(XXI)

A compound of formula (XIX) may be prepared by reacting a compound of formula (VI) with an aldehyde or ketone under standard reductive amination conditions.

A compound of formula (II) where $R^2$ represents a group of formula (XXII) may be prepared by reacting a compound of formula (XXIII) with a compound of formula (XXIV)

(XXII)

(XXIII)

(XXIV)

where $R^{43}$ is H or methyl and $R^1$, $R^3$, $R^4$ are as defined above. The reaction may be carried out under acid conditions, for example, in aqueous hydrochloric acid at elevated temperature.

A compound of formula (XXIII) may be prepared according to scheme 5:

Scheme 5

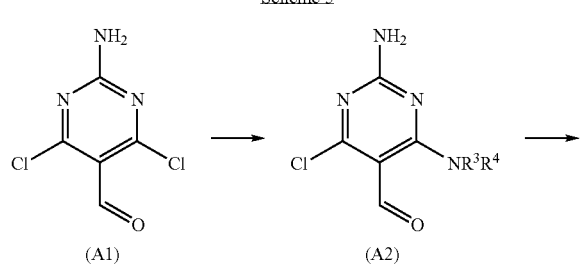

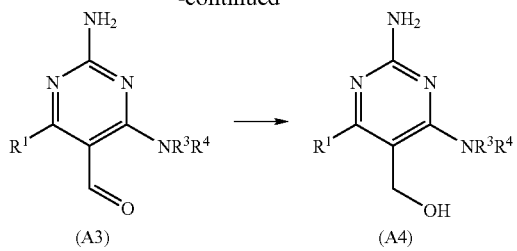

(A3)    (A4)

A compound of formula (A2) may be prepared by reacting a compound of formula (A1) with an amine of formula $R_3R_4NH$. The reaction may be carried out in the presence of a base such as triethylamine in an organic solvent such as methanol. Temperatures in the range of 50-100° C. are preferred.

A compound of formula (A3), where $R^1$ is methyl, may be prepared by reacting a compound of formula (A2) with tetramethylstannane. The reaction may be carried out in the presence of a catalyst such as $Pd(PPh_3)_4$ in an organic solvent such as dimethylformamide. Temperatures in the range of 50-120° C. are preferred. A compound of formula (A3), where $R^1$ is alkoxy or alkylthiol, may be prepared by reacting a compound of formula (A2) with the appropriate alcohol, or alkylthiol in the presence of a base such as sodium hydride.

A compound of formula (A4) may be prepared by reacting a compound of formula (A3) with a reducing agent such as sodium borohydride. The reaction may be carried out in an organic solvent such as methanol at a temperature in the range of 0-50° C.

A compound of formula (I) where $R^2$ represents a group of formula (Ia), wherein $X^1$ is $CH_2$ and $X^2$ is O may be prepared by reacting a compound of formula (XXV) with a compound of formula (XXVI)

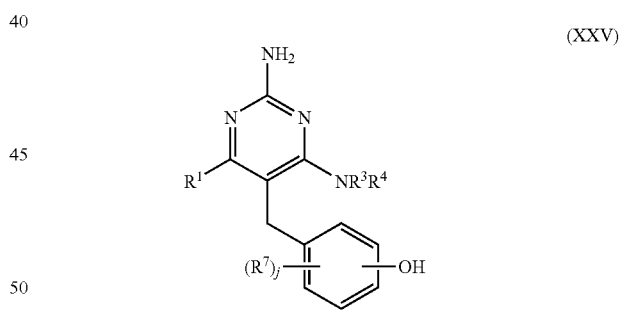

(XXV)

(XXVI)

where $LG^3$ is a leaving group such as chlorine, bromine or mesylate and j, $R^1$, $R^3$, $R^4$, $R^5$, $R^6$ and $R^7$ are as defined in formula (I). The reaction may be carried out in the presence of a base such as potassium carbonate in an organic solvent such as dimethylformamide at a temperature in the range from 20-100° C.

A compound of formula (XXV) may be prepared according to scheme 6 below:

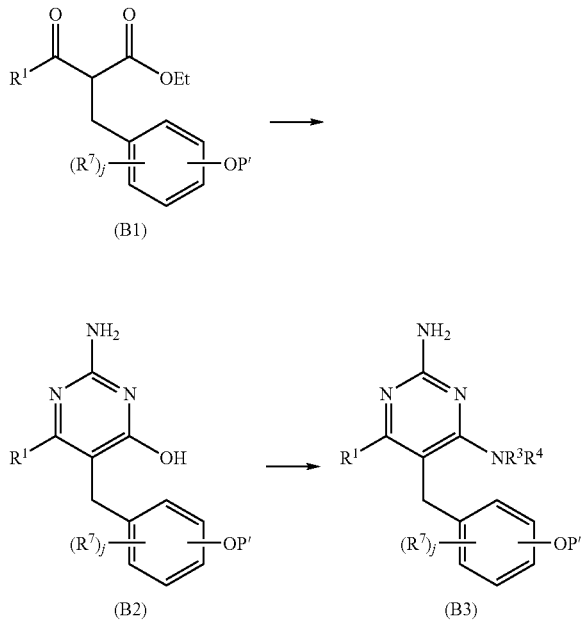

where j, $R^1$, $R^3$, $R^4$ and $R^7$ are as defined above and P' is hydrogen or a protecting group.

Compounds of formula (B2) may be prepared by reacting a compound of formula (B1) with guanidine or guanidine carbonate in a suitable solvent such as methanol or ethanol at a temperature, for example, in the range from 50° C. to 150° C.

Compounds of formula (B3) may be prepared in two steps by reacting a compound of formula (B2) with a compound of formula $^{41}RSO_2Cl$, followed with an amine of formula $R_3R_4NH$. The first step may be carried out in a suitable solvent, such as DCM, and a base such as triethylamine or Hunigs base at a temperature, for example, from 0° C. to 50° C. The second step may be carried out in a suitable solvent such as butanol or 1,2-dioxane at a temperature, for example, from 50° C. to 150° C. Alternatively the reaction can be performed in a microwave at a temperature, for example, from 50° C. to 200° C.

A compound of formula (I) where $R^2$ represents a group of formula (Ib), wherein $X^3$ is $NR^{12}CONR^{13}$ or $NR^{13}CONR^{12}$ may be prepared by reacting a compound of formula (XXVII) with a compound of formula (XXVIII)

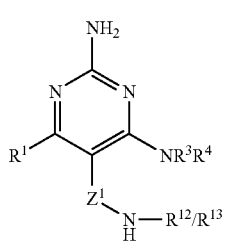

(XXVII)

(XXVIII)

where $R^{51}$ is defined as Cl—C(O)$NR^{12}/R^{13}$— and n, $R^1$, $R^3$, $R^4$, $R^{12}$, $R^{13}$, $Z^1$, $Y^1$, A, $X^4$, $R^9$, $R^{5a}$ and $R^8$ are as defined above. The reaction may be carried out in a suitable solvent, such as dichloromethane, and a base such as triethylamine or Hunigs base at a temperature, for example, from 0° C. to 50° C.

A compound of formula (I) where $R^2$ represents a group of formula (Ib) may be prepared from a compound of formula (XXIX) or (XXX) using the same methods as in scheme 1 and the enabling chemistry above. This route is suitable, for example, where $X^3$ in formulae (XXIX) and (XXX) is $S(O)_p$ or O.

(XXIX)

(XXX)

Compounds of formulae (XIX), (XX), (XXI), (XXII), (XXIII), (XXIV), (XXV), (XXVI), (XXVII), (XXVIII), (XXIX) and (XXX) are either commercially available, are well known in the literature or may be prepared easily using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, phosphate, acetate, fumarate, maleate, tartrate, lactate, citrate, pyruvate, succinate, oxalate, 1-hydroxy-2-napthoate (xinafoate), methanesulphonate or p-toluenesulphonate salt.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as modulators of toll-like receptor (especially TLR7) activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, malepattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;
3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;
4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvovaginitis; Peyronie's disease; erectile dysfunction (both male and female);
5. allograft rejection: acute and chronic following, for example, transplantation of kidney, heart, liver, lung, bone marrow, skin or cornea or following blood transfusion; or chronic graft versus host disease;
6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, candida, aspergillus, cryptococcal meningitis, pneumocystis carnii, cryptosporidiosis, histoplasmosis, toxoplasmosis, trypanosome infection and leishmaniasis.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the invention (including pharmaceutically acceptable salts) may be used in the treatment of asthma, COPD, allergic rhinitis, allergic conjunctivitis, atopic dermatitis, cancer, hepatitis B, hepatitis C, HIV, HPV, bacterial infections and dermatosis.

The invention still further provides a method of treating, or reducing the risk of, a disease or condition comprising or arising from abnormal cell growth (e.g. a cancer), which method comprises administering to a patient in need thereof a therapeutically effective amount of a compound of formula (I) or a pharmaceutically acceptable salt thereof as hereinbefore defined.

The invention also provides a method of treating, or reducing the risk of, an obstructive airways disease or condition (e.g. asthma or COPD) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals— The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the invention (including pharmaceutically acceptable salts) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU111248 (sunitinib; WO 01/60814), compounds such as those disclosed in International Patent Applications WO 97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Furthermore, for the treatment of the inflammatory diseases COPD, asthma and allergic rhinitis the compounds of the invention may be combined with agents such as tumour necrosis factor alpha (TNF-alpha) inhibitors such as anti-TNF monoclonal antibodies (for example Remicade, CDP-870 and adalimumab) and TNF receptor immunoglobulin molecules (such as Enbrel); non-selective cyclo-oxygenase COX-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocorticosteroids (whether administered by topical, oral, intramuscular, intravenous, or intra-articular routes); methotrexate, lefunomide; hydroxychloroquine, d-penicillamine, auranofin or other parenteral or oral gold preparations.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LTB4, LTC4, LTD4, and LTE4) selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention and an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present invention further relates to the combination of a compound of the invention and a chromone, such as sodium cromoglycate or nedocromil sodium.

The present invention still further relates to the combination of a compound of the invention together with an insulin-like growth factor type I (IGF-1) mimetic.

The present invention still further relates to the combination of a compound of the invention and a glucocorticoid, such as flunisolide, triamcinolone acetonide, beclomethasone dipropionate, budesonide, fluticasone propionate, ciclesonide or mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX3CR1 for the C—X3-C family.

The present invention still further relates to the combination of a compound of the invention together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present invention still further relates to the combination of a compound of the invention together with an immunoglobulin (Ig) or Ig preparation or an antagonist or antibody modulating Ig function such as anti-IgE (omalizumab).

The present invention further relates to the combination of a compound of the invention and another systemic or topically-applied anti-inflammatory agent, such as thalidomide or a derivative thereof, a retinoid, dithranol or calcipotriol.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

In a further aspect the present invention provides a combination (for example for the treatment of COPD, asthma or allergic rhinitis) of a compound of formula (I) or a pharmaceutically acceptable salt thereof as hereinbefore defined and one or more agents independently selected from:
- a non-steroidal glucocorticoid receptor (GR-receptor) agonist;
- a selective $\beta_2$ adrenoceptor agonist (such as metaproterenol, isoproterenol, isoprenaline, albuterol, salbutamol, formoterol, salmeterol, terbutaline, orciprenaline, bitolterol mesylate, pirbuterol or indacaterol);
- a phosphodiesterase inhibitor (such as a PDE4 inhibitor);
- a protease inhibitor (such as a neutrophil elastase or matrix metalloprotease MMP-12 inhibitor);
- a glucocorticoid;
- an anticholinergic agent;
- a modulator of chemokine receptor function (such as a CCR1 receptor antagonist); and
- an inhibitor of kinase function (such as the kinases p38 or IKK).

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is
- a non-steroidal glucocorticoid receptor (GR-receptor) agonist;
- a selective $\beta_2$ adrenoceptor agonist;
- a phosphodiesterase inhibitor;
- a protease inhibitor;
- a glucocorticoid;
- an anticholinergic agent;
- a modulator of chemokine receptor function; or
- an inhibitor of kinase function;

for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is
- a non-steroidal glucocorticoid receptor (GR-receptor) agonist;
- a selective $\beta_2$ adrenoceptor agonist;
- a phosphodiesterase inhibitor;
- a protease inhibitor;
- a glucocorticoid;
- an anticholinergic agent;
- a modulator of chemokine receptor function; or
- an inhibitor of kinase function;

and instructions for the simultaneous, sequential or separate administration of the preparations to a patient in need thereof.

The present invention will be further explained by reference to the following illustrative examples.

Unless otherwise stated reactions were run under nitrogen and organic solutions were dried over magnesium sulphate. RPHPLC means reversed phase preparative HPLC using Waters Symmetry C8, Xterra, XBridge or Phenomenex Gemini columns using acetonitrile and either aqueous ammonium acetate, ammonia, formic acid or trifluoroacetic acid as buffer where appropriate. Column chromatography was carried out on silica gel. Treating with SCX means the mixture was absorbed on SCX and eluted with an appropriate solvent such as methanol or acetonitrile then the free base product eluted with aqueous ammonia/methanol.

The following abbreviations are used in the Examples:
EtOAc ethyl acetate
DCM dichloromethane
NMP N-methylpyrrolidinone
NBS N-bromosuccinimide
DMF N,N-dimethylformamide
DMSO dimethylsulfoxide
THF tetrahydrofuran
MeOH methanol
EtOH ethanol
TFA trifluoroacetic acid
HCl hydrogen chloride
$K_2CO_3$ potassium carbonate
$NaHCO_3$ sodium hydrogen carbonate
TEA triethylamine
MeCN acetonitrile
Pd/C palladium on carbon
$T_3P$ 1-propanephosphonic acid cyclic anhydride
DMAP 4-dimethylaminopyridine
PS-TBD polystyrene bound 1,5,7-triazabicyclo[4.4.0]dec-5-ene
MTBE tert-butyl methyl ether
DIBAL-H diisobutylaluminium hydride
Pd-118 1,1'-Bis(di-tert-butylphosphino)ferrocenepalladium (II) chloride
KOH potassium hydroxide
sat. saturated
aq. aqueous
$Et_2O$ diethylether
DMA N,N-dimethylacetamide
TMS-Cl trimethylsilylchloride
conc. concentrated
rt room temperature
h hours
min minutes
M molar
MS mass spectrometry
PyBop Benzotriazol-1-yloxytripyrrolidinophosphonium hexafluorophosphate
HATU O-(7-azabezotriazol-1-yl)-N,N,N',N'-tetramethyluronium hexafluorophosphate
APCI atmospheric chemical ionisation method
ESI electron spray ionisation method
NMR nuclear magnetic resonance
Instrument Details:
XRPD—PANalytical CubiX PRO machine in Ø-Ø configuration over the scan range 2° to 40° 2Ø with 100-second exposure per 0.02° increment. The X-rays were generated by a copper long-fine focus tube operated at 45 kV and 40 mA. The wavelength of the copper X-rays was 1.5418 Å. Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

EXAMPLE 1

Methyl 2-(3-((3-(2-Amino-4-methyl-6-(pentylamino)pyrimidin-5-yl)propylamino)methyl)phenyl)acetate

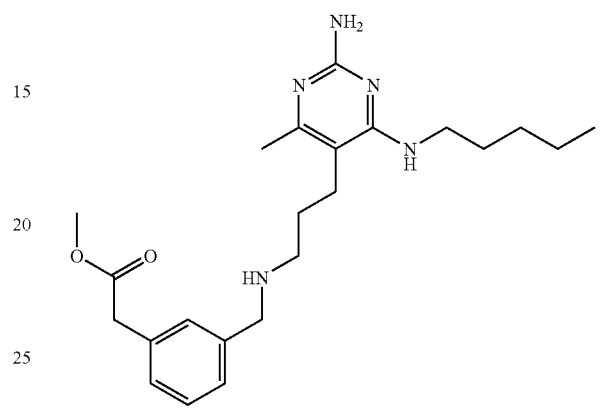

(i) 6-Methyl-N4-pentylpyrimidine-2,4-diamine

2-Amino-4-chloro-6-methylpyrimidine (10 g) and pentylamine (20 ml) were combined in dioxane (100 mL) and refluxed for 42 h. The solvents were evaporated, the product taken up in DCM, washed with water, sat. sodium bicarbonate solution, brine, dried, and the solvent evaporated to give the subtitle compound 8.3 g.
LC-MS m/z 195 ESI (ii)
5-Iodo-6-methyl-N4-pentylpyrimidine-2,4-diamine A solution of iodine (11.92 g) in DCM (300 mL) was added to a stirred mixture of the product from step (i) (8.3 g) and sodium hydroxide (3.42 g) in water (200 mL). The reaction mixture was stirred at rt overnight. The organic layer was separated and washed with sodium metabisulfate solution, then brine. The combined organic layers were dried, and the solvent evaporated under reduced pressure. The product was purified by chromatography eluting with DCM:MeOH; 95:5 to give the subtitle compound 11 g.
LC-MS m/z 321 ESI (iii) tert-Butyl 3-(2-amino-4-methyl-6-(pentylamino) pyrimidin-5-yl)prop-2-ynylcarbamate tert-Butyl prop-2-ynylcarbamate (7.27 g) was dissolved in THF (50 mL), briefly purged with nitrogen then copper(I) iodide (0.298 g) was added. The reaction mixture was stirred for 30 min then the product from step (ii) (5 g), tetrakis (triphenylphosphine)palladium(0) (0.903 g) and TEA (10 mL) were added. The reaction mixture was heated at 70° C. for 20 h then cooled to rt. The organic layer was washed with water and brine and the solvent evaporated under reduced pressure. The residue was taken up in MeOH and purified via SCX resin. The product was further purified by chromatography eluting with DCM:MeOH 95:5 to give the subtitle compound 3.7 g.
LC-MS m/z 348 ESI

(iv) tert-Butyl 3-(2-amino-4-methyl-6-(pentylamino) pyrimidin-5-yl)propylcarbamate The product from step (iii) (3.7 g) was dissolved in EtOH (100 mL) then 5% Pd/C (300 mg) was added. The reaction mixture was hydrogenated at 3 bar for 16 h. The catalyst was removed by filtration and the solvent evaporated to give the subtitle compound 3.8 g.
LC-MS m/z 352 ESI

(v) 5-(3-Aminopropyl)-6-methyl-N4-pentylpyrimidine-2,4-diamine

The product from step (iv) (3.8 g) was dissolved in DCM (100 mL) and TFA (35 mL) and the reaction mixture stirred at rt for 16 h. The solvent was evaporated and the residue taken up in MeOH. The product was purified via SCX resin to give the subtitle compound 2.3 g.
$^1$H NMR (DMSO-d6): δ 6.79-6.71 (m, 1H), 5.51-5.44 (m, 2H), 3.27-3.19 (m, 4H), 2.38-2.28 (m, 2H), 2.04 (s, 3H), 1.57-1.36 (m, 4H), 1.33-1.18 (m, 4H), 0.87 (t, 3H)
LC-MS m/z 252 ESI

(vi) Methyl 2-(3-((3-(2-Amino-4-methyl-6-(pentylamino)pyrimidin-5-yl)propylamino)methyl)phenyl)acetate The product from step (v) (1 g) was dissolved in THF (30 mL) then acetic acid (0.239 g, 0.23 ml) and methyl 2-(3-formylphenyl)acetate (0.709 g) were added followed by MeOH (0.5 mL). The reaction mixture was stirred at rt for 72 h then sodium borohydride (0.1506 g) was added. After 2 h a further portion of sodium borohydride (0.0452 g) was added and the reaction mixture stirred for 16 h. A further portion of sodium borohydride (0.1506 g) was added and stirred for 2 h. The reaction mixture was poured into saturated sodium bicarbonate solution and extracted with EtOAc. The solvents were evaporated and the product was purified by chromatography eluting with DCM:MeOH 97:3 to 80:20 to give the title compound 0.5 g.
$^1$H NMR (DMSO-d6): δ 7.31-7.18 (m, 3H), 7.12 (d, 1H), 6.54 (t, 1H), 5.48 (d, 2H), 3.65 (d, 4H), 3.60 (s, 3H), 3.27-3.17 (m, 2H), 2.49-2.44 (m, 2H), 2.35 (t, 2H), 2.05 (s, 3H), 1.55-1.39 (m, 4H), 1.29-1.16 (m, 4H), 0.84 (t, 3H)
LC-MS m/z 414 ESI

EXAMPLE 2

Methyl 2-(4-((3-(2-amino-4-methyl-6-(pentylamino)pyrimidin-5-yl)propylamino)methyl)phenyl)acetate

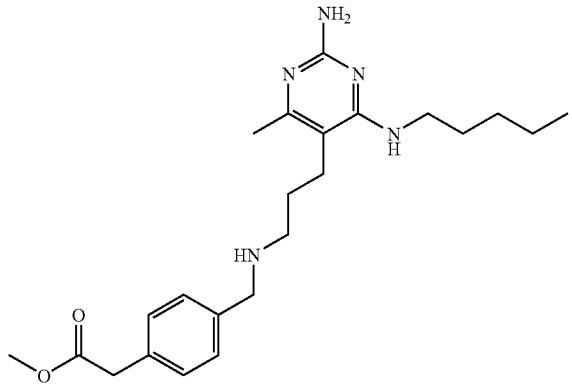

The product from Example 1 step (v) (0.3 g) and methyl 2-(4-formylphenyl)acetate (0.213 g) were combined in THF (20 mL), acetic acid (0.072 g) was added and the reaction mixture stirred at rt for 16 h. Sodium borohydride (0.0677 g) and MeOH (3 drops) were added and the reaction mixture stirred for 72 h. The solvents were evaporated and the product dissolved in MeOH and purified by RPHPLC to give the title compound 0.3 g.
$^1$H NMR (DMSO-d6): δ 7.28 (d, 2H), 7.19 (d, 2H), 6.58-6.54 (m, 1H), 5.50-5.45 (m, 2H), 3.64 (s, 3H), 3.61 (d, 2H), 3.29 (s, 4H), 3.25-3.18 (m, 2H), 2.47-2.40 (m, 2H), 2.38-2.30 (m, 2H), 2.05 (s, 3H), 1.54-1.39 (m, 4H), 1.28-1.18 (m, 3H), 0.85 (t, 31H)
LC-MS m/z 414 ESI

EXAMPLE 3

Methyl 2-(3-((N-(3-(2-amino-4-methyl-6-(pentylamino)pyrimidin-5-yl)propyl)-2-(dimethylamino)acetamido)methyl)phenyl)acetate

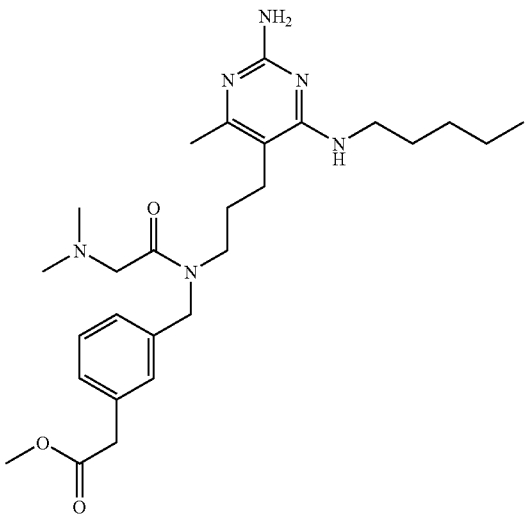

(i) Methyl 2-(3-((N-(3-(2-amino-4-methyl-6-(pentylamino)pyrimidin-5-yl)propyl)-2-chloroacetamido)methyl)phenyl)acetate The product from Example 1 (0.1 g) was dissolved in MeCN (10 mL) and chloroacetyl chloride (0.027 g) was added. The reaction mixture was stirred for 16 h and the solvents evaporated to give the subtitle compound which was used without further purification.
LC-MS m/z 490 ESI

(ii) Methyl 2-(3-((N-(3-(2-amino-4-methyl-6-(pentylamino)pyrimidin-5-yl)propyl)-2-(dimethylamino)acetamido)methyl)phenyl)acetate The product from step (i) (0.1 g) was dissolved in MeOH and dimethylamine (2M in MeOH, 0.61 ml) was added. The reaction mixture was stirred for 72 h at rt, the solvents were evaporated and the residue purified by RPHPLC to give the title compound 24 mg.
$^1$H NMR (DMSO-d6): δ 7.35-7.21 (m, 1H), 7.21-7.03 (m, 3H), 6.21-6.09 (m, 1H), 5.54-5.47 (m, 2H), 4.46 (s, 1H), 3.67 (s, 1H), 3.63 (s, 5H), 3.59 (s, 4H), 3.30-3.21 (m, 2H), 3.05-3.02 (m, 2H), 2.30-2.19 (m, 2H), 2.16 (d, 6H), 2.02 (s, 2H), 1.98 (s, 1H), 1.66-1.54 (m, 1H), 1.54-1.42 (m, 3H), 1.34-1.19 (m, 2H), 0.86 (t, 3H)
LC-MS m/z 499 ESI

EXAMPLE 4

Methyl 2-(4-((N-(3-(2-amino-4-methyl-6-(pentylamino)pyrimidin-5-yl)propyl)-2-(dimethylamino)acetamido)methyl)phenyl)acetate

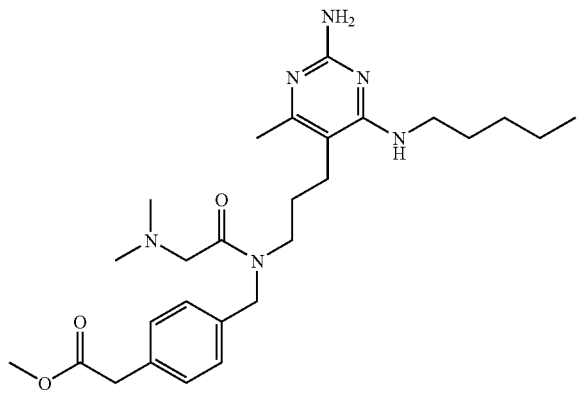

The title compound was prepared by the method of Example 3 using the product from Example 2 and the appropriate amine.

$^1$H NMR (DMSO-d6): δ 7.22 (dd, 2H), 7.17-7.11 (m, 2H), 6.20-6.11 (m, 1H), 5.53-5.47 (m, 2H), 4.45 (s, 2H), 3.65 (d, 2H), 3.60 (s, 3H), 3.27-3.20 (m, 2H), 3.04 (s, 2H), 2.30-2.20 (m, 2H), 2.19-2.13 (m, 7H), 2.02 (s, 2H), 1.99 (s, 1H), 1.64-1.54 (m, 1H), 1.53-1.42 (m, 3H), 1.33-1.19 (m, 5H), 0.86 (t, 3H).
LC-MS m/z 499 ESI

Examples 5-10 were prepared using the method of Example 3 and the appropriate amine.

EXAMPLE 5

(S)-Methyl 1-(2-((3-(2-amino-4-methyl-6-(pentylamino)pyrimidin-5-yl)propyl)(3-(2-methoxy-2-oxoethyl)benzyl)amino)-2-oxoethyl)pyrrolidine-2-carboxylate

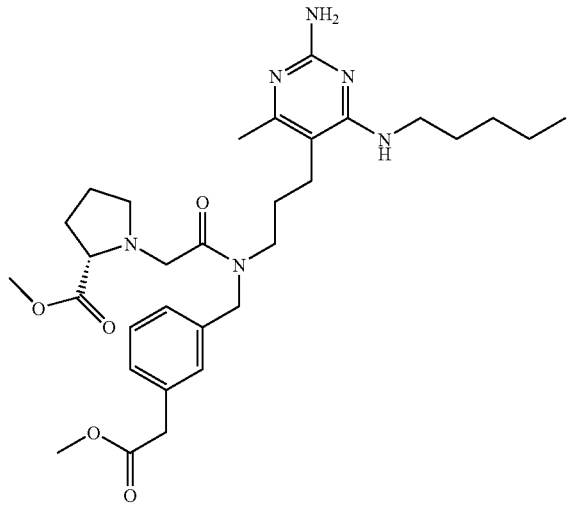

$^1$H NMR DMSO-d$_6$ @90° C.; δ7.33-7.19 (m, 1H), 7.19-7.03 (m, 3H), 5.80-5.70 (m, 1H), 5.21-5.12 (m, 2H), 3.68-3.51 (m, 6H), 3.45-3.21 (m, 5H), 2.98-2.92 (m, 6H), 2.33-2.22 (m, 2H), 2.00 (s, 4H), 1.84-1.71 (m, 3H), 1.59-1.45 (m, 4H), 1.34-1.22 (m, 6H), 0.86 (t, 3H)
LC-MS m/z 583 ESI

EXAMPLE 6

Methyl 2-(3-((N-(3-(2-amino-4-methyl-6-(pentylamino)pyrimidin-5-yl)propyl)-2-(4-methylpiperazin-1-yl)acetamido)methyl)phenyl)acetate

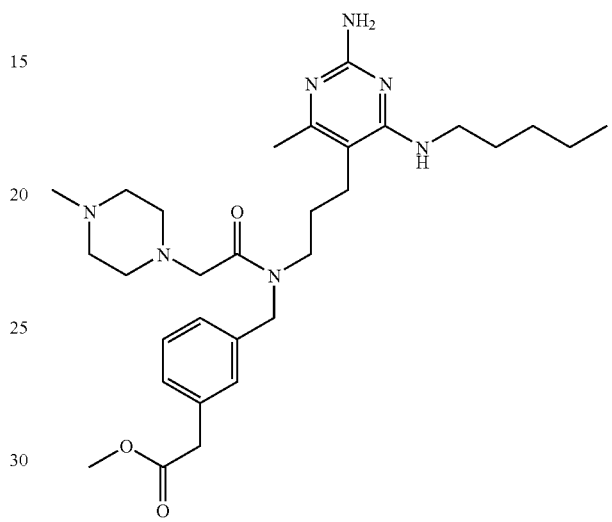

$^1$H NMR DMSO-d$_6$ @90° C.; δ 7.34-7.19 (m, 1H), 7.19-7.03 (m, 3H), 5.84-5.75 (m 1H), 5.20-5.11 (m, 2H), 3.61 (s, 4H), 336-3.23 (m, 4H), 3.08 (s, 2H), 2.98-2.93 (m, 2H), 2.47-2.17 (m, 10H), 2.13 (s, 3H), 2.02 (s, 3H), 1.60-1.47 (m, 4H), 1.34-1.23 (m, 5H), 0.86 (t, 3H)
LC-MS m/z 554 ESI

EXAMPLE 7

Methyl 2-(3-((N-(3-(2-amino-4-methyl-6-(pentylamino)pyrimidin-5-yl)propyl)-2-(4-hydroxypiperidin-1-yl)acetamido)methyl)phenyl)acetate

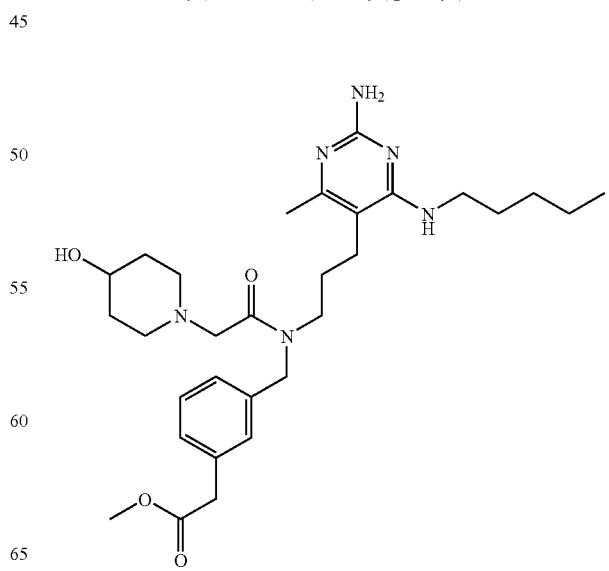

¹H NMR DMSO-d₆: δ 7.30-7.04 (m, 4H), 5.81-5.75 (m, 1H), 5.17 (s, 2H), 4.14 (s, 1H), 3.64-3.58 (m, 5H), 3.50-3.37 (m, 1H), 3.37-3.22 (m, 4H), 3.07 (s, 2H), 2.98-2.95 (m, 2H), 2.69-2.62 (m, 2H), 2.33-2.24 (m, 2H), 2.18-2.08 (m, 2H), 2.01 (s, 3H), 1.72-1.45 (m, 6H), 1.43-1.21 (m, 6H), 0.86 (t, 3H)
LC-MS m/z 555 ESI

EXAMPLE 8

Methyl 2-(3-((2-(4-acetyl-1,4-diazepan-1-yl)-N-(3-(2-amino-4-methyl-6-(pentylamino)pyrimidin-5-yl)propyl)acetamido)methyl)phenyl)acetate

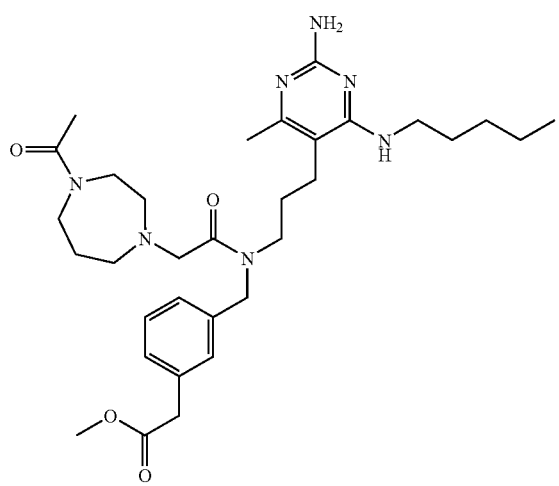

¹H NMR DMSO-d₆: δ 7.40-7.02 (m, 4H), 6.23-6.13 (m, 1H), 5.57-5.46 (m, 2H), 4.68-4.44 (m, 2H), 3.71-3.62 (m, 4H), 3.60 (s, 4H), 3.48-3.36 (m, 4H), 3.30-3.23 (m, 5H), 2.68 (s, 3H), 2.33 (s, 3H), 2.31-2.19 (m, 2H), 2.04-1.92 (m, 4H), 1.52-1.42 (m, 2H), 1.32-1.19 (m, 6H), 0.89-0.82 (m, 3H)
LC-MS m/z 596 ESI

EXAMPLE 9

Methyl 2-(3-((N-(3-(2-amino-4-methyl-6-(pentylamino)pyrimidin-5-yl)propyl)-2-(4-(3-(dimethylamino)propyl)piperazin-1-yl)acetamido)methyl)phenyl)acetate

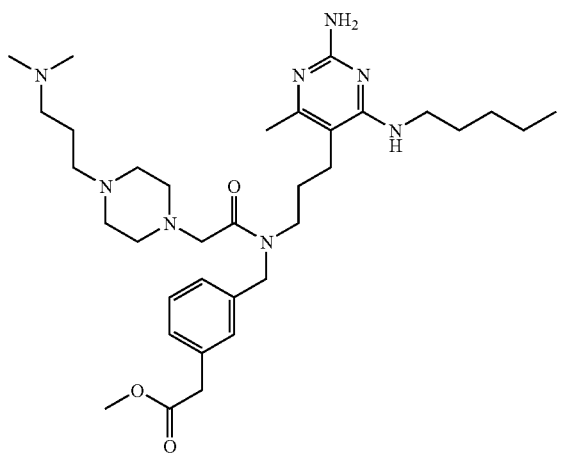

¹H NMR DMSO-d₆: δ 7.37-6.98 (m, 4H), 6.23-6.08 (m, 1H), 5.57-5.44 (m, 2H), 4.66 (s, 1H), 4.47 (s, 1H), 3.70-3.56 (m, 5H), 3.42-3.34 (m, 2H), 3.29-3.21 (m, 4H), 3.11-2.99 (m, 2H), 2.40-2.14 (m, 12H), 2.10 (s, 5H), 2.09-1.97 (m, 3H), 1.69-1.38 (m, 6H), 1.34-1.18 (m, 5H), 0.93-0.77 (m, 3H)
LC-MS m/z 625 ESI

EXAMPLE 10

Methyl 2-(3-[((N-(3-(2-amino-4-methyl-6-(pentylamino)pyrimidin-5-yl]propyl)-2-((2-hydroxyethyl)(methyl)amino)acetamido)methyl)phenyl)acetate

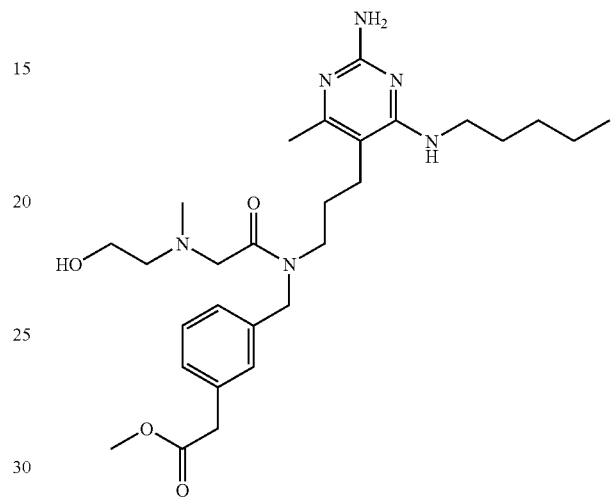

¹H NMR DMSO-d₆: δ 7.37-6.99 (m, 4H), 6.22-6.09 (m, 1H), 5.59-5.44 (m, 2H), 4.69 (s, 1H), 4.56-4.32 (m, 3H), 3.69-3.56 (m, 5H), 3.27-3.21 (m, 4H), 3.20-3.14 (m, 2H), 2.29-2.18 (m, 5H), 2.01 (d, 4H), 1.64-1.42 (m, 5H), 1.34-1.14 (m, 5H), 0.86 (t, 3H)
LC-MS m/z 529 ESI

EXAMPLE 11

Methyl 4-((3-(2-amino-4-methyl-6-(pentylamino)pyrimidin-5-yl)propyl)(3-(2-methoxy-2-oxoethyl)benzyl)amino)-4-oxobutanoate

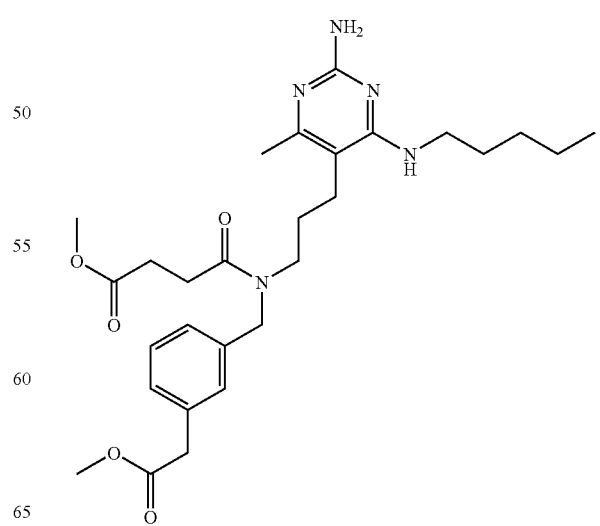

The product from Example 1 (61 mg), mono-methyl succinate (23.4 mg) and TEA (0.062 ml) were dissolved in DCM (15 ml) then HATU (61.7 mg) was added. The resulting solution was stirred at rt for 16 h. The solvents were evaporated, the residue was taken up in MeOH and the crude product was purified by RPHPLC to afford the title compound as a colorless gum 32 mg.

$^{1}$H NMR DMSO-$d_6$: δ 7.36-7.02 (m, 4H), 6.24-6.09 (m, 1H), 5.55-5.46 (m, 2H), 4.63-4.42 (m, 2H), 3.71-3.51 (m, 8H), 3.29-3.19 (m, 4H), 2.71-2.62 (m, 2H), 2.32-2.17 (m, 2H), 2.00 (s, 3H), 1.60-1.42 (m, 4H), 1.34-1.18 (m, 5H), 0.89-0.80 (m, 4H)

LC-MS m/z 528 ESI

EXAMPLE 12

Methyl 2-(3-((N-(3-(2-amino-4-methyl-6-(pentylamino)pyrimidin-5-yl)propyl)-4-(dimethylamino)butanamido)methyl)phenyl)acetate

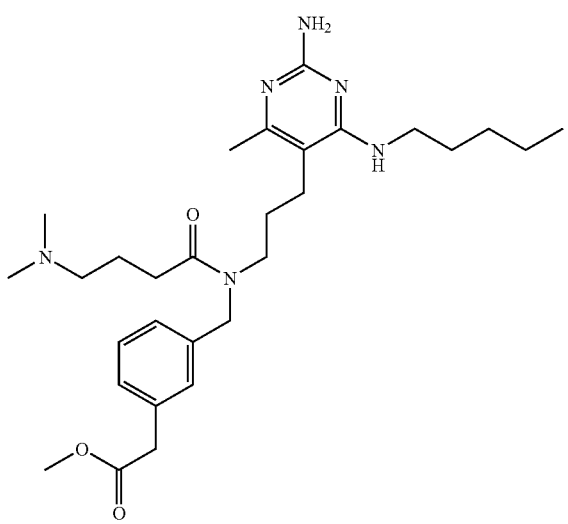

To a stirred DCM (15 mL) solution of the product from Example 1 (58 mg), 4-(dimethylamino)butyric acid hydrochloride (28.2 mg) and TEA (0.059 mL) was added HATU, (58.7 mg) under nitrogen. The resulting solution was stirred at rt for 16 h. The solvent was evaporated and the residue was taken up in MeOH and the crude product purified by RPHPLC to afford the title compound 5 mg.

$^{1}$H NMR DMSO-$d_6$: δ7.37-7.21 (m, 1H), 7.19-7.10 (m, 1H), 7.08-7.03 (m, 2H), 6.22-6.11 (m, 1H), 5.54-5.46 (m, 2H), 4.59-4.44 (m, 2H), 3.70-3.61 (m, 2H), 3.60 (s, 3H), 3.29-3.20 (m, 2H), 2.39-2.30 (m, 2H), 2.30-2.14 (m, 4H), 2.09 (s, 4H), 2.04 (s, 2H), 1.99 (s, 3H), 1.72-1.57 (m, 2H), 1.57-1.42 (m, 4H), 1.33-1.18 (m, 6H), 0.86 (t, 3H)

LC-MS m/z 527 ESI

EXAMPLE 13

Methyl 2-(3-((N-(3-(2-amino-4-methyl-6-(pentylamino)pyrimidin-5-yl)propyl)methylsulfonamido)methyl)phenyl)acetate

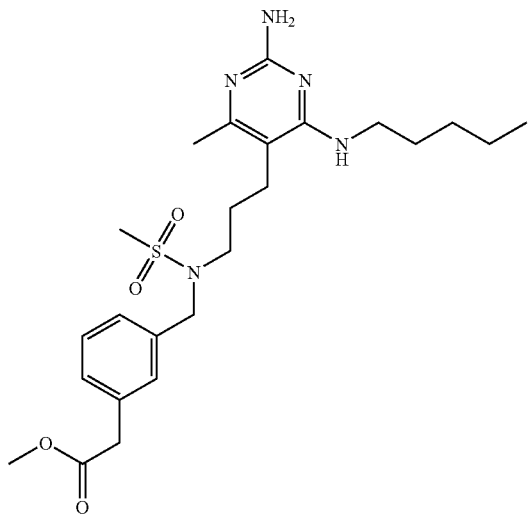

To a stirred solution of the product from Example 1 (70 mg) dissolved in DCM was added methanesulfonyl chloride (16 μl) and TEA (28.3 μl) under nitrogen. The resulting solution was stirred at rt for 16 h. The solvents were evaporated, the residue redissolved in MeOH and the crude product was purified by RPHPLC to afford the title compound 32 mg.

$^{1}$H NMR DMSO-$d_6$: δ 7.33-7.27 (m, 1H), 7.23-7.15 (m, 3H), 6.14-6.07 (m, 1H), 5.52-5.47 (m, 2H), 4.30 (s, 2H), 3.67 (s, 2H), 3.58 (s, 2H), 3.28-3.20 (m, 2H), 3.19-3.12 (m, 2H), 2.94 (s, 3H), 2.20-2.13 (m, 2H), 1.92 (s, 3H), 1.51-1.40 (m, 4H), 1.32-1.19 (m, 5H), 0.86 (t, 3H)

LC-MS m/z 492 ESI

EXAMPLE 14

Methyl 2-(3-((N-(3-(2-amino-4-methyl-6-(pentylamino)pyrimidin-5-yl)propyl)-1-methyl-1H-imidazole-4-sulfonamido)methyl)phenyl)acetate

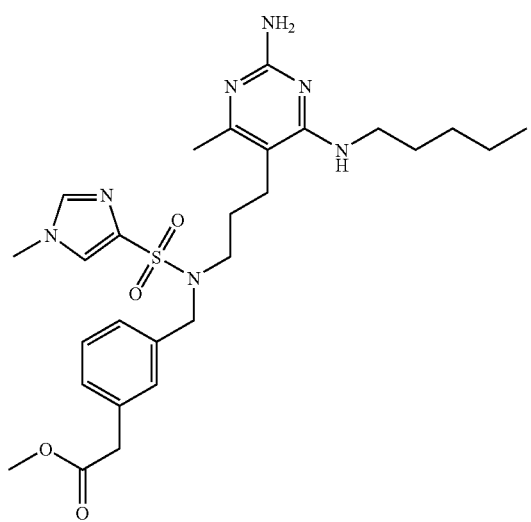

To a stirred solution of the product from Example 1 (80 mg) dissolved in DCM (5 mL) was added 1-methylimidazole-4-sulfonyl chloride (38.4 mg) and TEA (0.032 mL) under nitrogen. The resulting solution was stirred at rt for 16 h, the solvents were evaporated and the residue redissolved in MeOH and the crude product purified by RPHPLC to afford the title compound 69 mg.

$^1$H NMR DMSO-$d_6$: δ 7.83-7.81 (m, 1H), 7.78-7.76 (m, 1H), 7.33-7.10 (m, 4H), 6.07-6.02 (m, 1H), 5.48 (s, 2H), 4.28 (s, 2H), 3.71 (s, 3H), 3.64 (s, 2H), 3.58 (s, 3H), 3.25-3.11 (m, 4H), 2.14-2.07 (m, 2H), 1.85 (s, 3H), 1.49-1.39 (m, 2H), 1.40-1.17 (m, 6H), 0.85 (t, 3H)

LC-MS m/z 558 ES+

EXAMPLE 15

Methyl 2-(4-((N-(3-(2-amino-4-methyl-6-(pentylamino)pyrimidin-5-yl)propyl)-2-((2-methoxyethyl)(methyl)amino)acetamido)methyl)phenyl)acetate

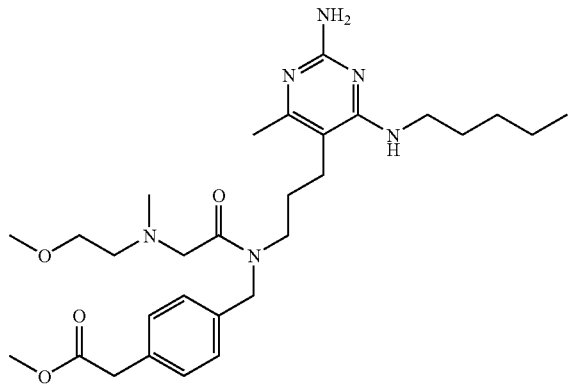

The title compound was prepared by the method of Example 3 using the product from Example 2 and N-(2-methoxyethyl)methylamine.

$^1$H NMR DMSO-$d_6$: δ 7.27-7.10 (m, 4H), 6.18-6.10 (m, 1H), 5.54-5.46 (m, 2H), 4.67 (s, 1H), 4.45 (s, 1H), 3.67-3.61 (m, 2H), 3.59 (s, 3H), 3.41 (t, 1H), 3.29-3.20 (m, 8H), 3.16 (s, 1H), 3.12 (s, 1H), 2.59-2.53 (m, 1H), 2.30-2.17 (m, 5H), 2.01 (d, 3H), 1.62-1.41 (m, 4H), 1.33-1.18 (m, 5H), 0.86 (t, 3H)

LC-MS m/z 543 ESI

EXAMPLE 16

Methyl 2-(3-((N-(3-(2-amino-4-methyl-6-(pentylamino)pyrimidin-5-yl)propyl)-3-(dimethylamino)propanamido)methyl)phenyl)acetate

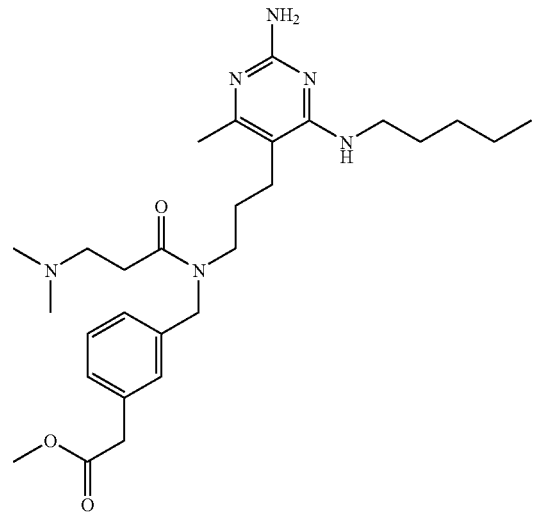

The product from Example 1 (80 mg) and 3-(dimethylamino)propanoic acid hydrochloride (45 mg) were combined in DCM (5 mL) then TEA (73 mg) and HATU (101 mg) were added. The reaction mixture was stirred at rt for 16 h. The solvents were evaporated, the residue dissolved in MeOH and purified by RPHPLC to give the title compound 32 mg.

$^1$H NMR DMSO-$d_6$: δ 7.37-7.02 (m, 4H), 6.24-6.11 (m, 1H), 5.55-5.45 (m 2H), 4.62-4.39 (m, 2H), 3.69-3.62 (m, 2H), 3.59 (s, 4H), 3.27-3.18 (m, 4H), 2.47-2.34 (m, 2H), 2.30-2.20 (m, 2H), 2.13 (s, 3H), 2.08-1.95 (m, 6H), 1.57-1.44 (m, 4H), 1.32-1.19 (m, 5H), 0.86 (t, 3H)

LC-MS m/z 513 ESI

EXAMPLE 17

Methyl 2-(3-((4-(2-amino-4-methyl-6-(pentylamino)pyrimidin-5-yl)butylamino)methyl)phenyl)acetate

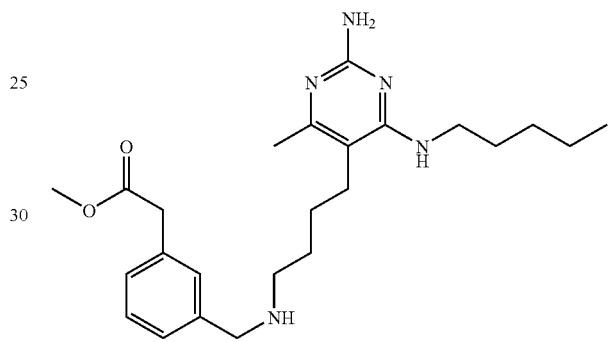

(i) Benzyl 4-(2-amino-4-methyl-6-(pentylamino)pyrimidin-5-yl)but-3-ynylcarbamate Benzyl but-3-ynylcarbamate (0.666 g) was dissolved in THF (20 mL), briefly purged with nitrogen and copper(I) iodide (0.042 g) was added. The reaction mixture was stirred for 30 min, the product from example 1 step (ii) (0.7 g), tetrakis(triphenylphosphine) palladium(0) (0.126 g) and TEA (5 mL) were added. The reaction mixture was heated to 70° C. for 16 h. The reaction mixture was cooled to rt and the organic layer washed with water and brine. The organic layer was evaporated under reduced pressure, MeOH added and the solid filtered off. The filtrate was purified via SCX resin then further purified by chromatography eluting with DCM:MeOH (95:5) to give the subtitle compound 0.4 g.

LC-MS m/z 396 ESI (ii) 5-(4-Aminobutyl)-6-methyl-N4-pentylpyrimidine-2,4-diamine The product from step (i) (0.2 g) was dissolved in EtOH (20 mL) then 5% Pd/C (100 mg) in EtOH (5 mL) was added. The reaction mixture was hydrogenated at 4 bar overnight. The catalyst was filtered off then 20% Pd(OH)$_2$/C (100 mg) in EtOH (5 ml) was added and the reaction mixture hydrogenated at 4 bar for 3 h. The catalyst was filtered off and the solvents evaporated to give the subtitle compound 0.06 g.

LC-MS m/z 266 ESI

(iii) Methyl 2-(3-((4-(2-amino-4-methyl-6-(pentylamino)pyrimidin-5-yl)butylamino)methyl)phenyl)acetate To the product of step (ii) (0.06 g), methyl 2-(3-formylphenyl)acetate (0.0403 g) and acetic acid (0.0136 g) in THF (10 mL) was added sodium triacetoxyborohydride (0.1102 g). The reaction mixture was stirred for 72 h, the solvents were evaporated and the residue dissolved in MeOH, acidified and purified via SCX resin, then RPHPLC to give the title compound 6 mg.
LC-MS m/z 428 ESI

EXAMPLE 18

(S)-Methyl 2-(4-((3-(2-amino-4-(1-hydroxyheptan-3-ylamino)-6-methylpyrimidin-5-yl)propylamino)methyl)phenyl)acetate

(i) (E)-tert-Butyl hept-2-enoate

To a solution of valeraldehyde (5.81 g) in THF (100 mL) was added tert-butoxycarbonylmethylenetriphenylphosphorane (25.4 g) and the reaction mixture stirred for 16 h at rt. The solvents were evaporated, the residue slurried in diethyl ether and filtered. The filtrate was evaporated and the residue purified by chromatography eluting with 3% EtOAc in isohexane to give the subtitle compound 8.5 g.
$^1$H NMR (CDCl$_3$); δ 6.86 (dt, 1H), 5.73 (dt, 1H), 2.25-2.09 (m, 2H), 1.47 (s, 9H), 1.47-1.27 (m, 4H), 0.90 (t, 3H)

(ii) (S)-tert-Butyl 3-(benzyl((S)-1-phenylethyl)amino)heptanoate n-Butyllithium (2.5M in hexanes, 27.66 ml) was added to a stirred solution of (S)—N-benzyl-1-phenylethanamine (15.59 g) in THF (150 mL) at −78° C. The reaction mixture was stirred for 30 mins then the product from step (i) (8.5 g) in THF (50 mL) was added and the reaction mixture stirred for 2 h at −78° C. The mixture was quenched with sat. NH$_4$Cl solution and warmed to rt. The product was partitioned between EtOAc and water, the organic phase was washed with water, dried, and evaporated. The residue was purified by column chromatography eluting with 5% EtOAc in isohexane to give the subtitle compound 12.7 g.
$^1$H NMR (CDCl$_3$); δ 7.49-7.15 (m, 10H), 3.87-3.70 (m, 2H), 3.48 (d, 1H), 3.35-3.21 (m, 1H), 1.99-1.78 (m, 2H), 1.53 (s, 3H), 1.39 (s, 9H), 1.36-1.14 (m, 6H), 0.88 (t, 3H)
LC-MS m/z 396 ESI

(iii) (S)-3-(Benzyl((S)-1-phenylethyl)amino)heptanoic acid

The product from step (ii) (12 g) was dissolved in DCM (40 mL) and TFA (2 mL) and the reaction mixture stirred for 24 h. The solvents were evaporated to give the subtitle compound 17 g.
LC-MS m/z 340 ESI

(iv) (S)-3-(Benzyl((S)-1-phenylethyl)amino)heptan-1-ol

The product from step (iii) (12 g) was dissolved in THF (120 mL) and borane-tetrahydrofuran complex (1M in THF, 132.3 ml) added dropwise. The reaction mixture was stirred at rt overnight then MeOH was added followed by 2M HCl (20 mL). The mixture was evaporated and the residue taken up in MeOH and purified via SCX resin and the residue was further purified via column chromatography eluting with 10-20% EtOAc in isohexane to give the subtitle compound 6 g.
$^1$H NMR (CDCl$_3$); δ 7.45-7.13 (m, 10H), 4.00-3.91 (m, 1H), 3.85 (d, 1H), 3.69 (d, 1H), 3.56-3.43 (m, 1H), 3.27-3.15 (m, 1H), 2.84-2.71 (m, 1H), 2.61 (s, 1H), 1.77-1.63 (m, 1H), 1.55 (s, 2H), 1.47-1.20 (m, 8H), 0.93 (t, 3H)
LC-MS m/z 326 ESI

(v) (S)-3-Aminoheptan-1-ol

A solution of the product from step (iv) (5 g) and 5% Pd/C (0.5 g) in EtOH (25 mL) was hydrogenated under 5 bar at rt for 5 days. A further portion of 5% Pd/C (1.5 g) was added, and the reaction mixture hydrogenated under 5 bar at rt for a further 1 day. The reaction mixture was filtered and the solvent evaporated to give the subtitle compound 1.8 g.
$^1$H NMR (CDCl$_3$); δ 3.89-3.74 (m, 2H), 2.94-2.84 (m, 1H), 2.79-2.41 (m, 3H), 1.70-1.60 (m, 1H), 1.55-1.38 (m, 2H), 1.39-1.19 (m, 5H), 0.96-0.83 (m, 3H)

(vi) tert-Butyl 3-(2-amino-4-chloro-6-methylpyrimidin-5-yl)prop-2-ynylcarbamate tert-Butyl prop-2-ynylcarbamate (3.11 g), 4-chloro-5-iodo-6-methylpyrimidin-2-amine (1.8 g) and bis(triphenylphosphine)palladium(II) chloride (0.469 g) were combined in TEA (100 mL). The reaction mixture was purged with nitrogen gas for 3 min then copper(I) iodide (0.254 g) added. The resulting mixture was stirred at 70° C. for 16 h, then cooled to rt and filtered. The filtrate was washed with water and brine, dried and the solvents evaporated. The crude material was dissolved in MeOH (20 mL), acidified with acetic acid (1 mL) and purified by SCX and further purified by chromatography eluting 10% MeOH and 0.25% Ammonia (7N) in DCM to afford the subtitle compound 0.93 g.
$^1$H NMR DMSO-d$_6$: δ 7.33 (s, 2H), 4.01-3.93 (m, 1H), 3.30 (s, 2H), 2.35 (s, 3H), 1.40 (s, 9H)
LC-MS m/z 297 ESI

(vii) (S)-tert-Butyl 3-(2-amino-4-(1-hydroxyheptan-3-ylamino)-6-methylpyrimidin-5-yl)prop-2-ynylcarbamate The product from step (vi) (200 mg) and the product from step (v) (177 mg) were combined in butan-1-ol (5 mL) and reacted in a CEM Microwave, at 120° C. for 1 h. The solvents were evaporated, and the crude product was purified by chromatography, eluting with 5% MeOH in EtOAc to afford the subtitle compound 170 mg.
LC-MS m/z 392 ESI

(viii) (S)-tert-Butyl 3-(2-amino-4-(1-hydroxyheptan-3-ylamino)-6-methylpyrimidin-5-yl)propylcarbamate The product from step (vii) (100 mg) and Pd/C (30 mg) in EtOH (5 mL) were hydrogenated under 3 bar at rt for 16 h. The catalyst was filtered off and the solvent evaporated to give the subtitle compound 76 mg.
LC-MS m/z 396 ESI

(ix) (S)-3-(2-Amino-5-(3-aminopropyl)-6-methylpyrimidin-4-ylamino)heptan-1-ol The product from step (viii) (76 mg) was dissolved in DCM (5 mL) and TFA (5 mL) and the mixture stirred at rt for 1 h. The solvent was evaporated and the crude material dissolved in MeOH (5 mL) and purified by SCX. The product was dissolved in THF (10 mL) then lithium hydroxide (12.2 mg) in water (5 mL) was added. The reaction mixture was heated to reflux for 1 h, the solvents were evaporated and the crude product purified by RPHPLC to afford the subtitle product 40 mg.
LC-MS m/z 297 ESI

(x) (S)-Methyl 2-(4-((3-(2-amino-4-(1-hydroxyheptan-3-ylamino)-6-methylpyrimidin-5-yl)propylamino)methyl)phenyl)acetate To a solution of the product from step (ix) (57 mg) in THF (5 mL) was added (4-formylphenyl)acetic acid methyl ester (51 mg) and acetic acid (0.011 mL). The resulting mixture was stirred for 5 h, sodium triacetoxyborohydride (90 mg) was added and the resulting solution stirred at rt for 16 h. TEA (0.013 mL) was added and the reaction mixture stirred for a further 2 h. The solvents were evaporated, the residue redissolved in MeOH and purified by RPHPLC to afford the title compound 2.7 mg.
$^1$H NMR DMSO-$d_6$: δ 7.28 (d, 2H), 7.20 (d, 2H), 6.09-6.03 (m, 1H), 5.53 (s, 2H), 4.53-4.43 (m, 1H), 4.19-4.09 (m, 1H), 3.64 (s, 3H), 3.61 (s, 2H), 3.42-3.35 (m, 2H), 3.30-3.28 (m, 2H), 2.40-2.31 (m, 2H), 2.06 (s, 3H), 1.70-1.58 (m, 2H), 1.56-1.39 (m, 4H), 1.31-1.18 (m, 5H), 0.84 (s, 3H)
LC-MS m/z 458 ESI

EXAMPLE 19

(S)-Methyl 2-(4-((N-(3-(2-amino-4-(1-hydroxyheptan-3-ylamino)-6-methylpyrimidin-5-yl)propyl)-2-(dimethylamino)acetamido)methyl)phenyl)acetate

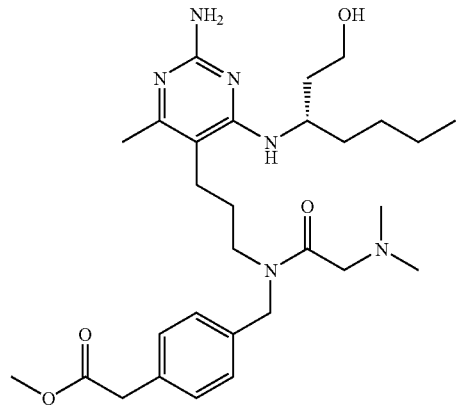

The product from Example 18 (5.7 mg) was dissolved in acetonitrile (2 mL) and chloroacetyl chloride (0.991 μL) added. The reaction mixture was stirred at rt for 16 h. The solvent was evaporated and dimethylamine (2M in MeOH, 0.016 mL) in MeOH (1 mL) was added. The reaction mixture was stirred for 5 h, then more dimethylamine (2M in MeOH, 0.016 mL) added and the reaction mixture stirred for a further 16 h. A further aliquot of dimethylamine (0.039 mL) was added and the reaction mixture stirred for 16 h. The solvents were evaporated and the residue purified by RPHPLC to afford the title compound 1.5 mg.
$^1$H NMR DMSO-$d_6$ @90° C.; δ 7.21 (d, 2H), 7.14 (d, 2H), 5.48-5.42 (m, 1H), 5.19 (s, 2H), 3.60 (s, 5H), 3.49-3.38 (m, 2H), 3.36-3.25 (m, 2H), 3.06 (s, 2H), 2.99-2.95 (m, 2H), 2.33-2.28 (m, 2H), 2.18 (s, 6H), 2.02 (s, 3H), 1.72-1.46 (m, 6H), 1.33-1.20 (m, 6H), 0.84 (t, 3H)
LC-MS m/z 543 ESI

EXAMPLE 20

Methyl 2-(3-((2-amino-4-methyl-6-(pentylamino)pyrimidin-5-yl)methyl)phenyl)acetate

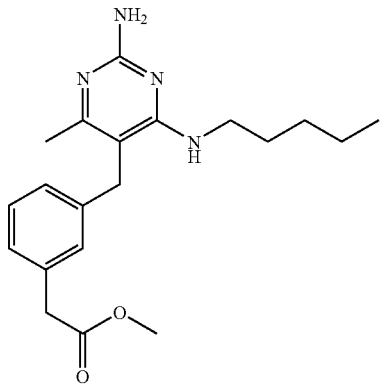

(i) [3-(2-Amino-4-hydroxy-6-methyl-pyrimidin-5-ylmethyl)]-benzoic acid ethyl ester Guanidine carbonate (2.71 g) was added to a stirred solution of 3-(2-ethoxycarbonyl-3-oxobutyl)-benzoic acid methyl ester (2.12 g) in EtOH (40 mL). The reaction mixture was heated to reflux for 6 h and allowed to cool. The solvent was evaporated under reduced pressure and the residue suspended in water (30 mL). The resulting precipitate was collected by filtration and the solid suspended in EtOAc (30 mL). The solid was collected by filtration to give the subtitle compound as a colourless solid 2.12 g that was used without further purification.
$^1$H NMR DMSO-$d_6$: δ 7.77-7.73 (m, 2H), 7.46-7.36 (m, 2H), 6.50 (s, 2H), 4.29 (q, 2H), 3.70 (s, 2H), 2.01 (s, 3H), 1.30 (t, 3H)

(ii) [3-(2-Amino-4-chloro-6-methyl-pyrimidin-5-ylmethyl)]-benzoic acid ethyl ester The product from step (i) (1.9 g) was added to phosphorous oxychloride (30 mL) and the mixture was heated at 100° C. for 15 h. The mixture was allowed to cool and the phosphorous oxychloride evaporated under reduced pressure. The residue was diluted with water (10 mL) and the pH of the mixture was adjusted to pH ~7 using sodium bicarbonate. The mixture was then heated at 50° C. for 2 h and the aqueous was extracted with EtOAc. The combined organic phase was dried and evaporated under reduced pressure to give the subtitle compound as a pale yellow solid 1.65 g that was used without further purification.

$^1$H NMR DMSO-d$_6$: δ 7.80 (d, 1H), 7.71 (s, 1H), 7.49-7.34 (m, 21H), 6.92 (s, 2H), 4.30 (q, 2H), 4.04 (s, 2H), 2.21 (s, 3H), 1.30 (t, 3H)

(iii) [3-(2-Amino-4-methyl-6-pentylamino-pyrimidin-5-ylmethyl)]-benzoic acid ethyl ester Pentylamine (2.5 mL) was added to a stirred solution of the product from step (ii) (1.65 g) in NMP (3 mL). The mixture was heated at 150° C. for 15 h and allowed to cool. The solution was diluted with EtOAc (50 mL) and saturated aqueous NaHCO$_3$ (50 mL) added. The aqueous phase was separated and the organic phase washed with water, dried and evaporated under reduced pressure. The residue was purified by chromatography eluting with 2% to 5% MeOH in DCM to give the subtitle compound as an orange solid. 0.7 g.

$^1$H NMR DMSO-d$_6$: δ 7.79-7.71 (m, 2H), 7.45-7.32 (m, 21H), 6.36 (s, 1H), 5.78 (s, 2H), 4.29 (q, 2H), 3.82 (s, 2H), 3.29-3.22 (m, 2H), 2.01 (s, 3H), 1.49-11.38 (m, 2H), 1.28-1.07 (m, 4H), 0.79 (t, 3H)

(iv) [3-(2-Amino-4-methyl-6-pentylamino-pyrimidin-5-ylmethyl)-phenyl]-methanol A solution of the product from step (iii) (0.7 g) in THF (10 mL) was added to a solution of lithium aluminium hydride (1M in THF, 4.1 mL) in THF (10 mL) at 0° C. The mixture was stirred at rt for 2 h, sodium sulfate decahydrate (10 g) was added and the suspension stirred for 1 h. The suspension was filtered and the filtrate diluted with saturated aq ammonium chloride (20 mL). The aqueous phase was separated and the organic phase dried and evaporated under reduced pressure to give the subtitle compound 0.60 g, which was used without further purification.

$^1$H NMR DMSO-d$_6$: δ 7.19 (t, 1H), 7.12-7.05 (m, 2H), 6.97 (d, 1H), 6.34-6.27 (m, 1H), 5.81 (s, 2H), 5.15-5.08 (m, 1H), 4.43 (d, 2H), 3.73 (s, 2H), 3.26 (q, 2H), 2.03 (s, 3H), 1.45 (quintet, 2H), 1.28-1.10 (m, 4H), 0.82 (t, 3H)

(v) 5-(3-Chloromethyl-benzyl)-6-methyl-N4-pentyl-pyrimidine-2,4-diamine

Thionyl chloride (0.17 mL) was added to a stirred solution of the product from step (iv) (0.60 g) in DCM (10 mL) at rt. The mixture was stirred for 1 h and the solvent evaporated under reduced pressure to give the subtitle compound as a yellow oil 0.62 g that was used without further purification.

$^1$H NMR DMSO-d$_6$: δ 8.03-7.94 (m, 1H), 7.50 (s, 2H), 7.34-7.26 (m, 3H), 7.21 (s, 1H), 7.13 (d, 1H), 4.72 (s, 2H), 3.87 (s, 2H), 3.37 (q, 2H), 2.20 (s, 3H), 1.47 (quintet, 2H), 1.26-1.17 (m, 2H), 1.15-1.06 (m, 2H), 0.80 (t, 3H)

(vi) [3-(2-Amino-4-methyl-6-pentylamino-pyrimidin-5-ylmethyl)-phenyl]-acetonitrile Potassium cyanide (0.61 g) was added to a stirred solution of the product from step (v) (0.62 g) in DMSO (5 mL) and DMF (5 mL) and the mixture stirred at rt for 1 h. The reaction mixture was diluted with saturated aqueous NaHCO$_3$ (10 mL) and the aqueous phase was extracted with EtOAc. The combined organic phase was washed with water, dried and evaporated under reduced pressure to give the subtitle compound as a yellow oil 0.59 g that was used without further purification.

$^1$H NMR DMSO-d$_6$: δ 7.27 (t, 1H), 7.15-7.04 (m, 31H), 6.17 (t, 1H), 5.66 (s, 2H), 3.97 (s, 2H), 3.75 (s, 2H), 3.24 (q, 2H), 2.01 (s, 3H), 1.49-1.39 (m, 2H), 1.27-1.09 (m, 4H), 0.82 (t, 3H)

(vii) Methyl 2-(3-((2-amino-4-methyl-6-(pentylamino)pyrimidin-5-yl)methyl)phenyl)acetate A 5M aqueous solution of potassium hydroxide (5 mL) was added to a stirred solution of the product from step (vi) (0.59 g) in MeOH (10 mL). The mixture was stirred at 65° C. for 15 h and allowed to cool. The organic solvent was removed under reduced pressure and the aqueous phase acidified to pH 7 with concentrated HCl. The aqueous phase was extracted with EtOAc and the combined organic phase dried and evaporated under reduced pressure. The residue was dissolved in MeOH (10 mL) and concentrated sulfuric acid (5 mL) added. The mixture was heated at 70° C. for 2 h and allowed to cool. The mixture was poured into saturated aqueous NaHCO$_3$ (30 mL) and the aqueous phase extracted with EtOAc. The combined organic phase was dried and evaporated under reduced pressure. The residue was purified by chromotography eluting with 5% MeOH in DCM to give the title compound 0.24 g.

$^1$H NMR DMSO-d$_6$: δ 7.36 (s, 1H), 7.23 (t, 1H), 7.11-6.98 (m, 3H), 6.77 (s, 2H), 3.79 (s, 2H), 3.62 (s, 2H), 3.59 (s, 3H), 3.30-3.26 (m, 2H), 2.12 (s, 3H), 1.47 (quintet, 2H), 1.29-1.06 (m, 4H), 0.81 (t, 3H)

LC-MS m/z 357 ESI

EXAMPLE 21

Methyl 2-(4-((2-amino-4-methyl-6-(pentylamino)pyrimidin-5-yl)methyl)-3-methoxyphenyl)acetate

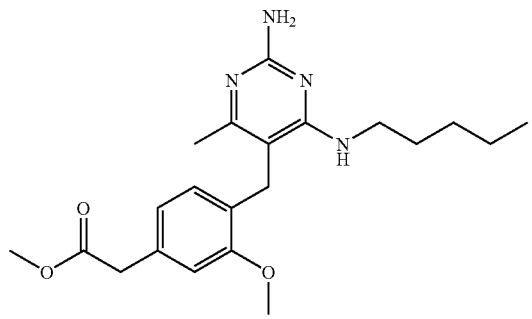

(i) Methyl 4-(2-(ethoxycarbonyl)-3-oxobutyl)-3-methoxybenzoate

Sodium hydride (60% in mineral oil; 1.45 g) was added portionwise over 10 min to a solution of ethyl acetoacetate (4.4 mL) in THF (60 mL) at 0° C. The resulting suspension was stirred at 0° C. for 10 min and a solution of methyl 4-(bromomethyl)-3-methoxybenzoate (7.5 g) in THF (40 mL) added portionwise over 10 min. The mixture was warmed to 70° C. and stirred for 15 h. The mixture was allowed to cool and then poured cautiously into ice/water (300 mL) and stirred for 30 min. The aqueous phase was extracted with EtOAc and the combined organic phase was dried filtered and evaporated to afford crude product. The reaction was repeated on an identical scale and the two batches of crude product were combined and purified by chromatography eluting with 20-30% EtOAc in isohexane to give the subtitle compound as a colorless oil 14.70 g.

$^1$H NMR DMSO-$d_6$: δ 7.48 (dd, 1H), 7.45 (d, 1H), 7.24 (d, 1H), 4.05 (q, 2H), 3.95 (dd, 1H), 3.86 (s, 3H), 3.84 (s, 3H), 3.10 (dd, 1H), 3.00 (dd, 1H), 2.17 (s, 3H), 1.09 (t, 3H)

(ii) Methyl 4-((2-amino-4-hydroxy-6-methylpyrimidin-5-yl)methyl)-3-methoxybenzoate Guanidine carbonate (8.73 g) was added in one portion to a solution of the product from step (i) (14.7 g) in MeOH (200 mL). The resulting mixture was stirred at 65° C. for 16 h and allowed to cool. The precipitate was collected by filtration and suspended in water (50 mL). The solid was collected by filtration, washed with MeOH (20 mL) and EtOAc (20 mL) to give the subtitle compound as a colourless solid 8.60 g that was used without further purification.

$^1$H NMR DMSO-$d_6$: δ 10.78 (s, 1H), 7.46 (d, 2H), 7.45 (s, 2H), 6.98 (d, 1H), 6.34 (s, 2H), 3.89 (s, 3H), 3.83 (s, 3H), 3.61 (s, 2H), 1.93 (s, 3H)

LC-MS m/z 304 ESI (iii) Methyl 4-((2-amino-4-chloro-6-methylpyrimidin-5-yl)methyl)-3-methoxybenzoate The product from step (ii) (8.6 g) was added to phosphorous oxychloride (50 ml) and the resulting suspension stirred at 100° C. for 15 h. The reaction mixture was allowed to cool and the phosphorous oxychloride evaporated under reduced pressure. The residue was diluted with water (100 mL) and the suspension adjusted to pH 7 with NaHCO$_3$. The mixture was heated at 50° C. for 1 h and allowed to cool. The solid was collected by filtration, washed with water, EtOAc and dried under vacuum to give the subtitle compound 9.05 g.

$^1$H NMR DMSO-$d_6$: δ 7.50 (s, 1H), 7.49 (d, 1H), 6.90 (s, 2H), 6.81 (d, 1H), 3.92 (s, 3H), 3.90 (s, 3H), 3.84 (s, 2H), 2.16 (s, 3H).

(iv) Methyl 4-((2-amino-4-methyl-6-(pentylamino)pyrimidin-5-yl)methyl)-3-methoxybenzoate Pentylamine (7.2 mL) was added to a solution of the product from step (iii) (5 g) in NMP (80 mL). The resulting solution was stirred at 150° C. for 15 h. The reaction mixture was allowed to cool, diluted with EtOAc and washed with water and brine. The organic phase was dried and evaporated under reduced pressure. The residue was suspended in diethyl ether (20 mL) and the solid was collected by filtration to give the subtitle compound as a colourless solid 1.2 g that was used without further purification.

$^1$H NMR DMSO-$d_6$: δ 7.48 (d, 1H), 7.45 (dd, 1H), 6.81 (d, 1H), 6.07 (t, 1H), 5.68 (s, 2H), 3.92 (s, 3H), 3.83 (s, 3H), 3.68 (s, 2H), 3.25-3.20 (m, 2H), 1.93 (s, 3H), 1.47-1.38 (m, 2H), 1.27-1.08 (m, 4H), 0.81 (t, 3H)

LC-MS m/z 374 ESI (v) (4-((2-Amino-4-methyl-6-(pentylamino)pyrimidin-5-yl)methyl)-3-methoxyphenyl)methanol A solution of the product from step (iv) (2.4 g) in THF (50 mL) was added portionwise over 10 min to a stirred solution of lithium aluminum hydride (1M in THF; 12.89 mL) in THF (50 mL) at 0° C. under nitrogen. The resulting mixture was stirred at 0° C. for 10 min and then at rt for 1 h. EtOAc (20 mL) was added portionwise over 10 min and the resulting mixture stirred for a further 20 min. The mixture was added portionwise to 2M NaOH (300 mL) and stirred for 30 min. The resulting suspension was filtered through a pad of celite and the resulting biphasic filtrate separated. The aqueous phase was extracted with EtOAc (200 mL) and the combined organic phase was dried, filtered and evaporated. The crude product was purified by chromatography, eluting with 5 to 10% MeOH in DCM. to afford the subtitle compound as a colourless gum 0.94 g.

$^1$H NMR DMSO-$d_6$: δ 6.94 (s, 1H), 6.75 (d, 1H), 6.66 (d, 1H), 6.03-5.96 (m, 1H), 5.67 (s, 2H), 5.10 (t, 1H), 4.44 (d, 2H), 3.84 (s, 3H), 3.59 (s, 2H), 3.25-3.19 (m, 2H), 1.98 (s, 3H), 1.43 (quintet, 2H), 1.30-1.10 (m, 4H), 0.82 (t, 3H)

LC-MS m/z 345 ESI (vi) 5-(4-(Chloromethyl)-2-methoxybenzyl)-6-methyl-N4-pentylpyrimidine-2,4-diamine Thionyl chloride (0.239 mL) was added portionwise to a solution of the product from step (v) (0.94 g) in DCM (20 mL) under nitrogen. The resulting solution was stirred at rt for 1 h. The solvent was evaporated under reduced pressure to give the subtitle compound as a colourless gum 0.99 g that was used without purification.

$^1$H NMR DMSO-$d_6$: δ 7.88 (t, 1H), 7.46 (s, 2H), 7.10 (d, 1H), 6.92 (dd, 1H), 6.79 (d, 1H), 4.73 (s, 2H), 3.86 (s, 3H), 3.69 (s, 2H), 3.38-3.33 (m, 2H), 2.11 (s, 3H), 1.48 (quintet, 2H), 1.30-1.11 (m, 4H), 0.83 (t, 3H)

LC-MS m/z 363 ES+

(vii) 2-(4-((2-Amino-4-methyl-6-(pentylamino)pyrimidin-5-yl)methyl)-3-methoxyphenyl)acetonitrile Potassium cyanide (0.53 g) was added to a solution of the product from step (vi) (0.99 g) in DMSO (10 mL) and DMF (10 mL) under nitrogen. The resulting mixture was stirred at rt for 20 h and diluted with saturated aqueous NaHCO$_3$ (50 mL). The mixture was extracted with EtOAc and the combined organic phase was washed with water and brine, dried, filtered and evaporated. The crude product was purified by chromatography, eluting with 5% MeOH in DCM to afford the subtitle compound as an orange solid 0.6 g.

$^1$H NMR DMSO-$d_6$: δ 6.97 (d, 1H), 6.80 (dd, 1H), 6.70 (d, 1H), 6.10 (t, 1H), 5.75 (s, 2H), 3.96 (s, 2H), 3.86 (s, 3H), 3.60 (s, 2H), 3.25-3.20 (m, 2H), 1.96 (s, 3H), 1.43 (quintet, 2H), 1.28-1.10 (m, 4H), 0.82 (t, 3H)

(viii) 2-(4-((2-amino-4-methyl-6-(pentylamino)pyrimidin-5-yl)methyl)-3-methoxyphenyl)acetic acid A 5M aqueous solution of potassium hydroxide (5 mL) was added to a solution of the product from step (vii) (0.60 g) in MeOH (10 mL). The resulting mixture was stirred at 65° C. for 15 h. The mixture was allowed to cool and the solvent evaporated under reduced pressure. The resulting aqueous mixture was neutralised with 2M HCl and extracted with EtOAc. The combined organic phase was dried, filtered and evaporated to give the subtitle compound as a colourless solid 0.329 g that was used without further purification.

$^1$H NMR DMSO-$d_6$: δ 6.88 (d, 1H), 6.70 (dd, 1H), 6.64 (d, 1H), 6.30-6.21 (m, 1H), 5.99 (s, 2H), 3.83 (s, 3H), 3.59 (s, 2H), 3.49 (s, 3H), 3.27-3.18 (m, 2H), 1.98 (s, 3H), 1.44 (quintet, 2H), 1.30-1.09 (m, 4H), 0.82 (t, 3H)

(ix) Methyl 2-(4-((2-amino-4-methyl-6-(pentylamino)pyrimidin-5-yl)methyl)-3-methoxyphenyl)acetate The product from step (vii) (0.329 g) was added in one portion to a mixture of sulfuric acid (2 ml) and MeOH (4 mL).

The resulting solution was stirred at 70° C. for 2 h. The mixture was allowed to cool and poured into saturated aqueous NaHCO$_3$ (20 mL). The aqueous was extracted with EtOAc and the combined organic phase was dried, filtered and evaporated. The crude product was purified by RPHPLC to afford a colourless gum that was triturated with hexane (5 mL). The solid was collected by filtration to give the title compound as a colorless solid 0.089 g.

$^1$H NMR DMSO-d$_6$: δ 6.89 (d, 1H), 6.70 (dd, 1H), 6.64 (d, 1H), 5.98 (t, 1H), 5.63 (s, 2H), 3.84 (s, 3H), 3.61 (s, 2H), 3.59 (s, 3H), 3.58 (s, 2H), 3.26-3.18 (m, 2H), 1.97 (s, 3H), 1.43 (quintet, 2H), 1.29-1.10 (m, 4H), 0.82 (t, 3H)

LC-MS m/z 387 ESI

EXAMPLE 22

Methyl 2-(4-((2-amino-4-methyl-6-(pentylamino) pyrimidin-5-yl)methyl)-3-fluorophenyl)acetate

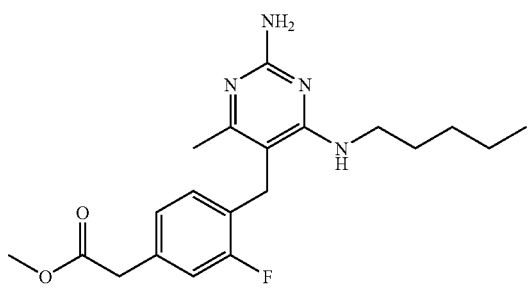

(i) Methyl 4-(2-(ethoxycarbonyl)-3-oxobutyl)-3-fluorobenzoate

Sodium hydride (60% dispersion in mineral oil; 2.45 g) was added portionwise over 10 min to a solution of ethyl acetoacetate (7.5 mL) in THF (60 mL) at 0° C. under nitrogen. The resulting mixture was stirred at 0° C. for 10 min and a solution of methyl 4-(bromomethyl)-3-fluorobenzoate (12.1 g) in THF (40 mL) added over 10 min. The mixture was heated to 65° C. for 15 h and allowed to cool. The mixture was poured cautiously into ice/water (300 mL) and the aqueous extracted with EtOAc. The combined organic phase was dried, filtered and evaporated. The crude product was purified by chromatography eluting with 10 to 20% EtOAc in isohexane to give the subtitle compound as a colorless oil 110.10 g.

$^1$H NMR DMSO-d$_6$: δ 7.73 (d, 1H), 7.64 (d, 1H), 7.46 (dd, 1H), 4.11-4.00 (m, 2H), 3.86 (s, 3H), 3.65-3.58 (m, 1H), 3.22-3.04 (m, 2H), 2.22 (s, 3H), 1.10 (t, 3H)

(ii) Methyl 4-((2-amino-4-hydroxy-6-methylpyrimidin-5-yl)methyl)-3-fluorobenzoate Guanidine carbonate (6.86 g) was added to a stirred solution of the product from step (i) (11.1 g) in MeOH (200 mL). The resulting mixture was stirred at 70° C. for 15 h. The mixture was allowed to cool to rt and the resulting precipitate collected by filtration. The solid was suspended in water (50 mL), collected by filtration and washed with MeOH to give the subtitle compound as a colourless solid 6.60 g that was used without further purification.

$^1$H NMR DMSO-d$_6$: δ10.83 (s, 1H), 7.68 (d, 1H), 7.63 (d, 1H), 7.23 (dd, 1H), 6.39 (s, 2H), 3.85 (s, 3H), 3.70 (s, 2H), 2.00 (s, 3H)

LC-MS m/z 292 ESI (iii) Methyl 4-((2-amino-4-chloro-6-methylpyrimidin-5-yl)methyl)-3-fluorobenzoate The product from step (ii) (6.6 g) was added to phosphorous oxychloride (40 ml) under nitrogen. The resulting mixture was stirred at 90° C. for 15 h. The phosphorous oxychloride was evaporated under reduced pressure and the residue cautiously diluted with water (50 mL). The aqueous phase was neutralised with NaHCO$_3$ and heated at 50° C. for 1 h. The mixture was allowed to cool and the precipitate was collected by filtration. The solid was suspended in MeCN (40 mL) and collected by filtration to give the subtitle compound as a cream solid 3.70 g that was used without further purification.

$^1$H NMR DMSO-d$_6$: δ 7.72 (d, 1H), 7.69 (d, 1H), 7.08 (dd, 1H), 6.95 (s, 2H), 4.02 (s, 2H), 3.85 (s, 3H), 2.22 (s, 3H)

LC-MS m/z 310 ESI (iv) Methyl 4-((2-amino-4-methyl-6-(pentylamino) pyrimidin-5-yl)methyl)-3-fluorobenzoate Pentylamine (5.82 mL) was added to a solution of the product from step (iii) (3.1 g) in dioxane (50 mL). The resulting mixture was stirred at 100° C. for 50 h. The mixture was allowed to cool and then the solvent was evaporated under reduced pressure. The crude product was purified by flash silica chromatography eluting with 2 to 5% MeOH in DCM. to give the subtitle compound as a yellow solid 1.52 g.

$^1$H NMR DMSO-d$_6$: δ 7.70-7.63 (m, 2H), 6.95 (dd, 1H), 6.31 (t, 1H), 5.75 (s, 2H), 3.84 (s, 3H), 3.80 (s, 2H), 3.28-3.20 (m, 2H), 1.94 (s, 3H), 1.51-1.36 (m, 2H), 1.31-1.10 (m, 4H), 0.81 (t, 3H)

(v) (4-((2-Amino-4-methyl-6-(pentylamino)pyrimidin-5-yl)methyl)-3-fluorophenyl)methanol A solution of the product from step (iv) (1.52 g) in THF (30 mL) was added portionwise to a stirred solution of lithium aluminium hydride (1M in THF; 8.43 mL) in THF (30 mL) at 0° C. under nitrogen. The resulting mixture was stirred at rt for 2 h. EtOAc (10 mL) was added cautiously to the reaction mixture and the mixture added portionwise to 2M NaOH (100 mL). The mixture was stirred for 30 min and the aqueous solution was extracted with EtOAc. The combined organic phase was dried, filtered and evaporated. The crude product was purified by chromatography eluting with 2 to 5% MeOH in acetonitrile to give the subtitle compound as a yellow oil 0.85 g.

$^1$H NMR DMSO-d$_6$: δ 7.22-6.90 (m, 2H), 6.79 (s, 1H), 6.28 (s, 2H), 5.36-5.09 (m, 1H), 4.47 (s, 2H), 4.11 (s, 1H), 3.72 (s, 2H), 3.29-3.12 (m, 2H), 1.97 (s, 3H), 1.57-1.39 (m, 2H), 1.37-1.15 (m, 4H), 0.94-0.78 (m, 3H)

(vi) 5-(4-(Chloromethyl)-2-fluorobenzyl)-6-methyl-N4-pentylpyrimidine-2,4-diamine Thionyl chloride (0.224 mL) was added to a solution of the product from step (v) (0.85 g) in DCM (15 mL) under nitrogen. The resulting mixture was stirred at rt for 2 h. The reaction mixture was evaporated to dryness under reduced pressure to give the subtitle compound as a yellow solid 0.85 g that was used without purification.

$^1$H NMR DMSO-d$_6$: δ 12.24 (s, 1H), 8.02 (t, 1H), 7.46 (s, 2H), 7.30 (dd, 1H), 7.17 (dd, 1H), 6.96 (dd, 1H), 4.74 (s, 2H), 3.83 (s, 2H), 3.39-3.32 (m, 2H), 2.14 (s, 3H), 1.54-1.41 (m, 2H), 1.32-1.08 (m, 4H), 0.82 (t, 3H)

(vii) 2-(4-((2-Amino-4-methyl-6-(pentylamino)pyrimidin-5-yl)methyl)-3-fluorophenyl)acetonitrile Potassium cyanide (0.473 g) was added to a stirred solution of the product from step (vi) (0.85 g) in DMSO (10 mL) and DMF (10 mL). The mixture was stirred at rt for 15 h, diluted with EtOAc, washed with saturated NaHCO₃ solution, saturated brine dried, filtered and evaporated. The crude product was purified by chromatography eluting with 0 to 5% MeOH in DCM to afford the subtitle compound as a yellow solid 0.530 g.

$^1$H NMR DMSO-$d_6$: δ 7.17 (d, 1H), 7.06 (d, 1H), 6.83 (dd, 1H), 6.34-6.25 (m, 1H), 5.76 (s, 2H), 4.01 (s, 2H), 3.72 (s, 2H), 3.27-3.22 (m, 2H), 1.95 (s, 3H), 1.45 (quintet, 2H), 1.30-1.11 (m, 4H), 0.83 (t, 3H)

(viii) 2-(4-((2-Amino-4-methyl-6-(pentylamino)pyrimidin-5-yl)methyl)-3-fluorophenyl)acetic acid A 5M aqueous solution of potassium hydroxide (3.10 mL) was added to a solution of the product of step (vii) (0.53 g) in MeOH (6 mL). The mixture was stirred at 65° C. for 15 h and allowed to cool. The solvent was evaporated under reduced pressure and the resulting aqueous solution adjusted to pH ~7 with conc. HCl. The aqueous phase was extracted with DCM and EtOAc, the combined organic phase was evaporated under reduced pressure to give the subtitle compound as a colourless solid 0.547 g.

$^1$H NMR DMSO-$d_6$: δ7.08 (dd, 1H), 6.95 (dd, 1H), 6.80 (dd, 1H), 6.52-6.42 (m, 1H), 3.74 (s, 2H), 3.55 (s, 2H), 3.28-3.24 (m, 2H), 2.03 (s, 3H), 1.50-1.43 (m, 2H), 1.29-1.11 (m, 4H), 0.83 (t, 3H)

(ix) Methyl 2-(4-((2-amino-4-methyl-6-(pentylamino)pyrimidin-5-yl)methyl)-3-fluorophenyl)acetate Sulfuric acid (3 ml) was added to a solution of the product from step (viii) (0.54 g) in MeOH (6 mL). The mixture was heated to 70° C. for 2 h and allowed to cool. The mixture was diluted with cold water (10 mL) and the pH adjusted to ~7 using NaHCO₃. The aqueous phase was extracted with EtOAc and the combined organic phase was dried, filtered and evaporated. The crude product was purified by RPHPLC to afford the title compound as a colourless solid 0.08 g.

$^1$H NMR DMSO-$d_6$: δ 7.08 (d, 1H), 6.95 (d, 1H), 6.76 (dd, 1H), 6.25 (t, 1H), 5.70 (s, 2H), 3.70 (s, 3H), 3.66 (s, 2H), 3.60 (s, 2H), 3.27-3.22 (m, 2H), 1.95 (s, 3H), 1.45 (quintet, 2H), 1.29-1.11 (m, 4H), 0.83 (t, 3H)

LC-MS m/z 375 ESI

EXAMPLE 23

Methyl 2-(4-(2-(3-(2-amino-4-methyl-6-(pentylamino)pyrimidin-5-yl)propylamino)-2-oxoethyl)phenyl)acetate

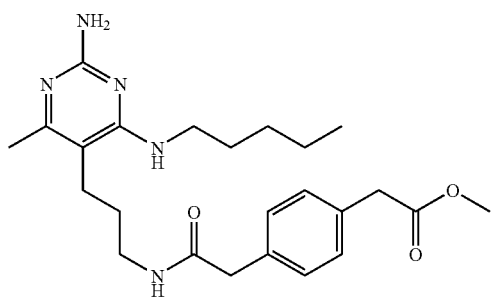

(i) {4-[2-({3-[2-Amino-4-methyl-6-(pentylamino)pyrimidin-5-yl]propyl}amino)-2-oxoethyl]phenyl}acetic acid A solution of T₃P (1.591 ml, 1.57M in THF) was added to a mixture of the product from example 1 step (v) (0.2 g), TEA (0.333 ml) and 2,2'-(1,4-phenylene)diacetic acid (0.463 g) in THF (15 mL) and the mixture stirred at rt overnight. The reaction was diluted with EtOAc, washed with water, dried and evaporated under reduced pressure. Used crude in next step.

LC-MS m/z 428 APCI+

(ii) Methyl 2-(4-(2-(3-(2-amino-4-methyl-6-(pentylamino)pyrimidin-5-yl)propylamino)-2-oxoethyl)phenyl)acetate The product from step (i) was dissolved in MeOH (20 mL) then a solution of HCl in dioxane (4M, 0.3 ml) was added and stirred overnight. Solvent was removed and the residue purified by RPHPLC to afford the title compound, 0.032 g.

$^1$H NMR DMSO-$d_6$: δ 8.06-7.98 (m, 1H), 7.23-7.14 (m, 5H), 6.19-6.12 (m, 1H), 5.52-5.45 (m, 2H), 3.67-3.57 (m, 7H), 3.13-3.02 (m, 2H), 2.32-2.20 (m, 2H), 2.00 (s, 3H), 1.55-1.37 (m, 4H), 1.33-1.22 (m, 4H), 0.85 (t, 3H).

LC-MS m/z 442 multimode+

EXAMPLE 24

Methyl 2-(3-(2-(3-(2-amino-4-methyl-6-(pentylamino)pyrimidin-5-yl)propylamino)-2-oxoethyl)phenyl)acetate

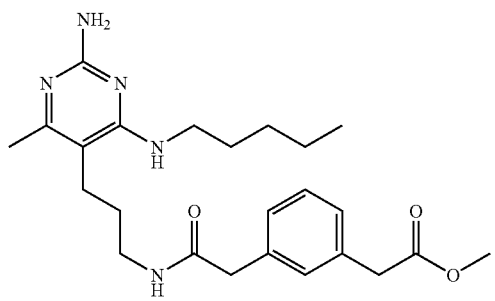

The title compound was prepared using the method of example 23.

$^1$H NMR DMSO-$d_6$: δ 8.05-7.98 (m, 1H), 7.28-7.21 (m, 1H), 7.16-7.09 (m, 3H), 6.18-6.13 (m, 1H), 5.52-5.47 (m, 2H), 3.64 (s, 2H), 3.60-3.58 (m, 3H), 3.39 (s, 2H), 3.29-3.22 (m, 2H), 3.12-3.04 (m, 2H), 2.30-2.22 (m, 2H), 1.97 (s, 1H), 1.53-1.41 (m, 4H), 1.35-1.19 (m, 4H), 0.86 (t, 3H)

LC-MS m/z 442 multimode+

EXAMPLE 25

Methyl 2-(3-((3-(2-amino-4-methyl-6-(pentylamino)pyrimidin-5-yl)propylamino)methyl)phenoxy)acetate

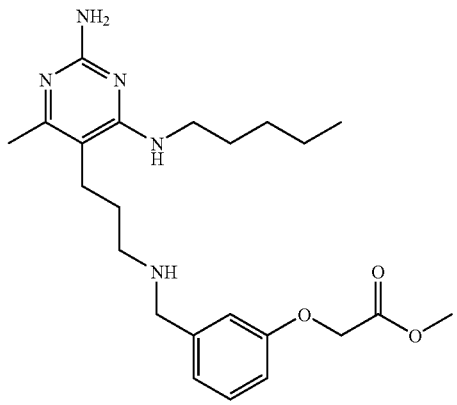

The product from example 1 step (v) (0.2 g) was dissolved in THF (10 mL) then methyl 2-(3-formylphenoxy)acetate (0.154 g) was added and stirred at rt overnight. Sodium borohydride (0.0301 mg) was added and stirred for 3 hr. The reaction was quenched with water and extracted with EtOAc, dried and solvent removed under reduced pressure. The residue was purified by RPHPLC to afford the title compound 0.038 g.

$^1$H NMR DMSO-$d_6$: δ 6.98-6.89 (m, 21), 6.82-6.72 (m, 1H), 6.67-6.58 (m, 1H), 5.61-5.52 (m, 2H), 4.81-4.70 (m, 2H), 3.71-3.67 (m, 3H), 3.68-3.65 (m, 2H), 3.27-3.18 (m, 2H), 2.48-2.41 (m, 2H), 2.38-2.31 (m, 2H), 2.07-2.04 (m, 3H), 1.57-1.42 (m, 4H), 1.30-1.17 (m, 4H), 0.85 (t, 3H)

LC-MS m/z 429 multimode+

EXAMPLE 26

Methyl 2-(4-((N-(3-(2-amino-4-methyl-6-(pentylamino)pyrimidin-5-yl)propyl)-2-(3-(4-(methylsulfonyl)phenyl)piperidin-1-yl)acetamido)methyl)phenyl)acetate

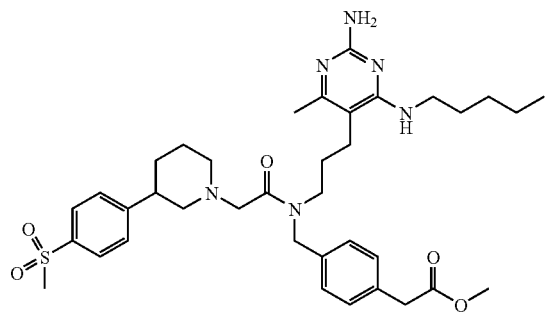

The title compound was prepared by the method of example 3 using the product from example 2 and the appropriate amine.

$^1$H NMR DMSO-$d_6$: δ 7.88-7.79 (m, 2H), 7.56-7.47 (m, 2H), 7.27 (d, 1H), 7.21-7.15 (m, 2H), 7.14-7.08 (m, 1H), 6.21-6.11 (m, 1H), 5.50 (s, 2H), 4.77-4.59 (m, 1H), 4.56-4.35 (m, 1H), 3.70-3.56 (m, 5H), 3.29-3.19 (m, 3H), 3.17 (s, 3H), 3.14-3.04 (m, 1H), 2.86-2.78 (m, 2H), 2.77-2.63 (m, 1H), 2.38-2.07 (m, 4H), 2.05-1.93 (m, 2H), 1.85-1.54 (m, 5H), 1.55-1.40 (m, 5H), 1.32-1.18 (m, 5H), 0.84 (sextet, 3H)

LC-MS m/z 693 multimode+

EXAMPLE 27

Methyl 2-(4-((N-(3-(2-amino-4-methyl-6-(pentylamino)pyrimidin-5-yl)propyl)-2-morpholinoacetamido)methyl)phenyl)acetate

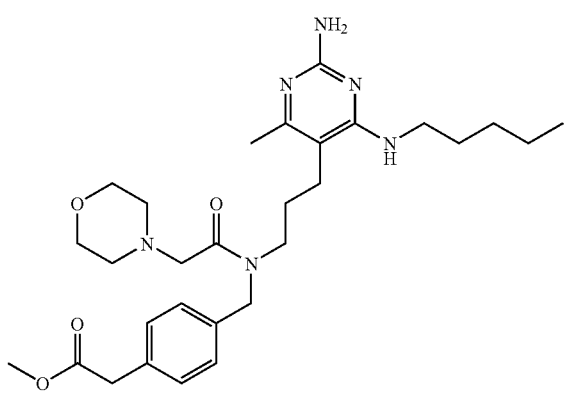

The title compound was prepared by the method of example 3 using the product from example 2 and the appropriate amine.

$^1$H NMR DMSO-$d_6$: δ 7.29-7.08 (m, 4H), 6.23-6.11 (m, 1H), 5.56-5.44 (m, 2H), 4.64 (s, 1H), 4.47 (s, 1H), 3.68-3.63 (m, 2H), 3.60 (s, 3H), 3.56-3.45 (m, 4H), 3.30-3.21 (m, 4H), 3.11 (s, TH), 3.05 (s, 2H), 2.41-2.30 (m, 4H), 2.02 (s, 2H), 1.98 (s, 1H), 1.66-1.57 (m, 1H), 1.52-1.43 (m, 3H), 1.33-1.19 (m, 5H), 0.88-0.82 (m, 3H)

LC-MS m/z 541 multimode+

EXAMPLE 28

Methyl 2-(4-((N-(3-(2-amino-4-methyl-6-(pentylamino)pyrimidin-5-yl)propyl)-2-(4-phenylpiperidin-1-yl)acetamido)methyl)phenyl)acetate

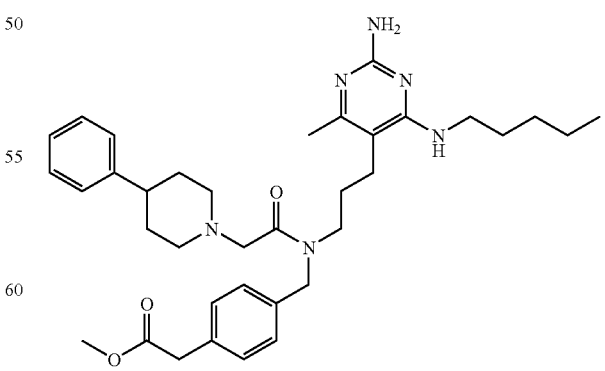

The title compound was prepared by the method of example 3 using the product from example 2 and the appropriate amine.

¹H NMR DMSO-d₆: δ 7.34-7.09 (m, 9H), 6.23-6.12 (m, 1H), 5.54-5.46 (m, 2H), 4.71 (s, 1H), 4.48 (s, 1H), 3.70-3.62 (m, 2H), 3.59 (s, 2H), 3.29-3.22 (m, 4H), 3.18-3.05 (m, 2H), 2.94-2.75 (m, 2H), 2.38-2.18 (m, 3H), 2.17-1.97 (m, 5H), 1.79-1.42 (m, 8H), 1.33-1.18 (m, 5H), 0.90-0.79 (m, 3H)
LC-MS m/z 615 multimode+

EXAMPLE 29

Methyl 2-(4-((N-(3-(2-amino-4-methyl-6-(pentylamino)pyrimidin-5-yl)propyl)-2-(piperidin-1-yl)acetamido)methyl)phenyl)acetate

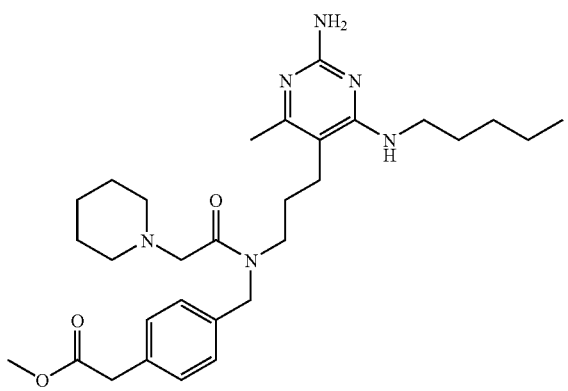

The title compound was prepared by the method of example 3 using the product from example 2 and the appropriate amine.
¹H NMR DMSO-d₆: δ 7.28-7.07 (m, 4H), 6.16 (t, 1H), 5.50 (d, 2H), 4.68 (s, 1H), 4.46 (s, 1H), 3.68-3.57 (m, 4H), 3.28-3.13 (m, 5H), 3.07-2.95 (m, 2H), 2.37-2.25 (m, 6H), 2.05-1.94 (m, 3H), 1.66-1.38 (m, 7H), 1.39-1.18 (m, 7H), 0.86 (t, 3H)
LC-MS m/z 539 multimode+

EXAMPLE 30

(S)-Methyl 2-(4-((2-amino-4-(1-hydroxypentan-2-ylamino)-6-methylpyrimidin-5-yl)methyl)-3-methoxyphenyl)acetate

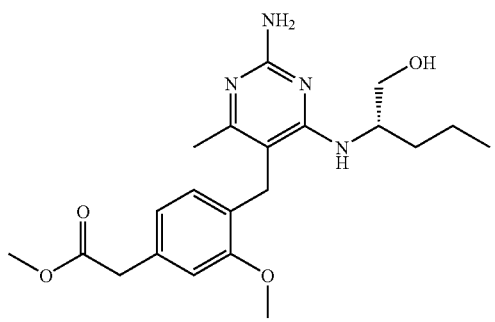

(i) (4-((2-Amino-4-chloro-6-methylpyrimidin-5-yl)methyl)-3-methoxyphenyl)methanol A solution of diisobutylaluminium hydride (1M in hexanes, 5.44 mL) was added over 10 min to a suspension of the product from example 21 step (iii) (0.5 g) in THF (10 mL) at 0° C. The mixture was allowed to warm to rt and stirred for 1 h. EtOAc (10 mL) was added cautiously and then the reaction mixture was added to ice/water (100 mL). The mixture was stirred for 30 min and then diluted with EtOAc (50 mL). The organic phase was separated and the aqueous was extracted with EtOAc. The combined organic phase was dried, filtered and evaporated to afford the subtitle compound, 0.39 g.
¹H NMR (DMSO-d₆); δ 6.96 (s, 1H), 6.84 (s, 2H), 6.78 (d, 1H), 6.58 (d, 1H), 5.13 (t, 1H), 4.45 (d, 2H), 3.83 (s, 3H), 3.81 (s, 2H), 2.15 (s, 3H)

(ii) 4-Chloro-5-(4-(chloromethyl)-2-methoxybenzyl)-6-methylpyrimidin-2-amine

Thionyl chloride (0.12 mL) was added to a solution of the product from step (i) (0.39 g) in DCM (10 mL) at 0° C. The reaction mixture was stirred at rt for 1 h and then the solvent was evaporated under reduced pressure to give the subtitle compound (0.40 g) which was used without purification.
¹H NMR DMSO-d₆: δ 7.09 (1H, s), 6.92 (1H, d), 6.66 (1H, d), 4.72 (2H, s), 3.92-3.73 (5H, m), 2.17 (3H, s)

(iii) 2-(4-((2-Amino-4-chloro-6-methylpyrimidin-5-yl)methyl)-3-methoxyphenyl) acetonitrile Potassium cyanide (0.17 g) was added to a stirred solution of the product from step (ii) (0.40 g) in DMSO (5 mL) and DMF (5 mL). The mixture was stirred at rt for 15 h, diluted with water and then extracted with EtOAc. The combined organic phase was dried, filtered and evaporated to give the subtitle compound, 0.20 g.
¹H NMR (DMSO-d₆); δ 6.98 (1H, d), 6.86 (2H, s), 6.83 (1H, dd), 6.66 (1H, d), 3.98 (2H, s), 3.85 (3H, s), 3.82 (2H, s), 2.16 (3H, s)

(iv) (S)-2-(4-((2-Amino-4-(1-hydroxypentan-2-ylamino)-6-methylpyrimidin-5-yl)methyl)-3-methoxyphenyl)acetonitrile (S)-2-Aminopentan-1-ol (0.136 g) was added to a solution of the product from step (iii) in NMP (2 mL). The resulting mixture was stirred at 140° C. for 50 h then diluted with EtOAc and washed with saturated NaHCO₃ solution and saturated brine. The organic phase was dried, filtered and evaporated. The crude product was purified by column chromatography, elution gradient 5 to 10% MeOH in DCM to give the subtitle compound, 0.095 g.
¹H NMR DMSO-d₆: 66.98 (1H, s), 6.84-6.78 (2H, m), 4.62 (1H, t), 4.21-4.12 (1H, m), 3.97 (2H, s), 3.86 (3H, s), 3.65 (2H, s), 3.41-3.33 (2H, m), 2.06 (3H, s), 1.55-1.41 (1H, m), 1.35-1.21 (1H, m), 1.15-1.00 (2H, m), 0.78 (3H, t)

(v) (S)-2-(4-((2-Amino-4-(1-hydroxypentan-2-ylamino)-6-methylpyrimidin-5-yl)methyl)-3-methoxyphenyl)acetic acid A 5M aqueous solution of potassium hydroxide (0.5 mL) was added to stirred solution of the product from step (iv) (0.095 g) in MeOH (1 mL). The mixture was stirred at 70° C. for 15 h and then the solvent was evaporated under reduced pressure. The resulting aqueous solution was adjusted to pH ~7 using concentrated HCl. The aqueous was extracted with EtOAc and the combined organic phase was dried, filtered and evaporated to give the subtitle compound, 0.09 g.
¹H NMR DMSO-d₆: δ 6.87 (1H, s), 6.66 (2H, s), 5.65 (2H, s), 5.45 (1H, d), 4.13-4.05 to (1H, m), 3.82 (3H, s), 3.58 (2H, s), 3.33 (2H, s), 3.42-3.34 (1H, m), 3.27-3.22 (1H, m), 3.17-3.11 (1H, m), 2.03 (3H, s), 1.53-1.41 (TH, m), 1.39-1.20 (1H, m), 1.20-1.05 (2H, m), 0.78 (3H, t)

(vi) (S)-Methyl 2-(4-((2-amino-4-(1-hydroxypentan-2-ylamino)-6-methylpyrimidin-5-yl)methyl)-3-methoxyphenyl)acetate Concentrated sulfuric acid (0.3 mL) was added to a solution of the product from step (v) (0.09 g) in MeOH (1 mL). The solution was heated at 70° C. for 3 h and then poured into saturated aqueous NaHCO$_3$ solution (10 mL). The aqueous was extracted with EtOAC and the combined organic phases were dried, filtered and evaporated. The crude product was purified by RPHPLC to give the title compound, 0.007 g.

$^1$H NMR DMSO-d$_6$: δ 6.89 (1H, s), 6.74-6.69 (2H, m), 5.62 (2H, s), 5.44 (1H, d), 4.59-4.53 (1H, m), 4.13-4.04 (1H, m), 3.84 (3H, s), 3.62 (2H, s), 3.59 (3H, s), 3.30-3.23 (4H, m), 2.03 (3H, s), 1.52-1.41 (1H, m), 1.33-1.21 (1H, m), 1.17-0.99 (2H, m), 0.77 (3H, t)

LC-MS m/z 403 multimode+

EXAMPLE 31

(S)-Methyl 2-(4-((2-amino-4-(1-hydroxyheptan-3-ylamino)-6-methylpyrimidin-5-yl)methyl)-3-methoxyphenyl)acetate

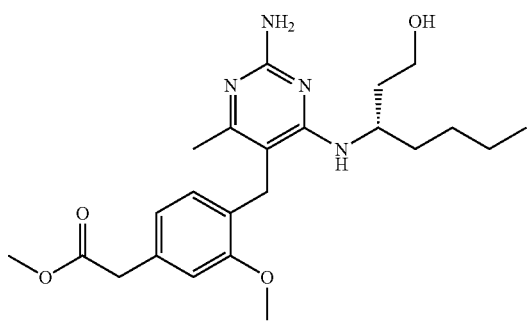

(i) (S)-2-(4-((2-Amino-4-(1-hydroxyheptan-3-ylamino)-6-methylpyrimidin-5-yl)methyl)-3-methoxyphenyl)acetic acid (S)-3-Aminoheptan-1-ol (108 mg) was added to a suspension of the product from example 30 step (iii) (0.1 g) in butan-1-ol (2 mL). The resulting mixture was stirred at 180° C. for 3 h in a CEM microwave. The mixture was then diluted with 5M aqueous potassium hydroxide (0.5 mL) and heated at 150° C. for 3 h in a CEM microwave. The mixture was adjusted to ~pH 7 with conc. HCl and the organic phase was separated. The aqueous was extracted with butan-1-ol and the combined organic phase was evaporated under reduced pressure to give the subtitle compound, 0.124 g.

$^1$H NMR (DMSO-d$_6$); δ 6.88 (1H, s), 6.70 (1H, d), 6.67 (1H, d), 5.90 (2H, s), 5.70 (1H, d), 4.23-4.12 (1H, m), 3.83 (3H, s), 3.60 (2H, s), 3.46 (2H, s), 3.35-3.27 (2H, m), 2.00 (3H, s), 1.65-1.52 (1H, m), 1.50-1.29 (3H, m), 1.27-0.97 (4H, m), 0.77 (3H, t)

(ii) (S)-Methyl 2-(4-((2-amino-4-(1-hydroxyheptan-3-ylamino)-6-methylpyrimidin-5-yl)methyl)-3-methoxyphenyl)acetate Concentrated HCl (1 mL) was added to a solution of the product from step (i) (0.1 g) in MeOH (2 mL). The mixture was heated at 70° C. for 2 h, poured into saturated aqueous NaHCO$_3$ solution (10 mL) and the aqueous was adjusted to pH 7 by adding NaHCO$_3$. The aqueous was extracted with EtOAc and the combined organic phase was dried, filtered and evaporated. The crude product was purified by RPHPLC to give the title compound, 0.018 g.

$^1$H NMR DMSO-d$_6$: δ 6.89 (1H, s), 6.71 (1H, d), 6.69 (1H, d), 5.66 (2H, s), 5.57 (1H, d), 4.37 (1H, t), 4.21-4.11 (1H, m), 3.84 (3H, s), 3.62 (2H, s), 3.60 (2H, s), 3.59 (3H, s), 3.29-3.26 (2H, m), 2.00 (3H, s), 1.62-1.52 (1H, m), 1.48-1.30 (3H, m), 1.27-1.01 (4H, m), 0.77 (3H, t)

LC-MS m/z 431 multimode+

EXAMPLE 32

(S)-Methyl 2-(4-((2-amino-4-(1-hydroxyhexan-2-ylamino)-6-methylpyrimidin-5-yl)methyl)-3-methoxyphenyl)acetate

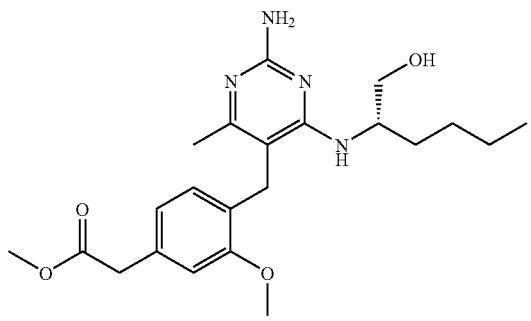

(i) (S)-2-(4-((2-Amino-4-(1-hydroxyhexan-2-ylamino)-6-methylpyrimidin-5-yl)methyl)-3-methoxyphenyl)acetic acid (S)-2-aminohexan-1-ol (0.077 g) was added to a suspension of the product from example 30 step (iii) (0.1 g) in butan-1-ol (2 mL). The resulting mixture was stirred at 180° C. for 2 h in a CEM microwave. The mixture was then diluted with 5M aqueous potassium hydroxide (0.5 mL) and heated at 100° C. for 15 h. The mixture was adjusted to ~pH 7 with conc. HCl and the organic phase was separated. The aqueous was extracted with butan-1-ol and the combined organic phase was evaporated under reduced pressure to give the subtitle compound, 0.1 g.

$^1$H NMR DMSO-d$_6$: δ 6.88 (1H, s), 6.69 (2H, s), 5.67 (2H, s), 5.45 (1H, d), 4.11-4.03 (1H, m), 3.83 (3H, s), 3.59 (2H, s), 3.43 (2H, s), 3.39-3.33 (1H, m), 3.28-3.22 (1H, m), 2.04 (3H, s), 1.58-1.46 (1H, m), 1.31-0.99 (3H, m), 0.90-0.82 (2H, m), 0.77 (3H, t)

(ii) (S)-Methyl 2-(4-((2-amino-4-(1-hydroxyhexan-2-ylamino)-6-methylpyrimidin-5-yl)methyl)-3-methoxyphenyl)acetate Concentrated hydrochloric acid (1 mL) was added to a stirred solution of the product from step (i) (0.1 g) in MeOH (2 mL) and the mixture was heated at 70° C. for 2 h. The mixture was allowed to cool and then poured into saturated aqueous NaHCO$_3$ solution (5 mL). The mixture was adjusted to pH ~7 by adding NaHCO$_3$ and the aqueous was extracted with EtOAc. The combined organic phase was dried, filtered and evaporated. The crude product was purified by RPHPLC to give the title compound, 0.014 g.

$^1$H NMR DMSO-$d_6$: δ 6.89 (1H, s), 6.74-6.69 (2H, m), 5.62 (2H, s), 5.43 (1H, d), 4.56 (1H, t), 4.12-4.02 (1H, m), 3.84 (3H, s), 3.61 (2H, s), 3.59 (5H, s), 3.39-3.33 (1H, m), 3.29-3.22 (1H, m), 2.03 (3H, s), 1.58-1.47 (1H, m), 1.30-0.99 (5H, m), 0.76 (3H, t)

LC-MS m/z 417 multimode+

EXAMPLE 33

(S)-Methyl 2-(4-((2-amino-4-(1-hydroxyheptan-3-ylamino)-6-methylpyrimidin-5-yl)methyl)-3-fluorophenyl)acetate

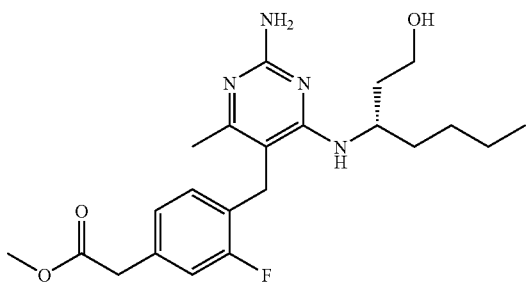

(i) (4-((2-Amino-4-chloro-6-methylpyrimidin-5-yl)methyl)-3-fluorophenyl)methanol A solution of diisobutylaluminium hydride (1M in hexanes, 8.8 mL) was added dropwise over 10 min to a suspension of the product from example 22 step (iii) (0.78 g) in THF (10 mL) at 0° C. The mixture was allowed to warm to rt and stirred for 1 h. EtOAc (10 mL) was added and then the mixture stirred for 10 min before being added to ice/water (100 mL). The mixture was stirred for 30 min and then diluted with EtOAc (50 mL). The organic phase was separated and the aqueous was extracted with EtOAc. The combined organic phase was dried, filtered and evaporated to afford the subtitle compound, 0.3 g.

$^1$H NMR (DMSO-$d_6$); δ 7.11 (d, 1H), 7.04 (d, 1H), 6.89 (s, 1H), 6.84 (dd, 2H), 5.27 (t, 1H), 4.46 (d, 2H), 3.92 (s, 2H), 2.21 (s, 3H)

(ii) 4-Chloro-5-(4-(chloromethyl)-2-fluorobenzyl)-6-methylpyrimidin-2-amine

Thionyl chloride (0.078 mL) was added to a stirred solution of the product from step (i) (0.30 g) in DCM (5 mL). The mixture was stirred at rt for 1 h and then the solvent was evaporated under reduced pressure. The crude product was purified by column chromatography to give the subtitle compound, 0.13 g.

$^1$H NMR DMSO-$d_6$: δ 7.29 (d, 1H), 7.19 (d, 1H), 6.96-6.87 (m, 3H), 4.73 (s, 2H), 3.94 (s, 2H), 2.22 (s, 3H)

(iii) 2-(4-((2-Amino-4-chloro-6-methylpyrimidin-5-yl)methyl)-3-fluorophenyl)acetonitrile Potassium cyanide (0.056 g) was added to a stirred solution of the product from step (ii) (0.13 g) in DMSO (1 mL) and DMF (1 mL). The mixture was stirred at rt for 15 h and then diluted with EtOAc (10 mL). The organic phase was washed with water and brine then dried, filtered and evaporated to give the subtitle compound, 0.12 g.

$^1$H NMR DMSO-$d_6$: δ 7.20 (d, 1H), 7.11 (d, 1H), 6.97-6.88 (m, 3H), 4.03 (s, 2H), 3.93 (s, 2H), 2.22 (s, 3H)

(iv) (S)-2-(4-((2-Amino-4-(1-hydroxyheptan-3-ylamino)-6-methylpyrimidin-5-yl)methyl)-3-fluorophenyl)acetonitrile (S)-3-Aminoheptan-1-ol (0.135 g) was added to a stirred solution of the product from step (iii) (0.12 g) in NMP (2 mL). The mixture was heated at 150° C. for 48 h, and then at 170° C. for a further 8 h. The mixture was allowed to cool, diluted with water (10 mL) and the aqueous extracted with EtOAc. The combined organic phase was dried and evaporated. The crude product was purified by column chromatography, to give the subtitle compound, 0.11 g.

$^1$H NMR DMSO-$d_6$: δ 7.17 (d, 1H), 7.05 (d, 1H), 6.86 (dd, 1H), 5.87 (s, 2H), 4.38 (t, 1H), 4.26-4.16 (m, 1H), 4.01 (s, 2H), 3.75 (s, 2H), 3.37-3.33 (m, 2H), 1.96 (s, 3H), 1.65-1.36 (m, 4H), 1.31-1.05 (m, 4H), 0.79 (t, 3H)

(v) (S)-2-(4-((2-Amino-4-(1-hydroxyheptan-3-ylamino)-6-methylpyrimidin-5-yl)methyl)-3-fluorophenyl)acetic acid A 5M aqueous solution of potassium hydroxide (0.58 mL) was added to a stirred solution of the product from step (iv) (0.11 g) in MeOH (1.5 mL). The mixture was heated at 70° C. for 15 h. The solvent was evaporated under reduced pressure and the aqueous residue was adjusted to pH ~7 with concentrated HCl. The aqueous was extracted with EtOAc and the combined organic phase was dried, filtered and evaporated to the subtitle compound, 0.102 g.

$^1$H NMR DMSO-$d_6$: δ 7.03 (d, 1H), 6.87 (d, 1H), 6.75-6.68 (m, 1H), 5.78-5.66 (m, 3H), 4.25-4.14 (m, 1H), 3.82-3.70 (m, 2H), 3.69 (s, 2H), 3.58 (s, 2H), 3.45-3.37 (m, 2H), 1.96 (s, 3H), 1.62-1.53 (m, 1H), 1.51-1.37 (m, 3H), 1.30-1.08 (m, 4H), 0.80 (t, 3H)

(vi) (S)-Methyl 2-(4-((2-amino-4-(1-hydroxyheptan-3-ylamino)-6-methylpyrimidin-5-yl)methyl)-3-fluorophenyl)acetate Concentrated sulfuric acid (0.3 mL) was added to a stirred solution of the product from step (v) (0.08 g) in MeOH (1 mL) and the mixture was heated to 70° C. for 2 h. The mixture was allowed to cool, diluted with water (2 mL) and neutralised with NaHCO$_3$. The aqueous was extracted with EtOAc and the combined organic phase was dried and evaporated. The crude product was purified by RPHPLC to give the title compound, 0.005 g.

$^1$H NMR DMSO-$d_6$: δ 7.09 (d, 1H), 6.95 (d, 1H), 6.78 (dd, 1H), 5.83 (d, 1H), 5.71 (s, 2H), 4.39 (t, 1H), 4.25-4.15 (m, 1H), 3.72 (s, 2H), 3.66 (s, 2H), 3.60 (s, 3H), 3.37-3.33 (m, 2H), 1.95 (s, 3H), 1.65-1.54 (m, 2H), 1.53-1.35 (m, 2H), 1.30-1.04 (m, 4H), 0.79 (t, 3H)

LC-MS m/z 419 multimode+

EXAMPLE 34

Methyl 2-(4-((2-amino-4-methyl-6-(pentylamino) pyrimidin-5-yl)methyl)phenyl)acetate, benzene sulphonic acid salt

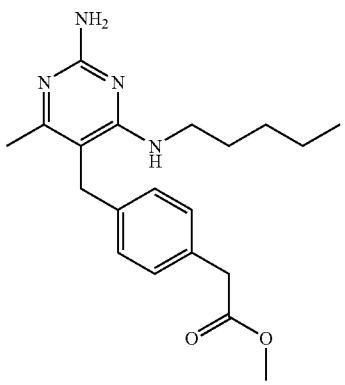

(i) Ethyl 3-oxo-2-(4-((tetrahydro-2H-pyran-2-yloxy) methyl)benzyl)butanoate

Ethyl acetoacetate (11.7 ml) was added to a stirred suspension of sodium hydride (60% disp. in oil, 3.8 g) in THF (200 ml) at 0° C. under nitrogen. After 1 h, a solution of 2-(4-(chloromethyl)benzyloxy)tetrahydro-2H-pyran (22.2 g) in THF (50 ml) was added, the mixture warmed to rt, then potassium iodide (16 g) added and heated under reflux for 48 h. The mixture was partitioned between water and ether, the organics separated, washed with water, dried and evaporated under reduced pressure. The residue was purified by column chromatography eluting with 20% EtOAc in isohexane to afford the subtitle compound, 15.66 g.
LC-MS m/z 333 APCI−

(ii) 2-Amino-6-methyl-5-(4-((tetrahydro-2H-pyran-2-yloxy)methyl)benzyl)pyrimidin-4-ol A mixture of the product from step (i) (15.66 g) and guanidine carbonate (8.7 g) in EtOH (150 ml) was heated under reflux for 48 h. The mixture was cooled, the solvent removed under reduced pressure and the residue triturated with water. The solid was filtered, washed with water then diethylether and dried to afford the subtitle compound, 11.58 g.
$^1$H NMR DMSO-$d_6$: δ 7.18 (d, 2H); 7.14 (d, 2H); 4.64 (t, 1H); 4.61-4.35 (m, 2H); 3.81-3.75 (m, 1H); 3.62 (s, 2H); 3.48-3.43 (m, 1H); 1.96 (s, 3H); 1.74-1.60 (m, 2H); 1.53-1.43 (m, 4H)
LC-MS m/z 330 APCI+

(iii) 2-Amino-6-methyl-S-(4-((tetrahydro-2H-pyran-2-yloxy)methyl)benzyl)pyrimidin-4-yl 2,4,6-trimethylbenzenesulfonate 2-Mesitylenesulfonyl chloride (3.65 g) was added to a stirred mixture of the product from step (ii) (5 g), TEA (4.2 ml) and DMAP (0.2 g) in DCM (100 ml) at rt under nitrogen. The mixture was stirred at rt for 4 h then partitioned between DCM and water. The organics were separated, washed with aq NaHCO$_3$ soln, water, dried and evaporated under reduced pressure to afford the subtitle compound, 6.49 g.
LC-MS m/z 512 APCI+

(iv) 6-Methyl-N4-pentyl-5-(4-((tetrahydro-2H-pyran-2-yloxy)methyl)benzyl)pyrimidine-2,4-diamine A mixture of the product from step (iii) (6.49 g) and n-pentylamine (7.34 ml) in 1-butanol was heated under reflux for 24 h. The solvent was evaporated and the residue partitioned between EtOAc and water. The organics were separated, dried and evaporated under reduced pressure. The residue was purified by column chromatography eluting with 8% MeOH/DCM to afford the subtitle compound, 3.4 g.
LC-MS m/z 399 APCI+

(v) (4-((2-Amino-4-methyl-6-(pentylamino)pyrimidin-5-yl)methyl)phenyl)methanol 2M HCl (10 ml) was added to a stirred solution of the product from step (iv) (3.4 g) in MeOH (30 ml). The mixture was stirred at rt for 3 days then the solvent evaporated under reduced pressure. The residue was partitioned between DCM/aq NaHCO$_3$ solution, the organics separated, dried and evaporated under reduced pressure to afford the subtitle compound, 2.38 g.
LC-MS m/z 315 APCI+

(vi) 5-(4-(Chloromethyl)benzyl)-6-methyl-N4-pentylpyrimidine-2,4-diamine

Thionyl chloride (1 ml) was added to a mixture of the product from step (v) (1.2 g) in DCM (20 ml) and stirred at rt for 2 h. The solvent was evaporated under reduced pressure and the residue used crude in the next step.

(vii) 2-(4-((2-Amino-4-methyl-6-(pentylamino)pyrimidin-5-yl)methyl)phenyl)acetonitrile Potassium cyanide (0.75 g) was added to a solution of the crude product from step (vi) in DMSO (10 ml) and DMF (10 ml). The mixture was stirred at rt for 18 h, then partitioned between EtOAc/water. The organics were separated, washed with aq NaHCO$_3$ solution, dried and evaporated under reduced pressure to afford the subtitle compound, 1.2 g.
LC-MS m/z 324 APCI+

(viii) 2-(4-((2-Amino-4-methyl-6-(pentylamino)pyrimidin-5-yl)methyl)phenyl)acetic acid A mixture of the product from step (vii) (1.2 g) and KOH (5M in water, 5 ml) in MeOH (15 ml) was heated under reflux for 18 h. The solvent was evaporated under reduced pressure and the residue dissolved in water (15 ml). The solution was adjusted to pH7 with 2M HCl then the solid filtered, washed with water then ether to afford the subtitle compound, 1.13 g
LC-MS m/z 343 multimode+

(ix) Methyl 2-(4-((2-amino-4-methyl-6-(pentylamino)pyrimidin-5-yl)methyl)phenyl)acetate, benzene sulphonic acid salt 2M HCl in ether (2 ml) was added to a mixture of the product from step (viii) (0.1 g) in MeOH (5 ml) and the mixture stirred at rt for 18 h. The solvent was evaporated and the residue purified by RPHPLC. The gum (0.06 g) was dissolved in MeCN (2 ml) then benzenesulphonic acid (0.027 g) added and the solvent evaporated under reduced pressure. The residue was triturated with ether and filtered to afford the title compound, 0.069 g.

¹H NMR DMSO-d₆: δ 11.87 (s, 1H); 7.93 (t, 1H); 7.62-7.59 (m, 2H); 7.41-7.25 (m, 4H); 7.18 (d, 2H); 7.09 (d, 2H); 3.82 (s, 2H); 3.63 (s, 2H); 3.59 (s, 3H); 3.39-3.34 (m, 2H); 2.18 (s, 3H); 1.51-1.44 (m, 2H); 1.27-1.07 (m, 4H); 0.81 (t, 3H)

LC-MS m/z 357 multimode+

EXAMPLE 35

2-Morpholinoethyl 2-(4-((2-amino-4-methyl-6-(pentylamino)pyrimidin-5-yl)methyl)phenyl)acetate, benzene sulphonic acid salt

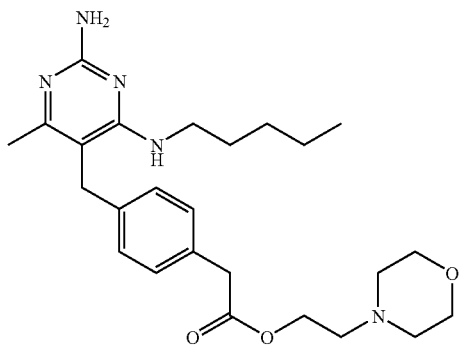

A solution of T₃P (1.57M in THF, 0.28 ml) was added to a mixture of the product from example 34 step (viii) (0.1 g), 4-(2-hydroxyethyl)morpholine (0.06 g), TEA (0.14 ml) and DMAP (0.01 g) in DMF (5 ml) and stirred at rt for 24 h. The mixture was partitioned between DCM/water, the organics separated, washed with aq NaHCO₃ soln, brine, dried and evaporated under reduced pressure. The residue was purified by RPHPLC to give a gum, 0.06 g. The gum was dissolved in MeCN (4 ml) and benzene sulphonic acid (0.021 g) was added, the solution evaporated under reduced pressure and the residue triturated with ether/EtOAc and the solid filtered and dried to afford the title compound, 0.042 g.

¹H NMR DMSO-d₆: δ 11.85 (brs, 1H); 7.94 (brs, 1H); 7.60 (m, 2H); 7.40-7.26 (brm, 4H); 7.20 (d, 2H); 7.09 (d, 2H); 4.14 (s, 2H); 3.82 (s, 2H); 3.62 (s, 2H); 3.52 (s, 4H); 3.37-3.31 (m, 2H); 2.37 (brs, 4H); 1.50-1.45 (m, 2H); 1.26-1.11 (m, 4H); 0.81 (t, 3H)

LC-MS m/z 456 multimode+

EXAMPLE 36

2-(Dimethylamino)ethyl 2-(4-((2-amino-4-methyl-6-(pentylamino)pyrimidin-5-yl)methyl)phenyl)acetate

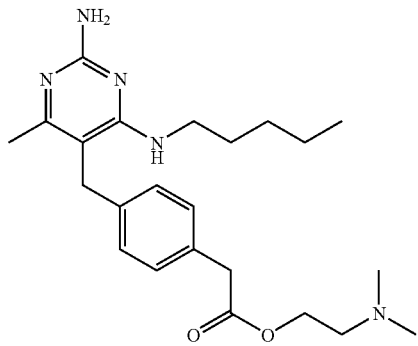

A solution of T₃P (1.57M in THF, 0.42 ml) was added to a mixture of the product from example 34 step (viii) (0.15 g), N,N-dimethylethanolamine (0.08 ml), TEA (0.3 ml) and DMAP (0.02 g) in DMF (5 ml) and stirred at rt for 24 h. The mixture was partitioned between DCM/water, the organics separated, washed with aq NaHCO₃ soln, brine, dried and evaporated under reduced pressure. The residue was purified by RPHPLC, then the product dissolved in MeCN (10 ml) and PS-TBD (0.1 g) added and left for 2 h. The mixture was filtered, the solvent evaporated under reduced pressure and the residue triturated with isohexane and filtered to afford the title compound, 0.034 g.

¹H NMR DMSO-d₆: δ 7.14 (d, 2H); 7.04 (d, 2H); 6.14 (t, 1H); 5.63 (s, 2H); 4.08 (t, 2H); 3.71 (s, 2H); 3.58 (s, 2H); 3.26-3.22 (m, 2H); 2.43 (t, 2H); 2.12 (s, 6H); 1.99 (s, 3H); 1.47-1.40 (m, 2H); 1.27-1.13 (m, 4H); 0.82 (t, 3H)

LC-MS m/z 414 multimode+

EXAMPLE 37

3-(Dimethylamino)propyl 2-(4-((2-amino-4-methyl-6-(pentylamino)pyrimidin-5-yl)methyl)phenyl)acetate

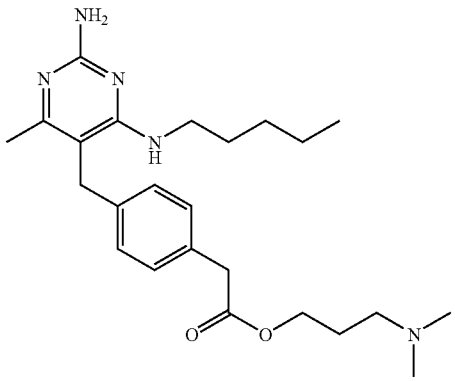

The title compound was prepared using the same method as example 36.

¹H NMR DMSO-d₆: δ 7.13 (s, 2H); 7.04 (s, 2H); 6.14 (t, 1H); 5.63 (s, 2H); 4.02 (t, 2H); 3.71 (s, 2H); 3.58 (s, 2H); 3.26-3.22 (m, 2H); 2.18 (t, 2H); 2.06 (s, 6H); 2.00 (s, 3H); 1.69-1.62 (m, 2H); 1.47-1.40 (m, 2H); 1.27-1.12 (m, 4H) 0.82 (t, 3H)

LC-MS m/z 428 multimode+

EXAMPLE 38

2-(4-Methylpiperazin-1-yl)ethyl 2-(4-((2-amino-4-methyl-6-(pentylamino)pyrimidin-5-yl)methyl)phenyl)acetate, di benzene sulphonic acid

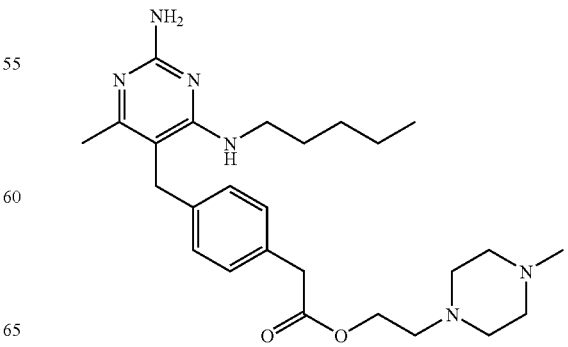

The title compound was prepared using the same method as example 36.

The dibenzene sulphonic acid salt was prepared by dissolving the product (0.098 g) in MeCN (4 ml) then benzene sulphonic acid (0.066 g) was added and the solution evaporated under reduced pressure to afford the title compound.

$^1$H NMR DMSO-$d_6$ (broad spectra, major peaks reported): δ 11.89 (s, 1H); 9.31 (s, 1H); 7.95 (s, 1H); 7.61-7.30 (m, 12H); 7.19 (d, 2H); 7.10 (d, 2H); 4.15 (s, 2H); 3.82 (s, 2H) 3.63 (s, 2H); 3.37 (brs, 4H); 3.00 (brs, 4H); 2.79 (s, 3H); 2.18 (s, 3H); 1.49-1.45 (m, 2H); 1.23-1.07 (m, 4H); 0.81 (t, 3H)

LC-MS m/z 469 multimode+

EXAMPLE 39

Methyl 2-(3-((2-amino-4-methyl-6-(pentylamino) pyrimidin-5-yl)methyl)-4-hydroxyphenyl)acetate

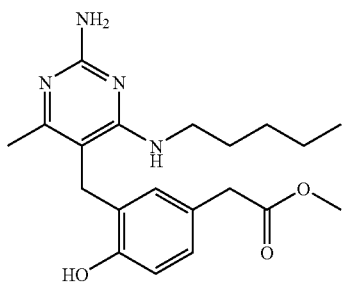

(i) 2-Amino-4-chloro-6-(pentylamino)pyrimidine-5-carbaldehyde

A mixture of 2-amino-4,6-dichloropyrimidine-5-carbaldehyde (30 g), pentylamine (18.5 ml) and TEA (22 ml) in MeOH (600 ml) were heated under reflux for 3 h then partitioned between EtOAc/water. The organics were separated, washed with water, dried and evaporated under reduced pressure. The residue was triturated with ether/iso-hexane to afford the subtitle compound, 20 g.

LC-MS m/z 243/5 APCI+

(ii) 2-Amino-4-methyl-6-(pentylamino)pyrimidine-5-carbaldehyde

A mixture of the product from step (i) (20 g), tetramethyltin (20 ml) and tetrakis(triphenylphosphine)palladium (0) (2 g) in DMF (200 ml) was heated at 100° C. for 16 h then evaporated under reduced pressure. The residue was partitioned between EtOAc/brine, the organics separated, dried and evaporated under reduced pressure. The residue was purified by chromatography on silica eluting with 50-60% EtOAc/isohexane to afford the subtitle compound, 14.4 g.

LC-MS m/z 223 APCI+

(iii) (2-Amino-4-methyl-6-(pentylamino)pyrimidin-5-yl)methanol

Sodium borohydride (0.6 g) was added to a solution of the product from step (ii) (2 g) in MeOH (30 ml) at 0-5° C. The mixture was warmed to rt, stirred for 3 h then the solvent evaporated under reduced pressure. The residue was partitioned between EtOAc and brine, the organics separated, dried and evaporated under reduced pressure to afford the subtitle compound, 1.78 g.

$^1$H NMR DMSO-$d_6$: δ 6.14 (t, 1H); 5.73 (s, 2H); 4.64 (t, 1H); 4.30 (d, 2H); 3.30-3.25 (m, 2H); 2.10 (s, 3H) 1.54-1.47 (m, 2H); 1.34-1.24 (m, 4H); 0.87 (t, 3H)

(iv) Methyl 2-(3-((2-amino-4-methyl-6-(pentylamino)pyrimidin-5-yl)methyl)-4-hydroxyphenyl) acetate A mixture of the product from step (iii) (1.5 g) and 4-hydroxyphenylacetic acid (1.02 g) in water (35 ml) and 2M HCl (5 ml) was heated at 100° C. for 48 h, cooled and evaporated under reduced pressure. The residue was azeotroped with toluene and the residue dissolved in MeOH (20 ml) Conc. HCl (1 ml) was added and the mixture stirred at rt for 4 h then evaporated under reduced pressure. The residue was partitioned between EtOAc/aq NaHCO$_3$ soln, the organics separated, dried and evaporated under reduced pressure. The residue was purified by column chromatography eluting with 8% MeOH/DCM to give a solid which was then purified by RPHPLC to afford the title compound, 0.23 g.

$^1$H NMR DMSO-$d_6$: δ 9.66 (s, 1H); 6.87 (d, 1H) 6.76 (d, 1H); 6.66 (s, 1H); 6.05 (brs, 1H); 5.61 (s, 2H); 3.56 (s, 2H); 3.54 (s, 3H); 3.43 (s, 2H); 3.25-3.20 (m, 2H); 2.07 (s, 3H); 1.48-1.40 (m, 2H); 1.28-1.14 (m, 4H); 0.83 (t, 3H)

LC-MS m/z 373 multimode+

EXAMPLE 40

Methyl 2-(4-((2-amino-4-methyl-6-(pentylamino) pyrimidin-5-yl)methyl)-3-methoxyphenoxy)acetate

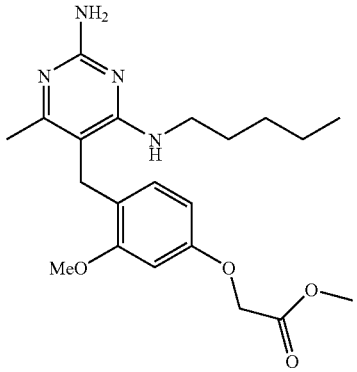

(i) Ethyl 2-(4-(benzyloxy)-2-methoxybenzylidene)-3-oxobutanoate

A solution of 4-(benzyloxy)-2-methoxybenzaldehyde (28.3 g), ethyl acetoacetate (18 ml), acetic acid (1.74 ml) and piperidine (0.56 ml) in toluene (400 ml) was heated under reflux for 48 h. A solution of acetic acid (1.74 ml) and piperidine (0.56 ml) in toluene (10 ml) was added and the solution heated under reflux for a further 48 h. The solvent was evaporated under reduced pressure and the residue partitioned between EtOAc and brine. The organics were separated, washed with aq NaHCO$_3$ soln, 1M HCl, brine, dried and evaporated under reduced pressure to give the subtitle compound, 40 g (used crude in next step).

(ii) Ethyl 2-(4-hydroxy-2-methoxybenzyl)-3-oxobutanoate

A mixture of the product from step (i) (40 g) and 5% Pd—C (3 g) in EtOAc were hydrogenated at 3 Bar for 48 h. The mixture was filtered through celite and evaporated under reduced pressure. The residue was purified by column chromatography eluting with 30% EtOAc/iso-hexane to afford the subtitle compound, 23.35 g.
LC-MS m/z 265 APCI−

(iii) 2-Amino-5-(4-hydroxy-2-methoxybenzyl)-6-methylpyrimidin-4-ol

A mixture of the product from step (ii) (23.35 g) and guanidine carbonate (15.9 g) in EtOH (300 ml) was heated under reflux for 24 h. The mixture was cooled and the solid filtered and washed with EtOH, water, EtOH then diethyl ether and dried to afford the subtitle compound, 11.36 g.
$^1$H NMR DMSO-$d_6$: δ 9.10 (s, 1H); 6.61 (d, 1H); 6.35 (s, 1H); 6.27 (s, 2H) 6.20 (d, 1H) 3.74 (s, 3H); 3.42 (s, 2H); 1.92 (s, 3H)

(iv) 4-((2-Amino-4-(mesitylsulfonyloxy)-6-methylpyrimidin-5-yl)methyl)-3-methoxyphenyl 2,4,6-trimethylbenzenesulfonate 2-Mesitylenesulfonyl chloride (5.25 g) was added to a mixture of the product from step (iii) (5 g), TEA (7 ml) and DMAP (120 mg) in DCM (100 ml) and stirred at rt for 24 h. DMF (10 ml) was added and the mixture heated under reflux for 12 h. Another portion of 2-mesitylenesulfonyl chloride (2 g) was added and heated under reflux for a further 24 h. The mixture was partitioned between DCM/water, the organics separated, washed with aq NaHCO$_3$ soln, brine, dried and evaporated under reduced pressure. The residue was triturated with ether/isohexane and filtered to afford the subtitle compound, 9.515 g.
LC-MS m/z 626 APCI+

(v) 4-((2-Amino-4-methyl-6-(pentylamino)pyrimidin-5-yl)methyl)-3-methoxyphenol

A mixture of the product from step (iv) (9.51 g) and pentylamine (12 ml) in dioxane (100 ml) was heated under reflux for 48 h. The solvent was evaporated and the residue partitioned between EtOAc/water. The organics were separated, washed with aq NaHCO$_3$ soln, water, dried and evaporated under reduced pressure. The residue was dissolved in MeOH (200 ml) then aq NaOH (2M, 40 ml) added and the mixture heated under reflux for 6 h. The mixture was acidified to pH 7 with aq 2M HCl, the solvent evaporated under reduced pressure and the residue partitioned between DCM/water. The organics were separated, washed with aq NaHCO$_3$ soln, brine, dried and evaporated under reduced pressure. The residue was triturated with ethyl acetate and filtered to afford the subtitle compound, 2.43 g.
$^1$H NMR DMSO-$d_6$: δ 9.24 (s, 1H); 6.56-6.54 (m, 2H); 6.43 (s, 1H); 6.29 (s, 2H); 6.23 (d, 1H); 3.78 (s, 3H); 3.51 (s, 2H); 3.27 (q, 2H); 2.04 (s, 3H); 1.48-1.40 (m, 2H); 1.29-1.11 (m, 4H); 0.83 (t, 3H)
LC-MS m/z 331 APCI+

(vi) Methyl 2-(4-((2-amino-4-methyl-6-(pentylamino)pyrimidin-5-yl)methyl)-3-methoxyphenoxy)acetate Methyl bromoacetate (57 ul) was added to a mixture of the product from step (v) (0.2 g) and K$_2$CO$_3$ (0.251 g) in DMF (10 ml) and the mixture stirred at rt for 24 h. The mixture was partitioned between EtOAc/water, the organics separated, dried and evaporated under reduced pressure. The residue was purified by RPHPLC to afford the title compound, 0.057 g
$^1$H NMR DMSO-$d_6$: δ 6.60-6.58 (m, 2H); 6.35 (dd, 1H); 5.92 (t, 1H); 5.62 (s, 2H); 4.73 (s, 2H); 3.83 (s, 3H); 3.68 (s, 3H); 3.52 (s, 2H); 3.22 (m, 2H); 1.97 (s, 3H); 1.46-1.39 (m, 2H); 1.27-1.09 (m, 4H); 0.83 (t, 31H)
LC-MS m/z 403 multimode+

EXAMPLE 41

Methyl 2-(4-((2-amino-4-(butylamino)-6-methylpyrimidin-5-yl)methyl)phenyl)acetate, benzene sulphonic acid

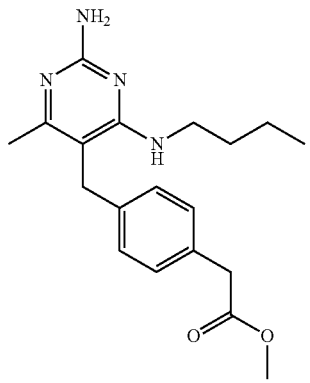

(i) 2-Amino-5-(4-(hydroxymethyl)benzyl)-6-methylpyrimidin-4-ol

Conc. HCl (4 ml) was added to a mixture of the product from example 34 step (ii) (5.2 g) in MeOH (100 ml) at rt and stirred for 30 min. The solvent was evaporated under reduced pressure and the residue dissolved in water (150 ml). Aq sat, NaHCO$_3$ soln was added until basic then the solid filtered, washed with water, ether and dried to afford the subtitle compound, 3.48 g.
LC-MS m/z 246 APCI+

(ii) 2-Amino-5-(4-(chloromethyl)benzyl)-6-methylpyrimidin-4-ol, hydrochloride

Thionyl chloride (6 ml) was added to a mixture of the product from step (i) (2.38 g) in DCM (80 ml) and the mixture stirred at rt under nitrogen for 18 h. The mixture was evaporated under reduced pressure to afford the subtitle compound, used crude in next step.
LC-MS m/z 264/266 APCI+

(iii) 2-(4-((2-Amino-4-hydroxy-6-methylpyrimidin-5-yl)methyl)phenyl)acetonitrile Potassium cyanide (2 g) was added to a solution of the product from step (ii) in DMF (20 ml) and DMSO (10 ml) and the mixture stirred at rt for 18 h. The mixture was flushed with nitrogen for 20 min, then diluted with brine (80 ml), stirred for 10 min and the precipitate filtered, washed with water then ether and dried to afford the subtitle compound, 2.46 g.
$^1$H NMR DMSO-$d_6$: δ 10.92 (s, 1H); 7.22-7.17 (m, 4H); 6.41 (s, 2H); 3.95 (s, 2H); 3.63 (s, 2H); 1.99 (s, 3H)

(iv) 2-Amino-5-(4-(cyanomethyl)benzyl)-6-methylpyrimidin-4-yl 2,4,6-trimethylbenzenesulfonate A mixture of the product from step (iii) (3.4 g), 2-mesitylenesulfonyl chloride (3.51 g), TEA (5.59 ml) and DMAP (82 mg) was stirred at rt for 18 h. The mixture was partitioned between DCM/water, the organics separated, washed with aq. NaHCO$_3$ soln, water, dried and evaporated under reduced pressure. The residue was triturated with ether/ethylacetate and filtered to afford the subtitle compound, 5.08 g.
LC-MS m/z 437 APCI+

(v) 2-(4-((2-Amino-4-(butylamino)-6-methylpyrimidin-5-yl)methyl)phenyl)acetonitrile A mixture of the product from step (iv) (0.3 g) and butylamine (1 ml) in 1,4-dioxane (6 ml) was sealed into a microwave tube and the reaction was performed in the CEM Microwave, at 160° C. and 100 W for 1 h. The solvent was evaporated under reduced pressure and the residue used crude in the next step.

(vi) 2-(4-((2-Amino-4-(butylamino)-6-methylpyrimidin-5-yl)methyl)phenyl)acetic acid The product from step (v) in MeOH (10 ml) and 5M KOH in water (3 ml) was heated under reflux for 18 h. The mixture was neutralised with acetic acid then purified by RPHPLC to afford the subtitle compound, 0.168 g.
$^1$H NMR DMSO-d$_6$: δ 7.06 (d, 2H); 6.91 (d, 2H); 6.11 (t, 1H); 5.64 (s, 2H); 3.67 (s, 2H) 3.27-3.22 (m, 2H); 3.15 (s, 2H); 2.00 (s, 3H); 1.47-1.40 (m, 2H); 1.26-1.17 (m, 2H) 0.84 (t, 3H)

(vii) Methyl 2-(4-((2-amino-4-(butylamino)-6-methylpyrimidin-5-yl)methyl)phenyl) acetate, benzene sulphonic acid A mixture of the product from step (vi) (0.146 g) and 4M HCl in dioxane (3 ml) in MeOH (7 ml) was stirred at rt for 18 h. The solvent was evaporated and the residue purified by RPHPLC to afford the ester, 0.098 g. The ester was dissolved in MeCN (4 ml) then benzene sulphonic acid (0.045 g) added. The solvent was evaporated to give a solid which was triturated with ether and filtered to afford the title compound, 0.111 g.
$^1$H NMR DMSO-d$_6$: δ 11.88 (s, 1H); 7.93 (t, 1H); 7.62-7.59 (m, 2H); 7.37-7.28 (m, 4H); 7.18 (d, 2H); 7.09 (d, 2H); 3.82 (s, 2H); 3.63 (s, 2H); 3.59 (s, 3H); 3.39-3.34 (m, 2H) 2.18 (s, 3H); 1.49-1.42 (m, 2H); 1.21-1.11 (m, 2H); 0.82 (t, 3H)
LC-MS m/z 343 multimode+

EXAMPLE 42

(S)-Methyl 2-(3-((2-amino-4-(1-hydroxyhexan-3-ylamino)-6-methylpyrimidin-5-yl)methyl)-4-fluorophenyl)acetate

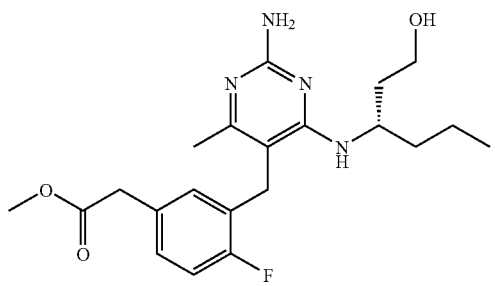

(i) Methyl 4-fluoro-3-methylbenzoate

Thionyl chloride (5.68 ml) was added dropwise to a solution of 4-fluoro-3-methylbenzoic acid (10 g) in MeOH (150 mL) at 0° C. over a period of 10 minutes under nitrogen. The resulting mixture was stirred at It for 24 h. The solvent was removed and the residue diluted with EtOAc, washed with sat. NaHCO$_3$, brine, dried, filtered and evaporated to afford the subtitle compound, 9.85 g.
LC-MS m/z 169 ESI (ii) Methyl 3-(bromomethyl)-4-fluorobenzoate NBS (14.60 g) and AIBN (2.89 g) were added to a solution of the product from step (i) (9.85 g) in EtOAc (200 mL). The resulting mixture was stirred at 80° C. for 20 h. After cooling the mixture was washed with sat. sodium thiosulphate, brine, dried, filtered and the solvent removed. The crude product was purified using chromatography, to give the subtitle compound, 5.30 g.
LC-MS m/z 248 ESI (iii) Methyl 3-((2-amino-4-chloro-6-methylpyrimidin-5-yl)methyl)-4-fluorobenzoate The subtitle compound was prepared using the product of step (ii) and the method of example 22 steps (i)-(iii).
$^1$H NMR DMSO-d$_6$: δ 7.92-7.87 (m, 1H), 7.51-7.49 (m, 1H), 7.37 (dd, 1H), 6.98 (s, 2H), 4.01 (s, 2H), 3.81 (s, 3H), 2.23 (s, 3H)
LC-MS m/z 310 ESI (iv) 2-(3-((2-Amino-4-chloro-6-methylpyrimidin-5-yl)methyl)-4-fluorophenyl)acetonitrile The subtitle compound was prepared using the product of step (iii) and the method of example 30 steps (i)-(iii).
$^1$H NMR DMSO-d$_6$: δ 7.27-7.20 (m, 2H), 6.95-6.87 (m, 3H), 3.97 (s, 2H), 3.95 (s, 2H), 2.22 (s, 3H)
LC-MS m/z 291 ESI.

(v) (S)-2-(3-((2-Amino-4-(1-hydroxyhexan-3-ylamino)-6-methylpyrimidin-5-yl)methyl)-4-fluorophenyl)acetonitrile (S)-3-Aminohexan-1-ol (101 mg) was added to a stirred solution of the product from step (iv) (100 mg) in butan-1-ol (2 mL). The reaction was performed in a microwave, at 180° C. for 2 h. The solvent was removed and the crude product was purified using chromatography, to give the subtitle compound, 70 mg.
$^1$H NMR DMSO d-6: δ 6.99 (s, 1H), 6.93-6.77 (m, 5H), 4.70 (t, 1H), 4.26-4.17 (m, 1H), 3.98 (s, 2H), 3.86 (s, 3H), 3.69 (s, 2H), 3.43-3.33 (m, 2H), 2.12 (s, 3H), 1.39-1.27 (m, 2H), 1.15-1.03 (m, 2H), 0.79 (t, 3H)
LC-MS m/z 370 ESI (vi) (S)-Methyl 2-(3-((2-amino-4-(1-hydroxyhexan-3-ylamino)-6-methylpyrimidin-5-yl)methyl)-4-fluorophenyl)acetate Aq. 5M KOH (0.5 mL) was added to a stirred solution of the product from step (v) (70 mg) in butan-1-ol (1 mL) and heated to 100° C. for 15 h. The mixture was allowed to cool, diluted with water (2 mL) and then adjusted to ~pH 7 with conc. HCl. The organic phase was separated and the aqueous was extracted with butan-1-ol (5 mL). The combined organic extracts were evaporated, the residue was dissolved in MeOH and conc. HCl (0.3 mL) was added and the mixture heated to 70° C. for 1 h. After cooling the reaction was poured into sat. NaHCO$_3$ (10 mL) and extracted with EtOAc, dried and the solvent removed. The crude product was purified by RPHPLC to afford the title compound as a colourless gum, 22 mg.

¹H NMR DMSO d-6: δ 7.12-7.06 (m, 2H), 6.76 (d, 1H), 5.83 (d, 1H), 5.72 (s, 2H), 4.38 (t, 1H), 4.30-4.17 (m, 1H), 3.73 (s, 2H), 3.58-3.51 (m, 5H), 3.39-3.34 (m, 2H), 1.95 (s, 3H), 1.68-1.33 (m, 4H), 1.30-1.11 (m, 2H), 0.80 (t, 3H)
LC-MS m/z 405 multimode+

EXAMPLE 43

(S)-Methyl 2-(4-((2-amino-4-(1-hydroxypentan-2-ylamino)-6-methylpyrimidin-5-yl)methyl)phenyl) acetate, benzenesulphonic acid salt

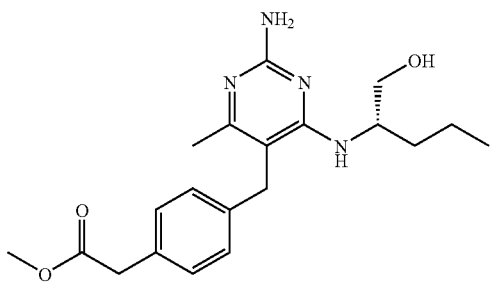

(i) (S)-2-(4-((2-Amino-4-(1-hydroxypentan-2-ylamino)-6-methylpyrimidin-5-yl)methyl)phenyl) acetonitrile To the product from example 41 step (iv) (300 mg) in butanol (2 ml), (S)-(+)-2-amino-1-pentanol (213 mg) was added and the reaction mixture heated in a microwave, at 180° C. for 2 h. The solvent was evaporated under reduced pressure and the crude product was purified using chromatography, to give the subtitle compound, 150 mg.
¹H NMR DMSO d-6: δ 7.26 (, 2H), 7.20-7.15 (m, 2H), 6.74 (s, 2H), 6.29 (s, 1H), 4.67 (t, 1H), 4.25-4.16 (m, 1H), 3.95 (s, 2H), 3.87 (d, 1H), 3.79 (d, 1H), 3.44-3.33 (m, 2H), 2.17 (s, 3H), 1.56-1.46 (m, 1H), 1.40-1.28 (m, 1H), 1.12-1.00 (m, 2H), 0.78 (t, 3H)
LC-MS m/z 340 ESI

(ii) (S)-2-(4-((2-Amino-4-(1-hydroxypentan-2-ylamino)-6-methylpyrimidin-5-yl)methyl)phenyl) acetic acid Aq. 5M KOH (1 ml) was added to a stirred solution of the product from step (i) (0.15 g) in butan-1-ol (2 mL). The mixture was heated at 100° C. for 15 h and then allowed to cool. The pH was adjusted to ~7 using conc. HCl and the organic phase was separated. The aqueous was extracted with butanol (5 mL) and then the combined organics were evaporated under reduced pressure. The crude product was purified by RPHPLC to afford the subtitle compound as a colorless solid, 0.041 g.
LC-MS m/z 359 multimode+

(iii) (S)-Methyl 2-(4-((2-amino-4-(1-hydroxypentan-2-ylamino)-6-methylpyrimidin-5-yl)methyl)phenyl) acetate, benzenesulphonic acid salt Conc. HCl (0.5 mL) was added to a stirred solution of the product from step (ii) (40 mg) in MeOH (1 mL) and the mixture heated at 70° C. for 2 h. The mixture was poured into sat aq NaHCO₃ (5 mL) and then adjusted to pH ~7 with solid sodium bicarbonate. The aqueous was extracted with EtOAc and the combined organics were dried, filtered and evaporated under reduced pressure. The crude product was purified by RPHPLC to give a gum. The salt was formed as in example 41 step (vii) to give a white solid, 12 mg.
¹H NMR DMSO d-6: δ 11.83 (s, 1H), 7.61-7.56 (m, 1H), 7.41-7.24 (m, 4H), 7.18 (d, 2H), 7.11 (d, 2H), 4.79-4.67 (m, 1H), 4.33-4.21 (m, 1H), 3.90 (d, 1H), 3.81 (d, 1H), 3.63 (s, 2H), 3.59 (s, 3H), 3.43-3.37 (m, 2H), 2.19 (s, 3H), 1.59-1.20 (m, 2H), 1.13-1.01 (m, 2H), 0.78 (t, 3H)
LC-MS m/z 373 multimode+

EXAMPLE 44

(S)-Methyl 2-(4-((2-amino-4-(1-hydroxyhexan-2-ylamino)-6-methylpyrimidin-5-yl)methyl)phenyl) acetate, benzene sulphonic acid salt

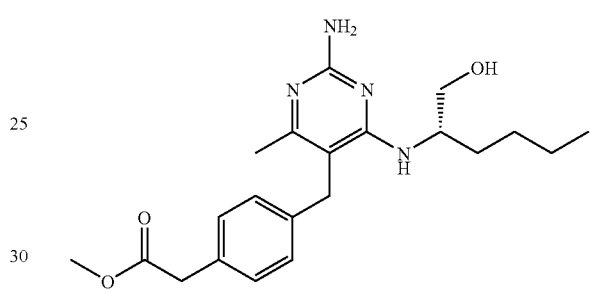

The title compound was prepared by the method of example 43 using (S)-2-amino-1-hexanol. The salt was formed as in example 41 step (vii) to give a white solid, 15 mg.
¹H NMR DMSO d-6: δ 7.24 (d, 2H), 7.15 (d, 2H), 6.23-6.02 (m, 3H), 4.61 (t, 1H), 4.17-4.05 (m, 1H), 3.97 (s, 2H), 3.82 (d, 1H), 3.75 (d, 1H), 3.43-3.35 (m, 2H), 2.07 (s, 3H), 1.60-1.48 (m, 1H), 1.37-0.97 (m, 5H), 0.77 (t, 3H)
LC-MS m/z 387 multimode+

EXAMPLE 45

(S)-Methyl 2-(4-((2-amino-4-(1-hydroxyhexan-3-ylamino)-6-methylpyrimidin-5-yl)methyl)-3-fluorophenyl)acetate

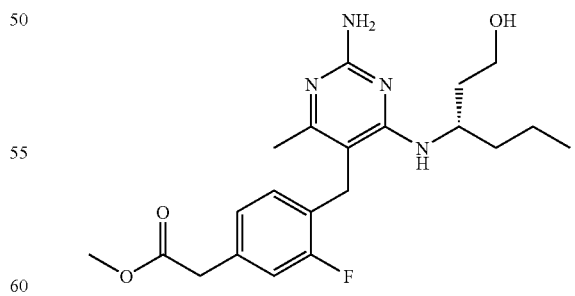

The title compound was prepared by the method of example 33 using (S)-3-aminohexan-1-ol to give a white solid, 102 mg.
¹H NMR DMSOd-6: δ 7.08 (dd, 1H), 6.95 (dd, 1H), 6.78 (dd, 1H), 5.83 (d, 1H), 5.71 (s, 2H), 4.39 (t, 1H), 4.28-4.17 (m, 1H), 3.72 (s, 2H), 3.66 (s, 2H), 3.60 (s, 3H), 3.36-3.32 (m, 2H), 1.94 (s, 3H), 1.65-1.54 (m, 1H), 1.53-1.32 (m, 3H), 1.22-1.08 (m, 2H), 0.79 (t, 3H)

LC-MS m/z 405 multimode+

EXAMPLE 46

Methyl 2-(4-((2-amino-4-(butylamino)-6-methylpyrimidin-5-yl)methyl)-3-methoxyphenyl)acetate, benzene sulphonic acid salt

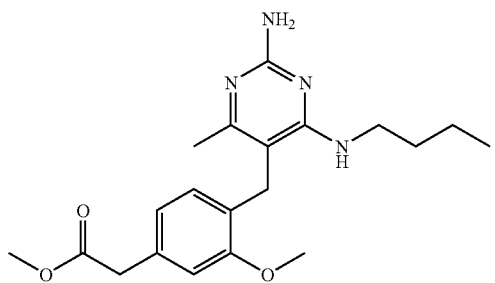

The title compound was prepared by the method of example 30 using butylamine. The salt was formed as in example 41 step (vii) to give a white solid, 140 mg.

¹H NMR DMSOd-6: δ 6.85 (s, 1H), 6.59 (d, 1H), 6.53 (d, 1H), 5.90 (t, 1H), 5.60 (s, 2H), 3.80 (s, 3H), 3.55 (s, 2H), 3.25-3.20 (m, 2H), 3.08 (s, 2H), 1.99 (s, 3H), 1.42 (q, 2H), 1.22 (sextet, 2H), 0.85 (t, 3H)

LC-MS m/z 373 multimode+

EXAMPLE 47

(S)-Methyl 2-(4-((2-amino-4-(1-hydroxypentan-2-ylamino)-6-methylpyrimidin-5-yl)methyl)-3-fluorophenyl)acetate, benzene sulphonic acid salt

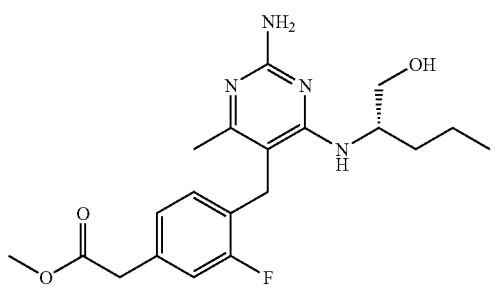

The title compound was prepared by the method of example 33 and (S)-2-aminopentan-1-ol. The salt was formed as in example 41 step (vii) to give a white solid, 34 mg.

¹H NMR DMSOd-6: δ 11.88 (s, 1H), 7.61-7.57 (m, 2H), 7.47 (d, 1H), 7.35-7.27 (m, 4H), 7.13 (dd, 1H), 7.00 (dd, 1H), 6.94 (dd, 1H), 4.72 (t, 1H), 4.35-4.25 (m, 1H), 3.85 (s, 2H), 3.69 (s, 2H), 3.60 (s, 3H), 3.44-3.35 (m, 2H), 2.12 (s, 3H), 1.59-1.46 (m, 1H), 1.44-1.32 (m, 1H), 1.28-1.06 (m, 2H), 0.80 (t, 3H)

LC-MS m/z 390 multimode+

EXAMPLE 48

(S)-Methyl 2-(4-((2-amino-4-(1-hydroxyhexan-3-ylamino)-6-methylpyrimidin-5-yl)methyl)-3-methoxyphenyl)acetate, benzene sulphonic acid salt

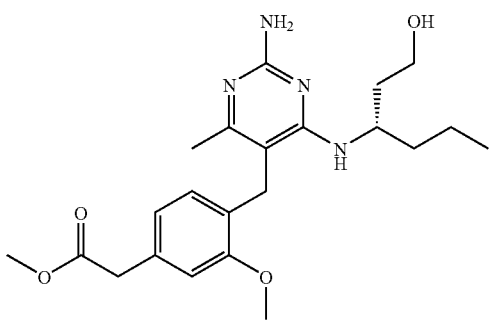

The title compound was prepared by the method of example 30 using (S)-3-aminohexan-1-ol. The salt was formed as in example 41 step (vii) to give a white solid, 76 mg.

¹H NMR DMSOd-6: δ 11.82 (s, 1H), 7.61-7.58 (m, 2H), 7.37 (d, 1H), 7.34-7.26 (m, 5H), 6.93 (s, 1H), 6.78-6.74 (m, 2H), 4.42-4.32 (m, 1H), 3.84 (s, 3H), 3.69 (s, 2H), 3.65 (s, 2H), 3.60 (s, 3H), 3.36-3.27 (m, 2H), 2.13 (s, 3H), 1.65-1.59 (m, 2H), 1.48-1.39 (m, 2H), 1.19-1.05 (m, 2H), 0.80 (t, 3H)

LC-MS m/z 417 multimode+

EXAMPLE 49

(S)-Methyl 2-(4-((2-amino-4-(1-hydroxyhexan-3-ylamino)-6-methylpyrimidin-5-yl)methyl)phenyl)acetate, benzene sulphonic acid salt

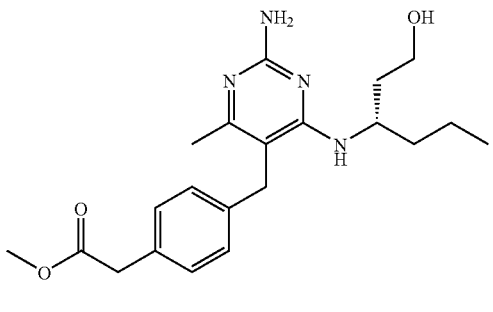

The title compound was prepared by the method of example 43 using (S)-3-aminohexan-1-ol. The salt was formed as in example 41 step (vii) to give a white solid, 56 mg.

¹H NMR DMSOd-6: δ 7.61-7.56 (m, 1H), 7.33-7.27 (m, 2H), 7.17 (d, 2H), 7.08 (d, 2H), 4.40-4.23 (m, 2H), 3.84-3.75 (m, 2H), 3.65-3.55 (m, 5H), 2.11 (s, 3H), 2.05-1.93 (m, 1H), 1.64-1.54 (m, 2H), 1.47-1.36 (m, 2H), 1.13-1.02 (m, 2H), 0.77 (t, 3H)

LC-MS m/z 387 multimode+

EXAMPLE 50

(S)-Methyl 2-(4-((2-amino-4-(1-hydroxyheptan-3-ylamino)-6-methylpyrimidin-5-yl)methyl)phenyl)acetate, benzene sulphonic acid salt

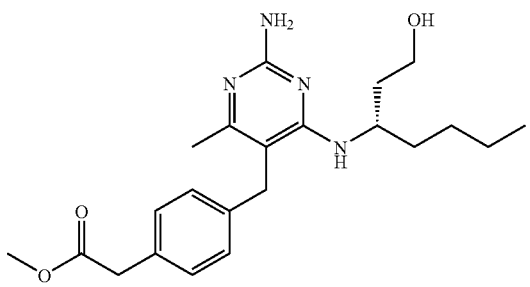

The title compound was prepared by the method of example 43 using (S)-3-aminoheptan-1-ol. The salt was formed as in example 41 step (vii) to give a white solid, 51 mg.

$^1$H NMR DMSOd-6: δ11.86-11.78 (m, 1H), 7.61-7.57 (m, 2H), 7.33-7.27 (m, 3H), 7.18 (d, 2H), 7.09 (d, 2H), 4.39-4.28 (m 2H), 3.87-3.80 (m, 2H), 3.61 (d, 5H), 2.17 (s, 3H), 2.05-1.94 (m, 1H), 1.67-1.59 (m, 2H), 1.50-1.39 (m, 2H), 1.26-1.0 (m, 3H), 1.07-0.99 (m, 2H), 0.77 (t, 3H)

LC-MS m/z 401 multimode+

EXAMPLE 51

Methyl 2-(4-((N-(3-(2-amino-4-methyl-6-(pentylamino)pyrimidin-5-yl)propyl)-1-methylpiperidine-4-carboxamido)methyl)phenyl)acetate, benzene sulphonic acid salt

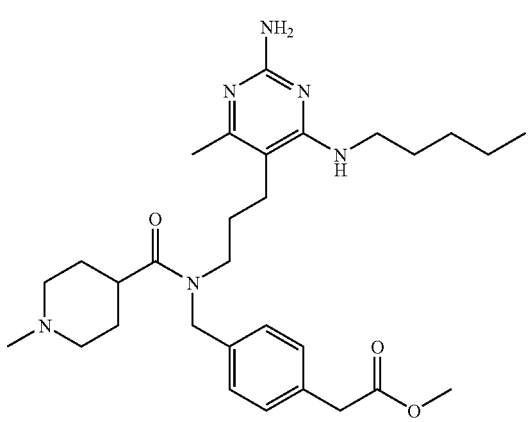

To the product of example 2 (50 mg) in DMF (4 ml) and TEA (0.118 ml), 1-methylpiperidine-4-carboxylic acid hydrochloride (23.89 mg) was added followed by T3P (1.57M in THF, 0.092 ml). The reaction mixture was stirred for 1 h. The solvents were evaporated, the crude product was purified by RPHPLC. The resulting gum was dissolved in MeCN, benzenesulfonic acid was added and the solvent removed to give the title compound as a white solid, 15 mg.

$^1$H NMR DMSO d-6 δ 7.65-7.59 (m, 1H), 7.32-7.18 (m, 5H), 7.16-7.08 (m, 2H), 4.60-4.42 (m, 2H), 3.66-3.57 (m, 5H), 3.41-3.23 (m, 4H), 2.40-2.16 (m, 9H), 2.11 (s, 3H), 1.82-1.43 (m, 9H), 1.35-1.18 (m, 5H), 0.87 (t, 3H)

LC-MS m/z 539 multimode+

EXAMPLE 52

Methyl 2-(4-((N-(3-(2-amino-4-methyl-6-(pentylamino)pyrimidin-5-yl)propyl)-2-(methylthio)acetamido)methyl)phenyl)acetate

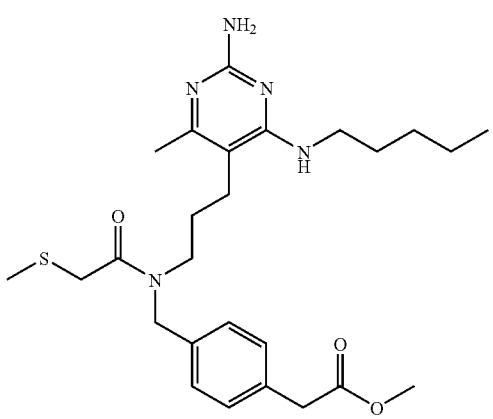

The title compound was prepared by the method of example 51 and 2-(methylthio)acetic acid to give a gum, 27 mg.

$^1$H NMR DMSOd-6: δ7.32-7.11 (m, 4H), 6.27-6.13 (m, 1H), 5.60-5.45 (m, 2H), 4.64-4.44 (m, 2H), 3.76-3.55 (m, 5H), 3.44-3.37 (m, 2H), 2.34-2.20 (m, 3H), 2.18-1.97 (m, 8H), 1.66-1.41 (m, 4H), 1.35-1.20 (m, 5H), 0.86 (t, 3H)

LC-MS m/z 502 multimode+

EXAMPLE 53

(S)-Methyl 2-(4-((2-amino-4-(2-hydroxybutylamino)-6-methylpyrimidin-5-yl)methyl)-3-methoxyphenyl)acetate, benzene sulphonic acid salt

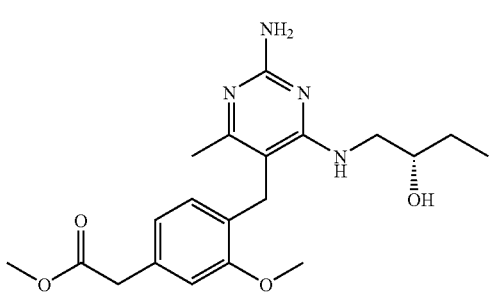

(i) (S)-2-(2-Hydroxybutyl)isoindoline-1,3-dione

To 1,2-Benzenedicarboximide (4.29 g) in DMF (10 ml), (S)-(−)-1,2-epoxybutane (2.1 g) was added followed by K$_2$CO$_3$ (4.03 g) and heated at 60° C. for 48 h. The reaction was diluted with water, extracted with EtOAc, dried and solvent removed to give the subtitle compound as a white solid, 1.8 g.

LC-MS m/z 220 ESI

(ii) (S)-1-Aminobutan-2-ol

To the product from step (i) (0.8 g) in MeOH (30 ml), hydrazine hydrate (60% in water, 0.6 ml) was added and the mixture stirred at rt for 48 h. The mixture was acidified with acetic acid, filtered and solvent removed. The product was purified on SCX resin to give the subtitle compound as a gum, 0.31 g.

$^1$H NMR DMSOd-6: δ 5.54-5.28 (m, 3H), 3.45-3.32 (m, 1H), 2.52-2.39 (m, 2H), 1.46-1.20 (m, 2H), 0.85 (t, 3H)

(iii) (S)-2-(tert-Butyldimethylsilyloxy)butan-1-amine

To the product from step (ii) (310 mg) in DMF (10 mL), tert-butylchlorodimethylsilane (734 mg) was added followed by imidazole (474 mg) and stirred at rt for 24 h. The mixture was washed with water and extracted with EtOAc, dried and the solvent removed to give the subtitle compound as a yellow oil, 610 mg.

LC-MS m/z 204 ESI

(iv) (S)-2-(4-((2-Amino-4-(2-hydroxybutylamino)-6-methylpyrimidin-5-yl)methyl)-3-methoxyphenyl)acetonitrile, hydrochloride The product of step (iii) (605 mg) was added to the product of example 30 step (iii) (300 mg) in butan-1-ol (3 mL) and stirred at 180° C. for 6 h in a microwave. The solvent was removed and the residue dissolved in EtOAc washed with water, dried and solvent removed. The product was purified using chromatography to give the protected compound (105 mg) as a white solid. (LC-MS m/z 470 ESI). This was dissolved in MeOH (5 ml) and 2M HCl (1 ml) was added and stirred overnight, the solvent was removed to give the subtitle compound as a yellow gum, 80 mg.

LC-MS m/z 356 ESI

(v) (S)-Methyl 2-(4-((2-amino-4-(2-hydroxybutylamino)-6-methylpyrimidin-5-yl)methyl)-3-methoxyphenyl)acetate, benzene sulphonic acid salt The title compound was prepared using the product of step (iv) (80 mg) and the method of example 42 step (vi). The benzene sulphonic acid salt was prepared as a white solid, 15 mg.

$^1$H NMR DMSOd-6: δ 11.91-11.87 (m, 1H), 7.69-7.63 (m, 1H), 7.63-7.56 (m, 1H), 7.35-7.27 (m, 2H), 3.85 (s, 3H), 3.70 (s, 2H), 3.66 (s, 2H), 3.62 (s, 3H), 3.57-3.51 (m, 1H), 3.41-3.25 (m, 2H), 2.18 (s, 3H), 1.36-1.17 (m, 2H), 0.89-0.81 (m, 3H)

LC-MS mm/z 389 multimode+

EXAMPLE 54

Methyl 2-(3-((2-amino-4-methyl-6-(pentylamino)pyrimidin-5-yl)methyl)-4-methoxyphenyl)acetate

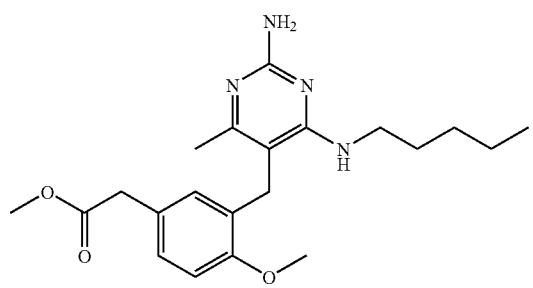

(i) 2-Amino-4-chloro-6-(pentylamino)pyrimidine-5-carbaldehyde

To 2-amino-4,6-dichloropyrimidine-5-carbaldehyde (30 g) in MeOH (600 ml) and TEA (22 ml), pentylamine (18.5 ml) was added and heated at reflux for 3 h. The solvent was removed and the residue partitioned between EtOAc and water, the organic layer was dried and the solvent evaporated. The residue was triturated with ether/isohexane to give the subtitle compound as a solid, 20.2 g.

LC-MS m/z 243 APCI+

(ii) 2-Amino-4-methyl-6-(pentylamino)pyrimidine-5-carbaldehyde

To the product from step (i) (20 g) in DMF (200 ml), Pd(PPh$_3$)$_4$ (2 g) was added followed by SnMe$_4$ (20 ml) and the mixture heated at 100° C. for 16 h. The solvent was evaporated and the residue partitioned between EtOAc and brine, the organics were dried and solvent removed. The product was purified by silica chromatography to give the subtitle compound, 14.4 g.

LC-MS m/z 233 APCI+

(iii) (2-Amino-4-methyl-6-(pentylamino)pyrimidin-5-yl)methanol

To the product from step (ii) (4 g) in MeOH (50 ml), sodium borohydride (0.7 g) was added portionwise over 5 min. The mixture was stirred at rt for 1 h then the solvent removed under reduced pressure. The residue was partitioned between EtOAc and water, the organics were separated, dried and evaporated under reduced pressure to give the subtitle compound, 3.89 g.

LC-MS m/z 225 APCI+

(iv) 2-(3-((2-Amino-4-methyl-6-(pentylamino)pyrimidin-5-yl)methyl)-4-methoxyphenyl)acetic acid To the product from step (iii) (0.8 g) in 1M aq HCl (20 ml), 4-methoxyphenylacetic acid (1.8 g) was added and heated under reflux for 48 h. The solvent was evaporated and the residue purified by SCX then by RPHPLC to give the subtitle compound, 164 mg.

LC-MS m/z 373 APCI+

(v) Methyl 2-(3-((2-amino-4-methyl-6-(pentylamino)pyrimidin-5-yl)methyl)-4-methoxyphenyl)acetate A solution of the product from step (iv) (135 mg) in MeOH (5 ml) and 4M HCl in dioxane (0.5 ml) was stirred at rt for 18 h. The solvent was evaporated and the residue purified by RPHPLC to give the title compound as a solid, 31 mg.

$^1$H NMR DMSO-d$_6$: δ 7.05 (d, 1H), 6.93 (d, 1H), 6.65 (s, 1H), 5.97 (t, 1H), 3.84 (s, 3H), 3.60 (s, 2H), 3.54 (s, 3H), 3.48 (s, 2H), 3.26-3.19 (m, 2H), 1.98 (s, 3H), 1.48-1.38 (m, 2M), 1.29-1.14 (m, 4H), 0.83 (t, 3H)

LC-MS m/z 387 multimode+

EXAMPLE 55

3-(Dimethylamino)-2,2-dimethylpropyl 2-(4-((2-amino-4-methyl-6-(pentylamino)pyrimidin-5-yl)methyl)phenyl)acetate, benzene sulphonic acid salt

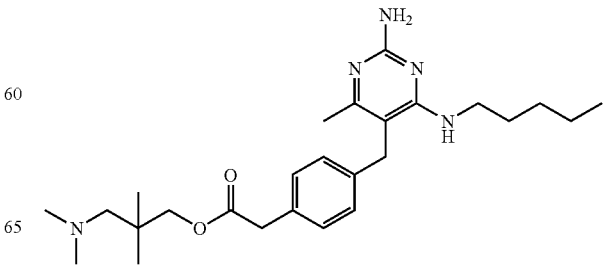

The title compound was prepared using the method of example 35 and 3-(dimethylamino)-2,2-dimethylpropan-1-ol to give a white solid, 65 mg.

$^1$H NMR DMSOd-6: δ 7.62-7.55 (m, 2H), 7.35-7.25 (m, 2H), 7.22-7.13 (m, 2H), 7.12-6.91 (m, 3H), 3.84-3.73 (m, 4H), 3.63 (s, 2H), 2.22-1.93 (m, 11H), 1.54-1.40 (m, 3H), 1.29-1.08 (m, 6H), 0.88-0.74 (m, 8H)

LC-MS m/z 456 multimode+

EXAMPLE 56

3-(4-Methylpiperazin-1-yl)propyl 2-(4-((2-amino-4-methyl-6-(pentylamino)pyrimidin-5-yl)methyl)phenyl)acetate, benzene sulphonic acid salt

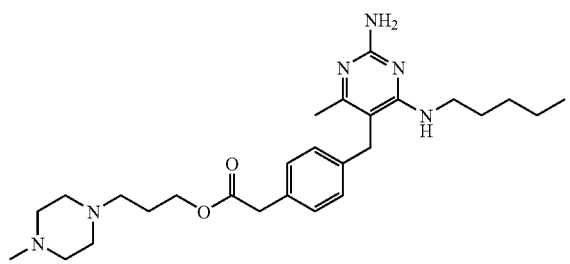

The title compound was prepared using the method of example 35 and 3-(4-methylpiperazin-1-yl)propan-1-ol to give a white solid, 63 mg.

$^1$H NMR DMSOd-6: δ 7.64-7.53 (m, 2H), 7.38-7.25 (m, 3H), 7.17 (d, 2H), 7.08 (d, 2H), 6.95-6.81 (m, 1H), 4.03 (t, 2H), 3.79 (s, 2H), 3.59 (s, 2H), 3.48-3.36 (m, 2H), 3.36-3.27 (m, 4H), 2.65-2.54 (m, 2H), 2.40-2.28 (m, 6H), 2.13 (s, 3H), 1.75-1.65 (m, 2H), 1.51-1.41 (m, 2H), 1.28-1.17 (m, 3H), 1.16-1.05 (m, 2H), 0.81 (t, 3H)

LC-MS m/z 483 multimode+

EXAMPLE 57

4-(Dimethylamino)butyl 2-(4-((2-amino-4-methyl-6-(pentylamino)pyrimidin-5-yl)methyl)phenyl)acetate, bis benzene sulphonic acid salt

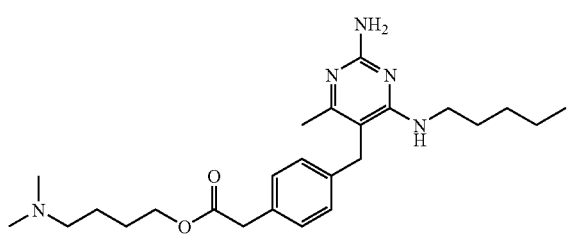

The title compound was prepared using the method of example 35 and 4-dimethylamino-1-butanol to give a foam, 131 mg.

$^1$H NMR DMSO-d$_6$: δ 7.94-7.30 (m, 10H); 7.18 (d, 2H); 7.09 (d, 2H); 4.03 (s, 2H); 3.82 (s, 2H); 3.63 (s, 2H); 3.37-3.32 (m, 2H); 3.04-3.01 (m, 2H); 2.75 (s, 6H); 2.18 (s, 3H) 1.61-1.44 (m, 6H); 1.23-1.10 (m, 4H); 0.80 (t, 3H)

LC-MS m/z 442 multimode+

4-(Dimethylamino)butyl 2-(4-((2-amino-4-methyl-6-(pentylamino)pyrimidin-5-yl)methyl)phenyl)acetate, monosaccharin salt To a stirred suspension of 4-(dimethylamino)butan-1-ol (1.54 g), the product from example 34 step (viii) (1.5 g) and Hunig's base (2.295 mL) in DMF (30 mL) was added HATU (1.666 g). After 4 h a further portion of HATU (250 mg) was added and stirring continued for 2 h. The solution was diluted with EtOAc and washed with brine, dried and concentrated to give a brown oil, 2 g. The crude product was purified by column chromatography eluting with DCM; MeCN; Et$_3$N (90:10:10 to 70:20:20) then by RPHPLC. The residue was dissolved in EtOAc, washed with sat NaHCO$_3$ soln., dried and concentrated to give a clear oil 0.45 g. The oil was dissolved in MeCN and saccharin (0.18 g) was added. Evaporation of the solvent gave a foam which was triturated under ether for 60 h to give a white solid which was collected, washed with ether and dried in vacuo at 40° C., yield 0.5 g.

$^1$H NMR DMSO-d$_6$: δ 7.66-7.56 (m, 4H), 7.2-7.18 (d, 2H), 7.17-7.06 (m 3H), 6.56 (s, 2H), 4.02 (t, 2H), 3.78 (s, 2H), 3.60 (s, 2H), 3.33-3.28 (m, 2H), 2.69-2.64 (m, 2H), 2.50 (s, 6H), 2.10 (s, 3H), 1.60-1.40 (m, 6H), 1.30-1.20 (m, 4H), 0.81 (t, 3H)

LC-MS m/z 442 multimode+

EXAMPLE 58

3-Morpholinopropyl 2-(4-((2-amino-4-methyl-6-(pentylamino)pyrimidin-5-yl)methyl)phenyl)acetate, benzene sulphonic acid salt

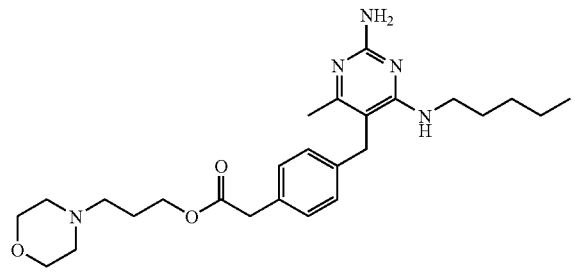

The title compound was prepared using the method of example 35 and 3-morpholinopropan-1-ol to give a white solid, 115 mg.

$^1$H NMR DMSO-d$_6$: δ 7.84 (s, 1H), 7.61-7.59 (m, 2H), 7.34-7.2 (m, 4H), 7.18 (d, 2H), 7.09 (d, 2H), 4.04 (t, 2H), 3.81 (s, 2H), 3.61 (s, 2H), 3.55 (brs, 4H), 3.38-3.33 (m, 2H), 2.33 (brs, 6H), 2.17 (s, 3H), 1.75-1.68 (m, 2H), 1.51-1.44 (m, 2H), 1.27-1.08 (m, 4H), 0.81 (t, 3H)

LC-MS m/z 470 multimode+

EXAMPLE 59

1-Methylpiperidin-4-yl 2-(4-((2-amino-4-methyl-6-(pentylamino)pyrimidin-5-yl)methyl)phenyl)acetate

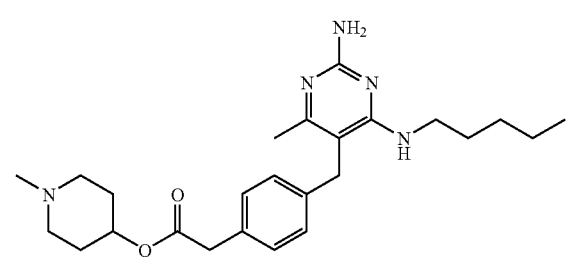

The title compound was prepared using the method of example 35 and 1-methylpiperidin-4-ol to give a white solid, 25 mg.

$^1$H NMR DMSO-d$_6$: δ 7.14 (d, 2H), 7.04 (d, 2H), 6.15 (t, 1H), 5.64 (s, 2H), 4.68-4.61 (m, 1H), 3.71 (s, 2H), 3.57 (s, 2H), 3.27-3.21 (m, 2H), 2.12 (s, 3H), 2.12-2.07 (m, 2H), 1.99 (s, 3H) 1.80-1.70 (brm, 2H) 1.59-1.39 (m, 4H), 1.27-1.13 (m, 4H), 0.82 (t, 3H)

LC-MS m/z 440 multimode+

EXAMPLE 60

(1-Methylpiperidin-4-yl)methyl 2-(4-((2-amino-4-methyl-6-(pentylamino)pyrimidin-5-yl)methyl)phenyl)acetate, benzene sulphonic acid salt

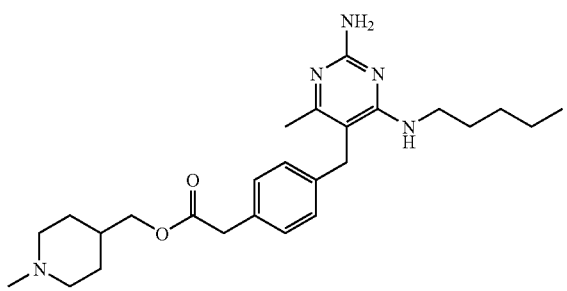

A solution of T$_3$P (1.57M in THF, 0.56 ml) was added to a mixture of the product from example 34 step (viii) (0.15 g), (1-methylpiperidin-4-yl)methanol (114 mg) and TEA (0.3 ml) in DMF (5 ml) and stirred at rt for 24 h. The mixture was partitioned between DCM/water, the organics separated, washed with aq NaHCO$_3$ soln, brine, dried and evaporated under reduced pressure. The residue was purified by RPHPLC to give a gum, 100 mg. The gum was dissolved in MeCN (5 ml) then benzenesulphonic acid (35 mg) added and the solvent evaporated under reduced pressure. The residue was triturated with ether and filtered, 103 mg $^1$H NMR DMSO-d$_6$: δ 7.61-7.59 (m, 2H); 7.34-7.28 (m, 3H); 7.16 (d, 2H) 7.08-7.06 (m, 3H); 6.54 (s, 2H); 3.90 (d, 2H); 3.77 (s, 2H); 3.62 (s, 2H); 3.33-3.27 (m, 2H); 3.07-3.04 (m, 2H); 2.45 (s, 3H); 2.45-2.34 (m, 2H); 2.09 (s, 3H); 1.71-1.65 (m, 3H); 1.50-1.42 (m, 2H); 1.33-1.09 (m, 6H); 0.82 (t, 3H)

LC-MS m/z 454 multimode+

EXAMPLE 61

4-(Pyrrolidin-1-yl)butyl 2-(4-((2-amino-4-methyl-6-(pentylamino)pyrimidin-5-yl)methyl)phenyl)acetate, benzene sulphonic acid salt

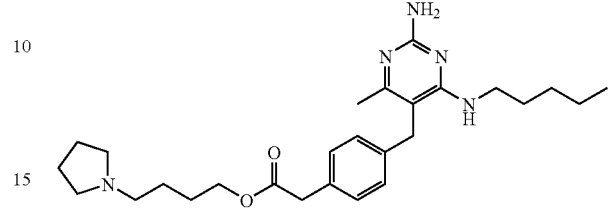

The title compound was prepared using the method of example 35 and 4-(pyrrolidin-1-yl) butan-1-ol to give a white solid, 26 mg.

$^1$H NMR DMSOd-6: δ 7.59 (dd, 2H), 7.34-7.28 (m, 3H), 7.16 (d, 2H), 7.07 (d, 2H), 4.03 (t, 2H), 3.75 (s, 2H), 3.60 (s, 2H), 2.95-2.76 (m, 5H), 2.07 (d, 4H), 2.03-1.91 (m, 1H), 1.89-1.74 (m, 2H), 1.64-1.51 (m, 5H), 1.49-1.39 (m, 2H), 1.29-1.19 (m, 4H), 1.18-1.09 (m, 2H), 0.82 (t, 3H)

LC-MS m/z 468 multimode+

EXAMPLE 62

(1-(2-Methoxyethyl)piperidin-4-yl)methyl 2-(4-((2-amino-4-methyl-6-(pentylamino)pyrimidin-5-yl)methyl)phenyl)acetate, bis benzene sulphonic acid salt

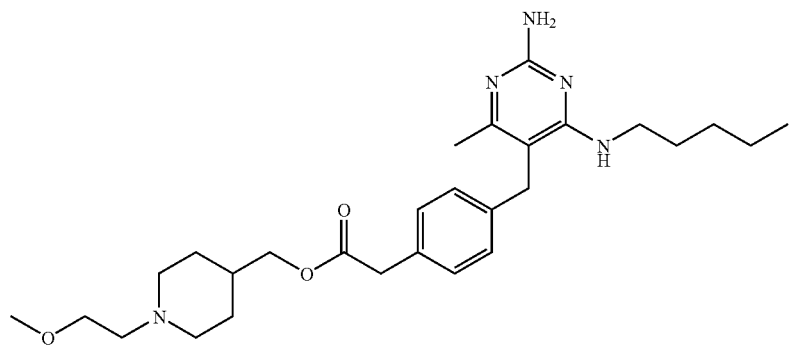

The title compound was prepared using the method of example 35 and (1-(2-methoxyethyl)piperidin-4-yl)methanol to give a foam, 168 mg.

$^1$H NMR DMSOd-6: δ 11.94 (s, 1H), 9.12 (s, 1H), 7.95 (t, 1H), 7.60 (d, 4H), 7.43 (brs, 2H), 7.34-7.27 (m, 6H), 7.19 (d, 2H), 7.10 (d, 2H), 3.90 (d, 2H), 3.82 (s, 2H), 3.66-3.61 (m, 4H), 3.49 (d, 2H), 3.39-3.33 (m, 2H), 3.31 (s, 3H), 3.27-3.18 (m, 2H), 2.98-2.89 (m, 2H), 2.18 (s, 3H), 1.89-1.78 (m, 3H), 1.52-1.42 (m, 4H), 1.25-1.07 (m, 4H), 0.81 (t, 3H)

LC-MS m/z 498 multimode+

EXAMPLE 63

4-(4-Methylpiperazin-1-yl)butyl 2-(4-((2-amino-4-methyl-6-(pentylamino)pyrimidin-5-yl)methyl)phenyl)acetate, benzene sulphonic acid salt

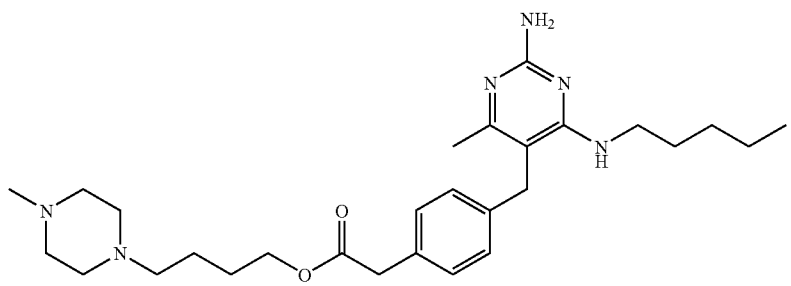

The title compound was prepared using the method of example 35 and 4-(4-methylpiperazin-1-yl)butan-1-ol to give a white solid, 151 mg.

$^1$H NMR DMSOd-6: δ 7.62-7.57 (m, 2H), 7.33-7.28 (m, 3H), 7.16 (d, 2H), 7.07 (d, 2H), 4.01 (t, 2H), 3.77 (s, 2H), 3.60 (s, 2H), 2.34-2.28 (m, 2H), 2.11 (s, 3H), 2.07 (s, 2H), 2.05-1.95 (m, 1H), 1.61-1.50 (m, 2H), 1.50-1.37 (m, 4H), 1.27-1.18 (m, 4H), 1.17-1.09 (m, 2H), 0.81 (t, 3H)

LC-MS m/z 497 multimode+

EXAMPLE 64

4-(1,1-Dioxidothiomorpholin-4-yl)butyl(4-{[2-amino-4-methyl-6-(pentylamino)pyrimidin-5-yl]methyl}phenyl)acetate, benzene sulphonic acid salt

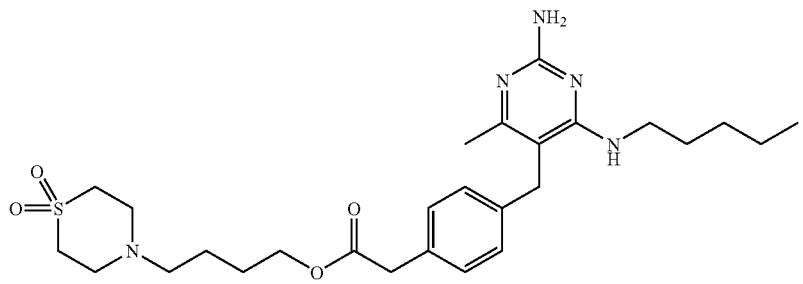

The title compound was prepared using the method of example 35 and 4-(4-hydroxybutyl)thiomorpholine 1,1-dioxide to give a white solid, 98 mg.

$^1$H NMR DMSOd-6: δ 7.95-7.88 (m, 1H), 7.60-7.56 (m, 2H), 7.33-7.29 (m, 3H), 7.20-7.16 (m, 2H), 7.12-7.07 (m, 2H), 4.06-3.99 (m, 2H), 3.82 (s, 2H), 3.61 (s, 2H), 3.40-3.34 (m, 1H), 3.09-3.02 (m, 4H), 2.85-2.79 (m, 4H), 2.46-2.39 (m, 2H), 2.19 (s, 3H), 1.59-1.50 (m, 1H), 1.50-1.36 (m, 4H), 1.26-1.17 (m, 2H), 1.15-1.06 (m, 2H), 0.81 (t, 3H)

LC-MS m/z 532 multimode+

EXAMPLE 65

4-Morpholinobutyl 2-(4-((2-amino-4-methyl-6-(pentylamino)pyrimidin-5-yl)methyl)phenyl)acetate, benzene sulphonic acid salt

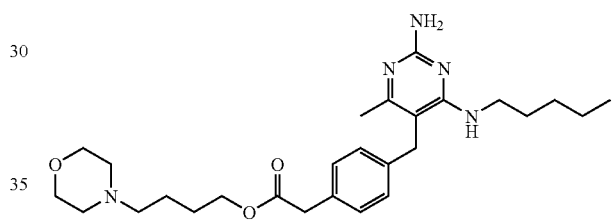

The title compound was prepared using the method of example 35 and 4-morpholinobutan-1-ol to give a white solid, 30 mg.

$^1$H NMR DMSOd-6: δ 7.60-7.55 (m, 2H), 7.33-7.28 (m, 3H), 7.19-7.14 (m, 2H), 7.09-7.04 (m, 2H), 4.02 (t, 2H), 3.77 (s, 2H), 3.62-3.51 (m, 5H), 3.31 (2H, m) 2.35-2.20 (m, 6H), 2.11 (s, 3H), 1.59-1.51 (m, 2H), 1.50-1.36 (m, 4H), 1.27-1.17 (m, 3H), 1.17-1.07 (m, 2H), 0.81 (t, 3H)

LC-MS m/z 484 multimode+

EXAMPLE 66

2-(1-Methylpiperidin-4-yl)ethyl 2-(4-((2-amino-4-methyl-6-(pentylamino)pyrimidin-5-yl)methyl)phenyl)acetate, benzene sulphonic acid salt

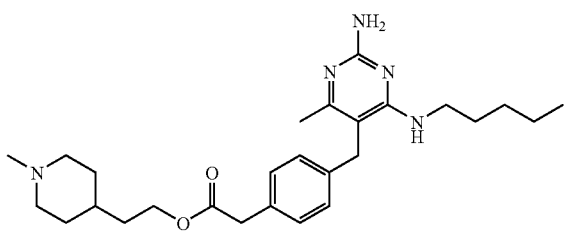

The title compound was prepared using the method of example 35 and 2-(1-methylpiperidin-4-yl)ethanol to give a gum, 90 mg.

$^1$H NMR DMSOd-6: δ 7.61-7.58 (m, 2H), 7.34-7.28 (m, 3H), 7.15 (d, 2H), 7.07 (d, 2H), 6.40 (s, 1H), 4.05 (t, 2H), 3.76 (s, 2H), 3.59 (s, 2H), 3.32-3.27 (m, 2H), 3.13-3.05 (m, 2H), 2.54-2.50 (m, 3H), 2.08 (s, 31H), 1.73-1.67 (m, 2H), 1.53-1.37 (m, 6H), 1.29-1.05 (m, 7H), 0.82 (t, 3H)
LC-MS m/z 468 multimode+

EXAMPLE 67

Piperidin-4-ylmethyl 2-(4-((2-amino-4-methyl-6-(pentylamino)pyrimidin-5-yl)methyl)phenyl)acetate

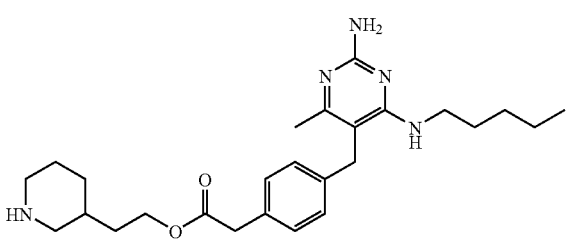

(i) tert-Butyl 4-((2-(4-((2-amino-4-methyl-6-(pentylamino)pyrimidin-5-yl)methyl)phenyl)acetoxy)methyl)piperidine-1-carboxylate The subtitle compound was prepared using the method of example 60 and tert-butyl 4-(hydroxymethyl)piperidine-1-carboxylate to give a crude solid, 237 mg.
LCMS m/z 540 APCI+ve (ii) Piperidin-4-ylmethyl 2-(4-((2-amino-4-methyl-6-(pentylamino)pyrimidin-5-yl)methyl)phenyl)acetate To the product of step (i) (237 mg) in DCM (7 ml), TFA (2 ml) was added and stirred at rt for 7 h. The solvent was removed and the crude product was partitioned between DCM/NaHCO$_3$ (aq), dried and evaporated under reduced pressure. The residue was purified by RPHPLC to give a white solid, 54 mg.
$^1$H NMR DMSOd-6: δ 7.13 (d, 2H), 7.04 (d, 2H), 6.14 (t, 1H), 5.63 (s, 2H), 3.83 (d, 1H), 3.71 (s, 2H), 3.59 (s, 2H), 3.27-3.22 (m, 2H), 2.90-2.84 (m, 2H), 2.41-2.33 (m, 2H) 1.99 (s, 3H), 1.66-1.55 (m, 1H), 1.51-1.40 (m, 4H), 1.27-0.95 (m, 6H), 0.82 (t, 31H)
LC-MS m/z 440 multimode+

EXAMPLE 68

4-(4-(Dimethylamino)piperidin-1-yl)butyl 2-(4-((2-amino-4-methyl-6-(pentylamino)pyrimidin-5-yl)methyl)phenyl)acetate, saccharin salt

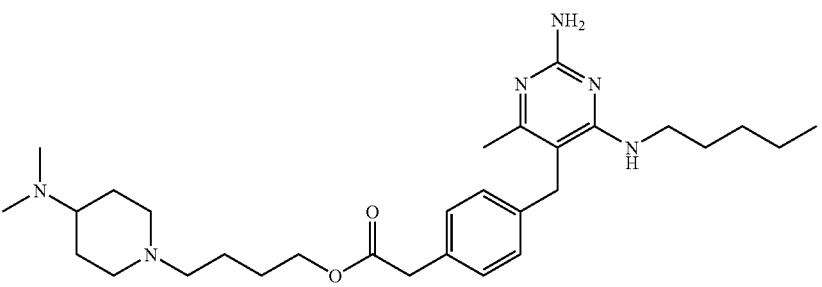

To the product from example 34 step (viii) (250 mg) in DMF (7 ml), 4-(4-(dimethylamino)piperidin-1-yl)butan-1-ol (292 mg) was added followed by Hunig's base and HATU (278 mg) and stirred at rt for 3 h. The product was then purified by RPHPLC, to give a gum (193 mg), this was dissolved in MeCN (6 ml) then saccharin (67 mg) was added and the solvent evaporated under reduced pressure. The residue was triturated with ether, filtered and dried under high vac to give the title compound as a white solid, 156 mg.
$^1$H NMR DMSOd-6: δ 7.66-7.55 (m, 4H), 7.16 (d, 2H), 7.07 (d, 2H), 6.88 (s, 1H), 6.38 (s, 2H), 4.02 (t, 2H), 3.76 (s, 2H), 3.60 (s, 2H), 3.32-3.27 (m, 2H), 2.95 (d, 2H), 2.68-2.60 (m, 1H), 2.33 (brs, 2H), 2.09 (s, 3H), 1.97 (brs, 2H), 1.84 (d, 2H), 1.57-1.39 (m, 8H), 1.26-1.09 (m, 4H), 0.81 (t, 3H)
LC-MS m/z 525 multimode+

EXAMPLE 69

(1-Methylpiperidin-4-yl)methyl 2-(4-((2-amino-4-(butylamino)-6-methylpyrimidin-5-yl)methyl)phenyl)acetate, saccharin salt

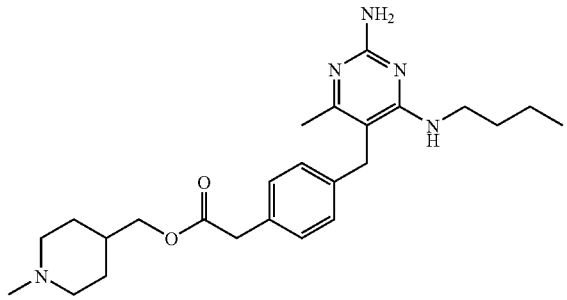

To the product from example 41 step (vi) (140 mg) in DMF (5 ml), (1-methylpiperidin-4-yl)methanol (0.11 g), DMAP (5 mg) and TEA (0.2 ml) were added followed by HAT (195 mg). The mixture was stirred for 18 h then purified by RPHPLC to give a gum (75 mg). The gum was dissolved in MeCN (5 ml), saccharin (31 mg) added and the solvent evaporated under reduced pressure. The residue was triturated with ether and the solid filtered and dried to give the title compound, 80 mg.

$^1$H NMR DMSOd-6: δ 7.66-7.55 (m, 4H), 7.16 (d, 2H), 7.07 (d, 2H), 6.57 (s, 2H), 3.90 (d, 2H), 3.77 (s 2H), 3.62 (s, 2H), 3.34-3.29 (m, 2H), 3.09-3.06 (m, 2H), 2.47 (s, 3H), 2.46-2.36 (m, 2H), 2.09 (s, 3H), 1.70-1.67 (m, 2H), 1.48-1.41 (m, 2H), 1.33-1.13 (m, 4H), 0.83 (t, 3H)

LC-MS m/z 440 multimode+

EXAMPLE 70

(S)-4-(Dimethylamino)butyl 2-(4-((2-amino-4-(1-hydroxypentan-2-ylamino)-6-methylpyrimidin-5-yl)methyl)phenyl)acetate, saccharin salt

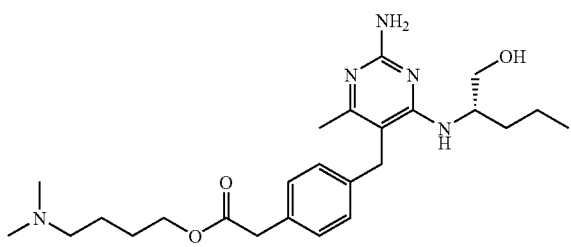

(i) 2-(4-((2-Amino-4-chloro-6-methylpyrimidin-5-yl)methyl)phenyl)acetonitrile

The product from example 41 step (iii) (3.7 g) and POCl$_3$ (30 ml) were heated at 100° C. for 18 h then evaporated under reduced pressure. The residue was diluted with cold water, and neutralised with aq 5M NaOH soln. and heated at 50° C. for 2 h. The subtitle compound was filtered, washed with water and dried under vacuum at 45° C., 1.81 g.

$^1$H NMR DMSOd-6: δ 7.27 (d, 2H), 7.12 (d, 2H), 6.88 (s, 2H), 3.98 (s, 2H), 3.96 (s, 2H), 2.21 (s, 3H)

LC-MS m/z APCI+273

(ii) (S)-2-(4-((2-Amino-4-(1-hydroxypentan-2-ylamino)-6-methylpyrimidin-5-yl)methyl)phenyl)acetic acid To the product of step (i) (0.4 g) in butan-1-ol (3 ml), (S)-(+)-2-amino-1-pentanol (0.5 g) was added and the reaction heated in a microwave, at 160° C. at 100 W for 1.5 h. After cooling, aq. 5M KOH (1 ml) was added and the mixture heated at 100° C. for 48 h. The mixture was cooled and the solvent evaporated under reduced pressure. The residue was purified by RPHPLC to give the TFA salt, which was purified by SCX, eluting with MeCN then 100% aq NH$_3$/MeCN to give the subtitle compound, 174 mg.

LC-MS m/z APCI+372

(iii) (S)-4-(Dimethylamino)butyl 2-(4-((2-amino-4-(1-hydroxyhexan-3-ylamino)-6-methylpyrimidin-5-yl)methyl)phenyl)acetate, 1.75 saccharin salt The title compound was prepared using the method of example 68 and the product of step (ii) with 4-(dimethylamino)butan-1-ol, yield 145 mg.

$^1$H NMR DMSOd-6: δ 7.68-7.58 (m, 8H), 7.19 (d, 2H), 7.11 (d, 2H), 4.37-4.30 (m, 1H), 4.04 (t, 2H), 3.90-3.80 (m, 2H), 3.63 (s, 2H), 3.37-3.29 (m, 2H), 3.06-3.02 (m, 2H), 2.76 (s, 6H), 2.20 (s, 3H), 1.66-1.58 (m, 6H), 1.46-1.40 (m, 2H), 1.09-1.04 (m, 2H), 0.77 (t, 3H)

LC-MS m/z 458 multimode+

EXAMPLE 71

(S)-(1-Methylpiperidin-4-yl)methyl 2-(4-((2-amino-4-(1-hydroxypentan-2-ylamino)-6-methylpyrimidin-5-yl)methyl)-3-methoxyphenyl)acetate, benzenesulfonic acid salt

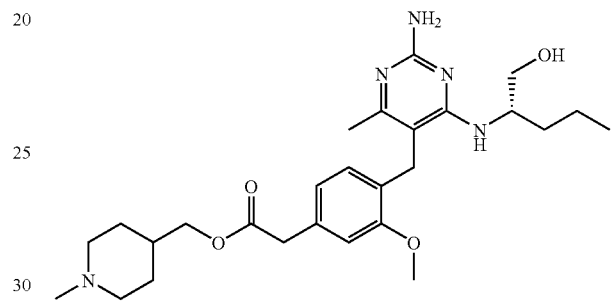

To the product from example 30 step (v) (100 mg) in DMF (3 ml), (1-methylpiperidin-4-yl)methanol (90 mg), TEA (0.17 ml) and DMAP (6.3 mg) were added, followed by T3P (1.57M in THF, 0.24 ml) and stirred at rt for 15 h. The reaction was diluted with EtOAc (10 mL), washed with water, dried, filtered and evaporated under reduced pressure. The crude product was purified by RPHPLC to give the product as a gum, this was dissolved in MeCN (0.5 mL) and benzenesulfonic acid (6.33 mg) was added and the solvent evaporated. The residue was triturated with Et$_2$O to give the title compound as a white solid, 25 mg.

$^1$H NMR DMSOd-6: δ 7.61-7.58 (m, 2H), 7.35-7.28 (m, 3H), 6.91 (s, 1H), 6.78 (d, 1H), 6.73 (d, 1H), 4.70-4.62 (m, 1H), 4.22-4.13 (m, 1H), 3.91 (d, 2H), 3.83 (s, 3H), 3.65 (s, 2H), 3.64 (s, 2H), 3.41-3.35 (m, 4H), 3.13-3.01 (m, 2H), 2.49-2.44 (m, 3H), 2.10 (s, 3H), 1.74-1.66 (m, 3H), 1.55-1.43 (m, 1H), 1.37-1.22 (m, 4H), 1.09 (t, 3H), δ 0.78 (t, 3H)

LC-MS m/z 500 multimode+

EXAMPLE 72

(1-Methylpiperidin-4-yl)methyl 2-(4-((2-amino-4-(butylamino)-6-methylpyrimidin-5-yl)methyl)-3-methoxyphenyl)acetate, bis benzenesulfonic acid salt

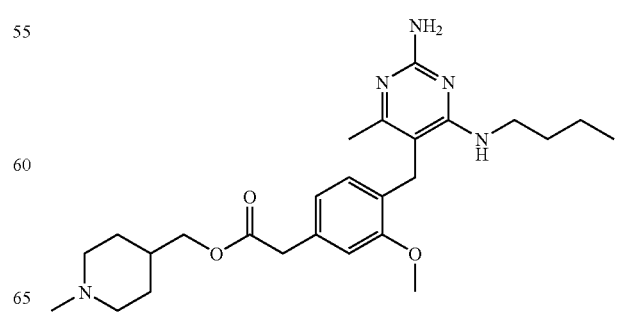

(i) 2-(4-((2-Amino-4-(butylamino)-6-methylpyrimidin-5-yl)methyl)-3-methoxyphenyl)acetic acid To the product of example 30 step (iii) (400 mg) in butan-1-ol (3 ml), butylamine (0.39 mL) was added and the reaction heated in a microwave, at 180° C. for 1 h. The reaction was repeated on an identical scale and the two batches were combined. Aq. 5M KOH (1 ml) was added and the mixture was heated at 100° C. for 36 h. After cooling, the solvent was evaporated under reduced pressure. The residue was diluted with water (5 mL) and the pH adjusted to ~7 using conc. HCl. The resulting precipitate was collected by filtration and the solid suspended in MeCN (10 mL) for 10 min. The suspension was filtered and the collected solid dried under vacuum to give to the subtitle compound as a white solid, 560 mg.
$^1$H NMR DMSOd-6: δ 6.88 (d, 1H), 6.70 (dd, 1.4 Hz, 2H), 6.64 (d, 2H), 6.23-6.18 (m, 1H), 5.91 (s, 1H), 3.83 (s, 3H), 3.59 (s, 2H), 3.49 (s, 2H), 3.27-3.21 (m, 8H), 1.98 (s, 3H), 1.42 (q, 2H), 1.25-1.16 (m, 3H), 0.84 (t, 3H)
LC-MS m/z 359 multimode+

(ii) (1-Methylpiperidin-4-yl)methyl 2-(4-((2-amino-4-(butylamino)-6-methylpyrimidin-5-yl)methyl)-3-methoxyphenyl)acetate, bis benzenesulphonic acid salt The title compound was prepared using the product from step (i) and the method of example 71 to give a white solid, 35 mg.
$^1$H NMR DMSOd-6: δ 11.90 (s, 1H), 7.90-7.86 (m, 1H), 7.62-7.57 (m, 4H), 7.35-7.26 (m, 6H), 6.92 (s, 1H), 6.76-6.72 (m, 2H), 3.92 (d, 2H), 3.83 (s, 3H), 3.67 (s, 2H), 3.65 (s, 2H), 3.46-3.32 (m, 4H), 2.97-2.85 (m, 2H), 2.79-2.73 (m, 2H), 2.52-2.51 (m, 3H), 2.10 (s, 2H), 1.90-1.80 (m, 2H), 1.52-1.30 (m, 4H), 1.28-1.15 (m, 4H), 0.85 (t, 3H)
LC-MS m/z 470 multimode+

EXAMPLE 73

4-(Pyrrolidin-1-yl)butyl 2-(4-((2-amino-4-(butylamino)-6-methylpyrimidin-5-yl)methyl)-3-methoxyphenyl)acetate, benzenesulphonic acid salt

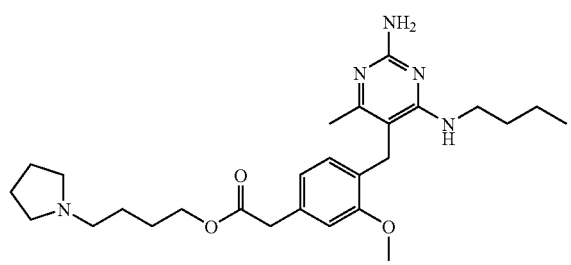

The title compound was prepared using the method of example 72 and 4-(pyrrolidin-1-yl)butan-1-ol to give a gum, 64 mg.
$^1$H NMR DMSOd-6: δ 7.60-7.57 (m, 2H), 7.34-7.28 (m, 3H), 6.90 (s, 1H), 6.72 (d, 1H), 6.68 (d, 1H), 4.04 (t, 2H), 3.84 (s, 3H), 3.62 (s, 2H), 3.61 (s, 2H), 2.92-2.78 (m, 2H), 2.58-2.50 (m, 4H), 2.02 (s, 3H), 1.85-1.75 (m, 4H), 1.65-1.50 (m, 4H), 1.48-1.38 (m, 4H), 1.31-1.14 (m, 4H), 0.84 (t, 3H)
LC-MS m/z 484 multimode+

EXAMPLE 74

(S)-(1-Methylpiperidin-4-yl)methyl 2-(4-((2-amino-4-(1-hydroxyhexan-3-ylamino)-6-methylpyrimidin-5-yl)methyl)-3-fluorophenyl)acetate, saccharin salt

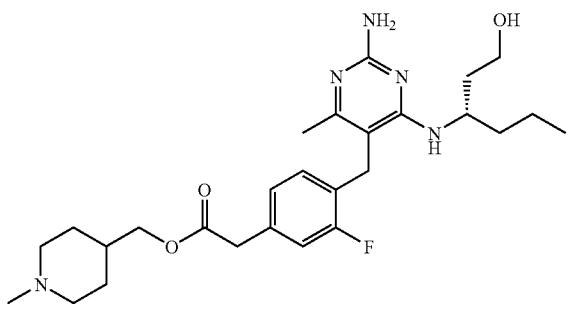

(i) (S)-2-(4-((2-Amino-4-(1-hydroxyhexan-3-ylamino)-6-methylpyrimidin-5-yl)methyl)-3-fluorophenyl)acetonitrile (S)-3-Aminohexan-1-ol (0.966 g) was added to a suspension of the product of example 33 step (iii) (1.2 g) in butan-1-ol (9 mL). The reaction was performed in the CEM Microwave, at 180° C. for 2 h. The solvent was evaporated under reduced pressure and the crude product was purified by flash silica chromatography, to give the subtitle compound as an orange solid, 0.98 g.
$^1$H NMR DMSO-$d_6$: δ 7.17 (dd, 1H), 7.06 (dd, 1H), 6.87 (dd, 1H), 6.01 (d, 1H), 5.91 (s, 2H), 4.44-4.36 (m, 1H), 4.30-4.19 (m, 1H), 4.01 (s, 2H), 3.75 (s, 2H), 3.41-3.23 (m, 2H), 1.96 (s, 3H), 1.65-1.32 (m, 2H), 1.30-1.05 (m, 4H), 0.79 (t, 3H)
LC/MS m/z 372 APCI+

(ii) (S)-2-(4-((2-Amino-4-(1-hydroxyhexan-3-ylamino)-6-methylpyrimidin-5-yl)methyl)-3-fluorophenyl)acetic acid 5M KOH (3 ml) was added to a stirred solution of the product from step (i) (0.98 g) in butan-1-ol (3 mL). The solution was heated to 100° C. for 15 h and then allowed to cool. The solvent was evaporated under reduced pressure and the residue was diluted with water (5 mL). The pH was adjusted to ~7 using conc. HCl and the aqueous was extracted with DCM/MeOH (9:1). The combined organics were evaporated to dryness. The aqueous was also evaporated to dryness and the residue suspended in MeOH (10 mL). The solids were removed by filtration and the filtrate was combined with the residues from the organic extracts and evaporated to dryness to give the subtitle compound as a light brown solid, 0.830 g.
$^1$H NMR DMSO-d6: δ 7.13-6.93 (m, 5H), 6.90-6.82 (m, 1H), 4.41-4.24 (m, 1H), 3.80 (s, 2H), 3.55 (s, 2H), 3.41-3.29 (m, 2H), 2.07 (s, 3H), 1.67-1.54 (m, 1H), 1.48-1.07 (m, 5H), 0.81 (t, 3H)
LC/MS m/z 391 APCI+

(iii) (S)-(1-Methylpiperidin-4-yl)methyl 2-(4-((2-amino-4-(1-hydroxyhexan-3-ylamino)-6-methylpyrimidin-5-yl)methyl)-3-fluorophenyl)acetate, saccharin salt To the product of step (ii) (157 mg) in DCM (1.5 ml)/DMF (1.5 ml), TEA (0.067 ml), DMAP (4.9 mg) and (1-methylpiperidin-4-yl)methanol (156 mg) were added followed by HATU (183 mg) and then stirred at rt for 1 h. The reaction was diluted with water (5 mL) and DCM (5 mL). The organic phase was separated and evaporated under reduced pressure. The crude product was purified by RPHPLC the resulting residue was diluted with methanol (0.5 mL) and saccharin (12.82 mg) was added and the solvent evaporated. The residue was triturated with diethyl ether (0.5 mL) to give the title compound as a colourless foam, 45 mg.

$^1$H NMR DMSOd-6: δ 7.66-7.54 (m, 4H), 7.11 (dd, 1H), 6.98 (dd, 1H), 6.85 (dd, 1H), 4.42-4.25 (m, 2H), 3.92 (d, 2H), 3.78 (s, 2H), 3.68 (s, 2H), 3.44-3.33 (m, 2H), 3.18-3.03 (m, 4H), 2.52-2.52 (m, 31H), 2.02 (s, 3H), 1.77-1.66 (m, 4H), 1.65-1.50 (m, 2H), 1.49-1.38 (m, 1H), 1.36-1.21 (m, 2H), 1.21-1.11 (m, 2H), 0.80 (t, 3H)

LC-MS m/z 502 multimode+

EXAMPLE 75

(S)-Methyl 2-(4-((2-amino-4-(1-hydroxyhexan-3-ylamino)-6-methylpyrimidin-5-yl)methyl)-3-hydroxyphenyl)acetate

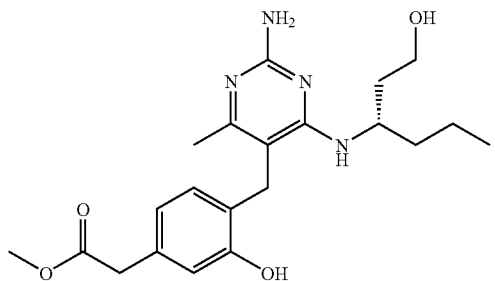

(i) Methyl 2-(benzyloxy)-4-iodobenzoate

A mixture of methyl 2-hydroxy-4-iodobenzoate (22.8 g), benzyl bromide (10.3 ml) and $K_2CO_3$ (22.67 g) in DMF (200 ml) was stirred at rt for 72 h. The mixture was partitioned between diethyl ether and water, the organics separated washed with water, dried and evaporated under reduced pressure to give a white solid, 29.5 g.

$^1$H NMR CDCl$_3$: δ 7.54-7.30 (m, 8H), 5.14 (s, 2H), 3.88 (s, 3H)

LC-MS m/z 369 APCI+

(ii) (2-(Benzyloxy)-4-iodophenyl)methanol

A solution of DIBAL-H (179 mL, 1M) was added to a solution of the product from step (i) (26.4 g) in THF (400 ml) at rt. The mixture was stirred for 3 h then a further 0 ml of DIBAL-H was added and stirred for a further 1 h. The mixture was quenched carefully with EtOAc and then with 2M aq HCl. The mixture was partitioned between ether/2M HCl, the organics were separated, washed with water, dried and evaporated under reduced pressure. The residue was triturated with isohexane and filtered to give the subtitle compound as a solid, 21 g.

LC-MS m/z 341 APCI+

(iii) Methyl 3-(benzyloxy)-4-(hydroxymethyl)benzoate

To a solution of the product from step (ii) (21 g) in MeOH (150 mL), hunig's base (53.9 ml), and dichloro[1,1'-bis(diphenylphosphino)ferrocene]palladium (II) dichloromethane adduct (2.54 g) was added. The resulting mixture was stirred at 90° C. for 16 h under carbon monoxide (4 bar) in a carbonylator. After cooling, the reaction mixture was filtered through a filter disc, evaporated and purified using chromatography, to give the subtitle compound as a white solid, 10 g.

LC-MS m/z 273 APCI+

(iv) Methyl 3-(benzyloxy)-4-(chloromethyl)benzoate

The product of step (iii) (9.5 g) was dissolved in DCM (200 ml), cooled to 0° C. and thionyl chloride (3.57 ml) was added and stirred at rt for 2 h. The solvents were evaporated and the residue taken up in DCM and washed with aq. NaHCO$_3$. The combined organics were dried, filtered and evaporated to give the subtitle compound as a brown oil, 9.60 g.

LC-MS m/z 291 APCI+

(v) Methyl 3-(benzyloxy)-4-(2-(ethoxycarbonyl)-3-oxobutyl)benzoate

The subtitle compound was prepared using the product from step (iv) (9.6 g) and the method of example 34 step (i), to give an oil, 8.6 g.

LC-MS m/z 385 APCI+

(vi) Methyl 4-((2-amino-4-hydroxy-6-methylpyrimidin-5-yl)methyl)-3-(benzyloxy)benzoate The subtitle compound was prepared using the product from step (v) (8.6 g) and the method of example 34 step (ii) to give a solid, 5.87 g.

$^1$H NMR DMSOd-6: δ 7.59-7.37 (m, 7H), 7.37-7.28 (m, 2H), 7.01 (d, 1H), 6.48-6.33 (m, 1H), 5.24 (s, 2H), 3.83 (s, 3H), 3.68 (s, 2H), 1.90 (s, 3H)

LC-MS m/z 380 APCI+

(vii) Methyl 4-((2-amino-4-chloro-6-methylpyrimidin-5-yl)methyl)-3-(benzyloxy)benzoate POCl$_3$ (25 ml) was added to the product from step (vi) (4.8 g) and stirred at 80° C. for 18 h. After cooling, the reaction was evaporated to dryness and the residue diluted with water (100 mL) and neutralized with solid NaHCO$_3$. The mixture was heated at 50° C. for 30 min and left to cool. The subtitle compound was collected by filtration as a solid, 3.78 g.

$^1$H NMR DMSOd-6: δ 7.63-7.29 (m, 8H), 6.93-6.77 (m, 2H), 5.28 (s, 2H), 3.97 (s, 2H), 3.83 (s, 3H), 2.15 (s, 3H)

LC-MS m/z 398 APCI+

(viii)(4-((2-Amino-4-chloro-6-methylpyrimidin-5-yl)methyl)-3-(benzyloxy)phenyl)methanol A solution of DIBAL-H (28.5 ml, 1M in THF) was added portion wise over 30 min to a stirred solution of the product from step (vii) (3.78 g) in THF (40 mL) at −20° C. The mixture was allowed to warm to 0° C. over 2 h and then EtOAc (30 mL) and isopropanol (10 mL) were added. The reaction was poured into a sat. solution of sodium sulfate and stirred for 1 h. The organics were separated, dried, filtered and the solvent evaporated under reduced pressure. The crude product was purified using chromatography to give the subtitle compound as a white solid, 2.60 g.

LC-MS m/z 370 APCI+

(ix) 5-(2-(Benzyloxy)-4-(chloromethyl)benzyl)-4-chloro-6-methylpyrimidin-2-amine Thionyl chloride (0.513 ml) was added to a stirred solution of the product from step (viii) (2.6 g) in DCM (120 mL) at 0° C. The mixture was allowed to warm tort and stirred for 1 h. The reaction mixture was poured into sat. sodium bicarbonate solution (100 mL) and extracted with EtOAc, the combined organics were dried filtered and the solvent evaporated under reduced pressure to give the subtitle compound as a yellow solid, 2.78 g.

LC-MS m/z 389 APCI+

(x) 2-(4-((2-Amino-4-chloro-6-methylpyrimidin-5-yl)methyl)-3-(benzyloxy)phenyl)acetonitrile The subtitle compound was prepared using the product from step (ix) (2.78 g) and the method of example 20 step (vi) to give a solid, 2.1 g.

$^1$H NMR DMSOd-6: δ 7.53-7.29 (m, 5H), 7.10 (d, 1H), 6.89-6.80 (m, 3H), 6.68 (d, 1H), 5.19 (s, 2H), 3.97 (s, 2H), 3.88 (s, 2H), 2.14 (s, 3H)

LC-MS m/z 379 APCI+

(xi) (S)-2-(4-((2-Amino-4-(1-hydroxyhexan-3-ylamino)-6-methylpyrimidin-5-yl)methyl)-3-(benzyloxy)phenyl)acetic acid The subtitle compound was prepared using the product of step (x) (250 mg) and the method of example 72 step (i) with (S)-3-aminohexan-1-ol to give a solid, 250 mg.

LC-MS m/z 479 APCI+

(xii) (S)-2-(4-((2-Amino-4-(1-hydroxyhexan-3-ylamino)-6-methylpyrimidin-5-yl)methyl)-3-hydroxyphenyl)acetic acid The product from step (xi) (250 mg) was dissolved in EtOH (25 mL) and Pd/C (200 mg) in EtOH (5 mL) was added, then the mixture stirred under hydrogen (4 bar) at rt for 16 h. The catalyst was filtered off and the solvent was evaporated. The crude product was purified by RPHPLC to give the subtitle compound as a white solid, 70 mg.

LC-MS m/z 460 APCI+

(xiii)(S)-Methyl 2-(4-((2-amino-4-(1-hydroxyhexan-3-ylamino)-6-methylpyrimidin-5-yl)methyl)-3-hydroxyphenyl)acetate The product from step (xii) (70 mg) was dissolved in MeOH (5 mL) and TMSCl (2 ml) was added and stirred for 1 h. The solvents were evaporated, the residue was purified on RPHPLC to give the title compound as a white solid, 50 mg.

$^1$H NMR DMSOd-6: δ 6.76-6.67 (m, 2H), 6.57-6.48 (m, 1H), 5.60 (s, 2H), 4.22-4.08 (m, 1H), 3.59-3.46 (m, 6H), 2.11 (s, 3H), 1.65-1.51 (m, 1H), 1.51-1.18 (m, 4H), 1.16-1.01 (m, 2H), 0.76 (t, 3H)

LC-MS m/z 403 multimode+

EXAMPLE 76

(S)-(1-Methylpiperidin-4-yl)methyl 2-(4-((2-amino-4-(1-hydroxypentan-2-ylamino)-6-methylpyrimidin-5-yl)methyl)-3-hydroxyphenyl)acetate

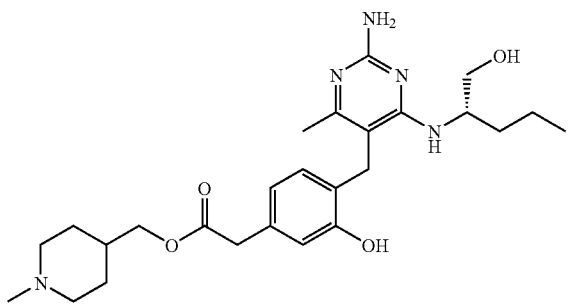

(i) (S)-2-(4-((2-Amino-4-(1-hydroxypentan-3-ylamino)-6-methylpyrimidin-5-yl)methyl)-3-(benzyloxy)phenyl)acetic acid The subtitle compound was prepared using the product of example 75 step (x) (200 mg) and (S)-(+)-2-amino-1-pentanol (188 mg), via the method of example 72 step (i) to give a yellow solid, 100 mg.

LC-MS m/z 479 APCI+

(ii) (S)-(1-Methylpiperidin-4-yl)methyl 2-(4-((2-amino-4-(1-hydroxypentan-2-ylamino)-6-methylpyrimidin-5-yl)methyl)-3-(benzyloxy)phenyl)acetate The subtitle compound was prepared using the product from step (i) (260 mg) and the method of example 71 to give a white solid, 100 mg.

LC-MS m/z 576 APCI+

(iii) (S)-(1-Methylpiperidin-4-yl)methyl 2-(4-((2-amino-4-(1-hydroxypentan-2-ylamino)-6-methylpyrimidin-5-yl)methyl)-3-hydroxyphenyl)acetate The product from step (ii) (100 mg) was dissolved in EtOAc (10 mL) and Pd/C (73.9 mg) in EtOAc (1 mL) was added and the reaction stirred under hydrogen (4 bar) at rt for 16 h. The catalyst was filtered off and the solvents were evaporated. The crude product was purified by RPHPLC to give the title compound as a white solid, 22 mg.

$^1$H NMR DMSOd-6: δ 6.74-6.70 (m, 2H), 6.56 (d, 1H), 5.62-5.54 (m, 3H), 4.14-3.99 (m, 1H), 3.86 (d, 2H), 3.55 (s, 2H), 3.50 (s, 2H), 3.24-3.19 (m, 1H), 2.75-2.62 (m, 2H), 2.15-2.04 (m, 6H), 1.82-1.71 (m, 2H), 1.59-1.43 (m, 4H), 1.34-0.98 (m, 6H), 0.77 (t, 3H)

LC-MS m/z 486 multimode+

EXAMPLE 77

Methyl 2-(4-((2-amino-4-(butylamino)-6-methylpyrimidin-5-yl)methyl)-3-hydroxyphenyl)acetate

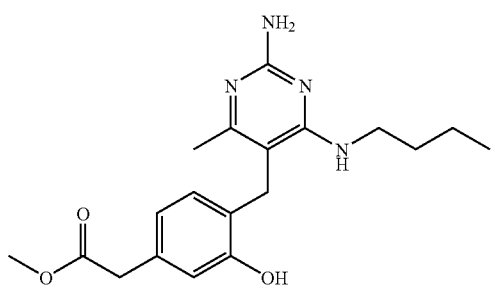

To the product from example 72 step (i) (550 mg) in DCM (20 mL), BBr$_3$ (0.29 ml) was added dropwise and the reaction mixture stirred for 5 h. MeOH (4 mL) was added followed by 4M HCl in dioxane (0.5 mL) and stirred for 16 h and the solvents evaporated. The residue was purified by RPHPLC to give the title compound as a white solid, 8 mg.

$^1$H NMR DMSOd-6: δ 6.73 (d, 1H), 6.69-6.65 (m, 1H), 6.58-6.53 (m, 1H), 6.12-5.98 (m, 1H), 5.59 (d, 2H), 3.58 (s, 3H), 3.55 (s, 2H), 3.51 (s, 2H), 3.24-3.17 (m, 2H), 2.05 (s, 3H), 1.47-1.35 (m, 2H), 1.26-1.15 (m, 3H), 0.84 (t, 3H)

LC-MS m/z 359 multimode+

EXAMPLE 78

(S)-4-(Pyrrolidin-1-yl)butyl 2-(4-((2-amino-4-(1-hydroxyhexan-3-ylamino)-6-methylpyrimidin-5-yl)methyl)-3-hydroxyphenyl)acetate

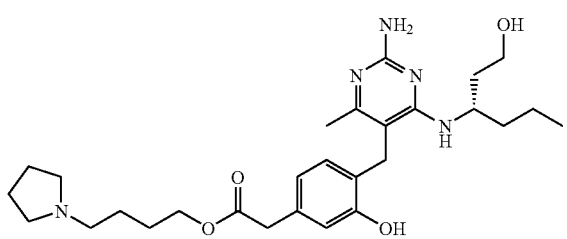

(i) (S)-2-(4-((2-Amino-4-(1-hydroxyhexan-3-ylamino)-6-methylpyrimidin-5-yl)methyl)-3-(benzyloxy)phenyl)acetic acid The subtitle compound was prepared using the product of example 75 step (x) and (S)-3-aminohexan-1-ol, via the method of example 72 step (i) to give a white solid, 300 mg.
LC-MS m/z 479 APCI+

(ii) (S)-4-(Pyrrolidin-1-yl)butyl 2-(4-((2-amino-4-(1-hydroxyhexan-3-ylamino)-6-methylpyrimidin-5-yl)methyl)-3-(benzyloxy)phenyl)acetate, bis trifluoroacetate salt The subtitle compound was prepared using the product of step (i) (154 mg) and 4-(pyrrolidin-1-yl)butan-1-ol (18 mg), via the method of example 74 step (iii). The product was purified by RPHPLC to give the product as the TFA salt, 170 mg.

LC-MS m/z 603 APCI+

(iii) (S)-4-(Pyrrolidin-1-yl)butyl 2-(4-((2-amino-4-(1-hydroxyhexan-3-ylamino)-6-methylpyrimidin-5-yl)methyl)-3-hydroxyphenyl)acetate The title compound was prepared using the product from step (ii) (170 mg) and the method of example 76 step (iii) to give a white solid, 50 mg.

$^1$H NMR DMSOd-6: δ 6.76-6.68 (m, 2H), 6.59-6.54 (m, 1H), 5.69-5.58 (m, 3H), 4.19-4.10 (m, 1H), 4.04-3.95 (m, 2H), 3.55 (s, 2H), 3.49 (s, 2H), 3.42-3.34 (m, 1H), 2.39-2.27 (m, 6H), 2.08 (s, 3H), 1.69-1.49 (m, 7H), 1.47-1.21 (m, 6H), 1.12-1.01 (m, 2H), 0.81-0.70 (m, 3H)

LC-MS m/z 514 multimode+

EXAMPLE 79

4-(Pyrrolidin-1-yl)butyl 2-(4-((2-amino-4-(butylamino)-6-methylpyrimidin-5-yl)methyl)-3-hydroxyphenyl)acetate

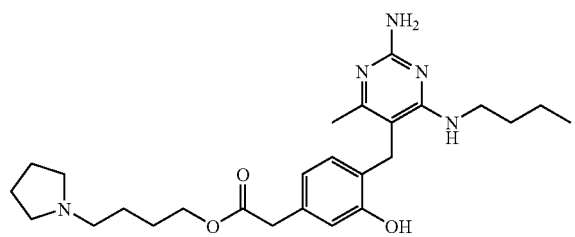

(i) 2-(4-((2-Amino-4-(butylamino)-6-methylpyrimidin-5-yl)methyl)-3-hydroxyphenyl)acetic acid To the product of example 77 (100 mg) in THF (5 mL), LiOH (35.1 mg) in water (5 mL) was added and stirred for 16 h at rt. The solvent was evaporated, the residue redissolved in water and AcOH was added. The precipitate was filtered and dried to give the subtitle compound as a white solid, 50 mg.

LC-MS m/z 345 APCI+

(ii) 4-(Pyrrolidin-1-yl)butyl 2-(4-((2-amino-4-(butylamino)-6-methylpyrimidin-5-yl)methyl)-3-hydroxyphenyl)acetate The title compound was prepared using the product of step (i) (50 mg), 4-(pyrrolidin-1-yl) butan-1-ol (64.2 mg) and the method of example 74 step (iii) to give a tan solid, 9 mg.

$^1$H NMR DMSOd-6: δ 6.75-6.64 (m, 2H), 6.57-6.51 (m, 1H), 5.60 (s, 2H), 4.01 (t, 2H), 3.58-3.51 (m, 2H), 3.52-3.45 (m, 2H), 3.25-3.15 (m, 2H), 2.38-2.24 (m, 6H), 2.05 (s, 3H), 1.68-1.50 (m, 5H), 1.51-1.33 (m, 4H), 1.29-1.11 (m, 3H), 0.84 (t, 3H)

LC-MS m/z 470 multimode+

EXAMPLE 80

(S)-Methyl 2-(3-((2-amino-4-(1-hydroxypentan-2-ylamino)-6-methylpyrimidin-5-yl)methyl)-4-methoxyphenyl)acetate, benzene sulphonic acid salt

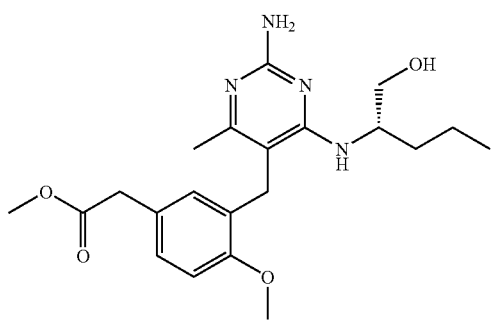

(i) 2-(3-(Bromomethyl)-4-methoxyphenyl)acetic acid

NBS (2.72 g) and AIBN (0.136 g) were added in one portion to a solution of 2-(4-methoxy-3-methylphenyl)acetic acid (2.99 g) in EtOAc (50 ml) and stirred at 80° C. for 2 h. Another portion of AIBN (0.136 g) was added and the suspension stirred for a further 2 h. The reaction mixture was diluted with EtOAc, washed with sat. sodium thiosulfate solution, 2M HCl, water, and sat. brine. The organic phase was dried, filtered and evaporated to afford the subtitle compound, 4.10 g.

LC-MS m/z 260 APCI+

(ii) Methyl 2-(3-(bromomethyl)-4-methoxyphenyl)acetate

Thionyl chloride (1.359 ml) was added dropwise to a solution of the product from step (i) (4.02 g) in MeOH (50 mL), the resulting suspension was stirred at 0° C. for 10 min then warmed to rt for 18 h. The solvent was evaporated and the residue was diluted with EtOAc washed with sat. NaHCO$_3$ and sat. brine. The organic phase was dried, filtered and evaporated. The crude product was purified by chromatography, to give the subtitle compound as a yellow oil, 1.47 g.

LC-MS m/z 274 APCI+

(iii) Ethyl 2-(2-methoxy-5-(2-methoxy-2-oxoethyl)benzyl)-3-oxobutanoate

The title compound was prepared using the product of step (ii) (1.2 g) and the method of example 34 step (i) to give a solid, 0.52 g.

$^1$H NMR DMSOd-6: δ 7.09 (dd, 1H), 6.96 (d, 1H), 6.90 (d, 1H), 4.08-3.99 (m, 3H), 3.77 (s, 3H), 3.58 (s, 3H), 3.54 (s, 2H), 3.03 (dd, 1H), 2.90 (dd, 1H), 2.15 (s, 3H), 1.10 (t, 3H)

LC-MS m/z 323 APCI+

(iv) Methyl 2-(3-((2-amino-4-hydroxy-6-methylpyrimidin-5-yl)methyl)-4-methoxyphenyl)acetate Guanidine carbonate (0.443 g) was added to a solution of the product from step (iii) (0.52 g) in MeOH (10 ml) and stirred at 50° C. for 15 h. The solvent was evaporated and the residue stirred in EtOAc (10 mL) and water (10 mL), the resulting solid was filtered off. Further product was collected by evaporation of the filtrate, the solids were combined to give the subtitle compound as a yellow solid, 0.607 g.

$^1$H NMR DMSOd-6: δ 7.01 (dd, 1H), 6.88 (d, 1H) 6.73 (d, 1H), 6.33 (s, 2H), 3.80 (s, 3H), 3.55 (s, 2H), 3.54 (s, 2H), 3.49 (s, 3H), 1.92 (s, 3H)

LC-MS m/z 318 APCI+

(v) Methyl 2-(3-((2-amino-4-(mesitylsulfonyloxy)-6-methylpyrimidin-5-yl)methyl)-4-methoxyphenyl)acetate The subtitle compound was prepared using the product from step (iv) (0.55 g) and the method of example 34 step (iii) to give a solid, 0.6 g.

$^1$H NMR DMSOd-6: δ 7.08-7.06 (m, 3H), 6.90 (d, 1H), 6.58 (d, 1H), 6.46 (s, 2H), 3.77 (s, 3H), 3.66 (s, 2H), 3.55 (s, 3H), 3.48 (s, 2H), 2.47 (s, 6H), 2.28 (s, 3H), 2.15 (s, 3H)

LC-MS m/z 500 APCI+

(vi) (S)-2-(3-((2-Amino-4-(1-hydroxypentan-2-ylamino)-6-methylpyrimidin-5-yl)methyl)-4-methoxyphenyl)acetic acid (S)-(+)-2-Amino-1-pentanol (100 mg) was added to a suspension of the product from step (v) (243 mg) in butan-1-ol (2 mL). The reaction was heated in a microwave at 160° C. for 2 h. 5M KOH (0.5 mL) was added and the mixture heated in a microwave at 100° C. for 1 h. The solvent was evaporated under reduced pressure and the residue purified by RPHPLC to give the subtitle compound as a white solid, 60 mg.

LC-MS m/z 389 APCI+

(vii) (S)-Methyl 2-(3-((2-amino-4-(1-hydroxypentan-2-ylamino)-6-methylpyrimidin-5-yl)methyl)-4-methoxyphenyl)acetate, benzene sulphonic acid salt The title compound was prepared using the product from step (vi) (50 mg) and the method of example 34 step (ix) to give a white solid, 36 mg.

$^1$H NMR DMSOd-6: δ 7.62-7.56 (m, 2H), 7.36-7.22 (m, 6H), 7.11 (dd, 1H), 6.97 (d, 1H), 6.79 (d, 1H), 4.74 (t, 1H), 4.33-4.21 (m, 1H), 3.83 (s, 3H), 3.72 (s, 2H), 3.56 (s, 3H), 3.53 (s, 2H), 3.44-3.33 (m, 2H), 2.16 (s, 3H), 1.59-1.44 (m, 1H), 1.42-1.29 (m, 1H), 1.17-1.04 (m, 2H), 0.79 (t, 3H)

LC-MS m/z 403 multimode+

EXAMPLE 81

(S)-(1-Methylpiperidin-4-yl)methyl 2-(4-((2-amino-4-(2-hydroxybutylamino)-6-methylpyrimidin-5-yl)methyl)phenyl)acetate, saccharin salt

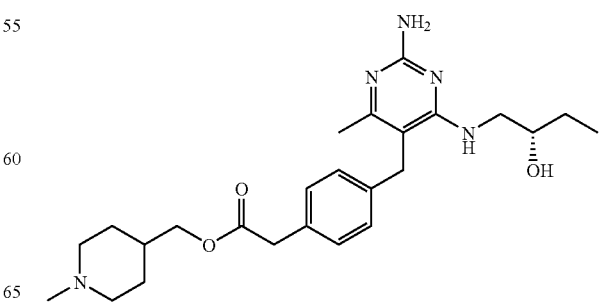

(i) Methyl 2-(4-(cyanomethyl)benzyl)-3-oxobutanoate

A stirred mixture of methyl 3-hydroxy-2-methylenebutanoate (19.5 g), 2-(4-bromophenyl)acetonitrile (40 g), PdOAc$_2$ (2 g), tetrabutylammonium bromide (40 g) and NaHCO$_3$ (31.5 g) in THF (300 ml) was heated under N$_2$ at reflux for 24 h. The mixture was cooled, diluted with ether (500 ml) and filtered through celite. The filtrate was washed with water, dried and evaporated under reduced pressure to give an oil, used crude in next step.
LC-MS m/z 244 APCI−

(ii) 2-(4-((2-Amino-4-hydroxy-6-methylpyrimidin-5-yl)methyl)phenyl)acetonitrile A mixture of the crude product from step (i) and guanidine (16 g) in EtOH (350 ml) was heated under reflux for 5 h. The mixture was cooled, neutralised with acetic acid, and the solid filtered and dried, 22.1 g.
$^1$H NMR DMSOd-6 δ 10.91 (brs, 1H), 7.20-7.17 (m, 4H), 6.38 (s, 2H), 3.95 (s, 2H), 3.63 (s, 2H), 2.00 (s, 3H)
LC-MS m/z 255 APCI+

(ii) 2-(4-((2-Amino-4-chloro-6-methylpyrimidin-5-yl)methyl)phenyl)acetonitrile The subtitle compound was prepared using the product from step (ii) (4 g) and the method of example 75 step (vii) to give a solid, 3.2 g.
LC-MS m/z 274 APCI+

(iv) (E)-N'-(4-Chloro-5-(4-(cyanomethyl)benzyl)-6-methylpyrimidin-2-yl)-N,N-dimethylformamide N,N-Dimethylformamide dimethyl acetal (0.147 ml) was added to a stirred suspension of the product from step (iii) (200 mg) in toluene (3 mL). The mixture was heated at 110° C. for 3 h and then the solvent evaporated under reduced pressure to give the subtitle compound as a brown oil, 240 mg.
$^1$H NMR DMSOd-6: δ 8.58 (s, 2H), 7.27 (d, 2H), 7.24 (d, 2H), 7.17 (d, 2H), 7.13 (d, 2H), 4.05 (s, 2H), 3.98 (s, 2H), 3.32 (s, 4H), 3.14 (s, 6H), 3.02 (s, 6H), 2.32 (s, 3H), 2.30 (s, 3H)
LC-MS m/z 328 APCI+

(v) (S)-5-Ethyloxazolidin-2-one

4-Nitrobenzoic acid (0.348 g) was added to a stirred solution of (R,R)-(−)-N,N'-bis(3,5-di-t-butylsalicylid-ene)-1,2-cyclohexanediaminocobalt(II) (0.628 g) in MTBE (10 mL). Urethane (3.09 g) and 2-ethyloxirane (6.02 ml) was added and the mixture stirred for 18 h at rt. The solution was then added portionwise to a suspension of sodium hydride (2.77 g) in THF (50 mL) and stirred for 3 h and then sat. NH$_4$Cl was added. The organic phase was washed with brine, dried, filtered and evaporated under reduced pressure. The crude product was purified using chromatography, to afford the subtitle compound as a white solid, 1 g.
$^1$H NMR DMSOd-6: δ 5.34 (s, 1H), 4.66-4.53 (m, 1H), 3.67 (dd, 1H), 3.25 (dd, 1H), 1.88-1.65 (m, 2H), 1.02 (t, 3H)

(vi) (S,E)-N'-(5-(4-(Cyanomethyl)benzyl)-4-(5-ethyl-2-oxooxazolidin-3-yl)-6-methylpyrimidin-2-yl)-N,N-dimethylformimidamide Palladium(II) acetate (8.22 mg) and 9,9-dimethyl-4,5-bis(diphenylphosphino)xanthene (42.4 mg) were added to dioxane (3 mL) and the solution stirred at rt for 10 min. The product from step (iv) (240 mg), (S)-5-ethyloxazolidin-2-one (169 mg) and K$_2$CO$_3$ (202 mg) were added and the mixture heated at 100° C. for 1 h. The solvent was evaporated under reduced pressure and the crude product was purified using chromatography, to give the subtitle compound as a white solid, 136 mg.
$^1$H NMR DMSOd-6: δ 8.59 (s, 1H), 7.24 (d, 2H), 7.02 (d, 2H), 4.49-4.37 (m, 1H), 3.97 (s, 2H), 3.96 (s, 2H), 3.17 (t, 2H), 3.12 (s, 3H), 3.01 (s, 3H), 2.32 (s, 3H), 1.54-1.42 (m, 2H), 0.84 (t, 3H)
LC-MS m/z 407 APCI+

(vii) (S)-2-(4-((2-Amino-4-(2-hydroxybutylamino)-6-methylpyrimidin-5-yl)methyl)phenyl)acetic acid Aq. 5M KOH (1 ml) was added to a stirred solution of the product from step (vi) (136 mg) in butan-1-ol (2 mL). The solution was heated at 100° C. for 15 h and the solvent evaporated under reduced pressure. The residue was diluted with MeOH (2 mL) and the pH adjusted to ~7 using acetic acid. The solution was purified by RPHPLC to give the subtitle compound as a white solid, 55 mg.
$^1$H NMR DMSOd-6: δ 7.06 (d, 2H), 6.93 (d, 2H), 5.94 (t, 1H), 5.70 (s, 2H), 3.67 (s, 2H), 3.41-3.29 (m, 2H), 3.18-3.06 (m, 3H), 2.03 (s, 3H), 1.38-1.17 (m, 2H), 0.83 (t, 3H)
LC-MS m/z 345 APCI+

(viii) (S)-(1-Methylpiperidin-4-yl)methyl 2-(4-((2-amino-4-(2-hydroxybutylamino)-6-methylpyrimidin-5-yl)methyl)phenyl)acetate, saccharin salt The title compound was prepared using the product from step (vii) and the method of example 74 step (iii) to give a white solid, 20 mg.
$^1$H NMR DMSOd-6: δ 7.65-7.61 (m, 1H), 7.60-7.55 (m, 3H), 7.15 (d, 2H), 7.07 (d, 2H), 4.78-4.72 (m, 1H), 3.90 (d, 2H), 3.75 (s, 2H), 3.62 (s, 2H), 3.52-3.45 (m, 2H), 3.23-3.16 (m, 2H), 3.06-2.93 (m, 2H), 2.43-2.36 (m, 3H), 2.06 (s, 3H), 1.71-1.60 (m, 4H), 1.35-1.14 (m, 5H), 0.82 (t, 3H)
LC-MS m/z 454 multimode+

EXAMPLE 82

4-(Pyrrolidin-1-yl)butyl 2-(4-((2-amino-4-(butylamino)-6-methylpyrimidin-5-yl)methyl)phenyl)acetate, saccharin salt

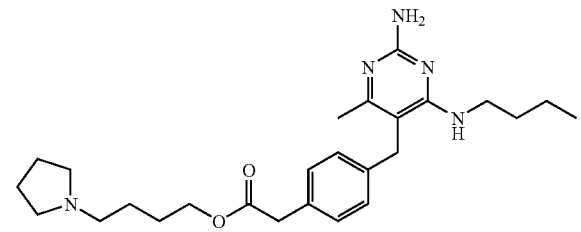

To a mixture of the product of example 41 step (vi) (240 mg) in DMF (10 ml), 4-(pyrrolidin-1-yl)butan-1-ol (209 mg) and Hunig's base (0.4 ml) were added followed by HATU (278 mg), and the mixture was stirred for 24 h then purified by RPHPLC. The product was dissolved in MeCN (5 ml) and saccharin (80 mg) added and the solvent evaporated under reduced pressure. The residue was triturated with ether and filtered to give the title compound as a solid, 195 mg.

$^1$H NMR DMSO-d6: δ 7.66-7.56 (m, 4H), 7.16 (d, 2H), 7.07 (d, 2H), 6.84 (s, 1H), 6.34 (s, 2H), 4.03 (t, 2H), 3.76 (s, 2H), 3.61 (s, 2H), 3.32-3.28 (m, 2H), 2.96-2.80 (m, 6H), 2.08 (s, 3H), 1.92 (s, 4H), 1.82 (s, 4H), 1.48-1.40 (m, 2H), 1.23-1.14 (m, 2H), 0.83 (t, 3H)

LC-MS m/z 454 multimode+

EXAMPLE 83

(1-Methylpiperidin-4-yl)methyl 2-(3-((2-amino-4-(butylamino)-6-methylpyrimidin-5-yl)methyl)-4-methoxyphenyl)acetate

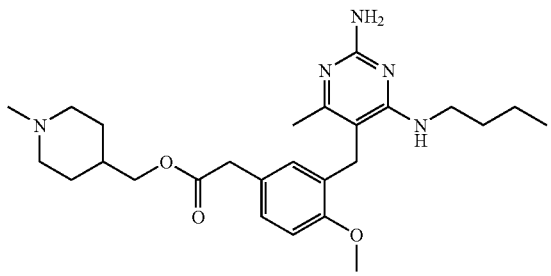

(i) Methyl 2-(5-(cyanomethyl)-2-methoxybenzyl)-3-oxobutanoate

N,N-dimethylacetamide (200 mL) was added to Pd-118 (1.009 g) and tetrabutylammonium chloride hydrate (0.916 g), followed by 2-(3-bromo-4-methoxyphenyl)acetonitrile (7 g). Methyl 3-hydroxy-2-methylenebutyrate (5.64 mL) and dicyclohexylamine (9.25 mL) were added and the solution was heated at 80° C. for 3 days. The reaction mixture was diluted with EtOAc (200 mL) and extracted with water. The organic phase was dried, filtered and evaporated under reduced pressure. The crude product was purified by chromatography to afford the subtitle compound as an orange oil, 5.01 g.

LC-MS m/z 276 APCI+

(ii) 2-(3-((2-Amino-4-hydroxy-6-methylpyrimidin-5-yl)methyl)-4-methoxyphenyl)acetonitrile Guanidine carbonate (5 g) was added to a stirred solution of the product from step (i) (5.01 g) in MeOH (80 mL). The suspension was heated at 50° C. for 15 h and then the solvent evaporated under reduced pressure. The residue was diluted with water (20 mL) and diethyl ether (20 mL). The resulting precipitate was collected by filtration and the solid was dried under vacuum to give the subtitle compound as an orange solid, 2.8 g.

$^1$H NMR DMSO-d6: δ7.11 (dd, 1H), 6.95 (d, 1H), 6.81 (d, 1H), 6.46 (s, 2H), 3.86 (s, 2H), 3.82 (s, 3H), 3.56 (s, 2H), 1.93 (s, 3H)

LC-MS m/z 285 APCI+

(iii) 2-(3-((2-Amino-4-chloro-6-methylpyrimidin-5-yl)methyl)-4-methoxyphenyl)acetonitrile The product from step (ii) (2.8 g) was added to POCl$_3$ (25 ml) and heated at 90° C. for 15 h and then evaporated under reduced pressure. The residue was diluted with ice/water (20 mL) and the mixture adjusted to pH ~7 with sodium bicarbonate. The mixture was heated at 50° C. for 1 h and the precipitate collected by filtration. The solid was dried under vacuum to give the subtitle compound as a brown solid, 2.88 g.

LC-MS m/z 303 APCI+

(iv) 2-(3-((2-Amino-4-(butylamino)-6-methylpyrimidin-5-yl)methyl)-4-methoxyphenyl)acetic acid Butylamine (0.393 mL) was added to a stirred suspension of the product from step (iii) (0.4 g) in butan-1-ol (3 mL) and heated in a microwave, at 150° C. for 1 h. The reaction was repeated on an identical scale and the two batches were combined. 5M KOH (3 mL) was added and the mixture was heated at 100° C. for 48 h. The solvent was evaporated under reduced pressure and the residue diluted with water (5 mL). The pH was adjusted to ~7 using conc. HCl and the precipitate was collected by filtration then dried under vacuum to give the subtitle compound, 0.7 g.

LC-MS m/z 359 APCI+

(v) Methyl 2-(3-((2-amino-4-(butylamino)-6-methylpyrimidin-5-yl)methyl)-4-methoxyphenyl)acetate 4M HCl in dioxane (1 mL) was added to a stirred suspension of the product from step (iv) (650 mg) in MeOH (2 mL). The suspension was heated at 60° C. for 2 h. The solvent was evaporated under reduced pressure to give the subtitle compound as a brown solid, 630 mg.

LC-MS m/z 373 APCI+

(vi) (1-Methylpiperidin-4-yl)methyl 2-(3-((2-amino-4-(butylamino)-6-methylpyrimidin-5-yl)methyl)-4-methoxyphenyl)acetate 4M HCl in dioxane (1.5 mL) was added to a mixture of the product from step (v) (300 mg) and (1-methylpiperidin-4-yl)methanol (520 mg). The suspension was heated at 80° C. for 24 h and the solvent evaporated under reduced pressure. The residue was purified by RPHPLC to give the title compound as a gum, 10 mg.

$^1$H NMR DMSO-d6: δ7.05 (d, 1H), 6.93 (d, 1H), 6.65 (s, 1H), 5.98 (t, 1H), 5.69 (s, 2H), 3.84-3.79 (m, 5H), 3.60 (s, 2H), 3.47 (s, 2H), 3.28-3.19 (m, 2H), 2.76-2.71 (m, 2H), 2.13 (s, 3H), 1.98 (s, 3H), 1.82-1.72 (m, 2H), 1.57-1.35 (m, 5H), 1.26-1.04 (m, 4H), 0.84 (t, 3H)

LC-MS m/z 470 multimode+

EXAMPLE 84

4-(Pyrrolidin-1-yl)butyl 2-(3-((2-amino-4-methyl-6-(pentylamino)pyrimidin-5-yl)methyl)phenyl)acetate, saccharin salt

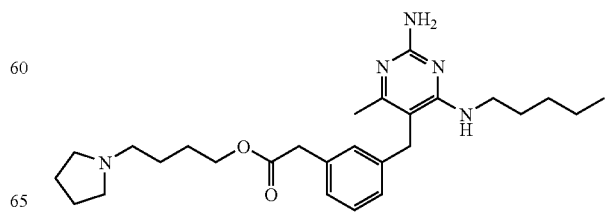

(i) Methyl 2-(3-(cyanomethyl)benzyl)-3-oxobutanoate

A stirred mixture of methyl 3-hydroxy-2-methylenebutanoate (11.37 ml), 2-(3-bromophenyl)acetonitrile (22 g) PdOAc$_2$ (3.15 g), tetrabutylammonium bromide (30.1 g) and NaHCO$_3$ (19.64 g) in THF (40 ml) was heated at reflux for 24 h. The mixture was partitioned between ether and water, the organics separated, washed with water, dried and evaporated under reduced pressure to give the subtitle compound, 22 g.
LC-MS m/z 244 APCI−

(ii) 2-(3-((2-Amino-4-hydroxy-6-methylpyrimidin-5-yl)methyl)phenyl)acetonitrile The title compound was prepared using the method of example 83 step (ii) and the product of step (i) (22 g) to give the title compound as a gum, 16.2 g.
LC-MS m/z 255 APCI+

(iii) 2-(3-((2-Amino-4-chloro-6-methylpyrimidin-5-yl)methyl)phenyl)acetonitrile The title compound was prepared using the method of example 83 step (iii) and the product of step (ii) (3 g) to give the title compound as a solid, 1.76 g.
LC-MS m/z 273 APCI+

(iv) 2-(3-((2-Amino-4-methyl-6-(pentylamino)pyrimidin-5-yl)methyl)phenyl)acetonitrile The product from step (iii) (Ig) was combined with butan-1-ol (25 mL) and pentan-1-amine (4 mL) was added. The reaction mixture was heated to 110° C. for 18 h. The solvents were evaporated and the product purified using chromatography to give the subtitle compound as an orange oil, 600 mg.
LC-MS m/z 324 APCI+

(v) 2-(3-((2-Hydroxy-4-methyl-6-(pentylamino)pyrimidin-5-yl)methyl)phenyl)acetic acid The product from step (iv) (600 mg) was dissolved in butan-1-ol (50 mL) and aq. 5M KOH (2 mL) was added. The reaction was heated in a microwave for 8 h at 160° C. The solvents were evaporated and the product purified by RPHPLC to give the subtitle compound as a solid, 252 mg.
$^1$H NMR DMSO-d6: δ7.20-7.12 (m, 1H), 7.03 (d, 2H), 6.92 (d, 1H), 6.23 (s, 1H), 5.81 (s, 2H), 3.71 (s, 2H), 3.40 (s, 2H), 3.28-3.18 (m, 2H), 2.00 (s, 3H), 1.49-1.39 (m, 2H), 1.29-1.19 (m, 2H), 1.20-1.09 (m, 2H), 0.82 (t, 3H)
LC-MS m/z 343 APCI+

(vi) 4-(Pyrrolidin-1-yl)butyl 2-(3-((2-amino-4-methyl-6-(pentylamino)pyrimidin-5-yl)methyl)phenyl) acetate, saccharin salt The title compound was prepared using the method of example 82 and the product from step (v) (115 mg) and 4-(pyrrolidin-1-yl)butan-1-ol (96 mg) to give a white solid, 29 mg.
$^1$H NMR DMSO-d6: δ7.66-7.53 (m, 1H), 7.26-7.19 (m, 4H), 7.11-7.06 (m, 1H), 7.05-6.99 (m, 1H), 4.07-3.98 (m, 2H), 3.79 (s, 2H), 3.61 (d, 3H), 3.11-3.02 (m, 4H), 3.02-2.93 (m, 2H), 2.13 (d 4H), 1.88 (s, 4H), 1.66-1.54 (m, 4H), 1.52-1.41 (m, 2H), 1.30-1.19 (m, 2H), 1.19-1.07 (m, 2H), 0.82 (t, 3H)
LC-MS m/z 468 multimode+

EXAMPLE 85

(1-Methylpiperidin-4-yl)methyl 2-(3-((2-amino-4-methyl-6-(pentylamino)pyrimidin-5-yl)methyl)phenyl)acetate

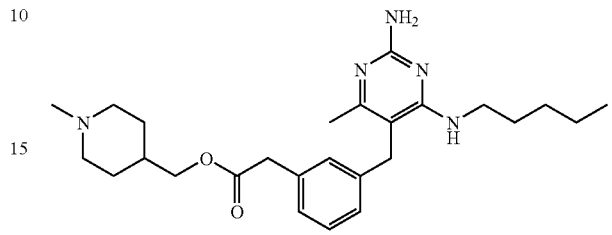

The title compound was prepared using the method of example 82 using the product of example 84 step (v) (115 mg) and (1-methylpiperidin-4-yl)methanol (87 mg) to give a solid, 19 mg.
$^1$H NMR DMSO-d6: δ7.22-7.17 (m, 1H), 7.07-6.96 (m, 3H), 6.17-6.11 (m, 1H), 5.63 (s, 2H), 3.88-3.83 (m, 2H), 3.71 (s, 2H), 3.59 (s, 2H), 3.27-3.21 (m, 2H), 2.74-2.67 (m, 2H), 2.12 (s, 3H), 1.99 (s, 3H), 1.81-1.73 (m, 2H), 1.57-1.40 (m, 5H), 1.27-1.11 (m, 6H), 0.82 (t, 3H)
LC-MS m/z 454 multimode+

EXAMPLE 86

(S)-4-(Dimethylamino)butyl 2-(4-((2-amino-4-(1-hydroxyhexan-3-ylamino)-6-methylpyrimidin-5-yl)methyl)-3-fluorophenyl)acetate, saccharin salt

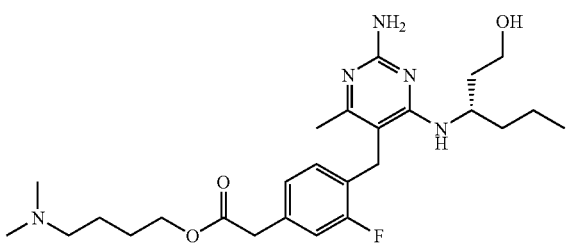

The title compound was prepared using the method of example 74 and 4-(dimethylamino)butan-1-ol to give a white solid, 9 mg.
$^1$H NMR DMSO-d6: δ7.67-7.54 (m, 51H), 7.10 (dd, 1H), 6.97 (dd, 1H), 6.82 (dd, 1H), 6.28 (s, 1H), 6.15 (s, 2H), 4.44-4.33 (m, 1H), 4.32-4.22 (m, 1H), 4.03 (t, 2H), 3.75 (s, 2H), 3.66 (s, 2H), 3.46-3.38 (m, 2H), 2.36 (s, 6H), 1.99 (s, 3H), 1.66-1.34 (m, 10H), 1.21-1.10 (m, 2H), 0.80 (t, 3H)
LC-MS m/z 490 multimode+

EXAMPLE 87

(S)-4-(4-Methylpiperazin-1-yl)butyl 2-(4-((2-amino-4-(1-hydroxyhexan-3-ylamino)-6-methylpyrimidin-5-yl)methyl)-3-fluorophenyl)acetate, saccharin salt The title compound was prepared using the method of example 74 and 4-(4-methylpiperazin-1-yl)butan-1-ol to give a foam, 63 mg.

$^1$H NMR DMSO-d6: δ7.65-7.55 (m, 4H), 7.11 (dd, 1H), 6.98 (dd, 1H), 6.86 (dd, 1H), 6.77-6.62 (m, 2H), 4.42-4.27 (m, 2H), 4.03 (t, 2H), 3.79 (s, 2H), 3.66 (s, 2H), 3.53-3.36 (m, 2H), 2.65-2.54 (m, 2H), 2.40-2.29 (m, 11H), 2.05 (s, 3H), 1.65-1.50 (m, 4H), 1.50-1.35 (m, 4H), 1.22-1.07 (m, 2H), 0.80 (t, 3H)

LC-MS m/z 545 multimode+

EXAMPLE 88

(S)-Methyl 2-(4-((2-amino-4-(1-hydroxypentan-2-ylamino)-6-methylpyrimidin-5-yl)methyl)-3-hydroxyphenyl)acetate (i) (S)-2-(4-((2-Amino-4-(1-hydroxypentan-2-ylamino)-6-methylpyrimidin-5-yl)methyl)-3-hydroxyphenyl)acetic acid To the product from example 30 step (v) (250 mg) in DMF (20 ml), sodium thiomethoxide (180 mg) was added and stirred at 100° C. for 16 h. The solvents were evaporated, and crude product purified by RPHPLC to give the subtitle compound as a colourless gum, 120 mg.

LC/MS m/z 375 APCI+

(ii) (S)-Methyl 2-(4-((2-amino-4-(1-hydroxypentan-2-ylamino)-6-methylpyrimidin-5-yl)methyl)-3-hydroxyphenyl)acetate The product from step (i) (120 mg) was dissolved in MeOH (10 mL) and TMS-Cl (0.205 ml) was added and stirred at rt overnight. The crude product was purified by RPHPLC to give the title compound as a white solid, 35 mg.

$^1$H NMR DMSOd-6: δ6.74-6.70 (m, 2H), 6.56 (dd, 1H), 5.62-5.54 (m, 3H), 4.11-4.01 (m, 1H), 3.59-3.53 (m, 5H), 3.52-3.48 (m, 2H), 3.40-3.32 (m, 1H), 3.30-3.17 (m, 1H), 2.10 (s, 3H), 1.55-1.45 (m, 1H), 1.33-1.21 (m, 2H), 1.15-0.99 (m, 2H), 0.76 (t, 3H).

LC-MS m/z 389 multimode+

EXAMPLE 89

2-Hydroxyethyl 2-(4-((2-amino-4-(butylamino)-6-methylpyrimidin-5-yl)methyl)-3-methoxyphenyl)acetate (i) Methyl 4-((2-amino-4-chloro-6-methylpyrimidin-5-yl)methyl)-3-methoxybenzoate The product from example 21 step (ii) (7 g) was added portion wise over 5 min to POCl$_5$ (32 ml) and heated at 100° C. for 20 h and then allowed to cool. The solvent was removed under reduced pressure and the residue was cautiously diluted with ice water (100 mL) and adjusted to pH ~7 using NaHCO$_3$ and then heated at 50° C. for 1 h. The precipitate was collected by filtration and dried under vacuum to give the subtitle compound as a cream solid, 3 g.

LC/MS m/z 322 APCI+

(ii) Methyl 4-((2-amino-4-(butylamino)-6-methylpyrimidin-5-yl)methyl)-3-methoxybenzoate A stirred mixture of the product from step (i) (8 g) and butylamine (7.40 ml) in dioxane (100 ml) was heated at 90° C. for 72 h. More butylamine (7.40 ml) was added and the reaction mixture stirred for a further 70 hrs. The solvent was evaporated and the crude product was purified by chromatography (5% MeOH/DCM) to afford the subtitle compound as a tan solid, 4.5 g.

$^1$H NMR DMSO d-6: δ 7.51-7.45 (m, 2H), 7.39-7.22 (m, 1H), 6.89 (d, 1H), 6.87-6.70 (m, 2H), 3.91 (d, 3H), 3.84 (s, 3H), 3.73 (s, 2H), 2.03 (s, 3H), 1.51-1.38 (m, 2H), 1.27-1.13 (m, 2H), 0.84 (t, 3H).

LC/MS m/z 359 APCI+

(iii) (4-((2-Amino-4-(butylamino)-6-methylpyrimidin-5-yl)methyl)-3-methoxyphenyl)methanol A solution of DIBAL-H (80 ml, 1M in hexanes) was added portion wise over 20 min to a stirred solution of the product from step (ii) (3.8 g) in THF (25 mL) at 0° C. The mixture was allowed to warm to rt, stirred for 2 h, then cooled to 0° C. Isopropanol (2 mL) was added, stirred for 10 min and then added to a saturated solution of sodium sulfate (50 mL). The mixture was diluted with DCM (100 mL) and then stirred for 1 h. The organic phase was separated and the aqueous was extracted with DCM. The combined organic extracts were dried and filtered. The crude product was purified via silica chromatography (10% MeOH/DCM) to give the subtitle compound as a cream solid, 2.2 g.

LC/MS m/z 331 APCI+

(iv) N4-Butyl-5-(4-(chloromethyl)-2-methoxybenzyl)-6-methylpyrimidine-2,4-diamine The product from step (iii) (2.2 g) in DCM (100 mL) was cooled to 0° C. and SOCl$_2$ (0.486 ml) was added dropwise. The reaction was allowed to warm up to rt over 1 hr, and poured cautiously into sat. NaHCO$_3$ and the aqueous phase was separated. The organic phase was dried, filtered and the solvent evaporated under reduced pressure to give the subtitle compound as a yellow solid, 2.260 g.

LC/MS m/z 349 APCI+

(v) 2-(4-((2-Amino-4-(butylamino)-6-methylpyrimidin-5-yl)methyl)-3-methoxyphenyl)acetonitrile KCN (0.844 g) was added to a stirred solution of the product from step (iv) (2.78 g) in DMF (10 mL) and DMSO (10 mL). The mixture was stirred at rt for 15 h. The reaction mixture was diluted with EtOAc (100 mL) and sat. NaHCO$_3$ (100 mL). The organic phase was separated, dried and solvent removed to give the subtitle compound as a solid, 2.2 g.

LC/MS m/z 340 APCI+

(vi) 2-(4-((2-Amino-4-(butylamino)-6-methylpyrimidin-5-yl)methyl)-3-methoxyphenyl)acetic acid The product from step (v) (2.1 g) was dissolved in butan-1-ol (20 mL) and aq. 5M KOH (3.71 ml) was added and the mixture was heated at 100° C. for 36 h. The mixture was allowed to cool and the solvent was evaporated under reduced pressure. The residue was diluted with water (5 mL) and the pH adjusted to ~7 using conc HCl. The resulting precipitate was collected by filtration and the solid was then suspended in MeCN (10 mL) for 10 min. The suspension was filtered and the solid dried under vacuum overnight to give the subtitle compound as a white solid, 2.60 g.

LC/MS m/z 359 APCI+

(vii) 2-Hydroxyethyl 2-(4-((2-amino-4-(butylamino)-6-methylpyrimidin-5-yl)methyl)-3-methoxyphenyl)acetate The product from step (vi) (100 mg), ethane-1,2-diol (0.031 ml) and Hunig's Base (0.146 ml) were combined in DMF (5 mL) and HATU (106 mg) was added and stirred at rt for 1 h. The reaction mixture was purified by RPHPLC to give the title compound as a solid, 6 mg.

$^1$H NMR DMSO d-6: δ 6.91 (s, 1H), 6.72 (d, 1H), 6.64 (d, 1H), 6.02-5.92 (m, 1H), 5.69-5.57 (m, 2H), 4.80 (t, 1H), 4.04 (t, 2H), 3.84 (s, 3H), 3.62 (s, 1H), 3.59-3.54 (m, 3H), 3.26-3.18 (m, 2H), 1.96 (s, 3H), 1.50-1.33 (m, 2H), 1.28-1.09 (m, 4H), 0.84 (t, 3H)

LC-MS m/z 403 multimode+

EXAMPLE 90

4-(4-(Dimethylamino)piperidin-1-yl)butyl 2-(4-((2-amino-4-(butylamino)-6-methylpyrimidin-5-yl)methyl)-3-methoxyphenyl)acetate, saccharin salt

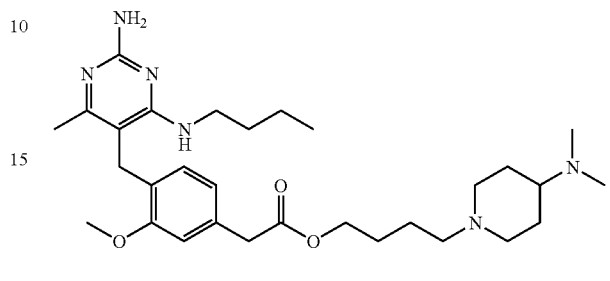

The title compound was prepared using the method of example 89 step (vii), using the product of example 89 step (vi) (150 mg) and 4-(4-(dimethylamino)piperidin-1-yl)butan-1-ol (168 mg). The saccharin salt was prepared to give the title compound as a white solid, 43 mg.

$^1$H NMR DMSO d-6: δ 7.66-7.54 (m, 5H), 6.90 (s, 1H), 6.75-6.66 (m, 2H), 6.64-6.49 (m, 1H), 6.28-6.13 (m, 2H), 4.03 (t, 2H), 3.83 (s, 3H), 3.61 (s, 3H), 3.31-3.23 (m, 2H), 2.96-2.87 (m, 2H), 2.44 (s, 5H), 2.35-2.26 (m, 2H), 2.02 (s, 3H), 1.99-1.85 (m, 2H), 1.85-1.77 (m, 2H), 1.60-1.51 (m, 2H), 1.49-1.37 (m, 6H), 1.27-1.13 (m, 3H), 0.84 (t, 3H)

LC-MS m/z 541 multimode+

EXAMPLE 91

4-Hydroxybutyl 2-(4-((2-amino-4-(butylamino)-6-methylpyrimidin-5-yl)methyl)-3-methoxyphenyl) acetate, saccharin salt

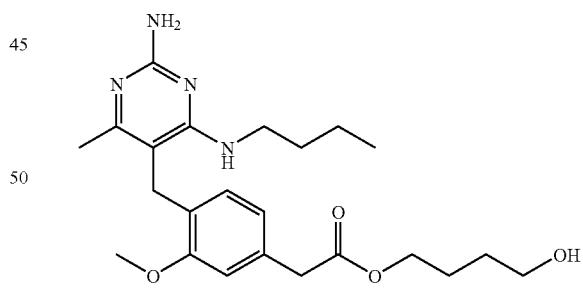

The title compound was prepared using the method of example 89 step (vii) and the product of example 89 step (vi) (150 mg) and butane-1,4-diol (75 mg). The saccharin salt was formed with one equivalent of saccharin in MeCN, to give the title compound, 30 mg.

$^1$H NMR DMSO d-6: δ 11.93-11.81 (m, 1H), 7.87 (t, 1H), 7.68-7.54 (m, 5H), 7.43-7.28 (m, 2H), 6.93 (s, 1H), 6.74 (s, 2H), 4.44-4.38 (m, 1H), 4.07-3.98 (m, 2H), 3.83 (s, 3H), 3.69-3.58 (m, 4H), 3.41-3.35 (m, 3H), 2.11 (s, 3H), 1.64-1.53 (m, 2H), 1.52-1.38 (m, 4H), 1.26-1.14 (m, 2H), 0.85 (t, 3H)

LC-MS m/z 431 multimode+

EXAMPLE 92

3-(Methylsulfonyl)propyl 2-(4-((2-amino-4-(butylamino)-6-methylpyrimidin-5-yl)methyl)-3-methoxyphenyl)acetate

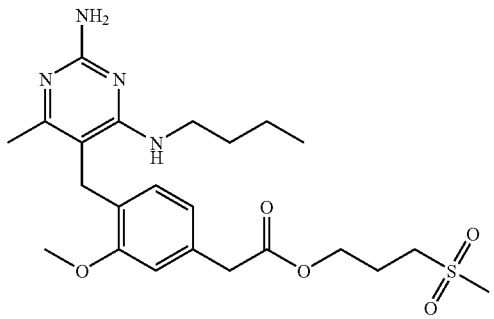

The title compound was prepared using the method of example 89 step (vii), using the product of example 89 step (vi) (150 mg) and 3-(methylsulfonyl)propan-1-ol (116 mg), to give the title compound as a gum, 6.3 mg.

$^1$H NMR DMSO d-6: δ 6.90 (d, 1H), 6.72 (dd, 1H), 6.65 (d, 1H), 6.02-5.95 (m, 1H), 5.66-5.61 (m, 2H), 4.15-4.08 (m, 2H), 3.84 (s, 3H), 3.63 (s, 2H), 3.58 (s, 2H), 3.26-3.19 (m, 2H), 3.17-3.09 (m, 2H), 2.96 (s, 3H), 2.05-1.97 (m, 2H), 1.97 (s, 3H), 1.46-1.34 (m, 2H), 1.26-1.14 (m, 2H), 0.84 (t, 3H)

LC-MS m/z 479 multimode+

EXAMPLE 93

3-Hydroxypropyl 2-(4-((2-amino-4-(butylamino)-6-methylpyrimidin-5-yl)methyl)-3-methoxyphenyl)acetate, saccharin salt

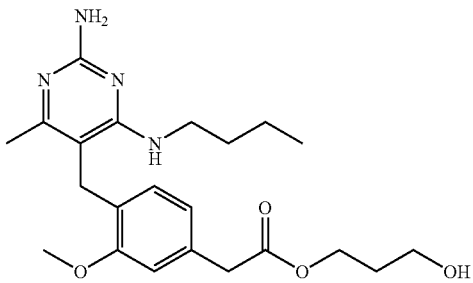

The title compound was prepared using the method of example 89 (step vii) and the product of example 89 step (vi) (150 mg) and propane-1,3-diol (63 mg). The saccharin salt was formed with one equivalent of saccharin in MeCN, to give the title compound, 30.6 mg.

$^1$H NMR DMSO d-6: δ 11.84 (s, 1H), 7.93-7.85 (m, 1H), 7.67-7.61 (m, 1H), 7.60-7.53 (m, 4H), 7.39-7.32 (m, 1H), 6.93 (s, 1H), 6.74 (s, 2H), 4.53-4.46 (m, 1H), 4.10-4.03 (m, 2H), 3.83 (s, 3H), 3.68 (s, 2H), 3.62 (s, 2H), 3.47-3.35 (m, 2H), 2.10 (s, 3H), 1.77-1.65 (m, 2H), 1.52-1.40 (m, 2H), 1.24-1.13 (m, 2H), 0.85 (t, 3H)

LC-MS m/z 417 multimode+

EXAMPLE 94

(S)-4-(Dimethylamino)butyl 2-(4-((2-amino-4-(1-hydroxyhexan-3-ylamino)-6-methylpyrimidin-5-yl)methyl)phenyl)acetate, bis saccharin salt

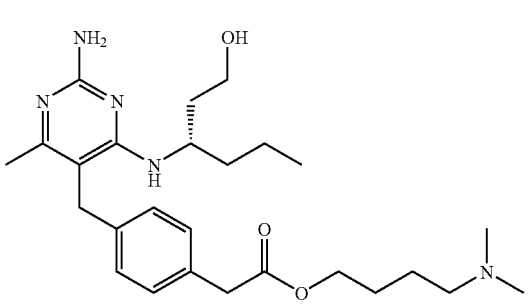

(i) (S)-2-(4-((2-Amino-4-(1-hydroxyhexan-3-ylamino)-6-methylpyrimidin-5-yl)methyl)phenyl) acetic acid A mixture of the product of example 81 step (iii) (0.4 g) and (S)-3-aminohexan-1-ol (0.5 g) in butan-1-ol (3 mL) was sealed into a microwave tube. The reaction was performed in the CEM Microwave, at 160° C. and 100 W for 1.5 h. Aq. 5M KOH (1 ml) was added and the mixture heated at 100° C. for 48 h. The mixture was cooled and the solvent evaporated under reduced pressure. The residue was purified by RPHPLC to give the subtitle compound, 174 mg.

LC/MS m/z 373 APCI+

(ii) (S)-4-(Dimethylamino)butyl 2-(4-((2-amino-4-(1-hydroxyhexan-3-ylamino)-6-methylpyrimidin-5-yl)methyl)phenyl)acetate, bis saccharin salt HATU (0.193 g) was added to a stirred solution of the product from step (i) (0.172 g), 4-(dimethylamino)butan-1-ol (0.216 g) and Hunig base (0.25 ml) in DMF (6 ml) at rt. The mixture was stirred at rt for 3 h then purified by RPHPLC to give a gum, 130 mg. The gum was dissolved in MeCN (4 ml) and saccharin (100 mg) added and the solvent evaporated under reduced pressure to give the title compound as a solid, 230 mg.

$^1$H NMR DMSO-d6/D$_2$O: δ 7.68-7.58 (m, 8H), 7.19 (d, 2H), 7.11 (d, 2H), 4.37-4.30 (m, 1H), 4.04 (t, 2H), 3.90-3.80 (m, 2H), 3.63 (s, 2H), 3.37-3.29 (m, 2H), 3.06-3.02 (m, 2H), 2.76 (s, 6H), 2.20 (s, 3H), 1.66-1.58 (m, 6H), 1.46-1.40 (m, 2H), 1.09-1.04 (m, 2H), 0.77 (t, 3H)

LC-MS m/z 472 multimode+

EXAMPLE 95

(1-Methylpiperidin-4-yl)methyl 2-(4-(2-amino-4-(butylamino)-6-methylpyrimidin-5-ylthio)phenyl)acetate, saccharin salt

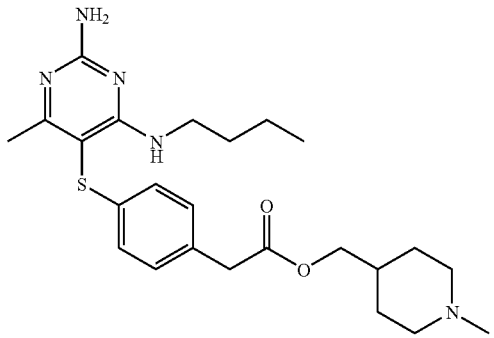

(i) 2-Amino-5-(4-(hydroxymethyl)phenylthio)-6-methylpyrimidin-4-ol

A stirred mixture of (4-mercaptophenyl)methanol (6.72 g), 2-amino-5-bromo-6-methylpyrimidin-4-ol (10.76 g) and $K_2CO_3$ (7.29 g) in ethylene glycol (120 ml) was heated at 155° C. for 9 h. After cooling the mixture was poured into water (500 ml) and neutralised with conc. HCl. The precipitate was filtered, washed with water then 50% EtOH/ether and dried to give the subtitle compound as a solid, 6.7 g.
$^1$H NMR DMSO-d6: δ11.07 (brs, 1H); 7.18 (d, 2H); 6.99 (d, 2H); 6.87 (brs, 2H); 5.09 (s, 1H); 4.41 (s, 2H); 2.24 (s, 3H)
LC/MS m/z 264 APCI+

(ii) 2-Amino-5-(4-(chloromethyl)phenylthio)-6-methylpyrimidin-4-ol $SOCl_2$ (20 ml) was added slowly to a stirred mixture of the product from step (i) (6.7 g) in DCM (50 ml) and stirred at rt for 24 h. The solvent was evaporated under reduced pressure to give the title compound, 8.7 g.
LC/MS m/z 282 APCI+

(iii) 2-(4-(2-Amino-4-hydroxy-6-methylpyrimidin-5-ylthio)phenyl)acetonitrile A mixture of the product from step (ii) (8.7 g) and KCN (8.28 g) in DMF (20 ml) and DMSO (20 ml) was stirred at rt for 2 h then 50° C. for 2 h. Water (150 ml) was added and stirred for 30 min. The solid obtained was filtered off and added to MeOH (150 ml), heated to reflux for 5 min then hot filtered and allowed to cool to rt. The precipitate was filtered and dried under high vacuum at 45° C., to give the subtitle compound as a brown solid, 23 g.
LC/MS m/z 273 APCI+

(iv) 2-(4-(2-Amino-4-chloro-6-methylpyrimidin-5-ylthio)phenyl)acetonitrile

A mixture of the product from step (iii) (2.3 g) and $POCl_3$ (25 ml) was heated under reflux for 8 h. The mixture was evaporated under reduced pressure and ice/water added to the residue. The mixture was stirred at rt for 15 min then neutralised with aq. 2M NaOH solution and heated at 40° C. for 2 h then extracted with DCM. The organics were dried, evaporated under reduced pressure and the residue purified by column chromatography (2% MeOH/DCM), to give the subtitle compound as a solid, 530 mg.
$^1$H NMR $CDCl_3$: δ 7.22 (d, 2H); 7.07 (d, 2H); 5.36 (s, 2H); 3.70 (s, 2H); 2.50 (s, 3H) LC/MS m/z 291 APCI+

(v) 2-(4-(2-Amino-4-(butylamino)-6-methylpyrimidin-5-ylthio)phenyl)acetonitrile A mixture of the product from step (iv) (525 mg) and butylamine (3 ml) in BuOH (14 ml) was heated under reflux for 5 h. The solvent was evaporated under reduced pressure and the residue partitioned between EtOAc/water. The organics were separated, dried and evaporated under reduced pressure to give the subtitle compound as a gum, 610 mg.
LC/MS m/z 328 APCI+

(vi) 2-(4-(2-Amino-4-(butylamino)-6-methylpyrimidin-5-ylthio)phenyl)acetic acid A mixture of the product from step (v) (610 mg) and aq. SM KOH (2 ml) in EtOH (8 ml) was heated under reflux for 18 h. The mixture was purified by RPHPLC to give the subtitle compound as a solid, 392 mg.
$^1$H NMR DMSO-d6: δ7.09 (d, 2H); 6.87 (d, 2H); 6.54 (t, 1H); 6.30 (s, 2H); 3.29-3.24 (m, 2H); 3.20 (s, 2H); 2.19 (s, 3H); 1.45-1.38 (m, 2H); 1.23-1.13 (m, 2H); 0.82 (t, 3H)
LC/MS m/z 347 APCI+

(vii) (1-Methylpiperidin-4-yl)methyl 2-(4-(2-amino-4-(butylamino)-6-methylpyrimidin-5-ylthio)phenyl)acetate, saccharin salt HATU (0.209 g) was added to a stirred mixture of the product from step (vi) (0.19 g), (1-methylpiperidin-4-yl)methanol (0.142 g), and Hunig's base (0.3 ml) in DMF (6 ml) at rt. The mixture was stirred for 24 h then purified by RPHPLC, to give a gum (130 mg). The gum was dissolved in MeCN (5 ml) and saccharin (52 mg) added and the solution evaporated under reduced pressure, triturated with ether and filtered to give the title compound as a solid, 173 mg.
$^1$H NMR DMSO-d6: δ 7.65-7.56 (m, 4H); 7.17 (d, 2H); 6.98 (d, 2H); 6.70 (s, 1H); 6.43 (s 2H); 3.93 (d, 2H); 3.62 (s, 2H); 3.31-3.23 (m, 2H); 2.91-2.81 (brm, 2H); 2.71 (s, 3H) 2.20 (s, 3H); 1.85-1.75 (m, 3H); 1.45-1.33 (m, 4H) 1.20-1.11 (m, 2H); 0.81 (t, 3H)
LC-MS m/z 458 multimode+

EXAMPLE 96

4-(Pyrrolidin-1-yl)butyl 2-(4-(2-amino-4-(butylamino)-6-methylpyrimidin-5-ylthio)phenyl)acetate, saccharin salt

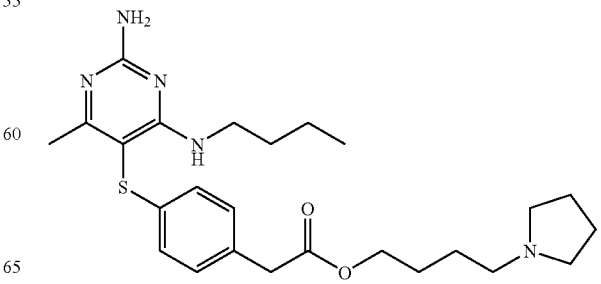

The title compound was prepared via the method of example 95, using the product of step (vi) (180 mg) and 4-(pyrrolidin-1-yl)butan-1-ol (149 mg), to give a solid, 189 mg.

$^1$H NMR DMSO-d6: δ 7.65-7.55 (m, 4H); 7.17 (d, 2H); 6.97 (d, 2H); 6.66 (s, 1H); 6.41 (s, 2H); 4.04 (t, 2H); 3.61 (s, 2H); 3.27 (m, 2H); 3.08 (brm, 2H); 2.20 (s, 3H) 1.91 (s, 4H); 1.65-1.58 (m, 4H); 1.44-1.37 (m, 2H) 1.20-1.07 (m, 2H); 0.81 (t, 3H)

LC-MS m/z 472 multimode+

EXAMPLE 97

4-(Dimethylamino)butyl 2-(3-((2-amino-4-(butylamino)-6-methylpyrimidin-5-yl)methyl)-4-methoxyphenyl)acetate, saccharin salt

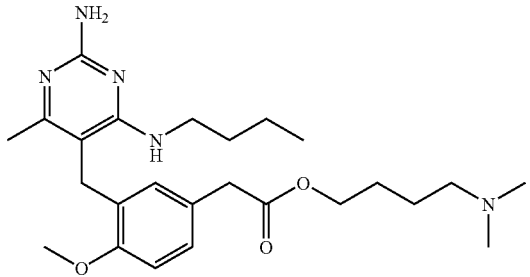

HATU (382 mg) was added to a stirred solution of the product from example 83 step (iv) (300 mg), 4-(dimethylamino)-1-butanol (196 mg) and triethylamine (0.233 ml) in DMF (3 mL). The mixture was stirred at rt for 1 h and then diluted with MeCN (2 mL) and purified via RPHPLC. The purified product was dissolved in MeCN (1 mL) and saccharin (14.84 mg) was added and the solution was stirred for 10 min. The solvent was evaporated under reduced pressure and the residue was triturated with diethyl ether to give the title compound as a white solid, 31 mg.

$^1$H NMR DMSO-d6: δ 7.66-7.55 (m, 7H), 7.10 (dd, 1H), 6.96 (d, 1H), 6.72 (d, 1H), 4.00 (t, 2H), 3.83 (s, 3H), 3.68 (s, 2H), 3.53 (s, 2H), 3.42-3.33 (m, 2H), 3.02-2.93 (m, 2H), 2.71 (s, 6H), 2.10 (s, 3H), 1.68-1.51 (m, 4H), 1.47 (q, 2H), 1.27-1.15 (m, 2H), 0.85 (t, 3H)

LC-MS m/z 458 multimode+

EXAMPLE 98

Methyl 2-(3-((2-amino-4-(butylamino)-6-methylpyrimidin-5-yl)methyl)-4-methoxyphenyl)acetate

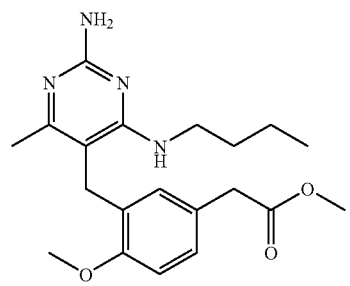

A solution of boron tribromide (13.95 ml, 1M in DCM) was added portionwise over 30 min to a stirred suspension of the product from example 83 step (iv) (1 g) in DCM (15 mL) at 0° C. The suspension was allowed to warm to rt and stirred for 5 h. The suspension was cooled to 0° C. and then MeOH (10 mL) and 4M HCl in dioxane (2 mL) were added and the mixture stirred for 1 h. The solvent was evaporated under reduced pressure and the residue was purified by flash silica chromatography (5% MeOH/DCM) to give the title compound (minor product) as a white solid, 51 mg.

$^1$H NMR DMSO-d6: δ 9.81 (s, 1H), 7.51 (s, 1H), 6.99 (s, 2H), 6.92 (dd, 1H), 6.79 (d, 1H), 6.70 (d, 1H), 3.63 (s, 2H), 3.55 (s, 3H), 3.47 (s, 2H), 3.38-3.33 (m, 2H), 2.16 (s, 3H), 1.53-1.41 (m, 2H), 1.28-1.16 (m, 2H), 0.85 (t, 3H)

LC-MS m/z 373 multimode+

EXAMPLE 99

Methyl 2-(3-((2-amino-4-(butylamino)-6-methylpyrimidin-5-yl)methyl)-4-hydroxyphenyl)acetate

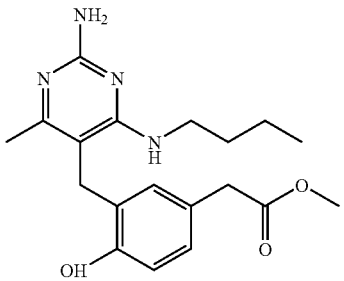

A solution of boron tribromide (2.51 ml, 1M in DCM) was added portionwise over 30 min to a stirred suspension of the product from example 83 step (iv) (300 mg) in DCM (5 mL) at 0° C. The suspension was allowed to warm to rt and stirred for 3 h. A further portion of boron tribromide (1.674 ml, 1M in DCM) was added and the mixture stirred at rt for a further 2 h. MeOH (2 mL) and 4M HCl in dioxane (2 mL) were added and the mixture stirred for 1 h. The solvent was evaporated under reduced pressure and the residue purified by RPHPLC, to give the title compound as a white solid, 27 mg.

$^1$H NMR DMSO-d6: δ 9.65 (s, 1H), 6.87 (dd, 1H), 6.76 (d, 1H), 6.66 (d, 1H), 6.05 (t, 1H), 5.61 (s, 2H), 3.56 (s, 2H), 3.54 (s, 3H), 3.43 (s, 2H), 3.26-3.20 (m, 2H), 2.06 (s, 3H), 1.43 (q, 2H), 1.21 (sextet, 2H), 0.84 (t, 3H)

LC-MS m/z 359 multimode+

EXAMPLE 100

(S)-2-(1-Methylpiperidin-4-yl)ethyl 2-(4-((2-amino-4-(1-hydroxyhexan-3-ylamino)-6-methylpyrimidin-5-yl)methyl)-3-fluorophenyl)acetate, saccharin salt

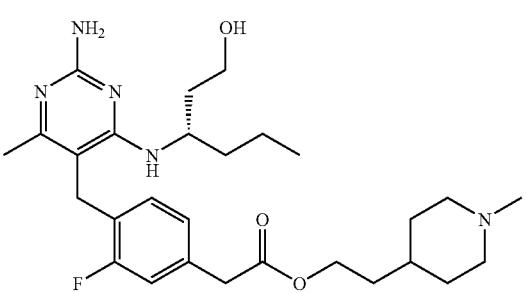

HATU (175 mg) was added to a stirred solution of the product from example 74 step (ii) (150 mg), 2-(1-methylpiperidin-4-yl)ethanol (110 mg) and triethylamine (0.107 ml) in DMF (2 ml). The mixture was stirred at rt for 1 h and then diluted with MeCN (3 ml). The solution was purified by RPHPLC, the resulting gum was dissolved in MeCN (0.5 mL) and saccharin (11.72 mg) was added and the solvent evaporated. The residue was triturated with diethyl ether to give the title compound as a solid, 22 mg.

$^1$H NMR DMSO-d6: δ 7.67-7.55 (m, 5H), 7.12 (d, 1H), 6.99 (d, 1H), 6.92-6.82 (m, 3H), 4.41-4.29 (m, 2H), 4.11-4.04 (m, 2H), 3.81 (s, 2H), 3.67 (s, 2H), 3.42-3.37 (m, 2H), 2.80-2.69 (m, 2H), 2.67 (s, 3H), 2.08 (s, 3H), 1.84-1.75 (m, 2H), 1.67-1.49 (m, 6H), 1.48-1.38 (m, 2H), 1.37-1.06 (m, 6H), 0.81 (t, 3H)

LC-MS m/z 516 multimode+

EXAMPLE 101

2-(4-Methylthiazol-5-yl)ethyl 2-(4-((2-amino-4-(butylamino)-6-methylpyrimidin-5-yl)methyl)-3-methoxyphenyl)acetate

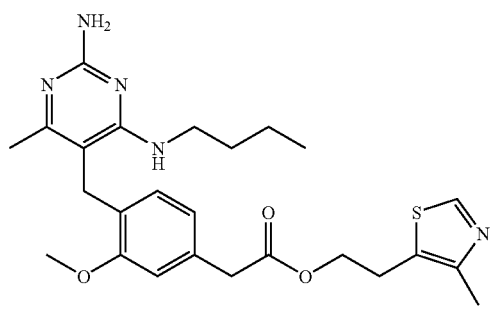

The title compound was prepared using the method of example 89 step (vii), using the product of example 89 step (vi) (150 mg) and 2-(4-methylthiazol-5-yl)ethanol (60 mg) to give the title compound as a gum, 10 mg.

$^1$H NMR DMSO-d6: δ 8.80 (s, 1H), 6.84 (d, 1H), 6.69-6.58 (m, 2H), 5.98 (t, 1H), 5.64 (s, 2H), 4.18 (t, 2H), 3.81 (s, 3H), 3.59 (d, 4H), 3.27-3.16 (m, 2H), 3.07 (t, 2H), 2.27 (s, 3H), 1.99 (d, 3H), 1.44-1.34 (m, 2H), 1.28-1.11 (m, 2H), 0.83 (t, 3H)

LC-MS m/z 484 multimode+

EXAMPLE 102

4-(Dimethylamino)butyl 2-(4-((2-amino-4-(butylamino)-6-methylpyrimidin-5-yl)methyl)-3-hydroxyphenyl)acetate

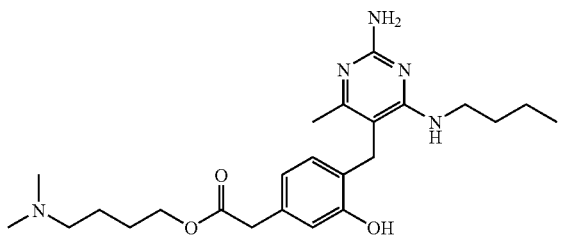

The title compound was prepared using product of example 79 step (i) (80 mg) and 4-(dimethylamino)butan-1-ol using the general coupling method of example 74 step (iii). The product was purified by RPHPLC to give the product, 25 mg.

$^1$H NMR DMSO-d6: δ 6.73-6.64 (m, 2H), 6.54-6.46 (m, 1H), 5.57 (s, 2H), 4.00 (t, 2H), 3.54 (s, 2H), 3.49-3.40 (m, 2H), 3.26-3.16 (m, 4H), 2.19-2.11 (m, 2H), 2.07 (s, 6H), 1.60-1.48 (m, 2H), 1.47-1.28 (m, 4H), 1.26-1.14 (m, 3H), 0.83 (t, 3H)

LC-MS m/z 444 APCI+

EXAMPLE 103

(1-Methylpiperidin-4-yl)methyl 2-(4-((2-amino-4-(butylamino)-6-methylpyrimidin-5-yl)methyl)-3-hydroxyphenyl)acetate, di-trifluoroacetic acid salt

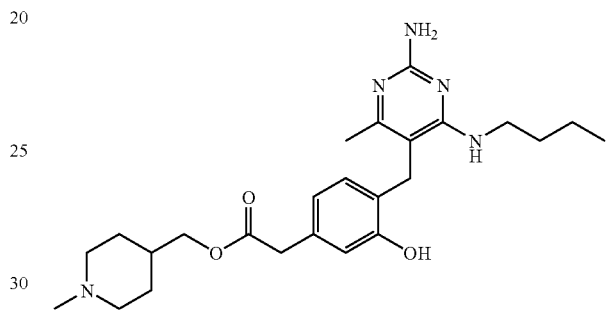

The title compound was prepared using product of example 79 step (i) (90 mg) and (1-methylpiperidin-4-yl)methanol using the general coupling method of example 74 step (iii). The product was purified by RPHPLC to give the product, 15.4 mg.

$^1$H NMR DMSO-d6: δ 12.32-12.11 (m, 1H), 10.04-9.86 (m, 1H), 9.40-9.18 (m, 1H), 7.92-7.78 (m, 1H), 7.57-7.42 (m 2H), 6.80-6.69 (m, 2H), 6.65-6.54 (m, 1H), 3.91 (s, 2H), 3.63 (s, 2H), 3.55 (s, 2H), 3.45-3.29 (m, 4H), 2.97-2.79 (m, 3H), 2.79-2.70 (m, 3H), 2.18 (s, 3H), 1.90-1.76 (m, 2H), 1.52-1.29 (m, 4H), 1.27-1.14 (m, 2H), 0.85 (t, 3H)

LC-MS m/z 456 APCI+

Biological Assay

Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound (pEC50). The results obtained are shown in Table 1 following.

TABLE 1

| Compound of Ex. No. | pEC50 | Compound of Ex. No. | pEC50 |
|---|---|---|---|
| 1 | 6.3 | 2 | 6.0 |
| 3 | 6.2 | 4 | 6.4 |
| 5 | 6.2 | 6 | 5.9 |
| 7 | 5.6 | 8 | 5.6 |
| 9 | 5.4 | 10 | 5.8 |
| 11 | 6.0 | 12 | 5.8 |
| 13 | 5.6 | 14 | 5.9 |
| 15 | 6.4 | 16 | 5.8 |
| 17 | 6.0 | 18 | 5.8 |
| 19 | 5.6 | 20 | 5.7 |
| 21 | 7.8 | 22 | 6.2 |
| 23 | 6.0 | 24 | 6.0 |
| 25 | 6.1 | 26 | 6.1 |
| 27 | 5.7 | 28 | 5.9 |
| 29 | 6.1 | 30 | 7.5 |
| 31 | 8.2 | 32 | 7.3 |
| 33 | 7.3 | 34 | 6.4 |
| 35 | 6.6 | 36 | 6.6 |
| 37 | 6.9 | 38 | 6.9 |
| 39 | 7.0 | 40 | 6.9 |
| 41 | 6.0 | 42 | 6.2 |
| 43 | 6.1 | 44 | 6.2 |
| 45 | 7.3 | 46 | 7.6 |
| 47 | 6.3 | 48 | 8.7 |
| 49 | 6.7 | 50 | 6.8 |
| 51 | 6.1 | 52 | 6.2 |
| 53 | 7.4 | 54 | 7.1 |
| 55 | 6.9 | 56 | 6.6 |
| 57 | 6.9 | 58 | 6.9 |
| 59 | 6.9 | 60 | 6.7 |
| 61 | 6.9 | 62 | 6.7 |
| 63 | 6.8 | 64 | 5.6 |
| 65 | 6.5 | 66 | 6.8 |

TABLE 1-continued

| Compound of Ex. No. | pEC50 | Compound of Ex. No. | pEC50 |
|---|---|---|---|
| 67 | 6.1 | 68 | 6.2 |
| 69 | 6.9 | 70 | 5.9 |
| 71 | 7.7 | 72 | 7.8 |
| 73 | 8.3 | 74 | 7.4 |
| 75 | 8.2 | 76 | 6.2 |
| 77 | 7.2 | 78 | 7.3 |
| 79 | 6.9 | 80 | 7.7 |
| 81 | 6.0 | 82 | 7.0 |
| 83 | 7.7 | 84 | 6.5 |
| 85 | 6.3 | 86 | 6.7 |
| 87 | 7.6 | 88 | 7.0 |
| 89 | 7.3 | 90 | 7.6 |
| 91 | 7.7 | 92 | 7.7 |
| 93 | 7.7 | 94 | 6.9 |
| 95 | 7.2 | 96 | 7.3 |
| 97 | 7.5 | 98 | 7.3 |
| 99 | 7.1 | 100 | 7.5 |
| 101 | 7.4 | 102 | 7.0 |
| 103 | 6.9 | | |

The invention claimed is:

1. A compound, which is 4-(dimethylamino)butyl 2-(4-((2-amino-4-methyl-6-(pentylamino)pyrimidin-5-yl)methyl) phenyl)acetate, or a pharmaceutically acceptable salt thereof.

2. A compound, which is 4-(dimethylamino)butyl 2-(4-((2-amino-4-methyl-6-(pentylamino)pyrimidin-5-yl)methyl) phenyl)acetate.

3. A compound, which is a pharmaceutically acceptable salt of 4-(dimethylamino)butyl 2-(4-((2-amino-4-methyl-6-(pentylamino)pyrimidin-5-yl)methyl)phenyl)acetate.

4. A pharmaceutical composition comprising a compound as claimed in any one of claims 1 to 3 in association with a pharmaceutically acceptable adjuvant, diluent or carrier.

* * * * *